US012605416B2

(12) United States Patent
Varma et al.

(10) Patent No.: US 12,605,416 B2
(45) Date of Patent: Apr. 21, 2026

(54) COMPOSITIONS AND METHODS FOR THE TREATMENT OF SKIN DISEASES AND CONDITIONS INCLUDING ECZEMA

(71) Applicant: PHI THERAPEUTICS, INC., San Francisco, CA (US)

(72) Inventors: Yug Varma, San Francisco, CA (US); Elijah Horwitz, San Francisco, CA (US)

(73) Assignee: PHI THERAPEUTICS, INC., San Francisco, CA (US)

( * ) Notice: Subject to any disclaimer, the term of this patent is extended or adjusted under 35 U.S.C. 154(b) by 0 days.

(21) Appl. No.: 19/003,326

(22) Filed: Dec. 27, 2024

(65) Prior Publication Data

US 2025/0134940 A1     May 1, 2025

Related U.S. Application Data

(63) Continuation of application No. PCT/US2024/022657, filed on Apr. 2, 2024.

(60) Provisional application No. 63/493,834, filed on Apr. 3, 2023.

(51) Int. Cl.
| | |
|---|---|
| *A61K 35/76* | (2015.01) |
| *A61K 9/00* | (2006.01) |
| *A61K 9/10* | (2006.01) |
| *A61K 36/899* | (2006.01) |
| *A61K 38/47* | (2006.01) |
| *A61P 17/00* | (2006.01) |
| *A61P 29/00* | (2006.01) |
| *A61P 31/02* | (2006.01) |

(52) U.S. Cl.
CPC ............ *A61K 35/76* (2013.01); *A61K 9/0014* (2013.01); *A61K 9/10* (2013.01); *A61K 36/899* (2013.01); *A61K 38/47* (2013.01); *A61P 17/00* (2018.01); *A61P 29/00* (2018.01); *A61P 31/02* (2018.01)

(58) Field of Classification Search
CPC ...................................................... A61K 35/76
See application file for complete search history.

(56) References Cited

U.S. PATENT DOCUMENTS

| | | | |
|---|---|---|---|
| 5,034,506 A | 7/1991 | Summerton et al. | |
| 5,235,033 A | 8/1993 | Summerton et al. | |
| 11,339,386 B2 | 5/2022 | Loessner et al. | |
| 2019/0249149 A1 | 8/2019 | Modlin et al. | |
| 2024/0415904 A1* | 12/2024 | Zelcbuch | ............... A61P 31/04 |

FOREIGN PATENT DOCUMENTS

| | | |
|---|---|---|
| WO | 2021207082 A2 | 10/2021 |

OTHER PUBLICATIONS

NCBI (https://blast.ncbi.nlm.nih.gov/Blast.cgi?PROGRAM=blastn&BLAST_SPEC=GeoBlast&PAGE_TYPE=BlastSearch) Blast results, SEQ ID NO. 45, Apr. 29, 2025.*

(Continued)

*Primary Examiner* — Sharmila G Landau
(74) *Attorney, Agent, or Firm* — QUARLES & BRADY LLP

(57)     ABSTRACT

Disclosed herein are therapeutic compositions comprising bacteriophage and colloidal oatmeal, and methods of using the compositions for the treatment of skin diseases and conditions including eczema.

17 Claims, 5 Drawing Sheets
Specification includes a Sequence Listing.

(56)  References Cited

OTHER PUBLICATIONS

Abo-elmaaty et al., "Improved antibacterial efficacy of bacteriophage-cosmetic formulation for treatment of *Staphylococcus aureus* in vitro," Annals of Agricultural Science 61(2):201-206, 2016.*

The Care and Keeping of Sensitive Skin A Practical Guide to Holistic Skin Care, Lissa Bell, iUniverse, Bloomington, Indiana, 2012, pp. 9-10.*

Duc et al (Applied Microbiology and Biotechnology, 2020, 104:5145-5158).*

Tabassum et al (Scientific Reports, 2022, 12:10008, pp 1-12).*

Ajuebor et al., Comparison of *Staphylococcus* Phage K with Close Phage Relatives Commonly Employed in Phage Therapeutics, Antibiotics, 2018, 7(2):37, pp. 1-14.

Altschul et al., Basic local alignment search tool, Journal of Molecular Biology, 1990, 215(3):403-410.

Altschul et al., Gapped BLAST and PSI-BLAST: a new generation of protein database search programs, Nucleic Acids Research, 1997, 25(17):3389-3402.

Aveeno, Colloidal Oatmeal: Composition, Benefits & Mechanism of Action, Retrieved from https://www.aveenomd.com/sites/aveenomd_us/files/colloidal_oatmeal.pdf, Version Accessed on Jun. 27, 2024, 2 pages.

Bolli et al., α-Bicyclo-DNA: Synthesis, Characterization, and Pairing Properties of α-DNA-Analogues with Restricted Conformational Flexibility in the Sugar-Phosphate Backbone, In "Carbohydrate Modifications in Antisense Research," ACS Symposium Series, 1994, vol. 580, Chapter 7, pp. 100-117.

Estrella et al., Characterization of novel *Staphylococcus aureus* lytic phage and defining their combinatorial virulence using the OmniLog® system, Bacteriophage, 2016, 6(3):e1219440, pp. 1-13.

Fang et al., Prebiotic Colloidal Oat Supports the Growth of Cutaneous Commensal Bacteria Including S. Epidermidis and Enhances the Production of Lactic Acid, Clinical, Cosmetic and Investigational Dermatology, 2021, 14:73-82.

Ganaie et al., Isolation and characterization of two lytic bacteriophages against *Staphylococcus aureus* from India: newer therapeutic agents against Bovine mastitis, Veterinary Research Communications, 2018, 42:289-295.

Gill, Revised genome sequence of *Staphylococcus aureus* bacteriophage K, Genome Announcements, 2014, 2(1):e01173-13, pp. 1-2.

Göller et al., Multi-species host range of staphylococcal phages isolated from wastewater, Nature Communications, 2021, 12(1):6965, pp. 1-17.

Gu et al., Complete genome sequence of *Staphylococcus aureus* bacteriophage GH15, Journal of Virology, 2012, 86(16):8914-8915.

Gu et al., Genomic characterization of lytic *Staphylococcus aureus* phage GH15: providing new clues to intron shift in phages, Journal of General Virology, 2013, 94(4):906-915.

Henikoff et al., Amino acid substitution matrices from protein blocks, Proceedings of the National Academy of Sciences, 1992, 89(22):10915-10919.

Herdewijn et al., Hexopyranosyl-Like Oligonucleotides, In "Carbohydrate Modifications in Antisense Research," ACS Symposium Series, 1994, vol. 580, Chapter 6, pp. 80-99.

Hsieh et al., Wide host range and strong lytic activity of *Staphylococcus aureus* lytic phage Stau2, Applied and Environmental Microbiology, 2011, 77(3):756-761.

Kim et al., Complete genome of *Staphylococcus aureus* phage SA11, Journal of Virology, 2012, 86(18):10232.

Kwan et al., The complete genomes and proteomes of 27 *Staphylococcus aureus* bacteriophages, Proceedings of the National Academy of Sciences, 2005, 102(14):5174-5179.

Łubowska et al., Characterization of the three new kayviruses and their lytic activity against multidrug-resistant *Staphylococcus aureus*, Microorganisms, 2019, 7(10):471, pp. 1-18.

National Institute of Health, National Library of Medicine: National Center for Biotechnology Information, *Staphylococcus phage* K, complete genome, GenBank: AY176327.1, Retrieved from https://www.ncbi.nlm.nih.gov/nuccore/AY176327, May 6, 2004, 50 pages.

National Institute of Health, National Library of Medicine: National Center for Biotechnology Information, *Homo sapiens* isolate JIANGXI10 D-loop, partial sequence; mitochondrial, GenBank: AY594960.1, Retrieved from https://www.ncbi.nlm.nih.gov/nuccore/AY594960, Sep. 17, 2004, 1 page.

National Institute of Health, National Library of Medicine: National Center for Biotechnology Information, Bacteriophage PT1028, complete genome, GenBank: AY954948.1, Apr. 15, 2005, 8 pages.

National Institute of Health, National Library of Medicine: National Center for Biotechnology Information, Bacteriophage 66, complete genome, GenBank: AY954949.1, Retrieved from https://www.ncbi.nlm.nih.gov/nuccore/AY954949, Apr. 15, 2005, 9 pages.

National Institute of Health, National Library of Medicine: National Center for Biotechnology Information, Bacteriophage 2638A, complete genome, GenBank: AY954954.1, Retrieved from https://www.ncbi.nlm.nih.gov/nuccore/AY954954, Apr. 15, 2005, 18 pages.

National Institute of Health, National Library of Medicine: National Center for Biotechnology Information, Bacteriophage ROSA, complete genome, GenBank: AY954961.1, Retrieved from https://www.ncbi.nlm.nih.gov/nuccore/AY954961, Apr. 15, 2005, 20 pages.

National Institute of Health, National Library of Medicine: National Center for Biotechnology Information, *Staphylococcus* phage JD007, complete genome, GenBank: JX878671.1, Retrieved from https://www.ncbi.nlm.nih.gov/nuccore/JX878671, Nov. 21, 2012, 59 pages.

National Institute of Health, National Library of Medicine: National Center for Biotechnology Information, *Staphylococcus* phage MCE-2014, complete genome, GenBank: KJ888149.1, Retrieved from https://www.ncbi.nlm.nih.gov/nuccore/KJ888149, Oct. 23, 2014, 58 pages.

National Institute of Health, National Library of Medicine: National Center for Biotechnology Information, *Staphylococcus* phage philPLA-RODI, complete genome, GenBank: KP027446.1, Retrieved from https://www.ncbi.nlm.nih.gov/nuccore/KP027446, Mar. 23, 2015, 58 pages.

National Institute of Health, National Library of Medicine: National Center for Biotechnology Information, Unverified: *Staphylococcus* phage vB_SauM-A, complete genome, GenBank: MN539736.1, Retrieved from https://www.ncbi.nlm.nih.gov/nuccore/MN539736.1/, Sep. 29, 2020, 32 pages.

National Institute of Health, National Library of Medicine: National Center for Biotechnology Information, Unverified: *Staphylococcus* phage vB_SauM-C, complete genome, GenBank: MN539737.1, Retrieved from https://www.ncbi.nlm.nih.gov/nuccore/MN539737, Sep. 29, 2020, 32 pages.

National Institute of Health, National Library of Medicine: National Center for Biotechnology Information, Unverified: *Staphylococcus* phage vB_SauM-D, complete genome, GenBank: MN539738.1, Retrieved from https://www.ncbi.nlm.nih.gov/nuccore/MN539738, Sep. 29, 2020, 32 pages.

National Institute of Health, National Library of Medicine: National Center for Biotechnology Information, *Staphylococcus* phage SaGU1 DNA, complete genome, GenBank: LC574321.1, Retrieved from https://www.ncbi.nlm.nih.gov/nuccore/LC574321, May 13, 2021, 62 pages.

National Innational Institute of Health, National Library of Medicine: National Center for Biotechnology Information, Unverified: *Staphylococcus* phage PG-2021_10, complete genome, GenBank: MZ417315.1, Retrieved from https://www.ncbi.nlm.nih.gov/nuccore/MZ417315, Sep. 24, 2021, 32 pages.

National Innational Institute of Health, National Library of Medicine: National Center for Biotechnology Information, Unverified: *Staphylococcus* phage PG-2021_12, complete genome, GenBank: MZ417316.1, Retrieved from https://www.ncbi.nlm.nih.gov/nuccore/MZ417316, Sep. 24, 2021, 33 pages.

National Innational Institute of Health, National Library of Medicine: National Center for Biotechnology Information, Unverified: *Staphylococcus* phage PG-2021_14, complete genome, GenBank: MZ417317.1, Retrieved from https://www.ncbi.nlm.nih.gov/nuccore/mz417317, Sep. 24, 2021, 33 pages.

National Innational Institute of Health, National Library of Medicine: National Center for Biotechnology Information, Unverified: *Staphylococcus* phage PG-2021_15, complete genome, GenBank:

(56) References Cited

OTHER PUBLICATIONS

MZ417318.1, Retrieved from https://www.ncbi.nlm.nih.gov/nuccore/ MZ417318, Sep. 24, 2021, 33 pages.
National Innational Institute of Health, National Library of Medicine: National Center for Biotechnology Information, Unverified: *Staphylococcus* phage PG-2021_16, complete genome, GenBank: MZ417319.1, Retrieved from https://www.ncbi.nlm.nih.gov/nuccore/ MZ417319, Sep. 24, 2021, 32 pages.
National Innational Institute of Health, National Library of Medicine: National Center for Biotechnology Information, Unverified: *Staphylococcus* phage PG-2021_17, complete genome, GenBank: MZ417320.1, Retrieved from https://www.ncbi.nlm.nih.gov/nuccore/ MZ417320, Sep. 24, 2021, 33 pages.
National Innational Institute of Health, National Library of Medicine: National Center for Biotechnology Information, Unverified: *Staphylococcus* phage PG-2021_18, complete genome, GenBank: MZ417321.1, Retrieved from https://www.ncbi.nlm.nih.gov/nuccore/ MZ417321, Sep. 24, 2021, 32 pages.
National Innational Institute of Health, National Library of Medicine: National Center for Biotechnology Information, Unverified: *Staphylococcus* phage PG-2021_1, complete genome, GenBank: MZ417323.1, Retrieved from https://www.ncbi.nlm.nih.gov/nuccore/ MZ417323, Sep. 24, 2021, 33 pages.
National Innational Institute of Health, National Library of Medicine: National Center for Biotechnology Information, Unverified: *Staphylococcus* phage PG-2021_22, complete genome, GenBank: MZ417324.1, Retrieved from https://www.ncbi.nlm.nih.gov/nuccore/ MZ417324, Sep. 24, 2021, 33 pages.
National Innational Institute of Health, National Library of Medicine: National Center for Biotechnology Information, Unverified: *Staphylococcus* phage PG-2021_23, complete genome, GenBank: MZ417325.1, Retrieved from https://www.ncbi.nlm.nih.gov/nuccore/ MZ417325, Sep. 24, 2021, 32 pages.
National Innational Institute of Health, National Library of Medicine: National Center for Biotechnology Information, Unverified: *Staphylococcus* phage PG-2021_27, complete genome, GenBank: MZ417326.1, Retrieved from https://www.ncbi.nlm.nih.gov/nuccore/ MZ417326, Sep. 24, 2021, 30 pages.
National Innational Institute of Health, National Library of Medicine: National Center for Biotechnology Information, Unverified: *Staphylococcus* phage PG-2021_33, complete genome, GenBank: MZ417330.1, Retrieved from https://www.ncbi.nlm.nih.gov/nuccore/ MZ417330, Sep. 24, 2021, 31 pages.
National Innational Institute of Health, National Library of Medicine: National Center for Biotechnology Information, Unverified: *Staphylococcus* phage PG-2021_38, complete genome, GenBank: MZ417332.1, Retrieved from https://www.ncbi.nlm.nih.gov/nuccore/ MZ417332, Sep. 24, 2021, 32 pages.
National Innational Institute of Health, National Library of Medicine: National Center for Biotechnology Information, Unverified: *Staphylococcus* phage PG-2021_40, complete genome, GenBank: MZ417333.1, Retrieved from https://www.ncbi.nlm.nih.gov/nuccore/ MZ417333, Sep. 24, 2021, 33 pages.
National Innational Institute of Health, National Library of Medicine: National Center for Biotechnology Information, Unverified: *Staphylococcus* phage PG-2021_43, complete genome, GenBank: MZ417335.1, Retrieved from https://www.ncbi.nlm.nih.gov/nuccore/ MZ417335.1/, Sep. 24, 2021, 33 pages.
National Innational Institute of Health, National Library of Medicine: National Center for Biotechnology Information, Unverified: *Staphylococcus* phage PG-2021_47, complete genome, GenBank: MZ417337.1, Retrieved from https://www.ncbi.nlm.nih.gov/nuccore/ MZ417337, Sep. 24, 2021, 33 pages.
National Innational Institute of Health, National Library of Medicine: National Center for Biotechnology Information, Unverified: *Staphylococcus* phage PG-2021_4, complete genome, GenBank: MZ417338.1, Retrieved from https://www.ncbi.nlm.nih.gov/nuccore/ MZ417338, Sep. 24, 2021, 22 pages.
National Innational Institute of Health, National Library of Medicine: National Center for Biotechnology Information, Unverified:

*Staphylococcus* phage PG-2021_64, complete genome, GenBank: MZ417340.1, Retrieved from https://www.ncbi.nlm.nih.gov/nuccore/ MZ417340, Sep. 21, 2021, 33 pages.
National Innational Institute of Health, National Library of Medicine: National Center for Biotechnology Information, Unverified: *Staphylococcus* phage PG-2021_68, complete genome, GenBank: MZ417342.1, Retrieved from https://www.ncbi.nlm.nih.gov/nuccore/ MZ417342, Sep. 24, 2021, 22 pages.
National Innational Institute of Health, National Library of Medicine: National Center for Biotechnology Information, Unverified: *Staphylococcus* phage PG-2021_84, complete genome, GenBank: MZ417345.1, Retrieved from https://www.ncbi.nlm.nih.gov/nuccore/ MZ417345, Sep. 24, 2021, 32 pages.
National Innational Institute of Health, National Library of Medicine: National Center for Biotechnology Information, Unverified: *Staphylococcus* phage PG-2021_86, complete genome, GenBank: MZ417346.1, Retrieved from https://www.ncbi.nlm.nih.gov/nuccore/ MZ417346, Sep. 24, 2021, 33 pages.
National Innational Institute of Health, National Library of Medicine: National Center for Biotechnology Information, Unverified: *Staphylococcus* phage PG-2021_87, complete genome, GenBank: MZ417347.1, Retrieved from https://www.ncbi.nlm.nih.gov/nuccore/ MZ417347, Sep. 24, 2021, 32 pages.
National Innational Institute of Health, National Library of Medicine: National Center for Biotechnology Information, Unverified: *Staphylococcus* phage PG-2021_8, complete genome, GenBank: MZ417350.1, Retrieved from https://www.ncbi.nlm.nih.gov/nuccore/ MZ417350, Sep. 24, 2021, 32 pages.
National Innational Institute of Health, National Library of Medicine: National Center for Biotechnology Information, Unverified: *Staphylococcus* phage PG-2021_9, complete genome, GenBank: MZ417354.1, Retrieved from https://www.ncbi.nlm.nih.gov/nuccore/ MZ417354, Sep. 24, 2021, 32 pages.
National Institute of Health, National Library of Medicine: National Center for Biotechnology Information, *Staphylococcus* phage 187, complete genome, GenBank: AY954950.1, Jan. 6, 2022, 20 pages.
National Institute of Health, National Library of Medicine: National Center for Biotechnology Information, *Staphylococcus* phage 69, complete genome, GenBank: AY954951.1, Retrieved from https:// www.ncbi.nlm.nih.gov/nuccore/AY954951, Jan. 6, 2022, 20 pages.
National Institute of Health, National Library of Medicine: National Center for Biotechnology Information, *Staphylococcus* phage 53, complete genome, GenBank: AY954952.1, Retrieved from https:// www.ncbi.nlm.nih.gov/nuccore/AY954952, Jan. 6, 2022, 21 pages.
National Institute of Health, National Library of Medicine: National Center for Biotechnology Information, *Staphylococcus* phage 85, complete genome, GenBank: AY954953.1, Retrieved from https:// www.ncbi.nlm.nih.gov/nuccore/AY954953, Jan. 6, 2022, 21 pages.
National Institute of Health, National Library of Medicine: National Center for Biotechnology Information, *Staphylococcus* phage 42E, complete genome, GenBank: AY954955.1, Jan. 6, 2022, 22 pages.
National Institute of Health, National Library of Medicine: National Center for Biotechnology Information, *Staphylococcus* phage 52A, complete genome, GenBank: AY954965.1, Retrieved from https:// www.ncbi.nlm.nih.gov/nuccore/AY954965, Jan. 6, 2022, 19 pages.
National Institute of Health, National Library of Medicine: National Center for Biotechnology Information, *Staphylococcus* phage 88, complete genome, GenBank: AY954966.1, Retrieved from https:// www.ncbi.nlm.nih.gov/nuccore/AY954966, Jan. 6, 2022, 20 pages.
National Institute of Health, National Library of Medicine: National Center for Biotechnology Information, *Staphylococcus* phage 92, complete genome, GenBank: AY954967.1, Retrieved from https:// www.ncbi.nlm.nih.gov/nuccore/AY954967, Jan. 6, 2022, 20 pages.
National Institute of Health, National Library of Medicine: National Center for Biotechnology Information, *Staphylococcus* phage X2, complete genome, GenBank: AY954968. 1, Retrieved from https:// www.ncbi.nlm.nih.gov/nuccore/AY954968, Jan. 6, 2022, 21 pages.
National Innational Institute of Health, National Library of Medicine: National Center for Biotechnology Information, *Staphylococcus* phage G1, complete genome, GenBank: AY954969.1, Retrieved from https://www.ncbi.nlm.nih.gov/nuccore/AY954969, Jan. 6, 2022, 60 pages.

(56)            References Cited

OTHER PUBLICATIONS

National Innational Institute of Health, National Library of Medicine: National Center for Biotechnology Information, *Staphylococcus* phage Twort, complete genome, GenBank: AY954970.1, Retrieved from https://www.ncbi.nlm.nih.gov/nuccore/AY954970, Jan. 6, 2022, 56 pages.

National Institute of Health, National Library of Medicine: National Center for Biotechnology Information, putative endolysin [*Staphylococcus* phage K], GenBank: AHB79986.1, Retrieved from https://www.ncbi.nlm.nih.gov/protein/564271309, Mar. 24, 2022, 2 pages.

National Institute of Health, National Library of Medicine: National Center for Biotechnology Information, *Staphylococcus* phage 47, complete genome, GenBank: AY954957.1, Retrieved from https://www.ncbi.nlm.nih.gov/nuccore/AY954957, Apr. 21, 2022, 21 pages.

National Institute of Health, National Library of Medicine: National Center for Biotechnology Information, *Staphylococcus* phage 37, complete genome, GenBank: AY954958.1, Retrieved from https://www.ncbi.nlm.nih.gov/nuccore/AY954958, Apr. 21, 2022, 21 pages.

National Institute of Health, National Library of Medicine: National Center for Biotechnology Information, *Staphylococcus* phage EW, complete genome, GenBank: AY954959.1, Retrieved from https://www.ncbi.nlm.nih.gov/nuccore/AY954959, Apr. 21, 2022, 21 pages.

National Institute of Health, National Library of Medicine: National Center for Biotechnology Information, *Staphylococcus* phage 71, complete genome, GenBank: AY954962.1, Retrieved from https://www.ncbi.nlm.nih.gov/nuccore/AY954962, Apr. 21, 2022, 20 pages.

National Institute of Health, National Library of Medicine: National Center for Biotechnology Information, *Staphylococcus* phage 55, complete genome, GenBank: AY954963.1, Retrieved from https://www.ncbi.nlm.nih.gov/nuccore/AY954963, Apr. 21, 2022, 20 pages.

National Institute of Health, National Library of Medicine: National Center for Biotechnology Information, *Staphylococcus* phage 29, complete genome, GenBank: AY954964.1, Retrieved from https://www.ncbi.nlm.nih.gov/nuccore/AY954964, Apr. 21, 2022, 20 pages.

National Institute of Health, National Library of Medicine: National Center for Biotechnology Information, *Staphylococcus* phage 3A, complete genome, GenBank: AY954956.1, Retrieved from https://www.ncbi.nlm.nih.gov/nuccore/AY954956, Jun. 13, 2022, 20 pages.

National Institute of Health, National Library of Medicine: National Center for Biotechnology Information, *Staphylococcus* phage 77, complete genome, GenBank: AY508486.1, Retrieved from https://www.ncbi.nlm.nih.gov/nuccore/AY508486, Nov. 1, 2022, 18 pages.

National Institute of Health, National Library of Medicine: National Center for Biotechnology Information, *Staphylococcus* phage phiP68, complete genome, NCBI Reference Sequence: NC_004679.1, Retrieved from https://www.ncbi.nlm.nih.gov/nuccore/NC_004679, Jan. 8, 2023, 11 pages.

National Institute of Health, National Library of Medicine: National Center for Biotechnology Information, *Staphylococcus* phage Stau2, complete genome, NCBI Reference Sequence: NC_030933.1, Retrieved from https://www.ncbi.nlm.nih.gov/nuccore/NC_030933, Jan. 8, 2023, 72 pages.

National Institute of Health, National Library of Medicine: National Center for Biotechnology Information, endolysin [*Staphylococcus* phage G15], NCBI Reference Sequence: YP_007002194.1, Retrieved from https://www.ncbi.nlm.nih.gov/protein/418487983, Jan. 8, 2023, 2 pages.

National Institute of Health, National Library of Medicine: National Center for Biotechnology Information, endolysin [*Staphylococcus aureus* bacteriophage Sb-1], NCBI Reference Sequence: YP_008873573.1, Retrieved from https://www.ncbi.nlm.nih.gov/protein/564292993, Jan. 8, 2023, 2 pages.

National Institute of Health, National Library of Medicine: National Center for Biotechnology Information, tail associated lysin [*Staphylococcus* phage Stau2], NCBI Reference Sequence: YP_009275797.1, Retrieved from https://www.ncbi.nlm.nih.gov/protein/1068512076, Jan. 8, 2023, 2 pages.

National Institute of Health, National Library of Medicine: National Center for Biotechnology Information, endolysin [*Staphylococcus* phage Stau2], NCBI Reference Sequence: YP_009275798.1, Retrieved from https://www.ncbi.nlm.nih.gov/protein/1068512077, Jan. 8, 2023, 2 pages.

National Institute of Health, National Library of Medicine: National Center for Biotechnology Information, putative tail lysin [*Staphylococcus* phage Stau2], NCBI Reference Sequence: YP_009275799.1, Retrieved from https://www.ncbi.nlm.nih.gov/protein/1068512078, Jan. 8, 2023, 2 pages.

National Institute of Health, National Library of Medicine: National Center for Biotechnology Information, tail protein with lysin activity [*Staphylococcus* phage Stau2], NCBI Reference Sequence: YP_009275801.1, Retrieved from https://www.ncbi.nlm.nih.gov/protein/1068512080, Jan. 8, 2023, 2 pages.

National Institute of Health, National Library of Medicine: National Center for Biotechnology Information, *Staphylococcus* phage phi44AHJD, complete genome, NCBI Reference Sequence: NC_004678.1, Retrieved from https://www.ncbi.nlm.nih.gov/nuccore/NC_004678, Jan. 10, 2023, 10 pages.

National Institute of Health, National Library of Medicine: National Center for Biotechnology Information, *Staphylococcus* phage IME-SA1, complete genome, NCBI Reference Sequence: NC_047729.1, Retrieved from https://www.ncbi.nlm.nih.gov/nuccore/NC_047729, May 8, 2023, 72 pages.

National Institute of Health, National Library of Medicine: National Center for Biotechnology Information, hypothetical protein QLX23_gp179 [*Staphylococcus* phage ISP], NCBI Reference Sequence: YP_009780264.1, Retrieved from https://www.ncbi.nlm.nih.gov/protein/1841992359, May 8, 2023, 2 pages.

National Institute of Health, National Library of Medicine: National Center for Biotechnology Information, hypothetical protein QLX23_gp177 [*Staphylococcus* phage ISP], NCBI Reference Sequence: YP_009780266.1, Retrieved from https://www.ncbi.nlm.nih.gov/protein/1841992361, May 8, 2023, 2 pages.

Needleman et al., A general method applicable to the search for similarities in the amino acid sequence of two proteins, Journal of Molecular Biology, 1970, 48(3):443-453.

Pearson et al., Improved tools for biological sequence comparison, Proceedings of the National Academy of Sciences, 1988, 85(8):2444-2448.

Sassi et al., Genome sequence of the clinical isolate *Staphylococcus aureus* subsp. *aureus* strain UAMS-1, Genome Announcements, 2015, 3(1):e01584-14, pp. 1-2.

Shimamori et al., Isolation and characterization of a novel phage SaGU1 that infects *Staphylococcus aureus* clinical isolates from patients with atopic dermatitis, Current Microbiology, 2021, 78:1267-1276.

Smith et al., Comparison of biosequences, Advances in Applied Mathematics, 1981, 2(4):482-489.

International Searching Authority, International Search Report and Written Opinion for corresponding International Application No. PCT/US2024/022657, mailed Aug. 23, 2024 [11 pgs].

Malik et al., Formulation, stabilisation and encapsulation of bacteriophage for phage therapy, Advances is Colloid and Interface Science, 2017, 249:100-133.

* cited by examiner

SEQUENCE LISTING

```
Sequence total quantity: 46
SEQ ID NO: 1            moltype = DNA  length = 17465
FEATURE                 Location/Qualifiers
source                  1..17465
                        mol_type = genomic DNA
                        organism = Staphylococcus phage MESA-01
SEQUENCE: 1
agggaaattt tttgtgtaaa tttacactac cccaccgttt aaaataaacg attaactaat   60
tcataactta ttaatcaact tataaattct tttataatct tatataatct gtgctactac  120
taataacatc tattcgaaac attcaaatat tctttaaacc aaaaaatatt caattgtaaa  180
ttcaaataat aaaaatataa ttatgtttta aaacaacatc acaactttat atacaacttt  240
aaataattta tgatataata agttataaaa tattttggag gtgtatatta aatgagtgag  300
tttgaagaaa ttgttaaatc tgatgaagaa actgaagaat caactgaaga atcaactgaa  360
gaatcaactg aagaatcaac tgaagaatct actgaagata aaacagtaga aacaattgaa  420
gaagaaaatg aaaacaaatt agaaccaact acaactgatg aagatagtgc aaaattagac  480
cctgttgttt tagaacaacg tattgcttca ttagaacaac gatttactaa ttttgaaaca  540
tcacaaatgc aacaaacaca acaagtagaa tcaactaacc cagatgtaac taatgctgat  600
aaagaagaca aagactattc agatgaagaa ttagtagata agttagattt agactaggag  660
gaaaataata tgtatgaagg taataacatg cgttctatga tgggaacatc atatgaagat  720
tcacgtttaa acaaacgtac agaattaaat gaaaatatgt caattgacgt taataaaagc  780
gaagatagtt atggggttca aattcattca ctatctaagc aaacatttac tggagacgta  840
gaggaggaat aataaattat ggctacaaca aaaaatgaaa ctgccctatt agttgctaaa  900
tcagcaaaag cagcattaca agattttaac catgattatt caaaatcttg gactttggt   960
gataagtggg ataatacaaa cacaatgttt gaaacatttg ttaataaata tttattccct 1020
aaaattaatg aaacattatt aattgatatt gcattaggta accgttttaa ttggttagca 1080
aaagagcaag actttatcgg acaatattca gaagaatatg taattatgga tactgttcca 1140
attaatatgg acttatcaaa aaacgaagaa ttaatgttaa aacgtaatta tccacgtatg 1200
gctactaagc tatatggtag tggtattgta aaaaaacaaa aattcacatt aaacaacaac 1260
gacgttcgtt ttaatttcca aacattagca gacgctacaa attatgcgtt aggtgtttat 1320
aaaagaaaa tttctgatat taatgtatta gaagaaaaag aaatgagagc aatgttagtt 1380
gattactcgt taaatcaatt atcagattca aacatacgca aaacaacatc aaaagaagat 1440
ttagcaagta aagtatttga agcgattctt aacttacaaa acaacagtgc aaaatacaat 1500
gaggtacatc gtgcttctgg cggcgctatt ggtcaataca caactgtgtc taagttaaaa 1560
gacattgtta ttttaacaac agattcatta aaatcttatt tattagatac aaaaattgcg 1620
aacactttcc aaatcgctgg tattgacttc acagaccatg ttattagctt tgatgattta 1680
ggtggcgtgt ttaaagtaac gaaagaattt aaattacaaa atcaagatac aattgatttc 1740
ttacgtgctt acggtgatta tcaagcacaa atcggtgata ctattccttt agatgctgta 1800
tttacttatg acgtttcaaa acttaaagag tttacaggta acgttgaaga gattaaacca 1860
aaatcagatt tatatgcgtt tattttagat attaattcaa ttaaatataa acgctataca 1920
aaaggtatgt taaaacaacc attctataat ggtgagtatg atgaggttac acattggata 1980
cattactatt catttaaagc tgtaagccca ttctttaaca aaattttaat tactgaccaa 2040
gatgttacac ctaaaccaga tactgtttca gaataggagg taaattatga caaatagcaa 2100
aagaggttta gatgttgaac tgtcaaaaca aattaataaa agagtagttg aacatcgtaa 2160
ccgtttttaaa cgtcttatgt ttaatcgtta tttggaattt ttacccctac taataaaacta 2220
taccaatcgt gatacggttg gtatagattt tattcagtta gaatccgcat taagacaaaa 2280
cattaatgtt gtggtaggag aagcgagaaa taaacaaatt atgattcttg gttatgttaa 2340
caatacttat ttcaaccaag cacctaattt ttcttcaaac tttaatttcc aattccaaaa 2400
aagattaaca aaagaagata tatattttat tgttcctgat tatttaatac ctgatgaatg 2460
tctacaaatt cataagcaat acgataattg catgagtggg aattttgttg ttatgcaaaa 2520
taaaccaata caatataaca gtgatattga aatcatagaa cattacacag atgaattagc 2580
tgaggttgtt ttatctcgtt tttcattgat tatgcaagca aaattcagca agatattaa 2640
atcagatatt aacgatgaat caattaatca acttgtatca gaaatttata acggtgcacc 2700
atttgttaag atgtcaccaa tgttcaatgc agatgatgat attattgatt taacaagtaa 2760
ttcagttatt ccagcattaa cagaaatgaa gagagaatat cagaataaaa ttagtgaatt 2820
aagtaactat ttaggtatta attcactagc tgttgataaa gaaagcggtg tttctgatga 2880
agaagcaaaa agtaatcgtg gttttactac gtcaaacagt aatatctatt taaaaggacg 2940
tgaaccgatt acatttttat caaaacgtta tggtttagat attaaaccgt attatgatga 3000
tgaaactacg tctaaaattt ctatggttga tacactgttt aaagatgaaa gtagtggtga 3060
aaatggctga atataccatg acattatatg attttataaa gtcagaactg attaaaaaag 3120
gttttaatga atttgtaaat aacaataaat taaccttta tgatgatgaa tttcaattta 3180
tgcaaaaaat gcttaaattt gataaagatg tacaagcaat tgtaaatgaa aaagtatttta 3240
```

-continued

```
aaggtttttc acttaaaaat gagttatcag atttactttt taaaaaatca tttacgattc  3300
acttttaga  tagagaaatt aacagacaaa ccgttgaagc gtttggcatg caagtgatta  3360
cagtgtgcat aacacatgag gattatttaa atgttgttta ttcatctagt gaagttgaaa  3420
agtatctaca agcacaaggg tttactgaac acaatgaaga tacaacaaac aatactgatg  3480
aaacatcgaa tcaaaatgct acatcattag acaattcaac aggtatgact gcaaacagaa  3540
atgctttttgt gacattacct caaagtgagg ttaatatcga tgttgataat acaacattac  3600
aatttgctga taacaatacc attgataatg gtaaatcagt gaataaatca agtagtgaaa  3660
gtaatcaaaa cgcaaaacgt aatcaaaatc aaaaaggaaa tgctaaaggt acacaattca  3720
caaaacaata cttaatcgaa aatatcgata aagcatatga tttaagaaaa aaaatattaa  3780
acgaatttga taaaagatgt ttttttacaaa tttggtaagg tggttaaaata atggcatata  3840
atgaaaatga ttttaaatat tttgaggata ttcgtccatt catagatgag atatataaaa  3900
caagagaaac atatacaccg ttctatgatg atagagctga ttataatact aattcaaaat  3960
cgtattatga ttatgtttca aaactatcac gactgattga agtattagca cgtcgtattt  4020
gggaatatga cggtgaatta aaaaaacgtt tcgaaaattg ggacgattta atgaaacaat  4080
ttccagatga cgctaaagaa ttatttagag gatggttaaa cgacggcacg attgataaaa  4140
tcattcatga tgagtttaca aaatattcag ctggtctaac ttcagctttt gctgtattta  4200
aaattgctga aatgaaacaa atgaatgatt ttaaagcaga agttaaagac ttaattaaag  4260
atattgaccg tttcgttaat gggtttgaat taaatgaact tgaaccaaag tttgttatgg  4320
gattcggtgg aatacgtaac gctgttaacc aatctgttaa tattgataaa gaaacaaatc  4380
atatttatac aacacaatca gactcacaat ctccagaggg cttttggata aataaaattaa  4440
cccctagtgg tgatttactt tcaagtatgc gtatcgtaca aggtgggcac ggcacaacag  4500
taggtttaga aagacaatca aacggtgaaa tgaaaatatg gttacatcat gacggtgtag  4560
ctaaactatt acaagtagct tataaagata attacgtttt agatttagaa gaggcaaaag  4620
gtttaacaga ttatacacca caatcacttt taaacaaaca tacatttaca ccattaattg  4680
atgaagcgaa tgacaaactc attttacgtt tcggagatgg gacaatacag gtacgttcaa  4740
gggtagatgt aaaaaatcat attgataacg tagaaaaaga aatgacaatt gataattcag  4800
aaaataacga tacacgctgg atgcaaggga tagctgttga tggggatgat ttatactggt  4860
taagtggtaa tagttctgtt aattcacatg ttcagattgg aaagtattca ttgaaaacag  4920
gggaaaaaat atacgattat ccgtttaaat tatcatatca agatggtatt aacttcccac  4980
gtgataattt caaagagcca gagggtattt gtatttatat taatccaaaa acaaaacgta  5040
aatcattatt acttgcaatg acaaatggcgc gcggtggtaa aagattccat aatttatatg  5100
gattcttcca aactggagaa tatgaacatt ttagtgcctt acgtgcaaga ggtgcacaaa  5160
actataaatt aacaaaagat gatggacgcg ctttatcaat accagactat atagatgatt  5220
taaacaactt aacacaagca ggattttatt atatcgatgg tggaacagca ggaaaactta  5280
aaaacatgcc tacaaacggt agtaagaaaa ttattgacgc aggttgcttt atcaatgtat  5340
accctacaac acaaacatta ggaacagtgc aagaaataac acgtttctca acaggtcgta  5400
aaatggttaa aattattcga ggtatgacgt tagatgtgtt tacattaaaa tgggattatg  5460
gtttatggac aacaatcaaa acagacgcac catatcaaga atatttggag gcaagtcaat  5520
acaacaattg gattgcatat gtaacaacac cgggtgagta ttacattaca ggtaatcaaa  5580
tggaattatt taaagacgca ccagatgata ttaaacacgt tggtgcatgg ttgaaagtgt  5640
caagtgggaa tgctgttggt gaggttagac aaacattaga agcaaatata gctgaatata  5700
aagaattctt tagtaatgtc aatgcggaaa caaaacatcg tgaatacgag tgggtagcaa  5760
aacataaata ggagatgaaa caatgaagtc attacaacaa gcaaaacaat gggattgatgt  5820
caatactggt agaggcattg actttgatgg cgcatatgga tttcaatgta tggatttagc  5880
tgtagcttat atgtattatg ttactgacgg aaaagtgcgt atgtggggta atgccaaaga  5940
cgcaattgat aataacttta aaggtttagc taaggtgtat caaaatacac ctagctttaa  6000
acctcaatta ggtgatattg ctgtttatac aaactcacaa tatggtcata ttcaagttgt  6060
gattagtggt aatttagatt attatacatg tctagagcaa aactggttaa atggtggtta  6120
tgacggttgg gaaaaagcaa caatcagaac acattattat gacggtgtaa cacactttat  6180
tcgtccaaac ttttcaaata gtaatagtaa agtattagaa caaaacattc aacaaacaaa  6240
taaatggaaa caaaatcaat acggtacatt atataaatct gaaaatggta catttacatg  6300
tggatttttta ccaatatttg cacgtgttgg aagtcctaaa ttaagtgaac cgaatgggta  6360
ttggttccaa ccaaacggct atacaccata tgatgaggtt tgtttatcag atggactagt  6420
gtggattggt tataattggc aaggtacacg ttattattta ccagtgagac aatggaacgg  6480
taaaacgggt aatagttata gcattggttt accatggggg gtgttctcat aatgggtatt  6540
ttaggttttt tctttgagtt tagttggaaa agatacaaat aagaggtgta aaatatggct  6600
gatagaatcg taagaagttt aagaggtatt gattcagtag agaagttaaa cgacaattta  6660
gtagaagcaa acgacttaat cacaaccaaa gacgataaca tatatataag acgtgatgag  6720
gattattata agctaacatt taaagatgaa ttattagaaa aaatcaatac aaacacaaaa  6780
gcgattgata aaaataaaaa tgacatcact acaaataaaa aaaatatatc tcaaaacgct  6840
acagatatta ttaacattaa agaagataat attcaacaag ataaaaaaat taaaaattta  6900
tctgacgttc aaacagaaca tgaaaataca ttaaacaatc atgatgacgc aattcgttta  6960
ttagatgatg aaaaatacaaa aaacaaatta gcaattgaaa agaataaaca agatattatc  7020
gctacaaaag atacaatcgg acaaaataaa caaagtattg aaaacttagc ttcaacggtt  7080
tcaaacaaca cgattgaaac aagtaaaaaa attgaatcaa ctaaaacaga attacaagaa  7140
caaatcaaat cttcaaaaac aagtgtgaat gatacaggtt ggttaaatat tcaacttgaa  7200
agtggtatca cagcaagtga ttcaagtggt ggatattcca caccacaata tcgaattata  7260
gatataaata acatcagaac tattcaatta agaggtgtat aaaaggtgt taagaaaaat  7320
ggagatatta aattaggcac gattaatgct aatttaaaag taacacatca ctatacacaa  7380
tgtgctattg attctaaaat gataaacaca agattatatg taaactttaa taacgaatta  7440
cattttgtta catcaggtta tcaagatagt gaactttctt ctggagataa acgttttgtt  7500
attgatacac aaatcattga ataaaaatga tataatagtc gtataaatta ttttatacga  7560
ctattttatt tggaggaaaa tctatgagga aattaacaaa ttttgtattt ttttataata  7620
cacctttac agattatcaa aatacaaatac attttaatag taataaagaa cgagatgatt  7680
attttttaaa aggtcgtcat tttaagtcat tagattattc aaaacaaccg tataacttca  7740
ttcgtgatag aatggaagtt aatgtagatt taagttggca tgacgcacaa ggtattaact  7800
atatgacgtt tttatctgat tttgaaaata gacgttatta tgcgtttgtg aaccaaattg  7860
aatatattaa cgatgttacg acaaaaattt attatgtcat tgatacagtt atgacgttca  7920
cacaaggtaa tgtgttagag caactctcaa acgtcaatat tgaacgacaa catttatcaa  7980
```

-continued

```
aacgtacgta taactatatg ttaccaatgt taagaaacaa cgatgatgtt ttaaaagtaa  8040
gtaataaaaa ctatgtttat aaccaaatgc aacagtattt gcaaaatgtt gtactatttc  8100
aatcaagtgc tgatttatct aaaaagtttg gtactaaaaa agagcctaat ttagacacat  8160
caaaaggaac aatatatgac aatatcacat caccagttaa tttgtatgtc atggaatata  8220
atgattttat taactttatg gataaaatga gcgcatatcc gtggattacg caaaacttcc  8280
aaaaagtaca aatgttacct aaagacttta ttaacgaaaa agatttagag gacgttaaaa  8340
caagtgaaaa aattactggt ttaaaaacat taaaacaagg tggtaaatct aaagagtgga  8400
gcttaaacga tttatcatta agttttttcaa aacttcaaga aatgatgttg tctaaaaaag  8460
atgaattaaa acacatgata cgcaatgaat acatgaccat tgaattttat gattggaatg  8520
gtaatacaat gttacttgac gctggtaaaa tttcagaaaa aacaggagtg aaactaagaa  8580
caaaatctat tattggttat cataatgaag ttagagttta tccagtagac tataacagcg  8640
ctgaaaacga tagaccgata cttgctaaaa acaaagacat attaattgat acaggttcat  8700
ttttaaatac aaatattaca tttaatagct ttgctcaagt tccaatttta attaataacg  8760
gtatattagg acaatcacaa caagcaaata gacaaaaaaa tgcagaaagt caattaatca  8820
caaatcgaat tgataacgtg ttaaatggta gtgaccctaa atcaagattt tacgacgctg  8880
tcagtgttgc tagtaatttta agtccaacag ctttatttgg taagtttaat gaagaatata  8940
atttttataa gcaacaacaa gctgaatata aagatttagc actacaacca ccgtctgtga  9000
cagaatcaga tatgggtaat gcattccaaa ttgcaaataa tattaacggt ttaacaatga  9060
agattagtgt accgtctcca aaagaaatta cattcttaca aaaatattac atgttatttg  9120
gttttgaagt gaatgactat aacaatttca ttgaacctat taatagtatg actgtatgta  9180
attacttaaa atgtaacgga acgtatacat tacgtgatat tgaccctatg ttaatggaac  9240
aactcaaagc aatattagaa tcggtgtga gattttggca tagtacggg tcaggtaatc  9300
caatgttaca aaatccatta aataataaat ttagataggg gtttttaattt tgaatgaagt  9360
aaaagtaaga tttacagata cagaagcatt tcatatgttt atttatgcag gagatttaaa  9420
attattatat ttcttatttg tattaatgtt tatcgacatt attacaggta tagcaaaagc  9480
cattaagaat aataatttat ggtcaaagaa atctatgaaa gggtttgcta aaaaattact  9540
catttttgt attattatac tagcaaatat cattgaccaa attttacaat taaaaggtgg  9600
gttactcatg ataacgatat tctattatat cgcaaatgag ggcttatcta ttgttgaaaa  9660
ttgtgcagaa atggatgtat tagtgccaga gcaaatcaaa gaacgattaa aagtaataaa  9720
aaacgagtct gaaaagagtg ataacaatga acgaccaaga gatgattgat aaatttaccc  9780
actcgtatat taatgatgac ttcggtttaa cgatagacca acttgtacca aaagttaaac  9840
cttacgggcg atttaatgta tggctaggtg gtaatgaaag taaaataaga caagtattaa  9900
atgcagtaaa gtcgataggt gtttcaccaa ccctttttgc tgtttatgaa aagaatgaag  9960
ggtatagtgc aggtttaggg tggttaaacc atacatctgc acaaggtgat tatttaactg 10020
atgctaaatt tgtagctaga aaattagtat cacaatcaaa acaagcagga catccgtctt 10080
ggtatgatgc aggtaacatt gtgcattttg tacctcaaga cgtacaaaga aaaggtaatg 10140
aagatttgc taagaaatatg aaagcaggta cagtcggacg tacctatatt ccattaacgg 10200
cggctgctac ttgggctgct tattacccac taggtctgaa agcttcatat aatagagtac 10260
aaaactatgg taatccattt tttagacggtg ctaataccat tttagaatgg ggcggtaaaa 10320
ttgacgggaa aggtggttca cctagtagtg gctcatctga tagtggttct gatagtggag 10380
gaaattcatt actagcccta gcaaaacaag ctatgcaaga attattaaaa aaagtgcaag 10440
acgcattaca atgggacgta cacagtatcg gtcatgataa atatttttagt aatgattatt 10500
ttacattaga aaaaacgttt aacaatacgt atcatattaa aatgactata gggttacttg 10560
attcactcaa aaaagattata gatagtattc atattgacag cggtggtagc tcatctaatc 10620
ctactgatga tgacggagat cataaaccaa ttagtggtaa atctgttaaa cctaacggaa 10680
aaagtggtcg tgttattggt ggtaactgga catatgacca attacctgaa aaatataaaa 10740
aggcaattgg tgtacctttg ttcaaaaaag aatatttata taaaccgggt aacatattcc 10800
ctcaaaccgg taatgcagga caatgtacag aattaacatg ggcgtatatg tcacaattac 10860
atggtaagcg tcaacctaca gacgacggtc aaattactaa cgggcaacgt gtatggtacg 10920
tttataagaa gttaggtgca aaaacaaccc ataacccaac agtaggttat ggtttttcaa 10980
gtaaaccacc atacttacaa gcaagtattt atggtattgg acacacaggt gttgtcgttg 11040
ctgtatttga cgatggttca ttcttagttga caaactataa cgtaccacct tacgttgcac 11100
cgtcacgagt gttattatat acactaatta atggtgtacc agaaaatgca ggtgataata 11160
ttgtattctt tagtggtatt gcttaacaag ttatgctata atgtaactat gctagattac 11220
tagtaaataa aatacaaaac ataatcaatt ttcgtacaca ttttttattg ttatctcaaa 11280
cttaaagggt agccgttatt ttaacggtta ccctttttcgt atgtcatcat gtatttgttt 11340
taattgattt aactttgaac gatattttgc agaacgttct actgggaata aatcatttaa 11400
tgaaaatgtg ccaatatcac tttcaatata tagaatatca tcatattcac tatgttcaaa 11460
attttctcta gcgtcttta gcaaaaattc tcttttttca tttaattcat ctgaaaagac 11520
atcatcatat acatctccgc ttacaatctc agtttttagac gggtaaatcg aaatcgtacc 11580
ctgctcatta tagatacttt tattgttgta aacaacagca ccatcaaaaa attgttcact 11640
gacaaatgtt tcaaaatcaa cgcttgtatc aaaagcgttt ttcggtatac cagcagaagc 11700
gattttaatt tttccgttcg tcacataagc atatttctta tgattgagta caaacatctt 11760
atctatctgt tcgtttttcaa tatcccattt acctaaggca atggtcgtga ataaatcggg 11820
gtttaacaag ggtttcacaa cggatttcat atacaaacta tcagtatcac aataaatgaa 11880
attatcgtct atttcacttt cagttaagta ttgaaacgga actaataagt tatataaatga 11940
gcgtgatgtt acaaaagtag aaaatagtaa attacgttct gtgttttttgt atccgtttat 12000
catattaaat aattcgttgt tttcatctaa acggaataaa ttaaagtgtg aacgtaaagc 12060
aggaatacca tataaaccgt ttaaaacgac tttagacagc ataacctctt catttgagta 12120
cgggtgttcg ttaatatcat cagtgatttt atagtcataa ggtgaagtca tattaatttt 12180
tgttttgagt ttcccttgtg ttttaataaa atagtttga aatataatat cacgagcatg 12240
aaagtattca cattcataca tcacaaatga attgacacgt attttttgtgc aatcaatatc 12300
tgtaatgtct tgaatcattc ttaatgtatt tgtgttgata ttaacgtaat cattatcatt 12360
attatagtat tttacaatca tttgacgtaa tacacgtgat tttattttta gtaatatatc 12420
atggttaaat gtatgcttat caatcttata taacgtaaaa taattatcat catctaaaaa 12480
agtaggaatt aacgttggtt ctgaatagtg ttcgtaaaag tataaccatg ttggaatttt 12540
ttcatgatac atcacatacg gataacttga attgatatca atagaaaaac aaggttcatc 12600
aacgattttg ttaatatact ttgtgttata catatttaac ccaccacgat aaaatgattt 12660
aatataatca taaaaattca tatcatggaa ttgataatgc gtatatgaaa tagcgatgtc 12720
```

```
atcgtattta ttaagtaatt gaaaacgtgt catttcatta tttaaatatg attccataat   12780
atttaatgaa aacgttaatt tattataatc aaaatttgga aaaatatcac tataatgtat   12840
atgacacata cctaaaataa ttacatcgtt atgaatatat gtaagttgtt ctgatgttaa   12900
ttttgtaaag catttagtag catagtcata agcttcactg tctgacatat ctgtttcttt   12960
atcaaagatt gtatagttaa aatcagtttt gagttggttt tctgtaagat aaccaccgtc   13020
taataacttt ttgccaagtg tagcgattga tgtattggtt ttcataaagt tatcaatgat   13080
attgaattta aatccgttta aaaacatcgt taaatctaaa ttaatagagg actttacacg   13140
ttttttcaagt atgacatttt gacttttaga taatatttga gcttctttca ttttttagggt   13200
gtgttcatta tcttcagctg attttaaaaa cacattttta cgtgtaatat tatcaaagta   13260
acgcatcgta tctttaagta aaaaatgatt gtcatactta ttacagttat gtgcaatcat   13320
aataatgtct gttttttgatt ttgtgattgt atcacgtcgt ttcacatact tataaaacga   13380
atcataaaat gcttcaaaac tagggaatac ctctacatca atttcataac cattaaacca   13440
accaatagca actgaatacg tgacgttttt atatttagtt ggtttttttac gtccattgat   13500
tttattatat gctaatgttt caatatccca atataaaatc attttacgtt catgtttatg   13560
atattgcata cactcaagta atcccataat cttacacacc tttattgttc gtattgttgc   13620
attaagtagc gtttttgtatt ttctatatag ttatcttcat atatctttttc ttttcgttca   13680
aactcactca tgttttttctt catttcattt ttaaatatgaa attttataat tttattcaca   13740
tctaaaatata aatacctatc attatcaaca acataatttt ttgaatatgc gttatcaaaa   13800
tgtaaatttg acggattata ataataacgc tccatatttt ctttataaaa catatcttct   13860
ctaagatatg tgacgttttc atcaaatatct ttgattttcg tacaaaattc atattctttt   13920
gtataaggta ttacaataat atttgctata aatgtagata cattatacat aattttaatg   13980
aatttatctt ctgttttgat atagaaaaaa tcaccgtttt gattaatatg tgaccgtata   14040
ctatcgttag ctaaattata ttcattaaaa tcaaattccc ctgttgtcat agcgtcctca   14100
tttgaattaa acgcacgtgt attacgtttt tcgttgacat aatcattacg tctcatctct   14160
aaaaaaaatgt ttttataaag tcgtgacgtg ttcattttat gttttttgtaa tagattatat   14220
atgtttaaat tagataaaat aggacttgaa aagttaacag cgttaccaag taaaaatatt   14280
ttaggaaatc cgatataatc tacattacca tgatttctat caatggactc ataaattgtt   14340
ttgagtttat cccactcatc atataaataa tcatcttcaa gtgctaaaaa ctcatcatat   14400
ataatgatag gatagtgttt taaaaagtta gaatgatatt tcaaatcagt tgcactattt   14460
aaatctgtta tcacacctat ttctttatct tggtatacaa tcgctaaata atctcttgcg   14520
cttctgaaag caacacgttt tgatttaaat aatggatttt tatcaataat ttcctcaata   14580
aaatcacggt atgcatcacg taacgtgtaa tgacgtgata gtaatgtaaa tttaatatca   14640
agtttcattg ctaaatataaa aaaaaaacgat acatagttaa atgatttacc gtctgaacgg   14700
tttgaaatag aaatatagta attctaaatca tcattcatta attcattgac taattcaatt   14760
tgattataat tatcaggtat cttttttctt acatgattga caacattttg ataatcccctt   14820
accatgtcta gcctgttttg ttttaccatg attatgctcc ttatagtaat ttataatatc   14880
ttcaattgat ttaaaatgtt tcatttttct attaaatgat aatataaaaa gttatatctg   14940
acttttttgt ttttgattgt tgtttttcggt ctgttagatt caccaatttc atcaaataat   15000
tcttcaatac ctttgatata tttatacatt gatgtattat tatctttagc agtttcatca   15060
tataaagtat atttatgtgt ttttgcattt ttgttattac tatcatcatt acgttcataa   15120
atgtttaata ttttttaacaa ttgttcacgt cgtttaccac gtactaaaga aacagcattt   15180
acataactca catgtttttc tttaggtaaa aatgtaagct ttgaaaaata ttcccaagcg   15240
tcaatatatt ctttttgtag tgatgcatct tcaaatttaa aactgacacc actaaagtca   15300
ttctttttttc ttttttttcttc atctgctttt cttgcttctc gttctttttt ccaacggtct   15360
gcttctgaca tacgtttacg cattgttatc aacctccata tatagcataa ataaccatta   15420
aaaagataat atagaatatg attagtgttg taaatagtac accaaatgac acacgtatat   15480
gcatgtgtcat aagaatgaca agtgtaatca ataatgctaa aagaaaaaatg ataattatat   15540
taagtaggtt attcatgttc tatcacattt ccgtttttat atataacttt gttttggtaa   15600
ataatcatta atccgctttc gagtggacaa tcaaaattta ctaatacatc gtctattgta   15660
acaccatatg aagtttctct tacaaatgtg ttatttacag aatctatata ataatactca   15720
agtaaaataaa aaacatgttt tttaatatca atatcaatat ctaacgtgaa taaatcattg   15780
ttaattgtta agtccgtatt atgactttca gaaaaattaa cacaaatatc atcatcgcta   15840
tcaataccta caaaattata accactatca gaaataaaatt gtatttttttt atcttgaaaa   15900
ttttttctgt tatcgttaat gtagcaaagt aagtcatata aattaaatga ttgtttttatt   15960
ttcatttttaa gtctcctcta tatattctat aacatacgca taattattat gaaatggatt   16020
gaattcataa taagagtata aaactttggc gttatacaaa tcttcaaaca ttaatatttg   16080
atgatgaaaa tcatttttcta ttgtgtcagt atataataag actgttttat atttttttcat   16140
tatatcctcc aataaaaaata gagggaatga aatccctcta tgaaatttta atattaaaat   16200
gatacttgac taaagttaat agaatatcct ttttgaccctt ttttgttttc gtattcataa   16260
attgagaaca caacttcacc tttattaata atgtctacaa catcttcatc ttgacgcatg   16320
tctttaatta attcagttaa gtgattcggt aagttaacat tataatcatc tgttacaata   16380
acaccttgtt caccgaattt tgattcttttg tttgtaaata atgctctaac gatgtattct   16440
tgtttgattc cgaatttttc aactaattcc gataatttga taaattctct ttcttttttcc   16500
tcaaattcaa atctcgctaa tgtgttttgg tgtctagata aaattcttttt tacgtttgtc   16560
ataataaata atctccttta aatttataat tttattttta ataactcgtt ataattaact   16620
ttaattgttt gtgtgtgtcg tgttgttgaa agtaatgtat atgtggcagg taataattct   16680
ttggcttgtt gtttagttaa atgatactca tgtaatggga aaaatttttc aatatattca   16740
tctttatcat cgagataatt aagaaatataa cctttaacac gtaaagtaac aatctcatca   16800
ggtttcatta tatcactcct ttctaaaaaa cgtaaacgtt atatgtttca taaaaacttt   16860
tatgcatatc ccattgttcc aaagcgtcat ctgtgatgta tgatagaaca gatgttggtt   16920
caatttcatt gttaagtttg tcgtttaaga acttaacaat agctgtgtta tagtttaata   16980
acagttgttg gcaagctgaa actaaattga tagcattatc aaatgtatat gctggattcc   17040
attcaattaa cttattgaac agttgcaaca tttcagtata tgcttgtcct ttttcatttg   17100
gtgcattatc tgcttgatc tttttattgt tacctccttg ttttgattac ataacaaata   17160
taacatacgt atttaaatta gtcaaacgtt tttgtgaaaa agttttaaag ttttttttaaa   17220
ataagaaaaa tcaatgtata taatgaagaa actagaaaat gcatattgtt ttaatttaat   17280
taaaattaaa atcgaatatt tttttcggttt aaagaatatt tgaatgtttc gaatagatgt   17340
tattagtagt agcacagatt atataagatt ataaagaat ttataagttg attaataagt   17400
tatgaattag ttaatcgttt atttttaaacg gtggggtagt gtaaatttac acaaaaaatt   17460
```

```
tccct                                                                   17465

SEQ ID NO: 2              moltype = DNA   length = 366
FEATURE                   Location/Qualifiers
source                    1..366
                          mol_type = genomic DNA
                          organism = Staphylococcus phage MESA-01
SEQUENCE: 2
atgagtgagt ttgaagaaat tgttaaatct gatgaagaaa ctgaagaatc aactgaagaa   60
tcaactgaag aatcaactga agaatcaact gaagaatcta ctgaagataa aacagtagaa   120
acaattgaag aagaaaatga aaacaaatta gaaccaacta caactgatga agatagtgca   180
aaattagacc ctgttgtttt agaacaacgt attgcttcat tagaacaacg atttactaat   240
tttgaaacat cacaaatgca acaaacacaa caagtagaat caactacacc agatgtaact   300
aatgctgata aagaagacaa agactattca gatgaagaat tagtagataa gttagattta   360
gactag                                                                  366

SEQ ID NO: 3              moltype = AA   length = 121
FEATURE                   Location/Qualifiers
source                    1..121
                          mol_type = protein
                          organism = Staphylococcus phage MESA-01
SEQUENCE: 3
MSEFEEIVKS DEETEESTEE STEESTEEST EESTEDKTVE TIEEENENKL EPTTTDEDSA   60
KLDPVVLEQR IASLEQRFTN FETSQMQQTQ QVESTTPDVT NADKEDKDYS DEELVDKLDL   120
D                                                                       121

SEQ ID NO: 4              moltype = DNA   length = 183
FEATURE                   Location/Qualifiers
source                    1..183
                          mol_type = genomic DNA
                          organism = Staphylococcus phage MESA-01
SEQUENCE: 4
atgtatgaag gtaataacat gcgttctatg atgggaacat catatgaaga ttcacgttta   60
aacaaacgta cagaattaaa tgaaaatatg tcaattgacg ttaataaaag cgaagatagt   120
tatggggttc aaattcattc actatctaag caaacattta ctggagacgt agaggaggaa   180
taa                                                                     183

SEQ ID NO: 5              moltype = AA   length = 60
FEATURE                   Location/Qualifiers
source                    1..60
                          mol_type = protein
                          organism = Staphylococcus phage MESA-01
SEQUENCE: 5
MYEGNNMRSM MGTSYEDSRL NKRTELNENM SIDVNKSEDS YGVQIHSLSK QTFTGDVEEE   60

SEQ ID NO: 6              moltype = DNA   length = 1218
FEATURE                   Location/Qualifiers
source                    1..1218
                          mol_type = genomic DNA
                          organism = Staphylococcus phage MESA-01
SEQUENCE: 6
atggctacaa caaaaaatga aactgcccta ttagttgcta aatcagcaaa agcagcatta   60
caagatttta accatgatta ttcaaaatct tggactttg gtgataagtg ggataataca   120
aacacaatgt ttgaaacatt tgttaataaa tatttattcc ctaaaattaa tgaaacatta   180
ttaattgata ttgcattagg taaccgtttt aattggttag caaaagagca agactttatc   240
ggacaatatt cagaagaata tgtaattatg gatactgttc caattaatat ggacttatca   300
aaaaacgaag aattaatgtt aaaacgtaat tatccacgta tggctactaa gctatatggt   360
agtggtattg taaaaaaaca aaaattcaca ttaaacaaca acgacgttcg tttaatttc    420
caaacattag cagacgctac aaattatgcg ttaggtgtt ataaaaagaa aatttctgat   480
attaatgtat tagaagaaaa agaaatgaga gcaatgttag ttgattactc gttaaatcaa   540
ttatcagatt caaacatacg caaaacaaca tcaaaagaag atttagcaag taaagtattt   600
gaagcgattc ttaacttaca aaacaacagt gcaaatacaa atgaggtaca tcgtgcttct   660
ggcggcgcta ttggtcaata cacaactgtg tctaagttaa aagacattgt tattttaaca   720
acagattcat taaaatctta tttattagat acaaaaattg caacacttt ccaaatcgct   780
ggtattgact tcacagacca tgttattagc tttgatgatt taggtggcgt gtttaaagta   840
acgaaagaat ttaaattaca aaatcaagat acaattgatt tcttacgtgc ttacggtgat   900
tatcaagcac aaatcggtga tactattcct ttagatgctg tatttactta tgacgtttca   960
aaacttaaag agtttacagg taacgttgaa gagattaaac caaatcaga tttatatgcg   1020
tttattttag atattaattc aattaaatat aaacgctata caaaaggtat gttaaaacaa   1080
ccattctata atggtgagta tgatgaggtt acacattgga tacattacta ttcatttaaa   1140
gctgtaagcc cattctttaa caaaattta attactgacc aagatgttac acctaaacca   1200
gatactgttt cagaatag                                                     1218

SEQ ID NO: 7              moltype = AA   length = 405
FEATURE                   Location/Qualifiers
source                    1..405
                          mol_type = protein
                          organism = Staphylococcus phage MESA-01
SEQUENCE: 7
```

```
MATTKNETAL LVAKSAKAAL QDFNHDYSKS WTFGDKWDNT NTMFETFVNK YLFPKINETL    60
LIDIALGNRF NWLAKEQDFI GQYSEEYVIM DTVPINMDLS KNEELMLKRN YPRMATKLYG   120
SGIVKKQKFT LNNNDVRFNF QTLADATNYA LGVYKKKISD INVLEEKEMR AMLVDYSLNQ   180
LSDSNIRKTT SKEDLASKVF EAILNLQNNS AKYNEVHRAS GGAIGQYTTV SKLKDIVILT   240
TDSLKSYLLD TKIANTFQIA GIDFTDHVIS FDDLGGVFKV TKEFKLQNQD TIDFLRAYGD   300
YQAQIGDTIP LDAVFTYDVS KLKEFTGNVE EIKPKSDLYA FILDINSIKY KRYTKGMLKQ   360
PFYNGEYDEV THWIHYYSFK AVSPFFNKIL ITDQDVTPKP DTVSE                  405

SEQ ID NO: 8              moltype = DNA   length = 984
FEATURE                   Location/Qualifiers
source                    1..984
                          mol_type = genomic DNA
                          organism = Staphylococcus phage MESA-01
SEQUENCE: 8
atgacaaata gcaaagagg tttagatgtt gaactgtcaa aacaaattaa taaaagagta     60
gttgaacatc gtaaccgttt taaacgtctt atgtttaatc gttatttgga attttttaccc  120
ctactaataa actataccaa tcgtgatacg gttggtatag attttattca gttagaatcc   180
gcattaagac aaaaacattaa tgttgtggta ggagaagcga gaaatataca aattatgatt  240
cttggttatg ttaacaatac ttatttcaac caagcaccta attttttctt aaactttaat   300
ttccaattcc aaaaaagatt aacaaaagaa gatatatatt ttattgttcc tgattatta    360
atacctgatg aatgtctaca aattcataag caatacgata attgcatgag tgggaatttt   420
gttgttatgc aaaataaacc aatacaatat aacagtgata ttgaaatcat agaacattac   480
acagatgaat tagctgaggt tgtttttatct cgttttcat tgattatgca agcaaaattc   540
agcaagatat ttaaatcaga tattaacgat gaatcaatta tcaacttgt atcagaaatt    600
tataacggtg caccatttgt taagatgtca ccaatgttca atgcagatga tgatattatt   660
gatttaacaa gtaattcagt tattccagca ttaacagaaa tgaagagaga atatcagaat   720
aaaattagtg aattaagtaa ctatttaggt attaattcac tagctgttga taaagaaagc   780
ggtgtttctg atgaagaagc aaaaagtaat cgtggtttta ctacgtcaaa cagtaatatc   840
tatttaaaag gacgtgaacc gattacattt ttatcaaaac gttatggttt agatattaaa   900
ccgtattatg atgatgaaac tacgtctaaa atttctatgg ttgatacact gtttaaagat   960
gaaagtagtg gtgaaaatgg ctag                                          984

SEQ ID NO: 9              moltype = AA   length = 327
FEATURE                   Location/Qualifiers
source                    1..327
                          mol_type = protein
                          organism = Staphylococcus phage MESA-01
SEQUENCE: 9
MTNSKRGLDV ELSKQINKRV VEHRNRFKRL MFNRYLEFLP LLINYTNRDT VGIDFIQLES    60
ALRQNINVVV GEARNKQIMI LGYVNNTYFN QAPNFSSNFN FQFQKRLTKE DIYFIVPDYL   120
IPDECLQIHK QYDNCMSGNF VVMQNKPIQY NSDIEIIEHY TDELAEVVLS RFSLIMQAKF   180
SKIFKSDIND ESINQLVSEI YNGAPFVKMS PMFNADDDII DLTSNSVIPA LTEMKREYQN   240
KISELSNYLG INSLAVDKES GVSDEEAKSN RGFTTSNSNI YLKGREPITF LSKRYGLDIK   300
PYYDDETTSK ISMVDTLFKD ESSGENG                                       327

SEQ ID NO: 10             moltype = DNA   length = 825
FEATURE                   Location/Qualifiers
source                    1..825
                          mol_type = genomic DNA
                          organism = Staphylococcus phage MESA-01
SEQUENCE: 10
atgatgatga aactacgtct aaaatttcta tggttgatac actgtttaaa gatgaaagta    60
gtggtgaaaa tggctagata taccatgaca ttatatgatt ttataaagtc agaactgatt   120
aaaaaaggtt ttaatgaatt tgtaaataac aataaaattaa cctttttatga tgatgaattt   180
caatttatgc aaaaaaatgct taaatttgat aaagatgtac aagcaattgt aaatgaaaaa   240
gtatttaaag gtttttcact taaaaatgag ttatcagatt tacttttttaa aaaatcattt   300
acgattcact ttttagatag agaaattaac agacaaaccg ttgaagcgtt tggcatgcaa   360
gtgattacag tgtgcataac acatgaggat tatttaaatg ttgtttattc atctagtgaa   420
gttgaaaagt atctacaagc acaagggttt actgaacaca aagaagatac aacaaacaat   480
actgatgaaa catcgaatca aaatgctaca tcattagaca attcaacagg tatgactgca   540
aacagaaatg cttttgtgac attacctcaa agtgaggtta tatcgatgt tgataataca   600
acattacaat ttgctgataa caataccatt gataatggta aatcagtgaa taaatcaagt   660
agtgaaagta atcaaaacgc aaaacgtaat caaaatcaaa aaggaaatgc taaaggtaca   720
caattcacaa aacaatactt aatcgaaaat atcgataaag catatgattt aagaaaaaaa   780
atattaaacg aatttgataa aagatgtttt ttacaaattt ggtaa                   825

SEQ ID NO: 11             moltype = AA   length = 274
FEATURE                   Location/Qualifiers
source                    1..274
                          mol_type = protein
                          organism = Staphylococcus phage MESA-01
SEQUENCE: 11
MMMKLRLKFL WLIHCLKMKV VVKMARYTMT LYDFIKSELI KKGFNEFVNN NKLTFYDDEF    60
QFMQKMLKFD KDVQAIVNEK VFKGFSLKNE LSDLLFKKSF TIHFLDREIN RQTVEAFGMQ   120
VITVCITHED YLNVVYSSSE VEKYLQAQGF TEHNEDTTNN TDETSNQNAT SLDNSTGMTA   180
NRNAFVTLPQ SEVNIDVDNT TLQFADNNTI DNGKSVNKSS SESNQNAKRN QNQKGNAKGT   240
QFTKQYLIEN IDKAYDLRKK ILNEFDKRCF LQIW                               274

SEQ ID NO: 12             moltype = DNA   length = 1941
```

-continued

```
FEATURE                  Location/Qualifiers
source                   1..1941
                         mol_type = genomic DNA
                         organism = Staphylococcus phage MESA-01
SEQUENCE: 12
atggcatata atgaaaatga ttttaaatat tttgaggata ttcgtccatt catagatgag   60
atatataaaa caagagaaac atatacaccg ttctatgatg atagagctga ttataatact   120
aattcaaaat cgtattatga ttatgtttca aaactatcac gactgattga agtattagca   180
cgtcgtattt gggaatatga cggtgaatta aaaaaacgtt tcgaaaattg ggacgattta   240
atgaaacaat ttccagatga cgctaaagaa ttatttagag gatggtaaa cgacggcacg   300
attgataaaa tcattcatga tgagtttaca aaatattcag ctggtctaac ttcagctttt   360
gctgtattta aaattgctga aatgaaacaa atgaatgatt ttaaagcaga agttaaagac   420
ttaattaaag atattgaccg tttcgttaat gggtttgaat taaatgaact tgaaccaaag   480
tttgttatgg gattcggtgg aatacgtaac gctgttaacc aatctgttaa tattgataaa   540
gaaacaaatc atatttatac aacacaatca gactcacaat ctccagaggg cttttggata   600
aataaattaa cccctagtgg tgatttactt tcaagtatgc gtatcgtaca aggtgggcac   660
ggcacaacag taggtttaga aagacaatca aacggtgaaa tgaaaatatg gttacatcat   720
gacggtgtag ctaaactatt acaagtagct tataaagata ttacgtttt agatttagaa   780
gaggcaaaag gtttaacaga ttatacacca caatcacttt taaacaaaca tacatttaca   840
ccattaattg atgaagcgaa tgacaaactc attttacgtt tcggagatgg gacaatacag   900
gtacgttcaa gggtagatgt aaaaaatcat attgataacg tagaaaaaga aatgacaatt   960
gataattcag aaaataacga tacacgctgg atgcaaggga tagctgttga tgggatgat   1020
ttatactggt taagtggtaa tagttctgtt aattcacatg ttcagattgg aaagtattca   1080
ttgaaaacag gggaaaaaat atacgattat ccgtttaaat tatcatatca agatggtatt   1140
aacttcccac gtgataattt caaagagcca gagggtattt gtatttatat taatccaaaa   1200
acaaaacgta aatcattatt acttgcaatg acaaatgggg gcgggtggtaa agaatccaat   1260
aatttatatg gattcttcca aactggagaa tatgaacatt ttagtgcctt acgtgcaaga   1320
ggtgcacaaa actataaatt aacaaaagat gatggacgcg ctttatcaat accagactat   1380
atagatgatt taaacaactt aacacaagca ggattttatt atatcgatgg tggaacagca   1440
ggaaaactta aaaacatgcc tacaaacggt agtaagaaaa ttattgacgc aggttgcttt   1500
atcaatgtat accctacaac acaaacatta ggaacagtgc aagaaataac acgtttctca   1560
acaggtcgta aaatggttaa aattattcga ggtatgacgt tagatgtgtt tacattaaaa   1620
tgggattatg gtttatggac aacaatcaaa acagacgcac catatcaaga atatttggag   1680
gcaagtcaat acaacaattg gattgcatat gtaacaacac cgggtgagta ttacattaca   1740
ggtaatcaaa tggaattatt aaagacgca ccagatgata ttaaacacgt tggtgcatgg   1800
ttgaaagtgt caagtgggaa tgctgttggt gaggttagac aaacattaga agcaaatata   1860
gctgaatata aagaattctt tagtaatgtc aatgcggaaa caaaacatcg tgaatacgag   1920
tgggtagcaa aacataaata g                                           1941

SEQ ID NO: 13          moltype = AA   length = 646
FEATURE                Location/Qualifiers
source                 1..646
                       mol_type = protein
                       organism = Staphylococcus phage MESA-01
SEQUENCE: 13
MAYNENDFKY FEDIRPFIDE IYKTRETYTP FYDDRADYNT NSKSYYDYVS KLSRLIEVLA   60
RRIWEYDGEL KKRFENWDDL MKQFPDDAKE LFRGWLNDGT IDKIIHDEFT KYSAGLTSAF   120
AVFKIAEMKQ MNDFKAEVKD LIKDIDRFVN GFELNELEPK FVMGFGGIRN AVNQSVNIDK   180
ETNHIYTTQS DSQSPEGFWI NKLTPSGDLL SSMRIVQGGH GTTVGLERQS NGEMKIWLHH   240
DGVAKLLQVA YKDNYVLDLE EAKGLTDYTP QSLLNKHTFT PLIDEANDKL ILRFGDGTIQ   300
VRSRVDVKNH IDNVEKEMTI DNSENNDTRW MQGIAVDGDD LYWLSGNSSV NSHVQIGKYS   360
LKTGEKIYDY PFKLSYQDGI NFPRDNFKEP EGICIYINPK TKRKSLLLAM TNGGGGKRFH   420
NLYGFFQTGE YEHFSALRAR GAQNYKLTKD DGRALSIPDY IDDLNNLTQA GFYYIDGGTA   480
GKLKNMPTNG SKKIIDAGCF INVYPTTQTL GTVQEITRFS TGRKMVKIIR GMTLDVFTLK   540
WDYGLWTTIK TDAPYQEYLE ASQYNNWIAY VTTPGEYYIT GNQMELFKDA PDDIKHVGAW   600
LKVSSGNAVG EVRQTLEANI AEYKEFFSNV NAETKHREYE WVAKHK               646

SEQ ID NO: 14          moltype = DNA   length = 750
FEATURE                Location/Qualifiers
source                 1..750
                       mol_type = genomic DNA
                       organism = Staphylococcus phage MESA-01
SEQUENCE: 14
atgaagtcat tacaacaagc aaaacaatgg attgatgtca atactggtag aggcattgac   60
tttgatggcg catatggatt tcaatgtatg gatttagctg tagcttatat gtattatgtt   120
actgacggaa aagtgcgtat gtggggtaat gccaaagacg caattgataa taactttaaa   180
ggtttagcta aggtgtatca aaatacacct agctttaaac ctcaattagg tgatattgct   240
gtttatacaa actcacaata tggtcatatt caagttgtga ttagtggtaa tttagattat   300
tatacatgtc tagagcaaaa ctggttaaat ggtggttatg acggttggga aaaagcaaca   360
atcagaacac attattatga cggtgtaaca cactttattc gtccaaactt ttcaaatagt   420
aatagtaaag tattagaaca aaacattcaa caaacaaata atggaaaca aaatcaatac   480
ggtacattat ataaatctga aaatggtaca tttacatgtg attttttacc aatatttgca   540
cgtgttggaa gtcctaaatt aagtgaaccg aatgggtatt ggttccaacc aaacggctat   600
acaccatatg atgaggtttg tttatcagat ggactagtgt ggattggtta taattggcaa   660
ggtacacgtt attatttacc agtgagacaa tggaacggta aaacgggtaa tagttatagc   720
attggtttac catggggggt gttctcataa                                   750

SEQ ID NO: 15          moltype = AA   length = 249
FEATURE                Location/Qualifiers
```

```
source                   1..249
                         mol_type = protein
                         organism = Staphylococcus phage MESA-01
SEQUENCE: 15
MKSLQQAKQW IDVNTGRGID FDGAYGFQCM DLAVAYMYYV TDGKVRMWGN AKDAIDNNFK   60
GLAKVYQNTP SFKPQLGDIA VYTNSQYGHI QVVISGNLDY YTCLEQNWLN GGYDGWEKAT  120
IRTHYYDGVT HFIRPNFSNS NSKVLEQNIQ QTNKWKQNQY GTLYKSENGT FTCGFLPIFA  180
RVGSPKLSEP NGYWFQPNGY TPYDEVCLSD GLVWIGYNWQ GTRYYLPVRQ WNGKTGNSYS  240
IGLPWGVFS                                                          249

SEQ ID NO: 16           moltype = DNA   length = 930
FEATURE                 Location/Qualifiers
source                  1..930
                        mol_type = genomic DNA
                        organism = Staphylococcus phage MESA-01
SEQUENCE: 16
atggctgata gaatcgtaag aagtttaaga ggtattgatt cagtagagaa gttaaacgac   60
aatttagtag aagcaaacga cttaatcaca accaaagacg ataacatata tataagacgt  120
gatgaggatt attataagct aacatttaaa gatgaattat tagaaaaaat caatacaaac  180
acaaaagcga ttgataaaaa taaaaatgac atcactacaa ataaaaaaaa tatatctcaa  240
aacgctacaa atattattaa cattaaagaa gataatattc aacaagataa aaaaattaaa  300
aatttatctg acgttcaaac agaacatgaa aatacattaa acaatcatga tgacgcaatt  360
cgtttattag atgatgaaaa tacaaaaaac aaattagcaa ttgaaaagaa taaacaagat  420
attatcgcta caaaagatac aatcggacaa aataaacaaa gtattgaaaa cttagcttca  480
acggtttcaa acaacacgat tgaaacaagt aaaaaaattg aatcaactaa aacagaatta  540
caagaacaaa tcaaatcttc aaaaacaagt gtgaatgata caggttggtt aaatattcaa  600
cttgaaagtg gtatcacagc aagtgattca agtggtggat attccacacc acaatatcga  660
attatagata taaataacat cagaactatt caattaagag gtgtattaaa aggtgttaag  720
aaaaatggag atattaaatt aggcacgatt aatgctaatt taaaagtaac aatcactat  780
acacaatgtg ctattgattc taaaatgata aacacaagat atatgtaaa ctttaataac  840
gaattacatt ttgttacatc aggttatcaa gatagtgaac tttcttctgg agataaacgt  900
tttgttattg atacacaaat cattgaataa                                   930

SEQ ID NO: 17           moltype = AA   length = 309
FEATURE                 Location/Qualifiers
source                  1..309
                        mol_type = protein
                        organism = Staphylococcus phage MESA-01
SEQUENCE: 17
MADRIVRSLR GIDSVEKLND NLVEANDLIT TKDDNIYIRR DEDYYKLTFK DELLEKINTN   60
TKAIDKNKND ITTNKKNISQ NATDIINIKE DNIQQDKKIK NLSDVQTEHE NTLNNHDDAI  120
RLLDDENTKN KLAIEKNKQD IIATKDTIGQ NKQSIENLAS TVSNNTIETS KKIESTKTEL  180
QEQIKSSKTS VNDTGWLNIQ LESGITASDS SGGYSTPQYR IIDINNIRTI QLRGVLKGVK  240
KNGDIKLGTI NANLKVTHHY TQCAIDSKMI NTRLYVNFNN ELHFVTSGYQ DSELSSGDKR  300
FVIDTQIIE                                                          309

SEQ ID NO: 18           moltype = DNA   length = 1755
FEATURE                 Location/Qualifiers
source                  1..1755
                        mol_type = genomic DNA
                        organism = Staphylococcus phage MESA-01
SEQUENCE: 18
atgaggaaat taccaaattt tgtatttttt tataatacac cttttacaga ttatcaaaat   60
acaatacatt ttaatagtaa taagaacga atgatgattat ttttaaaagg tcgtcatttt  120
aagtcattag attattcaaa acaaccgtat aacttcattc gtgatagaat ggaagttaat  180
gtagatttaa gttggcatga cgcacaaggt attaactata tgacgttttt atctgattt  240
gaaaatagac gttattatgc gtttgtgaac caaattgaat atattaacga tgttacgaca  300
aaaatttatt atgtcattga tacagttatg acgttcacac aaggtaatgt gttagagcaa  360
ctctcaaacg tcaatattga acgacaacat ttatcaaaac gtagtataa ctatatgtta  420
ccaatgttaa gaaacaacga tgatgtttta aaagtaagta ataaaaacta tgtttataac  480
caaatgcaac agtatttgca aaatgttgta ctatttcaat caagtgctga tttatctaaa  540
aagtttggta ctaaaaaaga gcctaattta gacacatcaa aaggaacaat atatgacaat  600
atcacatcac cagttaattt gtatgtcatg aatataatg attttattaa ctttatggat  660
aaaatgagcg catatccgtg gattacgcaa aacttccaaa agtacaaat gttacctaaa  720
gactttatta acgaaaaaga tttagaggac gttaaaacaa gtgaaaaaat tactggttta  780
aaaacattaa aacaaggtgg taaatctaaa gagtggagct aaacgatttt atcattaagt  840
ttttcaaaac ttcaagaaat gatgttgtct aaaaaagatg aattaaaaca catgatacgc  900
aatgaataca tgaccattga attttatgat tggaatggta atacaatgtt acttgacgct  960
ggtaaaattt cagaaaaaac aggagtgaaa ctaagaacaa aatcattatt tggttatcat  1020
aatgaagtta gagtttatcc agtagactat aacagcgctg aaaacgtag accgatactt  1080
gctaaaaaca aagacatatt aattgataca ggttcatttt taaatacaaa tattacattt  1140
aatagctttg ctcaagttcc aatttttaatt aataacggta tattaggaca tcacaacaa  1200
gcaaatagac aaaaaaatgc agaaagtcaa ttaatcacaa atcgaattga taacgtgtta  1260
aatggtagtg accctaaatc aagatttac gacgctgtta tactttaagt taatttaagt  1320
ccaacagctt tatttggtaa gtttaatgaa gaatataatt tttataagca acaacaagct  1380
gaatataaag atttagcact acaaccaccg tctgtgacag aatcagatat gggtaatgca  1440
ttccaaattg caaataatat taacggttta acaatgaaga ttagtgtacc gtctccaaaa  1500
gaaattcat tcttacaaaa atattacatg ttatttggtt ttgaagtgaa tgactataac  1560
aatttcattg aacctattaa tagtatgact gtatgtaatt acttaaaatg taacggaacg  1620
```

-continued

```
tatacattac gtgatattga ccctatgtta atggaacaac tcaaagcaat attagaaact   1680
ggtgtgagat tttggcataa tgacgggtca ggtaatccaa tgttacaaaa tccattaaat   1740
aataaattta gatag                                                    1755

SEQ ID NO: 19              moltype = AA  length = 584
FEATURE                    Location/Qualifiers
source                     1..584
                           mol_type = protein
                           organism = Staphylococcus phage MESA-01
SEQUENCE: 19
MRKLTNFVFF YNTPFTDYQN TIHFNSNKER DDYFLKGRHF KSLDYSKQPY NFIRDRMEVN   60
VDLSWHDAQG INYMTFLSDF ENRRYYAFVN QIEYINDVTT KIYYVIDTVM TFTQGNVLEQ   120
LSNVNIERQH LSKRTYNYML PMLRNNDDVL KVSNKNYVYN QMQQYLQNVV LFQSSADLSK   180
KFGTKKEPNL DTSKGTIYDN ITSPVNLYVM EYNDFINFMD KMSAYPWITQ NFQKVQMLPK   240
DFINEKDLED VKTSEKITGL KTLKQGGKSK EWSLNDLSLS FSKLQEMMLS KKDELKHMIR   300
NEYMTIEFYD WNGNTMLLDA GKISEKTGVK LRTKSIIGYH NEVRVYPVDY NSAENDRPIL   360
AKNKDILIDT GSFLNTNITF NSFAQVPILI NNGILGQSQQ ANRQKNAESQ LITNRIDNVL   420
NGSDPKSRFY DAVSVASNLS PTALFGKFNE EYNFYKQQQA EYKDLALQPP SVTESDMGNA   480
FQIANNINGL TMKISVPSPK EITFLQKYYM LFGFEVNDYN NFIEPINSMT VCNYLKCNGT   540
YTLRDIDPML MEQLKAILET GVRFWHNDGS GNPMLQNPLN NKFR                   584

SEQ ID NO: 20              moltype = DNA  length = 375
FEATURE                    Location/Qualifiers
source                     1..375
                           mol_type = genomic DNA
                           organism = Staphylococcus phage MESA-01
SEQUENCE: 20
atgtttattt atgcaggaga tttaaaatta ttatatttct tatttgtatt aatgtttatc   60
gacattatta caggtatagc aaaagccatt aagaataata atttatggtc aaagaaatct   120
atgaaagggt ttgctaaaaa attactcatt ttttgtatta ttatactagc aaatatcatt   180
gaccaaagtt tacaattaaa aggtgggtta ctcatgataa cgatattcta ttatatcgca   240
aatgagggct tatctattgt tgaaaattgt gcagaaatgg atgtattagt gccagagcaa   300
atcaaagaac gattaaaagt aataaaaaac gagtctgaaa agagtgataa caatgaacga   360
ccaagagaag attga                                                    375

SEQ ID NO: 21              moltype = AA  length = 124
FEATURE                    Location/Qualifiers
source                     1..124
                           mol_type = protein
                           organism = Staphylococcus phage MESA-01
SEQUENCE: 21
MFIYAGDLKL LYFLFVLMFI DIITGIAKAI KNNNLWSKKS MKGFAKKLLI FCIIILANII   60
DQILQLKGGL LMITIFYYIA NEGLSIVENC AEMDVLVPEQ IKERLKVIKN ESEKSDNNER   120
PRED                                                                124

SEQ ID NO: 22              moltype = DNA  length = 1440
FEATURE                    Location/Qualifiers
source                     1..1440
                           mol_type = genomic DNA
                           organism = Staphylococcus phage MESA-01
SEQUENCE: 22
atgaacgacc aagagaagat tgataaattt acccactcgt atattaatga tgacttcggt   60
ttaacgatag accaacttgt accaaaagtt aaaccttacg ggcgatttaa tgtatggcta   120
ggtggtaatg aaagtaaaat aagacaagta ttaaatgcag taaagtcgat aggtgtttca   180
ccaacccttt ttgctgttta tgaaaagaat gaagggtata gtgcaggttt agggtggtta   240
aaccatacat ctgcacaagg tgattattta actgatgcta aatttgtagc tagaaaatta   300
gtatcacaat caaaacaagc aggacatccg tcttggtatg atgcaggtaa cattgtgcat   360
tttgtacctc aagacgtaca aagaaaaggt aatgaagatt ttgctaagaa tatgaaagca   420
ggtacagtcg gacgtaccta tattccatta acggcggctc ctacttgggc tgcttattac   480
ccactaggtc tgaaagcttc atataataga gtacaaaact atggtaatcc atttttagac   540
ggtgctaata ccattttaga atggggcggt aaaattgacg ggaaaggtgg ttcacctagt   600
agtggctcat ctgatagtgg ttctgatagt ggaggaaatt cattactagc cctagcaaaa   660
caagctatgc aagaattatt aaaaaaagtg caagacgcat acaatgggga cgtacacagt   720
atcggtcatg ataaatattt tagtaatgat tattttacat tagaaaaaac gtttaacaat   780
acgtatcata ttaaaatgac tatagggtta cttgattcac tcaaaaagat tatagatagt   840
attcatattg acagcggtgg tagctcatct aatcctactg atgatgacgg agatcataaa   900
ccaattagtg gtaaatctgt taaacctaac ggaaaaagtg gtcgtgttat tggtggtaac   960
tggacatatg accaattacc tgaaaaatat aaaaaggcaa ttggtgtacc tttgttcaaa   1020
aaagaatatt tatataaacc gggtaacata ttccctcaaa ccggtaatgc aggacaatgt   1080
acagaattaa catgggcgta tatgtcacaa ttacatggta agcgtcaacc tacagacgac   1140
ggtcaaatta ctaacgggca acgtgtatgg tacgtttata agaagttagg tgcaaaaaca   1200
acccataacc caacagtagg ttatggtttt tcaagtaaac caccatactt acaagcaagt   1260
atttatggta ttggacacac aggtgttgtc gttgctgtat ttgacgatgg ttcattctta   1320
gttgcaaact ataacgtacc accttacgtt gcaccgtcac gagtgttatt atatacacta   1380
attaatggta taccagaaaa tgcaggtgat aatattgtat tctttagtgg tattgcttaa   1440

SEQ ID NO: 23              moltype = AA  length = 479
FEATURE                    Location/Qualifiers
source                     1..479
```

-continued

```
                        mol_type = protein
                        organism = Staphylococcus phage MESA-01
SEQUENCE: 23
MNDQEKIDKF THSYINDDFG LTIDQLVPKV KPYGRFNVWL GGNESKIRQV LNAVKSIGVS    60
PTLFAVYEKN EGYSAGLGWL NHTSAQGDYL TDAKFVARKL VSQSKQAGHP SWYDAGNIVH   120
FVPQDVQRKG NEDFAKNMKA GTVGRTYIPL TAAATWAAYY PLGLKASYNR VQNYGNPFLD   180
GANTILEWGG KIDGKGGSPS SGSSDSGSDS GGNSLLALAK QAMQELLKKV QDALQWDVHS   240
IGHDKYFSND YFTLEKTFNN TYHIKMTIGL LDSLKKIIDS IHIDSGGSSS NPTDDDGDHK   300
PISGKSVKPN GKSGRVIGGN WTYDQLPEKY KKAIGVPLFK KEYLYKPGNI FPQTGNAGQC   360
TELTWAYMSQ LHGKRQPTDD GQITNGQRVW YVYKKLGAKT THNPTVGYGF SSKPPYLQAS   420
IYGIGHTGVV VAVFDDGSFL VANYNVPPYV APSRVLLYTL INGVPENAGD NIVFFSGIA    479

SEQ ID NO: 24          moltype = DNA  length = 2280
FEATURE                Location/Qualifiers
source                 1..2280
                       mol_type = genomic DNA
                       organism = Staphylococcus phage MESA-01
SEQUENCE: 24
atgggattac ttgagtgtat gcaatatcat aaacatgaac gtaaaatgat tttatattgg    60
gatattgaaa cattagcata taataaaatc aatggacgta aaaaaccaac taaatataaa   120
aacgtcacgt attcagttgc tattggttgg tttaatggtt atgaaattga tgtagaggta   180
ttccctagtt ttgaagcatt ttatgattcg ttttataagt atgtgaaacg acgtgataca   240
atcacaaaat caaaaacaga cattattatg attgcacata actgtaataa gtatgacaat   300
cattttttac ttaaagatac gatgcgttac tttgataata ttacacgtaa aaatgtgttt   360
ttaaaatcag ctgaagataa tgaacacacc ctaaaaatga aagaagctca aatattatct   420
aaaagtcaaa atgtcatact tgaaaaacgt gtaaagtcct ctattaattt agatttaacg   480
atgttttaa acggatttaa attcaatatc attgataact ttatgaaaac caatacatca   540
atcgctcacac ttggcaaaaa gttattagac ggtggttatc ttacagaaaa ccaactcaaa   600
actgatttta actatacaat ctttgataaa gaaacagata tgtcagacag tgaagcttat   660
gactatgcta ctaaatgctt tacaaaatta acatcagaac aacttacata tattcataac   720
gatgtaatta ttttaggtat gtgtcatata cattatagtg atatttttcc aaatttttgat   780
tataataaat taacgttttc attaaatatt atggaatcat atttaaataa tgaaatgaca   840
cgttttcaat tacttaataa atacgatgac atcgctattt catatacgca ttatcaattc   900
catgatatga attttttatga ttatattaaa tcattttatc gtggtgggtt aaatatgtat   960
aacacaaagt atattaacaa aatcgttgat gaaccttgtt tttctattga tatcaattca  1020
agttatccgt atgtgatgta tcatgaaaaa attccaactt ggttatactt ttacgaacac  1080
tattcagaac caacgttaat tcctactttt ttagatgatg ataattattt tacgttatat  1140
aagattgata agcatacatt taaccatgat atattactaa aaataaaatc acgtgtatta  1200
cgtcaaatga ttgtaaaata ctataataat gataatgatt acgttaatat caacacaaat  1260
acattaagaa tgattcaaga cattacagat attgattgca caaaaatacg tgtcaattca  1320
tttgtgatgt atgaatgtga atactttcat gctcgtgata ttatatttca aaactatttt  1380
attaaaacac aagggaaact caaaacaaaa attaatatga cttcacctta tgactataaa  1440
atcactgatg atattaacga acacccgtac tcaaatgaag aggttatgct gtctaaagtc  1500
gttttaaacg gtttatatgg tattcctgct ttacgttcac actttaattt attccgttta  1560
gatgaaaaca acgaattatt taatatgata aacggataca aaaacacaga acgtaattta  1620
ctattttcta cttttgtaac atcacgctca ttatataact tattagttcc gtttcaatac  1680
ttaactgaaa gtgaaataga cgataatttc atttattgtg atactgatag tttgtatatg  1740
aaatccgttg tgaaaccctt gttaaaccoc gatttattcg acccgattgc cttaggtaaa  1800
tgggatattg aaaacgaaca gatagataag atgtttgtac tcaatcataa gaaatatgct  1860
tatgtgacga acggaaaaat taaaatcgct tctgctggta taccgaaaaa cgcttttgat  1920
acaagcgttg attttgaaac atttgtcagt gaacaatttt ttgatggtgc tgttgtttac  1980
aacaataaaa gtatctataa tgagcagggt acgattccga tttacccgtc taaaactgag  2040
attgtaagcg gagatgtata tgatgatgtc ttttcagatg aattaaatga aaaaagagaa  2100
tttttgctaa aagacgctag agaaaatttt gaacatagtg aatatgatga tattctatat  2160
attgaaagtg atattggcac attttcatta aatgatttat tcccagtaga acgttctgca  2220
aaatatcgtt caaagttaaa tcaattaaaa caaatacatg atgacatacg aaaagggtaa  2280

SEQ ID NO: 25          moltype = AA  length = 759
FEATURE                Location/Qualifiers
source                 1..759
                       mol_type = protein
                       organism = Staphylococcus phage MESA-01
SEQUENCE: 25
MGLLECMQYH KHERKMILYW DIETLAYNKI NGRKKPTKYK NVTYSVAIGW FNGYEIDVEV    60
FPSFEAFYDS FYKVKRRDT ITKSKTDIIM IAHNCNKYDN HFLLKDTMRY FDNITRKNVF    120
LKSAEDNEHT LKMKEAQILS KSQNVILEKR VKSSINLDLT MFLNGFKFNI IDNFMKTNTS   180
IATLGKKLLD GGYLTENQLK TDFNYTIFDK ETDMSDSEAY DYATKCFTKL TSEQLTYIHN   240
DVIILGMCHI HYSDIFPNFD YNKLTFSLNI MESYLNNEMT RFQLLNKYDD IAISYTHYQF   300
HDMNFYDYIK SFYRGGLNMY NTKYINKIVD EPCFSIDINS SYPVVMYHEK IPTWLYFYEH   360
YSEPTLIPTF LDDDNYFTLY KIDKHTFNHD ILLKIKSRVL RQMIVKYYNN DNDYVNINTN   420
TLRMIQDITD IDCTKIRVNS FVMYECEYFH ARDIIFQNYF IKTQGKLKTK INMTSPYDYK   480
ITDDINEHPY SNEEVMLSKV VLNGLYGIPA LRSHFNLFRL DENNELFNMI NGYKNTERNL   540
LFSTFVTSRS LYNLLVPFQY LTESEIDDNF IYCDTDSLYM KSVVKPLLNP DLFDPIALGK   600
WDIENEQIDK MFVLNHKKYA YVTNGKIKIA SAGIPKNAFD TSVDFETFVS EQFFDGAVVY   660
NNKSIYNEQG TISIYPSKTE IVSGDVYDDV FSDELNEKRE FLLKDARENF EHSEYDDILY   720
IESDIGTFSL NDLFPVERSA KYRSKLNQLK QIHDDIRKG                          759

SEQ ID NO: 26          moltype = DNA  length = 1248
FEATURE                Location/Qualifiers
```

-continued

```
source                1..1248
                      mol_type = genomic DNA
                      organism = Staphylococcus phage MESA-01
SEQUENCE: 26
atggtaaaac aaaacaggct agacatggta agggattatc aaaatgttgt caatcatgta    60
agaaaaaaga tacctgataa ttataatcaa attgaattag tcaatgaatt aatgaatgat   120
gatttagatt actatatttc tatttcaaac cgttcagacg gtaaatcatt taactatgta   180
tcgtttttta tttatttagc aatgaaactt gatattaaat ttacattact atcacgtcat   240
tacacgttac gtgatgcata ccgtgatttt attgaggaaa ttattgataa aaatccatta   300
tttaaatcaa aacgtgttgc tttcagaagc gcaagagatt atttagcgat tgtataccaa   360
gataaagaaa taggtgtgat aacagattta aatagtgcaa ctgatttgaa atatcattct   420
aacttttttaa aacactatcc tatcattata tatgatgagt ttttagcact tgaagatgat   480
tatttatatg atgagtggga taaactcaaa acaatttatg agtccattga tagaaatcat   540
ggtaatgtag attatatcgg atttcctaaa atattttac ttggtaacgc tgttaacttt   600
tcaagtccta ttttatctaa tttaaacata tataatctat tacaaaaaca taaaatgaac   660
acgtcacgac tttataaaaa catttttta gagatgagac gtaatgatta tgtcaacgaa   720
aaacgtaata cacgtgcgtt taattcaaat gaggacgcta tgacaacagg ggaatttgat   780
tttaatgaat ataatttagc taacgatagt atacggtcac atattaatca aaacggtaat   840
tttttctata tcaaaacaga agataaaattc attaaaatta tgtataatgt atctacattt   900
atagcaaata ttattgtaat accttataca aaagaatatg aatttgtac gaaaatcaaa   960
gatattgatg aaaacgtcac atatcttaga gaagatatgt tttataaaga aaatatggag  1020
cgttattatt ataatccgtc aaatttacat tttgataacg atatttatca aaattatgtt  1080
gttgataatg ataggtattt atatttagat gtgaataaaa ttataaaatt tcatattaaa  1140
aatgaaatga agaaaaacat gagtgagttt gaacgaaaag aaaagatata tgaagataac  1200
tatatagaaa atacaaaacg ctacttaatg caacaatacg aacaataa           1248
```

```
SEQ ID NO: 27          moltype = AA   length = 415
FEATURE                Location/Qualifiers
source                 1..415
                       mol_type = protein
                       organism = Staphylococcus phage MESA-01
SEQUENCE: 27
MVKQNRLDMV RDYQNVVNHV RKKIPDNYNQ IELVNELMND DLDYYISISN RSDGKSFNYV    60
SFFIYLAMKL DIKFTLLSRH YTLRDAYRDF IEEIIDKNPL FKSKRVAFRS ARDYLAIVYQ   120
DKEIGVITDL NSATDLKYHS NFLKHYPIII YDEFLALEDD YLYDEWDKLK TIYESIDRNH   180
GNVDYIGFPK IFLLGNAVNF SSPILSNLNI YNLLQKHKMN TSRLYKNIFL EMRRNDYVNE   240
KRNTRAFNSN EDAMTTGEFD FNEYNLANDS IRSHINQNGD FFYIKTEDKF IKIMYNVSTF   300
IANIIVIPYT KEYEFCTKIK DIDENVTYLR EDMFYKENME RYYYNPSNLH FDNAYSKNYV   360
VDNDRYLYLD VNKIIKFHIK NEMKKNMSEF ERKEKIYEDN YIENTKRYLM QQYEQ        415
```

```
SEQ ID NO: 28          moltype = DNA   length = 483
FEATURE                Location/Qualifiers
source                 1..483
                       mol_type = genomic DNA
                       organism = Staphylococcus phage MESA-01
SEQUENCE: 28
atgcgtaaac gtatgtcaga agcagaccgt tggaaaaaag aacgagaagc aagaaaagca    60
gatgaagaaa aaagaaaaaa gaatgacttt agtggtgtca gtttttaaatt tgaagatgca   120
tcactacaaa aagaatatat tgacgcttgg gaatattttt caaagcttac attttttacct   180
aaagaaaaac atgtgagtta tgtaaatgct gtttctttag tacgtggtaa acgacgtgaa   240
caattgttaa aaatattaaa catttatgaa cgtaatgatg atagtaataa caaaaatgca   300
aaaacacata aatatacttt atatgatgaa actgctaaag ataataatac atcaatgtat   360
aaatatatca aaggtattga agaattattt gatgaaattg gtgaatcaa cagaccgaaa   420
acaacaatca aaaacaaaaa agtcagatat aacttttttat attatcattt aatagaaaaa   480
tga                                                                483
```

```
SEQ ID NO: 29          moltype = AA   length = 160
FEATURE                Location/Qualifiers
source                 1..160
                       mol_type = protein
                       organism = Staphylococcus phage MESA-01
SEQUENCE: 29
MRKRMSEADR WKKEREARKA DEEKRKKNDF SGVSFKFEDA SLQKEYIDAW EYFSKLTFLP    60
KEKHVSYVNA VSLVRGKRRE QLLKILNIYE RNDDSNNKNA KTHKYTLYDE TAKDNNTSMY   120
KYIKGIEELF DEIGESNRPK TTIKNKKVRY NFLYYHLIEK                        160
```

```
SEQ ID NO: 30          moltype = DNA   length = 168
FEATURE                Location/Qualifiers
source                 1..168
                       mol_type = genomic DNA
                       organism = Staphylococcus phage MESA-01
SEQUENCE: 30
atgaataacc tacttaatat aattatcatt tttctttag cattattgat tacacttgtc    60
attcttatga ccatgcatat acgtgtgtca tttggtgtac tatttacaac actaatcata   120
ttctatatta tcttttttaat ggttatttat gctatatatg gaggttga               168
```

```
SEQ ID NO: 31          moltype = AA   length = 55
FEATURE                Location/Qualifiers
source                 1..55
```

```
                              mol_type = protein
                              organism = Staphylococcus phage MESA-01
SEQUENCE: 31
MNNLLNIIII FLLALLITLV ILMTMHIRVS FGVLFTTLII FYIIFLMVIY AIYGG          55

SEQ ID NO: 32              moltype = DNA   length = 417
FEATURE                    Location/Qualifiers
source                     1..417
                              mol_type = genomic DNA
                              organism = Staphylococcus phage MESA-01
SEQUENCE: 32
atgaaaataa aacaatcatt taatttatat gacttacttt gctacattaa cgataacaga    60
aaaaattttc aagataaaaa aatacaattt atttctgata gtggttataa ttttgtaggt    120
attgatagcg atgatgatat ttgtgttaat ttttctgaaa gtcataatac ggacttaaca    180
attaacaatg atttattcac gttagatatt gatattgata ttaaaaaaca tgttttttat    240
ttacttgagt attattatat agattctgta aataacacat ttgtaagaga aacttcatat    300
ggtgttacaa tagacgatgt attagtaaat tttgattgtc cactcgaaag cggattaatg    360
attatttacc aaaacaaagt tatatataaa aacggaaatg tgatagaaca tgaataa      417

SEQ ID NO: 33              moltype = AA   length = 138
FEATURE                    Location/Qualifiers
source                     1..138
                              mol_type = protein
                              organism = Staphylococcus phage MESA-01
SEQUENCE: 33
MKIKQSFNLY DLLCYINDNR KNFQDKKIQF ISDSGYNFVG IDSDDDICVN FSESHNTDLT    60
INNDLFTLDI DIDIKKHVFY LLEYYYIDSV NNTFVRETSY GVTIDDVLVN FDCPLESGLM    120
IIYQNKVIYK NGNVIEHE                                                  138

SEQ ID NO: 34              moltype = DNA   length = 174
FEATURE                    Location/Qualifiers
source                     1..174
                              mol_type = genomic DNA
                              organism = Staphylococcus phage MESA-01
SEQUENCE: 34
atgaaaaaat ataaaacagt cttattatat actgacacaa tagaaaatga ttttcatcat    60
caaatattaa tgtttgaaga tttgtataac gccaaagttt tatactctta ttatgaattc    120
aatccatttc ataataatta tgcgtatgtt atagaatata tagaggagac ttaa         174

SEQ ID NO: 35              moltype = AA   length = 57
FEATURE                    Location/Qualifiers
source                     1..57
                              mol_type = protein
                              organism = Staphylococcus phage MESA-01
SEQUENCE: 35
MKKYKTVLLY TDTIENDFHH QILMFEDLYN AKVLYSYYEF NPFHNNYAYV IEYIEET       57

SEQ ID NO: 36              moltype = DNA   length = 369
FEATURE                    Location/Qualifiers
source                     1..369
                              mol_type = genomic DNA
                              organism = Staphylococcus phage MESA-01
SEQUENCE: 36
atgacaaacg taaagaaat tttatctaga caccaaaaca cattagcgag atttgaattt     60
gaggaaaaag aaagagaatt tatcaaatta tcggaattgg ttgaaaaatt cggaatcaaa    120
caagaataca tcgttagagc attatttaca aacaaagaat caaaattcgg tgaacaaggt    180
gttattgtaa cagatgatta taatgttaac ttaccgaatc acttaactga attaattaaa    240
gacatgcgtc aagatgaaga tgttgtagac attattaata aaggtgaagt tgtgttctca    300
atttatgaat acgaaacaa aaaaggtcaa aaaggatatt ctattaactt tagtcaagta    360
tcattttaa                                                           369

SEQ ID NO: 37              moltype = AA   length = 122
FEATURE                    Location/Qualifiers
source                     1..122
                              mol_type = protein
                              organism = Staphylococcus phage MESA-01
SEQUENCE: 37
MTNVKEILSR HQNTLARFEF EEKEREFIKL SELVEKFGIK QEYIVRALFT NKESKFGEQG    60
VIVTDDYNVN LPNHLTELIK DMRQDEDVVD IINKGEVVFS IYEYENKKGQ KGYSINFSQV    120
SF                                                                  122

SEQ ID NO: 38              moltype = DNA   length = 225
FEATURE                    Location/Qualifiers
source                     1..225
                              mol_type = genomic DNA
                              organism = Staphylococcus phage MESA-01
SEQUENCE: 38
atgaaacctg atgagattgt tactttacgt gttaaaggtt atattcttaa ttatctcgat    60
gataaagatg aatatattga aaaatttttc ccattacatg agtatcattt aactaaacaa    120
```

```
caagccaaag aattattacc tgccacatat acattacttt caacaacacg acacacacaa  180
acaattaaag ttaattataa cgagttatta aaaataaaat tataa                  225

SEQ ID NO: 39           moltype = AA   length = 74
FEATURE                 Location/Qualifiers
source                  1..74
                        mol_type = protein
                        organism = Staphylococcus phage MESA-01
SEQUENCE: 39
MKPDEIVTLR VKGYILNYLD DKDEYIEKFF PLHEYHLTKQ QAKELLPATY TLLSTTRHTQ  60
TIKVNYNELL KIKL                                                    74

SEQ ID NO: 40           moltype = DNA   length = 300
FEATURE                 Location/Qualifiers
source                  1..300
                        mol_type = genomic DNA
                        organism = Staphylococcus phage MESA-01
SEQUENCE: 40
atgattcaag cagataatgc accaaatgaa aaaggacaag catatactga aatgttgcaa  60
ctgttcaata agttaattga atggaatcca gcatatacat ttgataatgc tatcaattta  120
gtttcagctt gccaacaact gttattaaac tataacacag ctattgttaa gttcttaaac  180
gacaaactta acaatgaaat tgaaccaaca tctgttctat catacatcac agatgacgct  240
ttggaacaat gggatatgca taaaagtttt tatgaaacat ataacgttta cgtttttag   300

SEQ ID NO: 41           moltype = AA   length = 99
FEATURE                 Location/Qualifiers
source                  1..99
                        mol_type = protein
                        organism = Staphylococcus phage MESA-01
SEQUENCE: 41
MIQADNAPNE KGQAYTEMLQ LFNKLIEWNP AYTFDNAINL VSACQQLLLN YNTAIVKFLN  60
DKLNNEIEPT SVLSYITDDA LEQWDMHKSF YETYNVYVF                          99

SEQ ID NO: 42           moltype = DNA   length = 174
FEATURE                 Location/Qualifiers
source                  1..174
                        mol_type = genomic DNA
                        organism = Staphylococcus phage MESA-01
SEQUENCE: 42
gtgctactac taataacatc tattcgaaac attcaaatat tctttaaacc gaaaaaatat  60
tcgattttaa ttttaattaa attaaaacaa tatgcatttt ctagtttctt cattatatac  120
attgattttt cttattttaa aaaaacttta aaacttttc acaaaaacgt ttga          174

SEQ ID NO: 43           moltype = AA   length = 57
FEATURE                 Location/Qualifiers
source                  1..57
                        mol_type = protein
                        organism = Staphylococcus phage MESA-01
SEQUENCE: 43
VLLLITSIRN IQIFFKPKKY SILILIKLKQ YAFSSFFIIY IDFSYFKKTL KLFHKNV      57

SEQ ID NO: 44           moltype = DNA   length = 17639
FEATURE                 Location/Qualifiers
source                  1..17639
                        mol_type = genomic DNA
                        organism = Staphylococcus phage MESA-05
SEQUENCE: 44
gtatttaaaa tctaatttct tctattaaat agtattttta aattatttaa acttttttaag  60
aaaaaacatt gacaaaactt ttaaacgttt gctatactat gtatgtaatc aaatcaagga  120
ggtaacaaaa tggaaaatgt acaacctta caaacttaca tttttaaaaaa tggtaatata  180
gttattgtta tgggtaatac atcaagttat gaattaacat tatttgtact tgaaaaggat  240
gattttgaac aattagacca taattcacct aaaaaaaatcg ttgatgaaat aaggaatgaa  300
atcaatgatt taaggagtga taataatggt taatgttgat aacgcacctg aagaaaaagg  360
gcaagcctat actgaaatgt tgcaactatt caataagttg attcaatgga atccagcttn  420
tactttcgac aatgctatta atttagtatc agcttgccaa caactattat aaaactataa  480
tagttctgtt gttaaattct taaatgatga actaaacaac gaaactaaac cagaatctat  540
tttatcttac attgctggtg atgacccaat agaacaatgg aatatgcaca aaggatttta  600
tgaaacgtat aacgtttacg ttttttagaa aggagtgata taataatgaa acctgatgat  660
attgttacat tacgaataaa aggttatatt tttcattatt tagatgataa aaatgaatat  720
gttgaagaat ttatcccact tcacgagtat catttatcaa aatcacaagc taaagactta  780
ttacctaata cacacaaact tttatccact acacgacata ctaaaactat gcaagtttat  840
tacaatgatt tactacaaat tgcaattgca gaaagcaaat aatttaaata agaggagaaa  900
taaaaatgac aaacgtaaaa gatatttat caagacacca aaacacatta gcgagattcg  960
aatttgagga aaagaaaga gaatttatca aactatcaga attagtagaa aaatacggta  1020
tgaaaaaaga gtatatcgtt agagcattat tcacaaacaa agaatcaaaa ttcggtgagc  1080
aaggtgttat cgtcactgac gactataacg taaacttacc gaatcactta actgaattaa  1140
ttaaagaaat gcgtcaagac gaggacgttg ttaacattat caacgctggc gaagttcaat  1200
tcacaattta tgagtatgaa aataaaaaag gtcaaaaagg ttactcaatc aactttggtc  1260
aagtatcatt ttaataaaaa tttcatagg gatatttatc ccctattttt atgaggtgct  1320
```

-continued

```
taaatggaat gtaaatacaa aacggtatta ttatattgtg atgagattaa aggaaattta   1380
ccacatcaaa tagcaatgtt tgaagaatta tatgacgcta aagttgtata ttcatattat   1440
gaatataatc catttactga aaaatatgcg tatatgatag aatacattaa ggagatataa   1500
aatgaaaatt acaacaacat taaatacaaa aaacaataat gatttattta ctttagatat   1560
tgacattgat attcatacac attgtttttga ttttcttatt gtttttttata gaatatatct   1620
aaatccaaat tataaaagag aagcatttac agattgcacc attgatgacg tattagaata   1680
ttttgagaat ccattattag ctgatattac aataatttat aaaaataagg taatttatga   1740
tttaggaaaa gtgattgacc atgaataacc tattagatat tattattgtt ttccttttag   1800
cattttaat tacacttgta atacttatga caatgcatat acgtgtgtca tttggtgttt   1860
tatttactac attgattata ttctacatta tctttttagt ggttatatat gggttatatg   1920
gaggtcgtta gcaatggtta gacatacgtc cgaaatggat aaatggaaaa aagaaagaga   1980
cgcaagaaaa gagcaggaaa aagaattgtt tttaaatgat tttagtactg ttaatttttaa   2040
atttgatgat aaagatttac aagaggcgta catagacgca tggaaacatt tcgcacattt   2100
gccctatttt ccaaaagaaa gaaacgtgtc atatgtaaat gctgtatcat tggtaagagg   2160
taaaagacat gaacaattaa actatatact tgaaatatat aaccgtaaag atgaatctaa   2220
taataaaaac gctaaaaaac ataaatatgc tttatatgaa ttacaagcta aaaataataa   2280
ttcttctatg tataaatata ttaaagaaat tgacacttta tacaaagaaa ttggtaaatc   2340
agacagacca gtgactacta ttgatgatga agatgtgagg ataacttttt tatattatgc   2400
aacatttgaa gactaatttt aatactgtaa acgacatcat aaactattat aaggagcaaa   2460
aacatggtga aacaaaatcg tttagacatg gtaagagatt atcaaaatgc tgtcaatcat   2520
gtcagaaaaa aaataccaga taactataat caaatagaat tagttgatga actcatgaat   2580
gatgatatag actattacat atctattttca aaccgttctg acggaaaatc gttcaactat   2640
gtttcattct ttatttattt agctataaaa cttgatatta aatttacttt attatcacgt   2700
cattatacat tacgtgacgc ttatcgtgat tttattgagg aaatcataga caaaaaccca   2760
ctattcaaat ctaagcgtgt cacattcaga agcgctaggg actatttagc tatcatctat   2820
caagataagg aaatcggtgc gattacagat ttgaatagtg caactgattt aaaatatcat   2880
tctaactttt taaaacacta ccctatcatt atatatgatg aatttttttagc acttgaagat   2940
gactatttaa ttgacgagtg ggataagtta aaaacaattt atgaatcaat cgaccgtaac   3000
catggtaatg ttgattatat cggcttccct aaaatgtttt tactaggtaa tgctgtcaac   3060
ttttcaagtc ctatattatc caatttaaat atatataact tattacaaaa acataaaatg   3120
aacacatcac gactttacaa aaatattttt ttagaaatgc gaagaaacga ttacgtaaat   3180
gaaaagcgta acacacgggc attcaattca aacgatgacg ctatgactac tggcgagttt   3240
gaatttaacg aatataattt ggcagatgat aatttaagaa atcatatcaa tcaaaacggt   3300
gatttttct atattaaaac tgacgataaa tatatataaa ttatgtataa tgttgataca   3360
tttaatgcta atattattgt tataccttat acaaaacaat atgaattttg tactaaaatc   3420
aaagatatag atgacaatgt tatttatttta agagaagata tgtttttataa agaaaacatg   3480
gagcgttatt attacaatcc aagcaattta cattttgata acgcttactc aaaaaattac   3540
gttgttgata atgatagata tttatattta gatatgaata aaattataaa atttcatata   3600
aaaaatgaaa tgaagaaaaa tatgagtgaa tttgaaagaa aagaaaaaat atatgaagat   3660
aactatattg aaaaatacaaa gaagtattta atgaaacaat acggcttata aaaggtgtgt   3720
aagattatgg gattactaga atgcatgcaa tatcataaac atgaacgtcg aatgatttta   3780
tactgggata tagaaacatt agcgtacaat aaagttaacg gacgaaaaaa accaaccaaa   3840
tataaaaacg taacgtattc agtagcaatt ggttggttta atggttatga gattgatgta   3900
gaagtatttc ctagtttttga atcgtttttat gacgcatttt atacgtatgt gaaacgacgt   3960
gatacaatca ctaagtcaaa aacagatatt atcatgattg cacataactg taataagtat   4020
gacaaccatt ttttacttaa agataccatg cgttattttg ataatatcac acgtgaaaat   4080
atatatttaa aatctgcaga agaaaacgaa cacacactaa agatgcaaga ggctactatt   4140
ttagctaaaa atcaaaatgt gattttagaa aaacgtgtga aatcgtctat taatttagac   4200
ttaacaatgt ttttaaatgg atttaaattt aatattattg ataactttat gaaaacaaat   4260
acatcaattg caacattagg taaaaagttg cttgacggtg gttatttaac agacgaccaa   4320
cttaaaacag attttaatta cacgatattt gataaagata acgatatgtc agataagtgaa   4380
gcctatgact atgctgttaa gtgtgtttgct aaactcacac ctgaacaact tacatacatt   4440
cataatgacg tgattatatt aggtatgtgc catattcatt atagtgatat atttccaaat   4500
tttgactata acaaattaac attttcattg aatattatgg aatcgtattt aaataatcaa   4560
atgacgcgtt ttcagttact caatcaatat caagatatta aaatatcata tacacattac   4620
catttccatg atatgaattt ttatgactat atcaaatcat tttatcgtgg tggtttaaat   4680
atgtataaca ctaaaatacat aaacaaactt attgatgagc cttgtttttc tattgatatc   4740
aattccagtt atccttatgt gatgtatcat gagaaaattc cgacatggtt atacttttat   4800
gaacattatt cagaacctac attaatccct acttttttaa atgatgacaa ttattttttca   4860
ttatataaga ttgataaaga tgtatttaac aatgatttat taattaaaat caaatcacgt   4920
gtattacgtc aaatgattgt aaaaatactat aataatgata atgattacgt taatattaat   4980
acaaatacat taagaatgat tcaagacatt acgggtattg attgtacgca tatacgtgtt   5040
aattcgtttg tgatatatga atgtgaatac tttcatgcac gtgatattat atttcaaaac   5100
tattttatta aaacacaagg taagttaaaa aacaaaatca acattacgac   5160
tatcatatta ctgatgacat caacgaacac cctactcaa atgaggaggt tatgttgtct   5220
aaagttgtac ttaacggatt atatggcata cctgcattac gttcacattt taacttattc   5280
cgtttagatg ataacaatga actatacaat attattaacg gttacaaaaa cacagaacgt   5340
aatattttat tttctacatt tgtaacatca cgttcattgt ataacttatt agtaccattc   5400
caatacttaa cggaaagtga aattgacgac aatttttattt attgtgatac tgatagtttg   5460
tatatgaaat ccgttgttaa acccttattg aaccccagtt tattcgaccc gatagcctta   5520
ggtaaatggg atattgaaaa cgaacagata gataagatgt ttgtactgaa tcataaaaaa   5580
tatgcatatg aagtgaatgg aaagattaaa attgcttctg ctggtatacc taaaagcgcc   5640
tttgatacaa gcgtcgattt tgaaaccttt gtacgtgaac aattctttga cggtgcgatt   5700
atagaaaaca ataaaagtat ctataatgaa cagggtacaa tatcgattta tccgtctaaa   5760
acagaaattg tatgtggtaa tgtatatgat gaatatttttt ctgatgaact taatatgaaa   5820
cgtgaattta tattaaaaga cgctagagaa aattttgacc atagtcaatt tgatgatatt   5880
ctttatattg aaagtgacat tggttcattt tcacttaacg acttatttcc tgttgaacgt   5940
tcagttcata acaaatctga tttgcatata ttaaaacgcg aacatgatga attaaaaaaa   6000
ggcaactgtt aaataacagt tgcctttttc ttttgagata acatgaaaaa tgtgtacgaa   6060
```

-continued

```
aattgattat gttttgtatt ttatttacta gcattactag catgtgttca ttatagcata  6120
gttaattaag caataccact gaagaataca atattatcac cagcgttatg aggtacacca  6180
ttaatcaatg tatataatac aacccgtgac ggtgcgacgt atggtggtac gttatagttt  6240
gctactaaga atgaaccatc gtcaaatact gccactacaa cacctgtgtg gccaatacca  6300
taagctgttg cttgtaagta tggtggttta cttgaaaaac cataaccaac agtagggttg  6360
tgtgttgttt tagcacctaa ctttttatag acgtaccata cacgttgacc gtttgtcact  6420
tgaccgtcgt ctgtcggttg tctttttacca tgtaattgtg acatatacgc ccatgttaat  6480
tctgtacact gacctgcatt acccgtttga ggaaatatgt tacctgtttt gtataaaatat  6540
tctttttttga ataaaggtac accaattgct tttttatatt tttctggtaa ctgtgcgtat  6600
gtccagttac caccaatgac gcgaccactt ttaccattag gtttgactga tttaccacta  6660
attggtttat ggtctccgtc atcatcagta gggtttgaac tactacccc actatctact  6720
tgcacgctat caatcagttt ttttaatgaa tcgagtagcc caatcgtcat tttaatatga  6780
tatgtgttgt taaatgtttt ttgtaatgta aaataatcat tactaaaaaa tttgtcgcta  6840
cctatactgt gtacatccca ttgtaatgcg tcttgtactt ttttaataa ttcttgcatg  6900
gcttgttttg ctaaagcgag cagtgaacta ccactgtcac cactactacc actgtcagac  6960
gaatcactag gtgaaccacc tttacgtct aatttaccac cccacgcaag aatagtattc  7020
gcaccgtcta aaaaaggatt accatagttt tgtactttat tatatgacgc tttcaaacct  7080
aggggataat atgccgccca agtagccgct gctgttaatg gaatatacgc acgtccgatt  7140
gtacctgctt tcatatttttt agcaaaatct gcattacctt ttctttgtac gtcttgcggt  7200
acaaaatgca ctggattacc gtaatcatac caagacggtt gtcctgcttg ttttgattgt  7260
gatactaatt ttcttgcaat gaatttagcg tctgttaaat agtcacctcg tgcagatgta  7320
tggttcaacc aacctaaacc cgcgctatac ccttcatttt tttcatatac agcaaaaaga  7380
gtaggtgaca cacctatctc ttttactgct tttaatactt gtctgattttt actttcatta  7440
ccacctagcc atacattaaa gcgtccatac ccttttactt tagggactaa ctggtctatc  7500
gttaaaccga aatcatcatt aatatacgaa tgcgtaaatt tatctatctt ctcttggtcg  7560
ttcattatta tcactctttt cagaatcatt tttaatttact cttaatttat ctttaatttg  7620
ttctgggact aacacgtcca tttctgcaca attttctacg atagataagc cctcattagc  7680
gatataatag aaaatcgtaa tcatgagtaa gccacctttt aattgtaaaa tctggtcaat  7740
gatgttagct aaaatgataa tacagaatat caataatttt ttagcaaaac ctttcattga  7800
ttttttagac catagattat tatttttaag agctttagca aaacctgtga taacatcaat  7860
aatcattaaa acaaataaaa agtatagtaa ttttaaatcc ccagcatata taaacatgtg  7920
aaacgcttct gagtctgtaa atctgaattt tacttcgttc atattatacc ccctctctaa  7980
atttgttatt taatggattt tgtaacattg gattacctga accgtcatta tgccaaaatc  8040
tcacaccaga ttctaaaatt gctttttaatt gttccattaa catggggtca atgtcacgta  8100
tggtatacgt acctgtacat tttaaatagt tgcaaacagt catactgtta attggttcaa  8160
taaatgaatt atagtcattc acttcaaaac caaacaacat ataatatttt tgtaaaaatg  8220
taatttcttt aggtgacggt acactaattt tcatcgttaa accgttaata ctgtttgcaa  8280
tttggaatgc gttgcccatt tccgactctg tcactgacgg tggttgtaat gctaaatctt  8340
tatattctgc ttgttgttgt ttgtagaaat tatattcttc attaaactta ccaaataaag  8400
cagtcggact taaattactt gctacactta ctgcgtcata aaaacgtgat tttgggtcac  8460
taccatttaa tacattatct atacgacttg tgattaattg actttctgca ttacgctgtc  8520
tattggcttg ttgtgattgt cctaaaattc cgttattaat taatataggc acttgcgcaa  8580
aactattaaa tgttatattt gtatttaaga atgaacctgt atcaattaat atatctttat  8640
tttttgcgag aataggtcta tcgtttttcag cactgttata atcaactgga tatactcgca  8700
cttcattatg ataaccaatg attgactttg tacgtaactt aacacctgtt ttttgtgaaa  8760
ttttaccagc gtcaagtaac attgtgttac cgttccagtc ataaaattca atcgtcatgt  8820
actcattacg tatcatatgt ttaaactcgt ctttttttaga caacatcatc tcttgaagct  8880
ttgtgaaact taatgataaa tcgtttaaac tccattcttt tgattttcca ccctgtttta  8940
acgtctttaa tccagtaatt ttttcacttg tttttaacgtc ctctaaatct tttgtattaa  9000
taaaatcttt aggtaacatt tgaacctttt gaaagttttg tgtaatccat ggatatgcac  9060
tcattttatc cataaagtta ataaagtcac catattccat aacgtataag ttgactggtg  9120
atgtgatatt gtcatatatc gtacccttag acgtatctaa gtttggctct tttttagtac  9180
caaatttctt tgataaatca gcgcttgact ggaataacac taaatttttcc aaatactgtt  9240
gcatttggtt atacacatag ttttttatttg atactttaa cacatcatca ttgttacgta  9300
acattggtaa catatagtta tacgtgcgtt ttgataagtg ttgacgttca atattaacgt  9360
ttgagagttg ctctaataca ttaccttgtg tatacgtcat aatagtatca atcacaaaat  9420
atattttttac cacaacatca ttcacgtatt cgatttgatt cacaaacgca taatatcgtc  9480
tgtcctcaaa atctgataaa aacgtcatgt agttaatccc ttgcgcgtca tgccactgca  9540
tatcaacatt gatttccatt ctatcacgta taaaattata cggttgtttg gaatagtcta  9600
atgatttaaa atgacgtcca tttaaaaaat aatcatcacg ctctttatta ctattaaaat  9660
gaatcgtatt ttgataatca gtaaacggtg tgttatagaa aaatttaaaa tttgttaatt  9720
ttctcatttt tacctccata aaaaatagtc gtataaataa tttatacgac tattataaca  9780
ttttttattca atgatttgtg tatctattgc aaaacgttta tcaccatttg aaagctcatt  9840
atcgctataa tttgatgtgg taaaatgtaa ttcattacta aagtttaaat ataatctttat  9900
attcatcatt ttattatcaa tcgcacattg tgtgtagtga tgtgttgatt ttaagtttgc  9960
gttaatcgta cctaatttaa tatcaccgtt tttcttaatc ccttttaaata cccctttttaa  10020
ttgtatggtt ttaacaccat taattgttac aatacgatat tgcggtgcgg gataaccccc  10080
gttgctatca cttgcaacaa taccactttc aagttgcaca tcttgccaac ctgtatcatt  10140
aaattgtaat tttgcactgt tgatttttttg atcaaaattt tgttcaattt ctgatttaga  10200
ttgtgcaatt ttagtatcta tatttaagtt atccacttttt gttgataaaa cgcttatact  10260
tgattcgttt gttgatgttt tttgttttaa atcactaata tcattatcat attttgataa  10320
atcaatatga ccgtttccgt caacaactgg tctatcttttt aattcttgaa taactttttc  10380
aatttttgat atttatcat tatttgtttt taaagtagcg atgtcagatt taattgaatt  10440
aatatcctgt gtataatctt tttggttaat actgttttcta actcttttat  10500
cttatcaagg ttggcatttg ctttgatgtc attaatggtt ttttctaaac tttcaagttt  10560
cccagcactt gaattttgtt ttaacttatt aatatcctct tgtatttctt gaattgtgtt  10620
atcattgttt tgtttagatt ttaataaattc aatttgactt tctatgtctt ttattttatc  10680
aagattaaca cttttttttaa cttcagctaa ttctcttttt aatgcgtcaa tgtttctctgc  10740
accagtattt gatttaatta tattaattttc atttgtgttt cgtcctacac tatctttaat  10800
```

-continued

```
agcgtttaac gattgtgtaa gtgtttcata tttatcatca tactttaaca ttgatttttc 10860
aaattcattt aattgtgttt gatgttgttc taaactttca tttaatatga catctttttc 10920
ttttaatgaa tcaatgtctt ttttattact atcaatcatt ggttggaatt tttttatttt 10980
ctctagaaat gttgatattt tttctttgtt atcattaatt gcaatatcat gatgttctat 11040
ttgaccactg tatttattaa tcaatgtttt taaatcatta taaaatgtta atttataata 11100
accagtatca gtacggacat aaaatatgtcc gtctgatgta ctgattaagt cattttcttc 11160
tgttaaaaaa tctgctaacc tgtctcattgt ttcaacttgt cttaaacttc ttacgattct 11220
atcagccatt gttcacacct cttatttgta tcgtttccaa ctaaactcaa agaaaaaacc 11280
taaaataccc attatgagaa caccccccaa ggaataccaa cactataact attacccgtt 11340
ttaccgttcc attttcttac tggtaaataa taacgtgtac cttgccagtt gtaaccaatc 11400
catacataac catctgataa acaaacttcg tcatatggtg tataaccatt tggttggaac 11460
caatatccat taggttcact taatttagga ctacctacac gtgcaaatat tggtaaaaat 11520
ccacatgtaa atgttgcatt ttcatttctg taatatgtgc catattggtt ttgtttccat 11580
tttccgaatg tgtttacttt tgatgtttct aattcgttgc tgttactagc agaaaattta 11640
ggtctaataa agtgtgttac accgtcataa taatgtgttc ttattgttgc ttttttcccaa 11700
ccgtcaaacc caccacctaa ccagtttttgc tctaaacatg tataataatc taaattacca 11760
cttaacacac attgaatatg tccatattgt ccatctgtat atacaccaac atcccctaat 11820
tgtggtttaa agttcggtgt atttttcatac accattgcta aaccttttaaa gtcattattg 11880
attgcgtctt tagcgttacc ccacatacga actttaccgt ctgtaatgta atatatataa 11940
gcaacagcta agtcagcgca ttgataacca aatgctaaat caaagtccac acctacaccc 12000
tcatgcttat atatccattc ttttgcttgt tgttgtgatt tcatgaaaca ttatcctttc 12060
ttgacccaac tatattgacg ttttttttgta tctgcattaa cgttactaaa gaattcttta 12120
tgttcggaca cattagcctc taatgttttgt cttacttcac cgacagcgtt accacttgaa 12180
acacgtaacc atgcacccac tttttttaatt tcttctggtg cgtctctaaa caattccatt 12240
tggttaccag taatataaata ttcaccaggt gtcgtaacgt aagctatcca gttattgtat 12300
tgacttgctt ctaaatactc ttgatatggt gcgtctgttt tgattgttgt ccataaaacca 12360
taatcccatt ttaatgtaaa tacatcgagc gtcataccac gcatgatttt aaccattttt 12420
cgaccagtag aaaaacgcgt taattcttgt actgtaccta atgtttgtgt tgtagggtat 12480
acattgatga aacaaccagc gtctataatt tttttactac cattcattgg catattttta 12540
agtttactag ctgtaccacc gtcaatataa tagaaccctg cttgtgttaa gtcatttaag 12600
tcgtcaatat ggtctggaat tgataacgca cgtccatcgt ctttttgttaa tttatagttt 12660
tgtgaacctc tcgcacgtaa tgcttcaaag tgttcatact caccaagttg aaagaaccca 12720
tataaattat tgaatcgttt tccaccaccg ccattagtca tagcaagtaa taacgattta 12780
cgttttgttt ttggattggt ataaatacaa ataccctccg gctctttaaa gttatcacgt 12840
ggaaaattaa taccgtcttg atatgataat ttaaacggat aatcataaat cttttgacca 12900
gttgttaatg aatatttacc aatttgaacg tgtgaattaa ctgaactgtt accacttaac 12960
cagtataaat catcaccatc aacggcaatc ccttgcatcc atcgattatc attgttttct 13020
gaattatcaa tcgtcatttc tttttctaca ttatcaatgt gattttttac gtcagctctt 13080
gaacgtacct gtattgtccc gtcaccgaat cttaaaacga ttttgtcatt ttcttcatca 13140
attaacggtg taaacgtgtg tttgtttaaa agtgactgtg gtgtataatc tgttaaccct 13200
ttagcctctt ctaaatctaa aatataatta tctttatatg cgacttgtaa cagttttgct 13260
acaccgtcat gatgtaacca tattttcatt tcaccgttag attgtctttc taaacctatt 13320
gtagtaccgt gaccaccttg tacaatacgc atactagaaa ttaagtcacc gctaggcgtt 13380
aatttattaa tccaaaaacc ttctgggttt tgtgaatctg attgtgtaga gtacatttga 13440
ttcgtttctt tatctatgtt tatagattgg ttaacagcat tacgaatacc accgaatccc 13500
ataacaaact ttggttcaag ctcatttaat tcaaaaccat taacaaaacg gtcaatgtct 13560
ttaattaagt cttttaacttc tgctttaaaa tcattcattt gtttcatttc tgcaacttta 13620
aataatgcaa atgcagatgt aagaccagta ctatatttag taaattcatc atgaataatt 13680
ttatctattg taccgtcgtt taaccaacct ctaaataagt ctttcgcttg gtctgggaat 13740
gctttcatta agtcgtccca atttttgaaa cgttttttta attcattgtc atagtcccaa 13800
atacgacgtg ctaatacttc aaattagtttt gataatcttg aaatataatc ataatatgat 13860
tttgaattgg tattataatc tgctctcatca tcgtaaaacg gtgtgtaacg ttctctcgtt 13920
ttatatattt cgtctaaaaa tggacgaatg tcgtcaaaat atttaaaatc gttttcatta 13980
tatgccataa ttttccacct ttaccaaatt tgtaaaaaac attttttatc aaattcattt 14040
aaaattttct ttcttaaatc gtatacttta tcaatattat caattaaata ctgttttgaa 14100
aattgtgtac ctttcgcatt accttttttga ttttgattac gttttgcgtt ttgattactt 14160
tcgttacttg atttattcac agtttttaccg ttgtcaattg tattattatc tgcaaatcgt 14220
aacgttgtgt tatctcacatc tatgttaacc tcgctttgtg gtaatgacac ataagcattt 14280
ctgtttgctg tcatgccagt tgaattgtct aaagatgttg cattttgatt tgaagtttca 14340
tcagtgttgc ttattgtatc ttcgttgtgt tctgtgaagc cttgtgattg aagatatttt 14400
tctacttcac ttgatgaata aaccacattc aaataatcct catgtgtgat acatacagta 14460
atcacttgca tgccaaaagc ttcaactgtt tgtctgttga tttctctatc taaaaagtgt 14520
attgtaaatg attttttaaa aagtaagtca gataagtcat ctttaagttt aaaaccttta 14580
aacactttt cattaacgat ggctaaaacg tctttgtcaa acttcaacat tttttgcatg 14640
aattgaaatt catcatcata aaacgttaat ttatcattat ttacaaattc attaaaacct 14700
tttttaatta attctgattt aataaaatca aataaagtca ttgtatatct agccattgta 14760
ttcactactt tcatcattag acaatgtatc tatcattgtg atttctgatg taacttcatc 14820
gtcgtaatac ggttttaatat ctaaaccata tcgtttttgat aagaatgtaa taggttcacg 14880
accttttaaa taaatattac tatttgatgt ggtaaaacct cggttgcttt ttgcctcttc 14940
gtcagaaaca ccgctttcct tatccactgc tagtgaatta atacctaaat agttacttaa 15000
ttcactaatt ttattttggt attcacgttt catctcagtt agtgctggaa tcacactatt 15060
actggttaaa tctatgatat catcatcggc gttaaacata ggtgacattt taacaaatgg 15120
tgcaccgttg tatatttccg atacaagttg attaactgac tcatcattaa tgtctgattt 15180
aaatattttg ctaaattttg cttgcataat taatgaaaaa cgagataaaa caacctcaga 15240
taattcatca gtataatgtt ctataatttc tatatcacta ttatattgaa tgggtttatt 15300
ttgcataaca acaaaaattac cactcataca gttatcatat attttatgaa tctgtaagca 15360
ttcatctggt attaaaatagt ctggaacaat gaaataaata tcatctttttg ttaatcgttt 15420
ttgaaattga aaattgaaat ttgatgaaaa gtttggggct tgattaaaat aagtgttgtt 15480
aacatagccc aaaatcataa tttgttcatt tcttgcttta ccaacaacaa cattaatgtt 15540
```

-continued

```
ttgccttaat gcagattcta attgaataaa atctatacca accgtatcac gattggtata  15600
gtttattaat aggggtaaaa attccaaata acgattaaac ataagacgtt taaatctgtt  15660
gcgatgttct acaacacgtt tattgatttc tttagataat tcaacctgta cgcctttatt  15720
atgtttagtc atttatatca cctctattat tctgttctcg gtgttacatc ttggtcagta  15780
attaaaattt tgttaaagaa tgggctaatg gctttaaatg aatagtaatg aatccagtgt  15840
gtaacttcat caaattcacc attatagaat ggttgtttta acatgccttt tgtgtaacgt  15900
ttatatttaa ttgaattaat atccaaaata aaagcgtata aatctgattt tggtttaatt  15960
tcttcaacac tatctttaaa ttcagatagt tttgatacat cgtaagtgaa tactgaacca  16020
actggaattg tatcaccttt atgagtttga taatcaccgt aagcacgtaa gaaattaact  16080
gattcatcac ttgatacgac aatatcttta gtgactttaa aaacaccacc taaatcgtcg  16140
aaactaataa catggtctgt aaagtcaatc cctgctactt ggaaagtgtt agcaatcttt  16200
gtatctaaaa gataagattt taagctatca gtcgttaaaa taacaatatc ttttaatttt  16260
gaaactgttg tatattgtcc gattgcacca cctgaagcac gatgaacttc attatattta  16320
gtgctgttgt tttgtaagtt aagaatagct tcaaaaactt tacttgctaa atcttctttt  16380
gatgttgctt tacgtacatt tgattcagat aattgattca atgagtaatc aactaacatt  16440
gcacgcattt cttttcttc taatacgtta atatcagaaa ttttcttttt atagacacct  16500
aatgcataat tagttgcgtc tgctaatgtt tggaaattga aacgtgtgtc attgttattt  16560
aatgtgaatt tttgtttctt cacaatacca ctaccatata acttagtagc catacgtggg  16620
taattacgtt tcaacattaa ttcttcattt ttagataagt ccatgttaat aggtactgta  16680
tccataatta catactcttc actgtattga cctataaagt cttgctcttt agctaaccaa  16740
ttaaaacggt tacctaatgc aatatcgatt aataacgttt cattaatctt agggaataaa  16800
aatttattta caaatgtttc aaacattgta ttagaattat cccacttatc gccaaacgtt  16860
catgatttttg aataagtatg attaaagtct tgtaatgcag atttagctga ctttgcaact  16920
aatagtgctg tttcgttttt tgtactcttt tctgccatga tttattattc ctcctctaca  16980
tcgccagtaa atgactgttt tgaaagtgaa tgaatttgta caccataact atcttcactt  17040
ttgtttgtat caattgacat attttcattt aattctgttc gtttatttaa tcttgaatct  17100
tcatatgatg ttcccatcat agaacgcata ttgttaccct catacatgtt taaattcctc  17160
ctaatctaaa tctaacttat ccactaattc ttcatctgaa tagtctttgt cgttgtcatc  17220
tgcttcagta acatctggtt ttggttgtgg ttgtggttgt ggttgttgca tttgtgatgt  17280
ttcaaaatta gtaaatcgtt gttctaaatga agcgatacgt tgttctaaaa caacagggtc  17340
taattttgca ctatcttcat cagtaatagt aggttctaat ttgtttttcat tttcttcttc  17400
gattgtttct actttttat cttcagtaga ttcttcagtt gattcttcag ttgattcttc  17460
ggttgattct gaagtttctt cagttgattc tgaagtttct tcagttgatt ctgaagtttc  17520
ttctttgtcg tctggttta cgatttcatc aaattctgtc attttgacac ctccaaatat  17580
tttataacta attatatcat agaatattta aataagtaaa ttaaatttat tatatgtta  17639
```

```
SEQ ID NO: 45          moltype = DNA   length = 18007
FEATURE                Location/Qualifiers
source                 1..18007
                       mol_type = genomic DNA
                       organism = Staphylococcus phage MESA-11
SEQUENCE: 45
cacttatcat ttctttacta aacttataaa cactgttcac caactttccc aacttatcta  60
acctattaca tattaattaa ttacatttat tatacatcta ttgactttta tcaaaagtta  120
tgatttgtat ttaaaatcta atttcttcta ttaaatagta tttttaaatt atttaaactt  180
tttaagaaaa aacattgaca aaacttttaa acgtttgcta tactatgtat gtaatcaaat  240
caaggaggta acaaaatgga aatgtacaa cctttacaaa cttacatttt aaaaaaatggt  300
aatatagtta ttgttatggg taatacatca agttatgaat taacattatt tgtacttgaa  360
aaggatgatt ttgaacaatt agaccataat tcacctaaaa aaatcgttga tgaaataagg  420
aatgaaatca atgatttaag gagtgataat aatggttaat gttgataacg cacctgaaga  480
aaaagggcaa gcctatactg aaatgttgca actattcaat aagttgattc aatggaatcc  540
agcttatact ttcaacaatg ctattaattt agtatcagct tgccaacaac tattattaaa  600
ctataatagt tctgttgtta aattcttaaa tgatgaacta aacaacgaaa ctaaaccaga  660
atctatttta tcttacattg ctggtgatga cccaatagaa caatggaata tgcacaaagg  720
attttatgaa acgtataacg tttacgtttt ttagaaagga gtgatataat aatgaaacct  780
gatgatattg ttacattacg aataaaaggt tatattcttc attatttaga tgataaaaat  840
gaatatgttg aagaatttat cccacttcac gagtatcatt tatcaaaatc acaagctaaa  900
gacttattac ctaatacaca caaactttta tccactacac gacatactaa aactatgcaa  960
gtttattaca atgatttact acaaattgca attgcagaaa gcaaataatt taaataagag  1020
gagaaataaa aatgacaaac gtaaaagata ttttatcaag acaccaaaac acattagcga  1080
gattcgaatt tgaggaaaaa gaaagagaat ttatcaaact atcagaatta gtagaaaaat  1140
acggtatgaa aaaagagtat atcgttagag cattattcac aaacaaagaa tcaaaattcg  1200
gtgaacaagg tgttatcgtc actgacgact ataacgtaaa cttaccgaat cacttaactg  1260
aattaattaa agacatgcgt caagacgagg acgttgttaa cattatcaat gctggtgaag  1320
ttcaattcac aatttatgag tatgaaaata aaaaaggtca aaaaggttat tcaatcaact  1380
ttggtcaagt atcattttaa tacaatttca taggggatat ttatccccta tttttatgag  1440
gtgctaaaca atggaaaaaa tatacactgc cgtattatta tacaatgtat caattaatga  1500
aacatatgaa catgaaattg aacaattcga aaaaataaat aaagctaagg taatatatag  1560
ttattttgat gcaaacttt ataaaaaagg tgcttatat ctttgtgtaa aatacattaa  1620
ggagatataa aaatgaatat tacaacaata ttaaacacaa aaaaattaat taattatatt  1680
ttagataata gagattgttt tatgaataaa ataacaaaat ttgaatcact aagtggaaaa  1740
tgtgttgttt ttgttagata cggtgaaatt tctattgaat actatgatag tgatacaaaa  1800
tacaatgatt tatttacttt agacattgac gttgatgttc gtacatatag tttttagttgt  1860
cttgaggttt tttatcggaga acatttaaac ccattatata aaaaagaagt ttttatggat  1920
tgtactattg atgacgtatt agaatatttc gagaaaccaa tagaaagtaa tataacaata  1980
atttttcaaa acaaagtgat atataataac gggaacgtga tagaacatga ctaatatatt  2040
aaacatagct attgttttcc ttttagcatt tttaattaca cttgtaatac ttatgacaat  2100
gcatatacgt gtgtcatttg gtgtttttatt tactacattg attatattct acattatctt  2160
tttagtggtt atatatgggt tatatggagg tcgttagcaa tggttagaca tacgtccgaa  2220
```

-continued

```
atggataaat ggaaaaaaga aagagacgca agaaaagagc aggaaaaaga attgtttta    2280
aatgatttta gtactgttaa tttttaaattt gatgataaag atttacaaga ggcgtacata    2340
gacgcatgga aacatttcgc acatttgccc tattttccaa aagaaagaaa cgtgtcatat    2400
gtaaatgctg tatcattggt aagaggtaaa agacatgaac aattaaacta tatacttgaa    2460
atatataacc gtaaagatga atctaataat aaaaacgcta aaaaacataa atatgcttta    2520
tatgaattac aagctaaaaa taataattct tctatgtata aatatataaa ggaaattgac    2580
actttataca aagaaatagg taaatcgac agaccagtga ctactattga tgatgaagat    2640
gtgagatata acttttttata ttatgcaaca tttgaagact aattttaata ctgtaaacga    2700
cataataaac tattacaagg agcaaaaaca tggtgaaaca aaatcgttta gacatggtaa    2760
gagattatca aaatgcggtc aatcatgtaa gaaaaaaaat accagaaaac tataatcaaa    2820
tagaattagt tgatgaactc atgaatgatg atatagacta ttatatatct atttcaaacc    2880
gttctgacgg aaaatcgttc aactatgttt cattctttat ttatttagct ataaaacttg    2940
atattaaatt tactttatta tcacgtcatt atacattacg tgacgcttat cgtgatttta    3000
ttgaggaaat catagacaaa aacccactat tcaaatctaa gcgtgtcaca ttcagaagcg    3060
ctagggacta tttagctatc atctatcaag ataaggaaat cggtgtgatt acagatttga    3120
atagtgcaac tgatttaaaa tatcattcta acttttttaaa acactaccct atcattatat    3180
atgatgaatt tttagcactt gaagatgact atttaattga cgagtgggat aagttaaaaa    3240
caatttatga atcaatcgac cgtaaccatg gtaatgttga ttatatcggc ttccctaaaa    3300
tgttttttatt aggtaatgcg gtcaacttttt caagtcctat attatccaat ttaaatatat    3360
ataacttatt acaaaaacat aaaatgaaca catcacgact ttacaaaaac atttttttag    3420
aaatgcgaag aaacgattac gtaaatgaaa agcgtaacac acgagcattc aattcaaacg    3480
atgacgctat gacaactggc gagtttgaat ttaacgaata taatttggca gatgataatt    3540
taagaaatca tatcaatcaa aacggtgatt ttttctatat taaaactgac gataaatata    3600
taaaaattat gtataatgtt gatacattta atgctaatat tattgttata ccttatacaa    3660
aacaatatga attttgtact aaaatcaaag atatagatga caatgttatt tatttaagag    3720
aagatatgtt ttataaagaa aacatggagc gttattatta caatccaagc aatttacatt    3780
ttgataacgc ttactcaaaa aattacgtgg ttgataatga tagatatta tatttagata    3840
tgaataaaat tataaaattt catataaaaa atgaaatgaa gaaaaacatc aacgaatttg    3900
aaagaaaaga aaaaatatat gaagataact atattgaaaa tacaaagaag tatttaatga    3960
aacaatacgg cttataaaag gtgtgtaaga ttatgggatt actagaatgc atgcaatatc    4020
ataaacatga acgtcgaatg attttatact gggatataga aacattagcg tacaataaag    4080
ttaacggacg aaaaaaacca accaaatata aaaacgtaac gtattcagta gcaattggtt    4140
ggtttaatgg ttatgagatt gatgtagaag tatttcctag ttttgaatcg tttttatgacg    4200
cattttatac gtatgtgaaa cgacgtgata caatcactaa gtcaaaaaca gatattatca    4260
tgattgcaca taactgtaat aagtatgaca accattttt acttaaagat accatgcgtt    4320
attttgataa tatcacacgt gaaaatatat atttaaaatc tgcagaagaa aacgaacaca    4380
cactaaagat gcaagaggct actattttag ctaaaaatca aaatgtgatt ttagaaaaac    4440
gtgtgaaatc gtctattaat ttagacttaa caatgttttt aaatggattt aaatttaata    4500
ttattgataa ctttatgaaa acaaatacat caattgcaac attaggtaaa aagttgcttg    4560
acggtggtta tttaacagac gaccaactta aaacagattt taattacacg atatttgata    4620
aagataacga tatgtcagat agtgaagcct atgactatgc tgttaagtgt tttgctaaac    4680
tcacacctga acaacttaca tacattcata atgacgtgat tatattaggt atgtgccata    4740
ttcattatag tgatatattt ccaaattttg actataacaa attaacattt tcattgaata    4800
ttatggaatc gtatttaaat aatcaaatga cgcgtttttca gttactcaat caatatcaag    4860
atattaaaat atcatataca cattaccatt tccatgatat gaattttttat gactatatca    4920
aatcatttta tcgtggtggt ttaaaatatgt ataacactaa atacataaac aaacttattg    4980
atgagccttg tttttctatt gatatcaatt ccagttatcc ttatgtgatg tatcatgaga    5040
aaattccgac atggttatac ttttatgaac attattcaga acctacatta atccctactt    5100
ttttagatga tgacaattat ttttcattat ataagattga taaagatgta tttaacaatg    5160
atttattaat taaaatcaaa tcacgtgtat tacgtcaaat gattgtaaaa tactataata    5220
atgataatga ttacgttaat attaatacaa atacattaag aatgattcaa gacattacgg    5280
gtattgattg tacgcatata cgtgttaatt cgtttgtgat atatgaatgt gaatactttc    5340
atgcacgtga tattatattt caaaactatt ttattaaaac acaaggtaag ttaaaaaaca    5400
aaatcaacat gacatcacct tacgactatc atattactga tgacatcaac gaacaccctt    5460
actcaaatga ggaggttatg ttgtctaaag ttgtacttaa cggattatat ggcataacctg    5520
cattacgttc acatttttaac ttattccgtt tagatgataa caatgaacta tacaatatta    5580
ttaacggtta caaaaacaca gaacgtaata ttttattttc tacatttgta acatcacgtt    5640
cattgtataa cttattagta ccattccaat acttaacgga aagtgaaatt gacgacaatt    5700
ttatttattg tgatactgat agtttgtata tgaaatccgt tgttaaaccc ttattgaacc    5760
ccagtttatt cgacccgata gccttaggta aatgggatat tgaaaacgaa cagatagata    5820
agatgtttgt actgaatcat aaaaaatatg catatgaagt gaatgggaag attaaaattg    5880
cttctgctgg tatacctaaa agcgcctttg atacaagcgt cgattttttgaa acctttgtac    5940
gtgaacaatt ctttgacggt gcgattatag aaaaacaataa aagtatctat aatgaacagg    6000
gtacaatatc gatttatccg tctaaaacag aaattgtatg tggtaatgta tatgatgaat    6060
atttttctga tgaacttaat atgaaacgtg aattattatt aaaagacgct agagaaaatt    6120
ttgaccatag tcaatttgat gatattcttt atattgaaag tgacattggt tcattttcac    6180
ttaacgactt atttcctgtt gaacgttcag ttcataacaa atctgatttg catatattaa    6240
aacgcgaaca tgatgaatta aaaaaaggca actgttaaat aacagttgcc ttttttcttt    6300
gagataacat gaaaatgtg tacgaaaatt gattatgttt tgtatttttat ttactagcat    6360
tactagcatg tgttcattat agcatagtta attaagcaat accactgaag aatacaatat    6420
tatcaccagc gttatgaggt acaccattaa tcaatgtata taatacaacc cgtgacggtg    6480
cgacgtatgg tggtacgtta tagtttgcta ctaagaatga accatcgtca aatactgcca    6540
ctacaacacc tgtgtggcca ataccataag ctgttgcttg taagtatggt ggtttacttg    6600
aaaaaccata accaacagta gggttgtgtg ttgttttagc acctaacttt ttatagacgt    6660
accatacacg ttgaccgttt gtcacttgac cgtcgtctgt cggttgtctt ttaccatgta    6720
attgtgacat atacgcccat gttaattctg tacactgacc tgcattaccc gtttgaggaa    6780
atatgttacc tggtttgtat aaatattctt ttttgaataa aggtacacca attgctttt    6840
tatattttc tggtaactgt gcgtatgtcc agttaccacc aatgacgcga ccacttttac    6900
cattaggttt gactgattta ccactaattg gtttatggtc tccgtcatca tcagtagggt    6960
```

-continued

```
ttgaactact accccccacta tctacttgca cgctatcaat cagttttttt aatgaatcga   7020
gtagcccaat cgtcatttta atatgatatg tgttgttaaa tgtttttttgt aatgtaaaat   7080
aatcattact aaaaaatttg tcgctaccta tactgtgtac atcccattgt aatgcgtctt   7140
gtactttttt taataattct tgcatggctt gttttgctaa agcgagcagt gaactaccac   7200
tgtcaccact actaccactg tcagacgaat cactaggtga accacctta cgtctaatt    7260
taccacccca cgcaagaata gtattcgcac cgtctaaaaa aggattacca tagttttgta   7320
ctttattata tgacgctttc aaacctaggg gataatatgc cgcccaagta gccgctgctg   7380
ttaatggaat atacgcacgt ccgattgtac ctgctttcat atttttagca aaatctgcat   7440
taccttttct ttgtacgtct tgcggtacaa aatgcactgg attaccgtaa tcataccaag   7500
acggttgtcc tgcttgtttt gattgtgata ctaattttct tgcaatgaat ttagcgtctg   7560
ttaaatagtc acctcgtgca gatgtatggt tcaaccaacc taaaccagcg ctataccctt   7620
catttttttc atatacagca aaaagagtag gtgacacacc tatctctttt actgcttta    7680
atacttgtct gattttactt tcattaccac ctagccatac attaaagcgt ccataccctt   7740
ttactttagg gactaactgg tctatcgtta aaccgaaatc atcattaata tacgaatgcg   7800
taaatttatc tatcttctct tggtcgttca ttattatcac tcttttcaga atcattttta   7860
attactctta atttatcttt aatttgttct gggactaaca cgtccatttc tgcacaattt   7920
tctacgatag ataagccctc attagcgata taatagaaaa tcgtaatcat gagtaagcca   7980
ccttttaatt gtaaaatctg gtcaatgatg ttagctaaaa taataataca gaatatcaat   8040
aattttttag caaaacctt  cattgatttt ttagaccata gattattatt tttaatagct   8100
ttagcaaaac cagtaacaac atctataatc atcaaaacaa ataaaaaata tagtaacttt   8160
aaatcacctg catatatgaa catatgaaat gcttctgtgt ccgtaaatct taattttacc   8220
tcattcattt tatacacctt ctctaaattt attatttaac gggttctgta acattggatt   8280
acctgaaccg tcattatgcc aaaatctcac accagattct aaaattgctt ttaattgttc   8340
cattaacata gggtcaatgt cacgtatggt atacgtacct gtacatttta aatagttgca   8400
tacagtcatg ctgttaatag gttcaatgaa tgtattatag tcatttactt caaaaccaaa   8460
caacataaa tattttttgta aaaatgtaat ttctttaggt gacggtacac taatttttcat  8520
cgttaaaccg ttaatgctat ttgcaatttg gaatgcgttt cccatttctg attctgtcac   8580
agatggtggt tgtaaggcta aatctttata ttctgcctgt tgttgtttgt agaaattata   8640
ttcttcatta aacttaccaa ataaagcggt tggacttaaa ttacttgcta cacttacagc   8700
gtcataaaaa cgtgattttg ggtcactacc atttaataca ttatctatac gacttgtgat   8760
taattgactt tctgcattac gctgtctatt ggcttgttgt gattgtccta aaattccgtt   8820
attaattaat ataggcactt gcgcaaaact attaaatgtt atattggtat ttaagaatga   8880
acctgtatca attaatatat cttttatttt agcaagtatc ggtctatcgt tttcagcact   8940
gttataatca actggatata ctcgcacttc attatgataa ccaatgatgg attttgtacg   9000
taacttaaca cctgtttttt gtgaaatttt accagcgtca agtaacattg tgttaccgtt   9060
ccagtcataa aattcaatcg tcatgtactc attacgtatc atatgtttaa actcgtcttt   9120
tttagacaac atcatctctt gaagctttgt gaaacttaat gataaatcgt ttaaactcca   9180
ttcttttgat tttccaccct gtttttaatgt ctttaatcca gtaatttttt cacttgtctt   9240
aacgtcctct aaatcttttg tattaataaa atctttaggt aacatttgaa ccttttgaaa   9300
gtttgtgta atccatggat atgcactcat tttatccata aagttaataa agtcaccata   9360
ttccataacg tataagttga ctggcgatgt gatattgtca tatatcgtac ctttagacgt   9420
atctaagttt ggctctttttt tcgtaccaaa tttctttgat aaatcagcgc ttgactggaa   9480
taacactaaa ttttccaaat actgttgcat ttggttatac acatagtttt tatttgatac   9540
ttttaacaca tcatcattgt tacgtaacat cggcaacata tagttatacg tacgctttga   9600
taagtgttga cgttcaatat taacgtttga aagttgttct aatacattac cttgtgtata   9660
cgtcataata gtatcaatca caaaatatat ttttaccaca acatcattca catattcgat   9720
ttgattcaca aaagcgtaat agcgtctgtc ctcaaaatct gataaaaacg tcatgtagtt   9780
aatcccttgt gcgtcatgcc actgcatatc aacattgatt tccattctat cacgtataaa   9840
attatacggt tgtttggaat agtctaatga tttaaaatga cgaccgttta aaaaataatc   9900
atcacgctct ttattactat taaaatgaat tgtattttga tagtctgtaa acggtgtgtt   9960
atagaaaaat ttaaaatttg ttaattttct catttttacc tccataaaaa atagtcgtat  10020
aaataattta tacgactatt ataacatttt tattcaatga tttgtgtatc tattgcaaaa  10080
cgtttatctc catttgttaa gtcactatcg ctataatttg atgtaacaaa atgtaattca  10140
ttattaaagt ttaaatataa tcttgtatta atcattttcg aatcaatcgc acattgtgtg  10200
tagtgatgtg ttgattttaa gttagtgtta atcgtaccta atttaatatc accgtttttc  10260
ttaatccctt ttaataccc  ttttaattgt atggtttttaa caccattaat tgttacaata  10320
cgatattgcg gtgcgggata accaccgttg ctatcacttg caactatacc actttctagc  10380
aatatatctt gccaacctgt atcattaaat tgtaattttg cactgttgat ttttttgatca  10440
aaattttgtt caatttctga tttagattgt gcaattttag tatctatatt taagttgtcc  10500
actcttgttg ataaagtgtt aatacttgat tcatttgttg atgtttttttg ttttaaatca  10560
ttaatatcat tatcatattt tgataaatca atatgtccgt ttccgtcaac aactggtcta  10620
tcttttaatt cttgaatatc tttttcaatt tttgatattt tatcattatt tgttttttaaa  10680
gcagcgatgt cagatttaat tgaattaata tcctgtgtat aatcttttttg gttaatactg  10740
tttaattttg ttttctaactc ttttatctta tcaaggttga catttgcttt gatgtcatta  10800
atggtttgtt ctaaacttttc aagtttccca gcacttgaat tttgtttttaa cttattaata  10860
tcctcttgta tttcttgaat tgtgttgtca ttgttttgtt tagattttttaa taattcaatc  10920
tgttgttcaa tatctttttat tttatcaaga ttgatacttt ttttaacttc agctaattct  10980
cttttaact cgtcaatgtt ttctgcacca gtattagctt taattaaatt aatttcattt  11040
gtgtttcgtc ctacactatc tttagtagcg tttaacgatt gtgtaagtgt ttcatattta  11100
tcatcatact gtaacattga tttttcaaat tcatttaatt gtgtttgatg ttgttctaaa  11160
ctttcatttta atatgacatc ttttttcttt aatgaatcaa tctcttttttt attactatca  11220
atcattggtt ggaatttttt tatttctct agaaatgttg atattttttctc tttattatca  11280
ttaattgcaa tatcatgatt ttctatttga ccactgtatt tattaatcaa tgtttttttaaa  11340
tcattataaa atgttaattt ataataacca gtatcagtac ggacataaat atgtccgtct  11400
gatgtactga ttaagtcatt ttcttctgtt aaaaaaatctg ctaacctgtc tattgtttca  11460
acttgtctta aacttcttac gattctatca gccattgttc acacctctta tttgtatcgt  11520
ttccaactaa actcaaagaa aaaacctaaa atacccatta tgagaacacc ccccacggaa  11580
taccaacact gtaactatta cctgtttttac cgttccattg tctcactggt aaataataac  11640
gtgtaccttg ccaattgtaa ccaatccata catacccgtc tgataaacaa acttcgtcat  11700
```

-continued

```
atggtgtata gccgtttggt tggaaccaat agccattaag ctcagataat ttaggactac    11760
cgacacgagc aaatattggt aaaaaaccac atgtaaatgt agcattttca tttctgtaat    11820
atgtgccgta ttggttttgt ttccagttgt tagtttgttg aatatttttt tctaatactt    11880
tactatcact atttgaaaat tttggacgaa taaagtgtgt tacaccgtca taataatgtg    11940
ttcttattgt tgctttttcc caaccatcat atccaccatt taaccagttt tgttctaagc    12000
atgtataata atcaagattt ccacttgtta cacattgaat atgcccatat tgagaattag    12060
tgtatacagc aacgtcacct aattgaggtt taaagctagg tgtattttca tacaccgctg    12120
ctaaaccttt aaagtcgttg ttaatggcgt ctttggcatt accccacatg cgaactttac    12180
cgtcagtaat gtaataaaca taagcaactg ctaagtccat acattgaaaa ccatatgctc    12240
catcaaagtc aacgccaaca ccctcatgtt tatatatcca atctttagct tgttgttgtg    12300
atttcattgc acattatcct ttcttaaccc aatcatactc acgatgtttc gtttccgcat    12360
taacgttact aaagaattct ttatgctctt taacattagc ctctaatgtt tgtctgactt    12420
caccaacggc gttaccactt gaaacacgta accatgcacc cacttttta atttcttctg     12480
gagcgtctct aaataattcc atttggttac ctgtaatata atattcacca ggtattgtaa    12540
cgtaagctat ccagttatta tattgacttg cttctaaata ctcttgatat ggtgcgtctg    12600
ttttgattgt tgtccataaa ccataatccc attttaatgt aaatacatcg agcgtcatac    12660
cacgcatgat tttaaccatt tttcgaccag tagaaaaacg cgttaattct tgtactgtac    12720
ctaatgtttg tgttgtaggg tatacattga tgaaacaacg agcgtctata attttttac    12780
taccattcat tggcatattt ttaagtttac tagctgtacc accgtcaata taatagaacc    12840
ctgcttgtgt taagtcattt aagtcgtcaa tatggtctgg aattgataac gcacgtccat    12900
cgtctttgt taatttatag ttttgtgaac ctctcgcacg taatgcttca aagtgttcat     12960
attctccaag ttggaagaaa ccatataaat tattgaatcg tttccacca cgcgccatttg     13020
tcatagcaag taataacgat ttacgttttg tttttggatt agtataaata caaataccct    13080
caggctcttt aaagttatca cgtgggaaat taattccgtc ttgatatgat aatttaaacg    13140
gataatcata aatctttga cctgttgtta atgaatattt accaatttga acgtgtgaat    13200
taactgaact gttaccactt aaccagtata aatcatcacc gtcaacagca atcccttgca    13260
tccatcgatt atcattgttt tctgaattgt caatcgtcat ttcttttct acattatcaa    13320
tgtgattttt tacgtcagct cttgaacgta cctgtattgt cccgtcgccg aatcttaaaa    13380
cgattttgtc atttgcttca tcaattaacg gtgtaaacgt gtgtttgttt aaaagtgaat    13440
gtggtgtata atctgttaag ccttttgctt cttctaaatc taaaatataa ttatctttat    13500
atgcaacttg taacagtttt gctacaccgt catgatgtaa ccatatttc atttcaccat     13560
tggattgacg ttctaaacct attgtagtac cgtgaccacc ttgtacaata cgcatactag    13620
atattaaatc accactaggc gttaatttat taatccaaaa accctctggt ttttgtgaat    13680
ctgattgtgt agagtacata tggtttgttt ctttatcaat attaatagat tggttaacag    13740
cattacgaat accaccaaaa cccatcacaa actttggttc aagttcattt aattcaaaac    13800
cattaacgaa acgtcaata tctttgatta agtctttcac ttctgcttta aagtcattca     13860
tttgtttcat ttctgcaact ttaaataatg caaatgcgga tgtaagacca gcactatatt    13920
tagtaaattc atcatgaatg atgttatcta ttgtaccgtc attgagccaa cctctaaata    13980
agtctttagc ctgttctggg aatgctttca ttaaatcgtc ccagtttcca aaacgtttt     14040
ttaactcacc gtcatagtcc caaatacgat gtgctaatac ttcaatgagc tttgataatc    14100
ttgaaaatata atcataatat gattttgaat tggtattata atctgctcta tcatcgtaaa    14160
acggtgtgta acgttctctc gttttatata tttcgtctaa aaatggacga atgtcgtcaa    14220
aatatttaaa atcgttttca ttatatgcca taattttcca cctttaccaa atttgtaaaa    14280
aacatttttt atcaaattca tttaaaattt tctttcttaa atcgtatact ttatcaatat    14340
tatcaattaa atactgtttt gaaaattgtg tgcctttcgc attacctttt tgattttgat    14400
tacgttttgc gttttgatta ctttcgttac ttgatttatt cacagtttta ccgttatcaa    14460
ttgtatatt atctgcaaat cgtaacgttg tattatctac atctatgtta acctcgcttt     14520
gtggtaatga cacataagca tttctgtttg ctgtcatacc agttgaattg tctaatgatg    14580
ttgcatttg atttgaggtt tcatcagtgt tgtttgttgt atcttcatta tgttctgtaa     14640
aaccttgtga ttgtagatat ttttcaactt cgcttgatga ataaacaaca ttcaaataat    14700
cctcagtgt gatacataca gtaatcactt gcataccaaa agcttcaact gtttgtcgt      14760
tgatttctct atctcaaaaag tgtattgtaa atgatttttt aaaaagtaag tcagataagt    14820
catctttaag tttaaaaacct ttaaacactt tttcattaac gatagctaaa acgtctttgt    14880
caaacttcaa catttttttgc atgaattgaa attcatcatc ataaacgtt aatttatcat     14940
tatttacaaa ttcattaaaa cctttttaa ttaattctga tttaataaaa tcaaataaag     15000
tcattgtata tctagccatt gtattcacta ctttcatcat tagacaatga ttctatcatt    15060
gtaaatctg aagtaacttc atcgtcgtaa tacggtttaa tatctaagcc ataacgtttt     15120
gataagaatg taatcggctc acgaccttt aaataaatat tactgtttga tgttgtaaaa     15180
cctcggttac tttttgcctc ttcgtcagaa acaccgcttt cctttatccac tgctagtgaa    15240
ttaataccta aatagttact taattcacta attttattt ggtattctct tttcatctca     15300
gttagtgctg gaatcacact attactggtt aaatctatga tatcatcatc ggcgttaaac    15360
ataggtgaca ttttaacaaa tggtgcaccg ttgtatattt ccgatacaag ttgattaact    15420
gactcatcat ttatgtctga tttaaatatt ttgctaaatt tcgcttgcat aattaatgaa    15480
aaacgagata aaacaacctc agataattca tcagtaatat gttctataat ttctatatca    15540
ctattatatt gaatgggttt attttgcata acaacaaaat taccactcat acagttatca    15600
tatattttat gaatctgtaa gcattcatct ggtattaaat agtctggaac aatgaaataa    15660
atatcatctt ttgttaatcg tttttgaaat tgaaaattga aatttgatga aaagtttggg    15720
gcttgattaa aataagtgtt gttaacatag cccaaaatca taatttgttc atttcttgct    15780
ttaccaacaa caacattaat gttttgcctt aatgcagatt ctaattgaat aaaatctata    15840
ccaaccgtat cacgattggt atagtttatt aataggggta aaaattccaa ataacgatta    15900
aacataagac gtttaaatct gttgcgatgt tctacaacac gtttattgat ttctttagat    15960
aattcaacct gtacgccttt attatgttta gtcatttata tcacctctat tattctgttc    16020
tcggtgttac atcttggtca gtaattaaaa ttttgttaaa gaatgggcta atggctttaa    16080
atgaatagta atgaatccag tgtgtaactt catcaaattc accattatag aatggttgtt    16140
ttaacatgcc ttttgtgtaa cgtttatatt taattgaatt aatatccaaa ataaaagcgt    16200
ataaatctga ttttggtttta atttcttcaa cactatcttt aaattcagat agtttttgata   16260
catcgtaagt gaatactgaa ccaactggaa ttgtatcacc tttatgagtt tgataatcac    16320
cgtaagcacg taagaaatta actgattcat cacttgatac gacaatatct ttagtgactt    16380
taaaaacacc acctaaatcg tcgaaactaa taacatggtc tgtaaagtca atccctgcta    16440
```

-continued

```
cttggaaagt gttcgcaatc tttgtatcta aaagataaga ttttaagcta tcagttgtta   16500
aaataacaat atcttttaat tttgaaactg ttgtatattg tccgattgca ccacctgaag   16560
cacgatgaac ttcattatat ttagtgctgt tgttttgtaa gttaagaata gcttcaaaaa   16620
ctttacttgc taaatcttct tttgatgttg ctttacgtac atttgattca gataattgat   16680
tcaatgagta atcaactaac attgcacgca tttctttttc ttctaatacg ttaatatcag   16740
aaattttctt tttatagaca cctaatgcat aattagttgc gtctgctaat gtttggaaat   16800
tgaaacgtgt gtcattgtta tttaatgtga attttttgttt cttcacaata ccactaccat   16860
ataacttagt agccatacgt gggtaattac gtttcaacat taattcttca tttttagata   16920
agtccatgtt aataggtact gtatccataa ttacatactc ttcactgtat tgacctataa   16980
agtcttgctc tttagctaac caattaaaac ggttacctaa tgcaatatcg attaataacg   17040
tttcattaat cttagggaat aaaaatttat ttacaaatgt ttcaaacatt gtattagaat   17100
tatcccactt atcgccaaac gtccatgatt ttgaataagt atgattaaag tcttgtaatg   17160
cagatttagc tgactttgca actaatagtg ctgtttcgtt ttttgtactc ttttctgcca   17220
tgatttatta ttcctcctct acatcgccag taaatgactg tttttgaaagt gaatgaactt   17280
gtacaccata actatcttca ctttttgtttg tatcaattga catattttca tttaattctg   17340
ttcgtttatt taatcttgaa tcttcatatg atgttcccat catagaacgc atattgttac   17400
cctcatacat gtttaaattc ctcctaatct aaatctaact tatccactaa ttcttcatct   17460
gaatagtctt tgtcgttgtc atctgcttca gtaacatctg gttttggttg tggttgtggt   17520
tgtggttgtt gcatttgtga tgtttcaaaa ttagtaaatc gttgttctaa tgaagcgata   17580
cgttgttcta aaacaacagg gtctaatttt gcactatctt catcagtaat agtaggttct   17640
aatttgtttt cattttcttc ttcgattgtt tctactttt tatcttcagt agattcttca   17700
gttgattctt cagttgattc ttcggttgat tctgaagttt cttcagttga ttctgaagtt   17760
tcttctttgt cgtctggttt tacgatttca tcaaattctg tcattttgac acctccaaat   17820
attttataac taattatatc atagaatatt taaataagta aattaaaatt attttaagtt   17880
caaatcataa cttttgataa aagtcaatag atacataaat tttgtatttg atgaatatgt   17940
tataggttag ataagttgga aaagtagacg tacagtgttt ataagtttag taaagaaatg   18000
ataagta                                                                 18007
```

SEQ ID NO: 46               moltype = DNA  length = 140909
FEATURE                     Location/Qualifiers
source                      1..140909
                            mol_type = genomic DNA
                            organism = Staphylococcus phage SaGU1
SEQUENCE: 46

```
atggatggaa aagaactaat taagatagca caagaaacat ttcaaactga aaaaataaca   60
agagaacaga tagaccatat aatcaatatg ttaaacccct ctacctatat gcttaagtat   120
cacacactaa gaggacaccc tataactttc agcattccta atagagatag aagtaaagca   180
caggctcata gaccatggca aactaggatt gtaaacgata ctcatcctaa taaggctgta   240
ataaaatcac gtcagttagg tcttagtgag atgggtgtaa tggaaatggt tcattttgca   300
gatatgcata gttatgccaa tgcaaagtgt ttatacacat tccctagatt ataagttggg   360
gaattaaaac tctgttaaac ggtcatagga aaataaagaa tatcctggta agagagacta   420
agtcctaatg gatagagtta ataccgtgct aaatcaacct aataagttgt aaatgccgaa   480
cgactaaatt tctagatagc ttattaaaag ggataagtga aaactagata agaaagtctt   540
gacaaaaata ccaaagtaag ttaatatatt aaataggagg tggaaaacaa atgcctagga   600
aaaaaacaca tgaagaattt gtaaaacaag taaaagatat agcaggaaat gaatacactg   660
taacaagaca ttatgaacac gcaaatcaaa atataaaaat gtttcataat gaatgtaagg   720
aagaatttga aataagacca aataaattct tacaaggtaa aagatgttct gcttgtgtag   780
gtaaaagaat aagtaagaca caagctaaac cacttagtaa agttaaaaga caattaaaag   840
agaaacataa tggtactata gagattatag gtgagtatac aaatactcac actaaaaacag   900
atttttaaatg tttaacatgc aatcatactt tctcttcaga acctaattct gttttaaggc   960
tgagtggatg tcctaaatgt aaagtttcta aaggggaaaa attaatagct gaattcctta   1020
aagaaaataa tatacgtttt aaagaacaga aaagatttaa agattgtgtt cataaaagac   1080
ctctaatatt tgatttctac ctattagatt taaatacttt aatagaatat gatgggattac   1140
agcacagtaa gccaatagat tattttggtg gtgttaaagc ttttgaagaa ttgaagtata   1200
gagatagctt aaaaagatgat tacgcaaaaa gaaataatat taggatgata agagtgtcct   1260
ataaacaaaa agagaaagag ataataagaag aattagaaag tgttttgggt gtggtaaccc   1320
gtcaagaaag taaagcagag agctcaacac caaaaagttg agttaagata tagtctagtc   1380
cgtatgtaaa tatcacgaaa gtgacggtag taacgactaa tgaacaaatg aaaaaaatttg   1440
ttcagtctcg tttgaaccct gtattagaaa aagaatattt tagagatatt gttgattggg   1500
ataaggactc tttaggtttt aaaaagataa gaaactctag tttattcttt agaacaagtt   1560
ctaaagcaag tactgtagag ggtgtggata ttgactactt atccttagat gagtatgata   1620
gggtaaactt attagcagag tcatctgcat tagagtcaat gtcttcatca cctttttagga   1680
ttgtgagaag atggagcaca ccatctgtac ccggtatggg tatacacaaa ttatatcaac   1740
aatctgacca atggtattat ggtcatagat gtcaacattg tgatttatta aatgaaatga   1800
gttataatga ttacaaccct gataatcttg aagaaagtgg gaatatgtta tgtgttaacc   1860
ctgaaggtgt agatgaacag gctaaaacag tacagaatgg tagttaccaa tttgtttgtc   1920
aaaaatgcgt taaaccacta gatagatggt ataatggta gtggcattgt aagtatcctg   1980
agcgtacaaa aggtaataaa ggggtacgag gatacctaat aacacaaatg aacgctgtat   2040
ggatttctgc tgatgaatta aaagaaaaag aaatgaatac agaatctaag caagcgtttt   2100
acaattatat tttggggttat ccatttgaag atgttaaact gagagttaat gaagaagacg   2160
tttatggtaa caaatcacct attgcagaaa cacaattaat gaaacgagat agatattctc   2220
atatagctat tggtatagat tggggaaata ctcattggat aactgttcat ggtatgttac   2280
ctaatggtaa ggtagactta atacgattat tctctgttaa aaagatgaca agacctgatt   2340
tagttgaagc agatttagaa aaaatcattt gggaaatatc taggtacgac cctgatatta   2400
taattgcaga taacgggagt tcaggaaaca atgttctaaa actcattaat cattttggaa   2460
aagataaagt atttggatgt acgtataaat cttctcctaa gtctacagga cagttggagac   2520
ctgaattaa tgagaacaat aatagggtta cagtagataa attaatgcag aataaaagat   2580
atatacaagc acttaagaca aaggatataa gtgtttatag tacagtagat gatgatttaa   2640
aaactttctt aaaacattgg caaaatgttg ttattatgga tgaagaagat gaaaaaactg   2700
```

-continued

```
gagaaatgta tcaagttatt aaacgtaaag gtgacgacca ttatgcacaa gcaagtgttt   2760
atgcctatat aggattaaca agaataaaag aacttcttaa agaaggaaat ggtacaagct   2820
ttggttctac atttgtttct actgattaca accaagaagg aaataaacaa ttctactttg   2880
atgaatagag gtgaaataga cttgacagat aaattatttt atggtacaat tagtaatgaa   2940
gaaattaata aaagtgtatt gaatttgtta ttaggtagag aattatcttt agattatgtt   3000
tctaaaaata gtgatacctt agatgttaaa tatgaacatg tttataaatc tctaggattc   3060
gataaatttct ttgattgttt tttatatgct aatagagaac ctgaaatagt ccataaaggt   3120
ggagataaaa atcttggtgg gctaaataag gttaaacgta ctgttattcg taatggtaaa   3180
gaaatggaaa tgacagttta cgaagacggt aataaagaaa atgatagtaa agaaaaacaa   3240
gaaggcaaag aagaagttag tagaagtgca gtaggagcaa gagctatttc taatggtgaa   3300
gaaggaaagg taaaccctaa aaaggtagca aattcattat ctagtttaag taaaaaaggt   3360
gtcgatgtat cacatgttag tacaaactca tcattgtaca aagagtttgt tgatgataat   3420
ggggatacat taggaattac atcttttaaa agaactgaaa atgatataat attagaatct   3480
tatgcaagtt cacccgattc agatggtgta ggggctagag ctattatgga actattacgt   3540
ttaagtatta aggaaaataa aaatgcagtt gtgtatgaca tagaattgcc tgaagctata   3600
gagtatttaa aaactttagg atttaaacct aataaagatg gatacatctt aagaaaaaaa   3660
gatgtaaaac aattcttagg tgattatagt gattttattt agcactgtag tcatctattc   3720
tattgtattt attctctata ttatattaaa aacaatttat gtaaagtcta atatgaatag   3780
aatagataac acaactgaat tattaaaaat attacaggaa gatattgaag gaaagataaa   3840
aaaggaagga agaaataaat gactttagaa gaaaataaat taacattaga agaatcaata   3900
actccactta gtaaagagga gaaagaggat agtattaaag aatttagtag tttattatgt   3960
gaaatggtaa atagattata caagtcttac aatgtattta gacaagaccc tatggatgaa   4020
acgcaacgtt tagatggttc tctaatggtc tttcaaagta gactaaatga cccctttaaca   4080
ggagatttac atgacaagat gtataaactt gctttttcaa aacgcattga tatttttgaa   4140
gctaacaagc aattcagaaa agatgtagaa tcaggtaagg caattgaact aggtgatgta   4200
gctattatag atacagcatt aagtaatatt ctttcaggta acgagttcca aggaagtatt   4260
tcgtttatgc ttagaaaaga ctttgaagaa aaagaaagaa ttagaaaaga agaagaagag   4320
aaacttaata acttataaaa gggaagaatt atgagactat ataaaatgag gtatcataat   4380
tgaaaaagaa accacaaggc aatgagataa tcataaccat aataacggtt atgatagcaa   4440
tatttgtagt cattatgacc atatttttta ataaatacca agatgctaaa gaagataaaa   4500
atagatatca gagattagtt gagatttata aaaaagcaga tgataatgat ggagagacta   4560
aaaagaaata cgtaaaaaga ttaaataaag ctgaagaaga acttaaaaaa gtaaagaaag   4620
aaacaaatta taaagactat aataagaagt caaataaaga aagacaaaag gaagataaag   4680
aaactagaga gaaaatatat gatgtaactg gtgatgatga cttaatatta gtaaaaaata   4740
atattgagtt tagtgataag gtagataaac ctgaaatact tattagtgaa gatggaattg   4800
gtacgataac tgtccctaca aacagtggtt atgaaaaaca aacagtaggt tctattatta   4860
ctagtgtatt aggttccccg ttcttatcaa ctgattcacc cggtatagat agtttaggta   4920
tcattaatag taatgtttat ccaaatacag tagatagtat agtagaagat acaaatactt   4980
ctactgataa tgtactaaag gataatccta ttataacaaa tccagttgaa ccaaccacac   5040
cttcagatat attacctcct attgataatc cgtcagttcc tatattacct gaaaatcctg   5100
tagacaataa ttcaggaaat atagataata cggataatcc aaaccctcca cctccaggat   5160
atacagatga agatggaggt agaggctcag gtggtgagg taatgttgaa cccccaccaa   5220
cggaagaacc ttcagataac ggtaatacag gaggaggaga ttgggaagaa aaacctgacc   5280
caggagaaga gccatcagat aatggtaata caggagacaa tgaaggagag gtaactcctg   5340
aacctgaccc tacaccttct gagcctgaac aacctaatga aaaacctaat gagggtaatg   5400
gtaatgaaga aaaaccatcc gaaccatcag ataatcctga tgaaaatgga ggatgggaaa   5460
ctgagccttc cgaacctgaa acacccttctg agccggacga taagggtggac gaagaggata   5520
aaaacgaaga tacaacagag gataaacaac ctacagaaca accggacgat aataatacag   5580
ataatgagga taaaactgaa gaggagtaat tactcctctt ttttgtttgc tatattaaat   5640
aagagataaa tataaaaaaa ttgaacatta cggtggtgaa aactttgata ggaatgaatg   5700
ttataacgtc actatcagta gtatttaccct gtttaagtct tttaacttta atgattttg   5760
ttcacagtaa gttctccagt aaaaaacgttt ttgtttcgta tgtaatttat gctataatag   5820
gaataggtac atacatagtt ttaactatgt ttcaaacaac atctgtactt attaagaatg   5880
atgtaataga ttccatagaa aatactgaac attatattgg attcaatgac cctataatta   5940
tatttactat aagtttttata ggggcaatac ttggaggaat ttggtacaag atgatgaaaa   6000
ttattaaaaa gagtaacttt aaagataaaa aataaaaaag acggtgaata ggttgatatt   6060
ctctaaagat aagaaatggg atgaagcaaa agatttcatc aaaggtcaag ggatgcaaga   6120
taattggata gagattgtag attattatag acagataggt ggaaaacacg tagctgtttt   6180
tattgcttta aacaaagtaa aatacatgat tctagaagca acaaaagaca ataaagtaat   6240
attagtagat aaagataata atatactatt agaagattat gatattgtta tggaaagtaa   6300
aaaaatgttt tattacattg aagaaccgtt cgaggttaaa ataaatatcc ctcgacatat   6360
tagagatgta acttataata atactgttgt attaactaca gtaagaggga gtagaggtga   6420
ctagtaattg gcagatttat ttaagcaatt cagattaggt aaggactatg gtaataatag   6480
taccattgct caagttccta ttgatgaagg attacaagct aacattaaaa aaatagaaca   6540
agacaataaa gagtaccaag acttaactaa gtctttatac ggacaacaac aggcttatgc   6600
agagccattt atagaaaatga tggatactaa tcctgaattt agagataaga gaagttacat   6660
gaagaatgaa cataatttac acgatgtttt gaaaaagttt ggtaataatc ctattcttaa   6720
tgctatcata cttacacgtt caaatcaagt agctatgtat tgtcaacctg caagatactc   6780
agagaaaggt ttaggttttg aggtaagatt aagagaccta gatgcagaac caggtagaaa   6840
agaaaaagaa gaaatgaaac gtatagaaga tttttattgtt aatacaggta aagataaaga   6900
tgtagataga gattcgtttc aaactttctg taagaaaatt gttagagata cttatatata   6960
tgaccaagtt aactttgaaa aagtatttaa taagaacaat aaaactagat tagaaaaatt   7020
catagcagta gaccctccta ctattttta tgcaacagat aaaaaaggta aaattattaa   7080
gggtggtaag aggtttggtt c aagtagtaga taaaagagta gtagctagtt ttacttctag   7140
agaattagct atgggtataa gaaatcctag aactgaatta tcttcttcag ggtacggatt   7200
atcagaagta gagatagcta tgaaagaatt tattgcttat aataatactg aatcattta   7260
cgatagattt ttctcacatg gtggtactac aagaggtatt ttacaaatac gttcagacca   7320
acaacaatca caacatgcat tagagaactt caagcgtgaa tggaaatcaa gtttatcggg   7380
tatcaatggt tcatggcaaa ttccagtggt aatggcagac gatattaaat ttgttaatat   7440
```

```
gacaccgact gctaatgata tgcaatttga gaaatggtta aattatctta ttaatattat   7500
atctgctttg tatggtattg accctgcaga aattggtttc cctaatagag gaggagctac   7560
aggttctaaa ggtggttcta ctttaaatga ggctgaccca ggtaaaaaac aacaacaatc   7620
tcaaaataaa ggtttacaac ctttacttag atttattgaa gatttagtta atagacatat   7680
tatatcagaa tatggagata aatatacatt ccaattcgta ggtggagata ctaagagtgc   7740
tacggacaaa cttaatattc ttaaactaga aactcaaata tttaaaacag tcaatgaggc   7800
tagagaagaa caaggtaaga aacctattga aggtggagac attatcttag atgcttcatt   7860
cttacaagga acagcacaat tacaacaaga taaacaatat aatgatggta aacagaaaga   7920
acgtttacaa atgatgatga gtttactaga aggagataat gacgattcag aagaaagtca   7980
atcaacagat tctagtaatg ctgataaaga aataggaaca gatgcgcaaa taaaaggtga   8040
cgataatgtt taccgaactc aaacatctaa taaaggtcaa gggagaaaag gagaaaaatc   8100
ttctgacttt aaacattaat taataagcct agaataaatc taggctttgt ttatttttt   8160
gtaatttaat tttgataaag ggaataacta tgatatacta tatgtaattg atattaatac   8220
ataaaaaata ttaatatttc acttacaagt tattattgtt atattattaa cgtaaaagta   8280
aataaaataa caagtggagg tgtagacacc tttggaagaa ataaaattta atgctttgt   8340
acctatggat ttgaagaaat ctgtatcaac agcttctgat actaatgagt attctatagt   8400
ttcaggatgg gctagtactc caagtatgga tttacagaat gatatagtta atcctaaagg   8460
aatagatata gagtatttta agtcacaagg gtacattaat tatgagcatc aaagtgataa   8520
agttgtaggt atacctacag agaattgcta tgtggatata gaaaaaggtt tatttattga   8580
agcaaagcta tggaagaatg atgaaaatgt tgttaagatg cttgatttag ctgagaaatt   8640
agaaaaatca ggtagtggaa gacgtttagg tttttctatt gaaggtgcag ttaaaaaacg   8700
taacataaat gacaatagag ttattgatga agttatgata acaggagttg cattagttaa   8760
aaatcctgct aatcctgaag caacatggga aagcttttatg aaatcatttt taactggtca   8820
cggtacatca cctgacactc aagttgatgc aggagcttta aggaaagaag aaatagcatc   8880
tagcattaca aatttagctt acgtcactaa gattaaagat ttaaaagagt ttaatgatgt   8940
atggaatggc gttgttgaag atttgagtaa atctaatagt atgggatatg aggaatcagt   9000
ccttacgtta caactagcta aaggtttatc tcgtaaagat gcagaactag cagtaatgga   9060
tataaacaaa caaaaactag aataggtaag gagaatacat tctatgagta aagaaatgca   9120
aaatatttta gaagagtatg ataagttaaa tgctcaagag gcagtttcga aatctgtaga   9180
agatgatgaa aagaatacag tagaatctac cgaagaacaa gtagcagaaa caactgaaga   9240
accggctaaa gaacctgaaa aggttactga ggaagatgct aaagaagcac aagagcaagg   9300
tgaaaaagtt gaatctgaag aggtaacaga ggacactgaa gatgaggaag ttgaaaaatc   9360
agctaaagaa tcaaaagacc ctgtagacca aaaagatact aaaacagaaa ataaagacaa   9420
cgagaaacgt aaaaataaaa aagataaaaa agaagattct gaatctgatg gtaagacaa   9480
agatactgac gatgataaag ataagaaaga agataagaag gaaaaaactt ctaaatcaat   9540
ttctgatgag gatatcacaa cagtatttaa atctatccta acatcttttg aaaacttaaa   9600
taaggagaaa gaaaactttg ctactaaaga cgatttaagt gaagttagta aatctattaa   9660
tgagttatca gcaaaaattt ctgaaatcca atctgaagat gtttctaaat cagtagacac   9720
tgatgaagaa gaagctgtag aaaaatcagt aacatctaca aatgggggagc aagaaaaagt   9780
agaaggttat gtttctaaat cagtagacac tgaagagcaa gctgaaactg gtgaagcaaa   9840
atcagagagat gctgaagaag tacaagagga taacacattt aaaggattaa gtcaagaaga   9900
aagaactaag ttcatggatt cttataaagc acaagctaaa gaccctagag cttctaaaca   9960
tgacttacaa tcagcttatc aatcttactt gaacattaac actgacccta ctaatgcatc   10020
agagaaagat attaaaactg taaaagactt tgcacaaatt taattaatgc acaaagttgt   10080
gttatattat acggtgtaac taaagaatat aaatagggta catttactg tacccctacat   10140
aaaataaaaa gaacacaaat gaaaggtgat aaatttatat gactatcgaa aagaacctgt   10200
cagacgttca acaaaagtac gctgaccaat tccaagaaga cgtagtaaag tcattccaaa   10260
ctggttatgg aatcactcct gatacacaaa ttgacgcagg agctttacgt agagaaattt   10320
tagatgacca aatcacaatg ttaacatgga ctaatgaaga tttaatcttc tatcgtgata   10380
tctcacgccg tcctgctcaa tctacagtag taaaatacga ccaatattta cgtcacggta   10440
acgtaggtca ctctcgtttc gttaaagaaa tcggagtagc accagtatct gacccaaata   10500
tccgtcaaaa aaccgtatca atgaaatacg tttctgatac taaaaacatg tcaattgcat   10560
caggtttagt aaataacatt gctgacccat cacaaatcct tacagaagat gctatcgcag   10620
ttgttgcaaa aacaattgag tgggcttcat tctacggtga tgcttcatta acttctgaag   10680
ttgaaggtga aggtttagaa tttgatggtt tagctaaatt gattgacaaa aataacgtaa   10740
ttaacgctaa aggtaaccaa ttaactgaga aacacttaaa cgaggcggct gtacgtatcg   10800
gtaaaggttt cggtacagct acagatgctt acatgcctat tggtgtacac gcagacttcg   10860
ttaactcaat cttaggtcgt caaatgcaat aatgcaaga caacagcggt aacgttaaca   10920
ctggttacag tgtaaatggt ttctactcat ctcgtggatt cattaaatta catggttcta   10980
cagtaatgga aaatgaatta atcttagatg aatcattacca accattacca aacgctcctc   11040
aacctgctaa agttacagct acagttgaaa ctaagcaaaa aggtgctttt gaagatgaag   11100
aagaccgtgc aggattatca tataaagtag tagttaactc agatgacgct caatcagctc   11160
cttctgaaga agtaacagct acagtatcta acgttgacga tggtgttaaa ctttcaatca   11220
gtgttaacgc tatgtaccaa caacaaccac aatttgtttc tatctaccgt caaggtaaag   11280
aaacaggtat gtacttccta atcaaacgtg taccagttaa agatgcacaa gaagatggaa   11340
caatcgtatt cgtagataag aacgaaacat tgcctgaaac agcagacgta ttcgttggtg   11400
aaaatgtcacc acaagtagtt cacttattcg aattacttcc aatgatgaaa ttaccattag   11460
ctcaaattaa tgcttctatt acatttgcag tattatggta ggtgcatta gcattacgtg   11520
ctcctaaaaa atgggctcgt attaaaaacg ttcgttatat cgcagtttaa tagaataaga   11580
aaaactgaat acaagagaat agggataaac ttagggttta tcccttttt attaaaataa   11640
acttgaaggg actcaataaa tatgttatac tataagaaat tactaaatac aaaaatggct   11700
accatttatg gtacagtaga tattgacaaa gatggagtag ttaaaggatt aactaaggaa   11760
caagaaaaag agtttgcaaa tgttccaggt tttgaatttg aagaagaaaa gaaaactact   11820
agaaaacaat cagcttctac tagtaaagaa gaagaaccta aagaagagga aaagaaagcc   11880
tctactagaa aaactacaag tactactaga aaatctacag cacgtaaaac aacagccaaa   11940
aaagatgaaa ataagtaaag ggtgaattaa atggttaact caatgtttgg aggggactta   12000
gacccttatg aaaaatcatt aaactatgaa tatccttatc atcctagtgg taatcctaaa   12060
catatagacg taagtgagat agataacta acattagctg attatggatg gtcacctgat   12120
gcagttaaag cttatatgtt tggtattgta gtacaaaaacc ctgatacagg acagcccatg   12180
```

```
ggtgatgagt tttataacca tatattagaa agagcagtag gtaaagctga gagagcgcta   12240
gatatttcta tactacctga tactcaacat gagatgagag attatcatga gacagagttt   12300
aatagttata tgtttgtaca tgcttacaga aaacctatat tacaggtaga gaacttacag   12360
ctacaattta atggtagacc tatatataaa taccctgcta actggtggaa agtagagcat   12420
ttagcaggtc atgttcaatt gttccctaca gcacttagtc aaacaggaca atcaatgtca   12480
tatgatgctg tattcaatgg ataccctcaa ttagcaggtg tatacccacc atcaggagca   12540
acctttgcac ctcaaatgat acgactagaa tacgtatcag gtatgcttcc acgtaaaaaa   12600
gcaggtagaa ataaaccttg ggagatgcct cctgagttag aacagctagt tataaaatat   12660
gcattgaaag aaatatacca agtatggggt aacttaatca ttggtgccgg tattgctaat   12720
aaaacattag aagtagacgg tatcacagaa acaataggaa ctactcaatc agctatgtat   12780
ggtggagcta gtgctcagat acttcaaata aatgaagata taaaagaact attggatggt   12840
ttaagagctt actttggata taatatgata ggattataag gagggttaga aaatggaaaa   12900
accgtatatg ataggagcca actctaaccc taatattatt aataagtcaa caacatacac   12960
tactacaaca caagcagatg aacaggataa acctaagtat actactaggc tagagtttga   13020
tactattgat atgattaggt ttattaatga taggggtata aaagtactat gggaagaagc   13080
atattttgt ccgtgtctta atcctgacac aggtcatcct agagtagatt gtcctagatg   13140
tcatggtaaa ggtattgctt atttacctcc taaagagact ataatggcaa tacagtccca   13200
agagaaagga actaaccaat tagatatagg gatattagat acaggtactg caataggtac   13260
aactcaatta gaaaagagaa tatcctatag agataggttt actgttcctg aagtattaat   13320
gcctcaacaa atgatttatt ttgtaaataa agatagaatt aaaaaaggta taccattata   13380
ctacgatgta aaagaagtaa cttatatagc cactcaagat ggtacagtct atgaagaaga   13440
ttatgaaatt aagaataaaa gattgtattt aaatgaaaaa tatgagaacc atacagtaac   13500
tttaaagata cttatgactt taagatatgt agtatcagat atactaaagg aaagtcgtta   13560
tcaatatact aaatttaatc aacctaaatc aaaaatttgaa aacttacctc aaaaaattact   13620
tcttaaaagg gaagatgtta ttgtactaca agacccttat aaagttaatg atggtataga   13680
agaagaccta gaaattcaag tagatgaccc taaagcttcc gcatctaatc ctagtaattt   13740
aggtggattc ttcggaggtg catttaaata atgccagttc acggaaagag acctaattta   13800
tttaaaaata aaaactataa gcaggtaggt aagagaacca ttgatggcat gcgttcagaa   13860
gttcttgaca agctacaagc aacagcacag caagtagaga atactagtat taaacgtatg   13920
cctacttatc tacaagtaac agagaaaaag cttgaaaaag aaggagtagt agaccttaaa   13980
aaagcatttg ctcactcatc taaaaagaaa actagtaaag acggaggatg gtatttaact   14040
gtaccaatcc gcattaaaac tagtagaatg aacaacagta cttatcaaga tatgaggact   14100
ttaaaagtag ataaaggcac aggttcagtt tctaagataa ctgattatct agaaggacgt   14160
agaaagaatg taagtcaccc gtcaatgaaa ccggaaccta tgactcataa catgactaaa   14220
gttaaaagag gaaagcaatc ttcttacttt atatttagaa ctgtttctag taaatcacct   14280
gctagttcct ggatacttaa tagagataaa gttaatgaga ataatttctc taaaacaact   14340
ctaaaaactg ttaagcaact aatgaactgg aagatgaaaa atttaaatta agaggagggt   14400
tagtattaaa tggcaataac atcagttgat tcatatttat tatcagaaat aaagcctaga   14460
cttaacactg tgctagagaa ttgttatatt atagatgaag tttttaaaaga ctttgattat   14520
caaactagag agagctttaa agaagctttc tgcggtaaga atgcacaaca tgaagtaacg   14580
gtaggattta acttcccaaa atttaaaaat aactatgaag ctcattactt gatacaatta   14640
ggtcaaggac aagagacaaa aaactctta gggagtattc agtcatctta ctttgaggca   14700
acaggagata ccttagtcga atcttctaca gcaataagga aagatgataa gttagttttt   14760
actgtttcta aacctatagg agaattaata aaagtagaag atatagagtt tgctaaaatac   14820
gataatcttc aagttgaagg taataaggta tcatttaagt accaaacaaa tgaagattat   14880
gagaattata atgctaatat tatctttact gaaaagaaaa acgactctaa aggtttagta   14940
aaaggattca cagttgaaga acaagtaaca gttgtagctc tatcatttaa tgtagatgtt   15000
gcacgatgtt tagatgctgt attaaaaaatg attttaatat ctatgagaga tagtatagaa   15060
gagcaacaaa cattccaatt acagaatttg tcctttggtg atattgcacc aataatagaa   15120
gacggtgact caataatttt tggtagaccg acaattatta agtacacaag ttctctagac   15180
ttgattaca ctattacaca agatattaat aaactaactt ttaaagaaag aaaggatttg   15240
aagtaggatg gctagaaaaa agacacctga aaataacact cctaaattta atggttatgt   15300
tcatatagat acattccttg atactgcaaa aacccttttt aacatgaggg attcacaagt   15360
agcaggattt aaagcttata tggaaggtag tcattatttg tttagtgagc aagaattctt   15420
accatcatta gagaagtatt taggtaggaa attagatata taataacatt cagataagga   15480
gaattaaata tggcagtaga accattccca agaagaccta ttacccgtcc tcatgcatct   15540
attgaagtag atacttcagg tatcggtggc tcagcaggtt caagtgaaaa agtattttgc   15600
ttaatcggtc aggctgaagg cggagaacca aatacagttt atgaattacg taactatgca   15660
caagctaaac gtttattccg ttcaggagaa ttacttgatg caattgaatt agcatggggt   15720
tctaaccta actatacagc aggacgtatt ttagctatgc gtatagaaga tgctaaacct   15780
gcaacagcag aagttggcgg actaaaaaatt acatctaaaa tcttcggtaa tgttgctaac   15840
aacattcaag taggattgga aaagaacaca ttaagtgatt cattacgttt aagagtaata   15900
ttccaagatg accgtttcaa tgaggtttat gataatatcg gtaatatctt cacaatcaag   15960
tataaaggag aagaagctaa cgcaacttttt tctgtagaac atgatgaaga aactcaaaaa   16020
gcaagtcgtt tagtattaaa agttggagac caagaagtta agtcatatga tttaactggc   16080
ggagcttatg actatactaa tgctattatt acagacatta tcaattacc tgatttcgaa   16140
gctaaattat caccttttcgg agataagaac ttagaatcta gtaaattaga taaaattgaa   16200
aatgcagata ttaaagacaa agctgtatat gttgaaagcag ttttcggtga cttagaaaaa   16260
caaacagcat ataacggtat tgtatctttc gagcaactta atgcagaagg agaagtacca   16320
agtaatgtag aggttgaagc aggagaagaa tcagctacag taactgctac ttcacctatt   16380
aaaactattg agccgttcga attaactaag ttaaaaggcg gtactaacgg tgaaccacct   16440
gctacatggg cagataaatt agataaattt gcacatgaag gtggatactta cattgttcca   16500
ttatcatcta aacaatcagt tcatgcagag gtagcttctt cgttaaaaga acgttctgac   16560
gcaggagaac caatgagagc tattgttggt ggaggattca gtaatctaa agaacaattg   16620
ttcggtagac aagcatcatt atctaatcca cgtgtatcat tagtagctaa ctcaggtact   16680
tttgttatgg atgatggacg taaaaaccat gtacctgctt atatggtagc tgtagcttta   16740
ggtggtcttg caagtggttt agaaatcggt gaatcaatca cattcaaacc attacgtgta   16800
agttcattag accaaatcta tgaatcaata gacttagatg aattaaatga aaatggtatt   16860
attagtatag agttttgttcg taaccgtact aatacattct tcagaatcgt tgatgacgta   16920
```

```
actacattca atgataaatc agacccagtt aaggctgaaa tggctgttgg ggaagctaat  16980
gacttcttag taagtgagct taaagttcaa cttgaagacc aatttattgg tactcgtact  17040
atcaatacaa gtgcttcaat tattaaagac tttatccaat cttacttggg tcgtaagaaa  17100
cgtgataatg aaaattcaaga cttccctgct gaagacgtac aagttattgt tgaaggtaac  17160
gaagcaagaa tttcaatgac agtttaccca atcagaagct tcaagaaaat ctctgttagc  17220
ttggtttaca agcaacagac attacaagcc taatctaggt gatggagtac ctggattagg  17280
tactcctatt aatataattt gaatacttta ggagagtgaa tacagatggc atcagaagct  17340
aaacaaaccg tccatactgg taataccgtc ctacttatga ttaaaggtaa accggtagga  17400
agagcacaat cagcatcagg tcaacgtgaa tacggtacaa ctggtgtata cgaaatcggt  17460
tctatcatgc ctcaagaaca cgtatactta cgttatgaag gtacaattac agtagaacgt  17520
ttacgtatga aaaaagaaaa ctttgcagat ttaggatatg cttcacttgg tgaagaaatt  17580
cttaagaaag atatcattga tattttagtt gtagataact taacgaaaca agttattatc  17640
tcatatcatg gttgctctgc aaataactac aatgaaactt ggcagacaaa tgaaattgta  17700
acagaagaaa tcgagtttag ttacttaaca gcaagtgaca aagcacgtac ttaatatact  17760
agaccaacta aaaagttggt cttttttttat tgacattata aaatttatat gatattataa  17820
taaacaggtt aggagtaatg agtatgaata atagacaagc taaaatacaaa ggttataatc  17880
aatttcatta ttatgatttt ccaacaacta aaggtaagtt taaagatata atgaaaagaa  17940
agtctagaac agaacttaaa aaagatttac aaaaagagag aagagattat cttgacaaat  18000
aagagaaaaa caataggaaa aatgagtaat acgagagcaa catggaatat caaccctgta  18060
actaaggtta aaaaagataa aacaaaatat tctagaaaaa ataagcataa aggtcttgac  18120
aactataatt aactaaggta tattattagt ataacaaaaa aggagatgaa ttacatgagt  18180
acatttggt caaaaagaag aacaacaggt aaggacagac aagtaaagaa acattatact  18240
caaatgtctt tacaagaaaa gaagaagtgt gttaatctat tacaagatac aattaatacg  18300
cataagtatt tagaactatc aagtcattgt aaaactaaac ttaaaaataa aattaatttt  18360
agtaatctag taagatttat ttttaaggat agaaatgcac catttaatat tattgagtat  18420
aatattacag attttcatgg taaagaacaa agaagaataa tttttaaaag ccctactatt  18480
gtaactatag aaggagtaag tagttatcag tacttagtta ttaacttaga agatggtaca  18540
ataataacta catactataa tggtattaca gatacacata aaacattaga tttaaaatat  18600
tataataaaa acttgacaat taaataagga ggaattataa tgggattaat atttgtaaat  18660
agttatttta taatatcaaa catattaatt attgtgtttta gtaaattaaa tagtaaaaaa  18720
aaggtaacag aaaaaactct agctacaagt aatcttttat taacaatatc atatattcaa  18780
ctattagcat ttttaatcat taatggtatt tactactcat taaaatatat gtaaaaaaag  18840
tattgacaga ataaaaataa taaactataa tacagatata acaaattaaa ggagaagata  18900
taaaatgtca caagataaat taagagcaat ttacacagaa gtgaaagtag aattacacaa  18960
atttcctaaa gaggtagatg taacaagtaa atcaactgca attgcaatca atcagattct  19020
agataaattt aaaacattaa ctgaacaagc agggaaaatt acgagaaaat atctagaagg  19080
tcaagaaata ttaactattg attatgagta ttatgattca ttacaagaat actatatcta  19140
cctacttaga aacagtgaaa agattgaaca aagtttacaa gaaatcacta agcgtacagg  19200
tgaatatgta agtaattttt gatttaaaaa caaaatatga tatactatgt ttaaagtagt  19260
aagcctacac tagtccgtgt tatattaata ttgaatcgga taagcgtagg ctttattaat  19320
atttaaaaaa ggaaggtata tcatattatg gcagaagaaa ttaaaaaagga acaagatgta  19380
caagaaacaa ctaaagaaga taaaaaagat gttagtaaaa tgacaccgga agaaatagat  19440
aaattaaaat atcaagataa gcaagaaaaa gaacaagtaa taacaaagt tattaaaggt  19500
gttaatgata cttgggaaaa agaatataac tttgaagaat tagatttaag atttaaagtt  19560
aaaattaaat tacctaatgc acgagaacaa ggtaacatat ttgcgttacg ttctgcttac  19620
ttaggtggta tggatatgta tcaaacagac caagtaatta gagcatacca aatgttagct  19680
acattacaag aagtaggtat tgaagttcct aaggaattcc aagaccctga tgatatctat  19740
aacttatatc ctttaactgt tatgtatgaa gattggttag gattcttaaa ctcctttcgt  19800
tactaatagt atagaaacat tagataaaga tatagaacga ttgggtggta tggaatcaat  19860
tgttaaacaa ccttttatcta gaaatctatg ggctattatg aaagagttta atgttttgcc  19920
tactgagcaa agatttaagg atttagacga ttatcaaata gagtttatta ttggtaaatt  19980
gaatagagat gtttatgaac ataataaaca acttaaacaa gctcaaaaag gtggaaaatt  20040
cgatagtcaa tttgaagatg acgatagtag ttggtggaat gaatctcatg aagactttga  20100
cccggtacct gatttcttag atgccgatga cttagcacaa cagatggaag ctaaattatc  20160
tgatagagat aaggaagaaa gagctaagag aaatgatgca gagttaaatg atgaaacaga  20220
aggactcact acacaacatc ttgctatgat ggaatacatt agaagaaaac aagaagaatt  20280
agatgatgaa gtaggaaatg gtaaaactag tgaagatgat gctactataa cacaagagag  20340
cgttaataaa gcactagaag acctagatga tgactggtat atgtaaaggg tggtaggtga  20400
tactaccatc cttatttttt taaaatggat ggtgaataat gatggcaatg aatgacgatt  20460
atagattggt cttatccggt gatagttcgg atttagagaa tagtctgaag gcaatagaac  20520
tttatatgga ttccctagaa tctaaaaata ttgatgcccc tttagacaat ttcttaaaga  20580
aattaaaagt aattgctaaa gaagttaaaa atgtacagaa ctcaatggat aaacaagaag  20640
gtaaatctgt catatcttct aaagatatgg atgaatctat taaatccact caatctgcta  20700
caaagaatat aaatgaatta aagaaagcct tagatgaccc tcaaaaagaa aatatatcta  20760
aaggtattgc acctgaccct gaagttgaaa aagcatatgc taagatgggt aaagttgtag  20820
atgaaactca agaaaaactt gagaaaatgt cttcacaaaa aataggctca gacgctagta  20880
tacaaaatag aattaaggaa atgaaaaacct taaatcaagt aacagaagaa tataataaga  20940
taagtaaaaga ttctagtgct actaaagact atactaaacg tttaagagct aatcgtaata  21000
tgactagagg gtatatggag cgttcagaag gaacaggacg tttaacatat gaccaagggg  21060
cacgagttag aagtgaacta ggtaagatag gttcttatga aagtcaaaga aaacaaaatc  21120
aacgcaactt aggtcaagca agagaacaat atagtaatta tagaaaccaa caacaagacc  21180
tgactaaacg tagagctagt ggtcaaataa ataaagctca gtatgaacaa gaattagctt  21240
ctattaagca ggaaatgaaa gctagagaag aacttatatc taactatgag aaaattaggag  21300
cagagcttga taaaactgtt caatactata aaggttcagt tcagaaagat ttccaatcta  21360
gagatgtaga ccaacaacga ggaacatttg gtagaatggt tcaagagcgt ttaccatcta  21420
tcggttctca tgctatgatg ggaactacag ctatggctac gggtttatac atgaaaggtg  21480
cttcattaag tgaaactaat agaccaatgg ttacatcact aggtcaaaac tcagataata  21540
tggatataga ttctgtaaga aatgcatatg gagacttgtc aattgataac aaaattaggtt  21600
ataatagtac tgacatgttg aaaatggcta cttcatatga agcatctgta ggacataaaa  21660
```

```
gtgatgagga tacaatggca ggaactaaac aacttgctat tggaggacgt tctttaggta 21720
ttaaagacca agaagcttat caagagtcta tgggtcagat aatgcatact ggtggagtaa 21780
attccgataa catgaaggag atgcaagatg cattcctagg cgggattaaa caatcaggta 21840
tggttggtcg tcaagatgaa caacttaaag cattaggttc tatagctgaa caatcaggag 21900
aaggaagaac tttaactaaa gaccaaatga gtaatcttac tgctatgcaa tctacttttg 21960
cagagtcagg aagtaaagga ttacaaggtg aacaaggtgc caatgctatt aatagtatag 22020
accaaggact taaaaatggt atgaatagtt cttatgctcg tatagcaatg ggatggggaa 22080
cacagtacca aggtcttgaa ggtggatatg atttacaaaa acgtatggat gaaggtatat 22140
ctaaccctga aaacttgaca gacatggctg atatggctac tcaaatgggt ggtagtgaaa 22200
aagaacaaaa atacctattc aatagaagta tgaaagaaat aggtgctaac ttaactatgg 22260
agcaatctga tgagatattt aaagatgctc aatccggaaa attatctaaa gaagagttag 22320
ctaaaaaagc taagaaaatg gaaaaagaag gtaaaaaaga aggagaagat aacgccactg 22380
attataaaga atctaaatca ggaaaaaatg accaaaataa atctaagact gatgataagg 22440
cagaagatac ttatgatatg gctcaaccat taagagatgc tcatagtgct ttagcaggcc 22500
tacctgctcc tatatattta gcaataggag ctattggagc atttacagca tcactaattg 22560
catctgcaag tcaatttggg gcaggtcatt taataggtaa aggagctaaa ggacttagaa 22620
ataaatttgg cagaaataag ggtggtagct ccggaggtaa ccctatggca ggaggaatgc 22680
ctactggagg aggttcacct aaaggcggag gctctcctaa aggtggcggt actcgttcta 22740
ctggaggtaa aatacttgat agtgctaaag gattaggagg attcctagtc ggtggagcag 22800
gatggaaagg tatgtttggt ggagaatcta aaggtaaagg atttaaacaa acatctaaag 22860
aagcctggtc aggtactaga aaagtattta acagagacaa tggtagaaaa gccatggata 22920
aatctaaaga tatagctaaa ggtactggta gcggtcttaa agatatttat aatgatagta 22980
tatttggaaa agaaagaaga caaaatctag gagataaagc taaaggtttt ggtgaaaaag 23040
ctaaaggtct ctatggtaaa tttgctgata agtttggtga tggtggtaaa aatggtatcc 23100
tttcacaatc accaaaagca ggcggtagcg ggctaggaaa actaggaaaa cttgcaggtg 23160
gacttggaaa aggagccgga gttttaggtg ttgctacatc tgccttatca ttgatacctg 23220
ctttagcttc cggtgatagt aaagctatcg gcggaggtat aggctctatg ggcgggaggaa 23280
tggcaggtgc atcagcagga gcttctattg gagctttatt tggtggtgta ggtgcaatac 23340
ctggagcttt aataggcgga gctataggtt cttttggtgg aggagctgtt ggtgaaaaag 23400
tcggagacat ggctaagaag gctaacacta aagaaggatg gaacctagga tggactaatg 23460
gagataaaga cggtaagaat aaattccaag attctttatt aggaaaacct atatctaaag 23520
catggagcgg tataacaggt ctctttgata atgacgctga agcatctgaa gaagatagca 23580
aagataagaa aaaaggcgtt aaaggtgtta aaggagatac taagaagaaa gaaaaaatga 23640
cagcagaaca acttagagaa aagaataacc aatctgaaac taagaatctt aaaatctata 23700
gtgatttact tgatagggct cagaaaaatta ttgagagtgc taaaggtatt aatatagatg 23760
gaggaacttc tgatagtggt tctgatagcg gaggctctgc atctgatgta ggtggagaag 23820
gcgcagagaa aatgtataag ttccttaaag gaaaaggact atctgacaat caggtaggag 23880
ctgttatggg gaacttacaa caagaatcta atcttgaccc taatgctaag aatgcctcta 23940
gtggtgcatt tggtattgct cagtggttag gggctagaaa aacaggatta gaaaactttg 24000
ctaaatctaa aggtaaaaaa tctagtgaca tggatgttca attagattac ctatggaaag 24060
agatgcagtc tgattatgaa agtaataatc ttaaaaatgc cggatggagt aaaggcggaa 24120
gcttagaaca gaatacaaaa gcatttgcta ccggatttga acgtatggga gcaaacgagg 24180
ctatgatggg tactcgtgtt aacaatgcta aagaattcaa gaagaaatac ggaggctccg 24240
gtggcggagg aggtggagga gctctatcct ctacttacca agaagctatg agtaaccctg 24300
tattaactac tggttctaac tataaaggct ctaatgatgc ttctaatgct tctacaacta 24360
atagaataac agttaatgtt aacgttcaag gtggaaataa tcctgaagaa actggagaca 24420
ttatcggagg aagaattaga gaagttctag acagcaacat ggatattttt gcaaatgaac 24480
ataagagaag ttactagtaa ttttgtattg cacacaagagt agtatcatag tatactactc 24540
ttatacatat aaaaataaaa ggaagtatgt gtatatgaaa agattaagaa gacctaaggt 24600
aagaatagag atagttacag atgataatac atttacatta agatttgaag atacacgtga 24660
ctacaatggt gatgagttcg gagctaaact tttaggtttc caaactaaaa actctatgga 24720
agatgatagt tctgtattcc aaatcaatat ggcaggagat acttactggg ataagttagt 24780
tatggctaac gatataatca gaatatttat tacacctaat gatgaccccta atgataaaga 24840
aggtcgtcaa gaacgtttaa tccaagtagg tatggtatca caagtatcaa aagtaggtag 24900
ttatgtaat gaccaaactc aatttaggat aacaggtcaa tcttttgtaa aacctttttat 24960
gaaatttgga ttaggagtta ttcaggaagt tcaagctgta ttacctgaag taggttggct 25020
tattgatggt gacggagata atgaagtaaa atttactggt agctcagccc atgaagtaat 25080
gacaggaatt atacgtagat tcataccata tatgaagtat aactatactg aaaaaaacata 25140
taatacaatt gataactatc ttgattatga tgatttaagt agttgggatg aatttgaaaa 25200
tttgacagaa gtatctgctt ttactaattt tgatggctca ttaaaacagt tgatggatat 25260
ggtaacagct agacccttta atgaattgtt cttcaaaaac tctgaaaaaa cacctggtaa 25320
agcacaactt gtattaagaa aaaccccttt taatcctact gagtggagag ctttagatat 25380
gattaaagta cctactgaag actttattga agaagatgta ggtaaaagtg acgtagagac 25440
atattctata tttacagcta cacctgcagg tatgttaaaa gaacttaatg gtgatgtatt 25500
ttctaaacca caatttcacc ctgaattgac tgatagatat gggtatacta aatttgaagt 25560
agaaaaatatc tatcttagta ctaaatcagg ttcagctact gaagactcag attcttcggg 25620
tgatgacaat ggtactgaaa gaggaactta ctctaaaatt atgaaagatt taagtaacta 25680
tggaagagat aatatatcta aaggtataga taagtataca agtaaaattat cttcaaaaata 25740
taaaaactta aaaaaagctc aagctaaaaa aattatagag aaatttgtca aagaaggaaa 25800
agtaacagaa aaagaatacg agaagataac aggtaataaa gtagatgatg aattaacatc 25860
agataacaga ccgaagttga caaaggataa attaaagagt atactaaaag agaagtttaa 25920
aacacaagat gattttaata actctaagaa aaagaaaaaa gctaagacag atgcacttaa 25980
agaattgaca actaaatatc gtttcggtaa caaaacacac gctacaactt gttagatga 26040
atatattaaa tacaaaggag aaccaccgaa tgatgaagtc tttgataaat atcttaaagc 26100
tattgaaggt gttagtaacg tagctacaga cacaggttca gatgcaagtg atagtccttt 26160
agttatgttc tctagaatgc tatttaattg gtatcatggg aaccctaact tctacgcagg 26220
agatattatt gtttttaggag accctaagta tgacctaggt aaaaggttat ttattgagga 26280
taaacaacgg ggagatactt gggaattcta tattgagtct gtagaacata aatttgatta 26340
taaacaaggt tattatacaa ctgtaggagt aactagaggt ttaaaagatg ctatcctaga 26400
```

-continued

```
agatggtaag ggtagtcctc ataggtttgc aggtttatgg aatcaatcat cagacttcat   26460
gggaggtctt atgggtgaag atacttctaa agaactcaaa gaaaaaggtg tagcagagaa   26520
gaaaagtagt ggagataaag acggtggctc tgatagtggt ggagcacaag atggaggttc   26580
tctagattca cttaaaaaat ataatggtaa acttcctaaa catgacccaa gtttcgttca   26640
gcccggtaac cgacattaca agtatcaatg tacttggtat gcttataata gaagaggtca   26700
attaggcatt cctgtgcctt tatgggggga tgccgccgac tggattggtg gtgctaaaag   26760
tgcaggatat ggagtaggta agacaccaaa acaaggtgcc tgtgttattt ggcaacgagg   26820
agacaaaggt ggttctaatg cttatggtca cgttgccttt gtggaaaaag ttttagatgg   26880
tgggaagaaa atattcattt ctgaacataa ctgggctacg cctaatggtt atggtactag   26940
aacaatagac atgagctctc aaataggtaa agaagctcaa ttcatttacg ataagaaata   27000
aaggaggata gtcatggca acagataaag aagctaaaga tgttattgat aaatttatg   27060
ataatgtgtt taattttgat gtattaacta cggaaagagt taaagaaaaa gatgaagaaa   27120
tcaaaaaaat aactacagat gatatgtatg aaaaagttgt gtatatacga ccttatgttg   27180
gagtaataca aagtcttaac cctcaacatg tacaatatga atcattttct aataatggtt   27240
acgatataga agcagaatta agttttagga aagtaagtta tttagttgat aaagggtcta   27300
tacctacaga ttctttatcc actttaacag ttcacttagt agaaagaaat caggagttat   27360
taatagatta ctttgatgag atacaagatg tgttgtatgg ggagtatatg gaagaagaat   27420
atgtatttga tgaagatgta ccattaagta ctatactagc attagactta aatgataatc   27480
ttaaatcctt atcaaatata aagtatatgt tcaaaggagc ccctaaagat aatcctttg   27540
gaacagataa agatgtttat atagatactt ataatttatt atattggttg tatttaggtg   27600
aagatgaaga attagcatat cctatgaata ttaactattt ctttacagaa ggtagatttt   27660
ttactgtttt tggtaaaggt cataagtata aagtagatgt tagtaaattt atagttggag   27720
atatattatt ctttggtaga agtgatacta atataggtat ttatgtaggt gatggagagt   27780
ttatatctat gataggtaaa tttccaaaag atgagacacc tataggaaaa tacaaacttg   27840
atgattactg gaatgaattt aacggaagag ttatgagatt cgatgaagag gtgtatattt   27900
aatggtagta agattccaat cttccatggg gagaagtcta aaaagagtag attcagatga   27960
cttaaatgta aaagggttag ttttagctac agttagtaaa attaattata agtatcaatc   28020
agtagaagtt aaagttaata acttgacttt aggaagccgt ataggtgatg atggtagctt   28080
agctgtacct tatcctaaat cttttcatagg tagaacacct gagggaagcg tattcggtac   28140
aaaaccactt attactgaag gttctgtagt attaataggg ttcctaaatg atgatataaa   28200
tagtcctata atcttgagtg tttatggtga taatgaacaa aataaaatga ttaatactaa   28260
ccccttagat ggaggtaagt ttgatacaga aagtgtttac aaatacagta gttcactata   28320
tgaaatttta ccatctttaa attataaata tgatgatgga gaagggacaa gtattagaac   28380
ttataatggt aaatcattct tctctatgac atcaggtgaa gagagaaaac cgcaggcaac   28440
agattttat actggaactg agtatcaaga tttatttact tcctattatg gtaataaaac   28500
attgattgaa cctagaatac aaaaggctcc taatatgtta ttcaaacatc aaggagtttt   28560
ttatgatgat ggcacgccgg ataatcacat aactacttta tttatatctg aaagaggaga   28620
tatcagagct tcagttttaa atacagaaac acagaaaaga actacacaag aaatgtcaag   28680
tgatgttct tatagggtta ttaaacagga tgacgattta atgttggatg aggctcaagt   28740
ttggattgaa tatggtatta gtgaagataa taaatttat attaaaaatg ataagcataa   28800
atttgaattt actgatgaag gaatttatat agacgataag cctatgctag aaaatttaga   28860
tgagagtata gcagaggcta tgaagaattt aaatgaaata caaaaagaac tagatgatat   28920
aaactatctt cttgagggtg taggtaagga taatttagaa aatccacaaa aatccacaaa   28980
agagtctata gaagcgtcta aaaaagcaac ttcagatgtt aatagactta caactcagat   29040
atcagaggtt agtggtagaa ctgagggtat tataactcaa ttccaaaaat ttagagatga   29100
gacttttaaa gactttatg aagatgcttc tactgttatt aatgaagtaa atcagaattt   29160
ccctagtatg aaaacagatg ttaataatct aaaaactaaa gttaataact tagagaaaac   29220
tgagatacca aatatcaaaa ataggttaac agaactagag aataataata acaatgcaga   29280
taaaataatt tcagatagag gagagcatat aggtgctatg atacagttag aggaaaatgt   29340
tactgtacca atgagaaaat atatgccaat accttggagt aaagttactt ataataatgc   29400
tgagtttttgg gattctaata accctactag attagtagta cctaagggaa taacaaaagt   29460
aagagttgca ggtaatgtcc tatgggattc taacgctaca ggacaacgta tgttgagaat   29520
attgaaaaat ggtacttata gtttaggggt accttataca agggatgtag ctatatctac   29580
cgcacctcag aatggtacta gtggagttat tcctgttaaa gaaggagact actttgagtt   29640
tgaggctttt caagattcag aaggtgacag acaattcaga gcagacccctt atacatggtt   29700
tagtattgaa gctatagaat tagaaactga aaccatggag aaagacttta tgcttatagg   29760
tcatagggga gcaactggat atacagatga acatacaata aaagggtatc aaatggcttt   29820
agataaaggt gcagattata tagaattgga tttacaatta acaaaagata ataagttatt   29880
gtgtatgcat gattctacta tagatagaac aacaacagga acaggtaagg tagggggatat   29940
gacttatct tatatacaaa ctaactttac atctcttaat ggtgagccta taccatctct   30000
tgatgatgta ttaaatcatt ttggaacaaa agttaaatac tatatagaaa ctaaacgtcc   30060
ttttgatgct aatatggata aagaattatt aactcagtta aaatcaaaag gattaatagg   30120
aattggttca gaaagattcc aagtaattat tcaatcattt gctagggaat cattaattaa   30180
tattcataat caattctcta atatcctttt agcttactta acaagtacat tctctgtgaag   30240
tgaaatggat gattgtttaa gttatggttc ttatgctatt gctcctaagt atacaactat   30300
aactaaagaa ttagtagatt tagcccatag taaaggactt aaagtacacg catggacggt   30360
aaatacaaaa gaagaaatgc aaagcttgat acaaatgggt gtagatggat ctttacaaa   30420
ctacttagat gaatataaaa agatttaata ttaaagacct attaatttag gtctttttttt   30480
agttgtaatt taaactagtt cgtgatatat tagtagtatg agatttatat acatactgaa   30540
aaggagagga taaaatgcca caatcagatg gaataagtaa tcttcataga atagctttac   30600
gcttccctaa agaaggcggt ggttatgata tgtatagatt taaagttaac cctgagaact   30660
acacaataga ttcaccacaa cgtacgcacg caattaaaac aaaatcagat attgtaatag   30720
aagattatgg taaagacata gaagttatta acttcacagg tacaactggt tttagacctg   30780
ttagagaagc agacggatta aaaacaggta aagaaagatta caaagtaag   30840
ttagtgaata tgctatgcaa ggtggtagtg gtaatgtaag tggttcttac ttacaatttt   30900
ttaacttta c agatgatagc tactataaag ttcattagc tcctcaaggg ttaaagataa   30960
ctaggtctaa agatgaacca ttactttta gatatgaaat aacattagta gttattggtt   31020
cgttaacaga agcagataga agtgctgtaa caacagaaga gtttggtaat gttaaaccta   31080
atgcttctca aagagtagat gagggtataa aagaattaga taaaaatgct cgtaaaacga   31140
```

-continued

```
gagatagaaa taatcaagaa atatctaaaa gagaaaatac aataacctaaa tctacaggag    31200
ataatacgaa tgagggtaat agacttaagc aaagcttccc tagtagttct atatataatc    31260
ctagacaatc tactaacgga ttaaaaggga atattgacaa tatggctctg ataataggtt    31320
acggtgatgg aggtgtatct agctaatgaa taattttata ccacaacctc aaggtctact    31380
cagattttta aatgccctag atacagattt aacttcttct cacatgaatt tactggatga    31440
agaggtatca tttgtatcta aattttacac accacagcta caattaagtg aattagcaaa    31500
aaaagtattg acaaatataa agacagatga tatacctgta ttagaaagag aatttaatga    31560
taatacaatt atccataaag ctaatgatac attactaaaa gtacaggctc caagaatgta    31620
tatgattcta cagtctattg tgcttgaagc atatgctatt gttaattgct ttgtagaaaa    31680
tccaagctct ttaaaatact taactgaaga agatgttagt ataacacgag aaaacttaaa    31740
ttatgtagct gactacttag gtaactatga tgactacaat agtgttgtct tagacttaag    31800
agatttagac ttatgtttta gtgcgataga attacaatta cctctaatta aaaaggaggc    31860
taatgtataa tgagatttaa gaaacacgta gttcaacatg aagaaacgat gcaagcaata    31920
gcacagagat actatggtga tgttagttat tggatagacc tagtagagca taataattta    31980
aagtatccct atttagtaga aactaatgaa gaaaaaatga aagaccctga acgattagct    32040
tctacaggtg atacactgat tatacctata gaatctgatt taacagatgt atcagcaaaa    32100
gaaattaatt ctagggataa agatgtacta gttgaattag ctttaggaag agatttaaat    32160
attactgcag atgaaaagta ttttaatgaa catggtacta gtgataatat actagcattc    32220
agcacaaatg gtaacggaga tttagatact gtaaaaggca tagataatat gaaacagcaa    32280
ttacaggcac gtttattaac tcctaggggt tccttaatgc tacatcctaa ttatggttca    32340
gatttgcata atttatttgg tcttaatata cctgaacaag ctacattaat agaaatggaa    32400
gtattgagaa cattaacatc agataaataga gtaaaatctg ctaatctaat tgattggaaa    32460
atacaaggta atgtttattc aggtcaattt tcagtggaaa taaaatctgt tgaagaatca    32520
ataaattttg tcttagggca agatgaggaa ggaattttg ctttatttga ataggaaagg    32580
attaaattat gaaaactaga aaattaacta acatactatc aaaattaata gataagacaa    32640
tggcaggtac aagcaagata acagacttta ctcctggttc agcttctcgt tcattattag    32700
aagctgtatc attagaaata gagcaattct atattctaac aaaagaaaat attgattggg    32760
gtatacaaga gggtatcatt gaagccttg atttttcaaaa aagacaatct aaaagagctt    32820
atggtgatgt tactattcaa ttctaccaac ccttagatat gagaatgtat atacccgcag    32880
gaacaacttt tacttcaaca cgacaagaat atcctcagca atttgaaaca ttagttgatt    32940
attatgcaga gcctgattct actgagattg ttgttgaagt ttattgtaaa gaaacaggg    33000
ttgcaggtaa tgttcctgaa ggaacaatta atactatagc atcaggttct agtttgatta    33060
gaagtgttaa taacgagtat tcttttaata caggaactaa agaagagagc caagaagact    33120
ttaagcgcag attccactct tttgtagaat ctagagtag agcaactaat aaatcagtaa    33180
gatatggtgc attgcagata cctgatgtag aaggtgttta tgtttatgaa gaaacaggac    33240
atattacagt atttgctcat gatagaaatg gtaatttatc agataccta aaagaagata    33300
taattgatgc tttacaagac tatagaccaa gtggtataat gttagatgtt acaggtgtag    33360
aaaaagaaga agtaatgtt tctgctcag taactatatc taataaaatct agaattggtg    33420
atacattaca aaaaacatc gaaggtgtta ttagaaagtaca tttaaataat ctaaaaacttt    33480
ctgatgactt aataaattaca gaccttattc aagctataat gaatattgat gatgtactaa    33540
tatatgatgt gtcatttgat aacctagatg agaacattat agtaccacca caaggaatta    33600
ttagagcagg agaaataaaa gtagaactaa agtaaagaga ggtgaaactt aagtcgtggc    33660
taatttttta aagaatcttc atccattatt aagaagagat agaaataaaa aagatatca    33720
agaccctaac tttgctctga tagatgcact caatgaagag atgaatcaag tagagaaaga    33780
tgctatagaa agtaagttac aatcttctct aaagacatct acaagtgaat atttagataa    33840
gtttggggat tggtttggag tttatcgtaa gacagatgag aatgatgatg tttatagagc    33900
aagaattata aaatatttac tcttgaaaag aggaactaat aatgctataa tagatgctat    33960
aaaagattat ttaggtaggg atgatattga tgtaagtgta tatgaacctt ttacaaatat    34020
tttctatact aacaaaatcac atttaaatgg tgaagaccac ttaatgggat actattatag    34080
atttgctgtt attaatgtct ctataggtga ttatttccct gtagagatta tagatgtaat    34140
taatgaattc aaacctgcag gtgtaacttct gtatgtcact tatgatggag cttctactat    34200
tagaggtgga gcaattatta agtggttaga tgggttacct aaaaatagaaa catatcaaga    34260
gtttgatagg tttacaggat acgatgatac attctatggt catattaaca tgaatcaaag    34320
taaagatact gataatagta catcagatat ttttaaaaca aaccatagct taattaatag    34380
tttagatgtt ttaacaggtt cctctagcgt aggtagacag tatgttaact atggatatat    34440
aacgtcatat gtttataatc caggtatgac atcttctgta aatcaaataa gcgctagtac    34500
agaaggtaga gggcaagaag tacctactga ctattatatg tatactagta ctaagaataa    34560
caatacagta gaacttagta tgcaaactac ttccggtgtg tcttatttat ataataactt    34620
taattttagg gattatatga gtaaaatatag acctcaagta aattacaat ctgatgagga    34680
tagaagaatt gtatctgatt atatataaaga attaagtatt gattattatc tcagtgctgt    34740
aatacctcct gatgaaagta tagaaattaa attacaagtt tatgattttt ctattaatag    34800
atggcttaca gtatcaatta ataatttatc tttctatgaa aaaatatcg gtagcaatat    34860
aggatatata aaagattatt taaacagtga attaaatatg tttactagat tagagataaa    34920
cgcaggtaaa agagattcag tagatattaa agttaattac tgtttaatta tgggatatat    34980
ttatgaacga ggtatttata caataaaacc ttataaagcc ttagtagaaa attatttaga    35040
tatatctaga gagacttacg tagaggcatt taaaatagca tcactatcta atggagagat    35100
tataactaaa acaggctatt tacctatagg ttatctaaga gtatcaggag gtattgataa    35160
cctaagtaac catatagaaa ttattactac ag ataataac actaatagta ttccaagtac    35220
tattttagaa gataactcta atagtgttga attatcgtat ggtaacgtca aaaccaatat    35280
acacagtttt gaattaaata gtgatgtttc aatttcaaat attaaatttg aatactctta    35340
ttatggtgat gcttgggaag aactgacagc attaactgaa atatctgagg gtgaaactat    35400
agtacctaat atattaatag atttttatatg gattacagaca gtagattatt ctaatataaa    35460
tccaatgtca aaagtgtcat tacgttctat ttggaatgtt aagctaggtg aattgaacaa    35520
tcaagaaggt tccttatcta atatgcctaa tgattacttt aatgctgtat ggcaggatat    35580
agataaatta tcagatattg agttaggttc tatgagaatg attaaagaca ctgagggtgg    35640
agtatttgat ggagctacag gtgaaattat taaggctact ctatttaatg tcggtgctta    35700
tactgattta gacatgttag cttatacttt gactaactat actgaaccat taacgttagg    35760
ctctagtcga ttaataagtg agctaaaaga agaactatta acatcagaat catttaatgt    35820
cgataataga attaaaagta attgactcaat atctgagcag ttacctaata acaatatatt    35880
```

-continued

```
aagtaactct taccaaacac aaactattac acagaatgga tttgctaagt ataatttgaa   35940
agaacctata gagcgagaa aacaatacaa tctaagaata catggagatt ttaaagaagg    36000
gttagaaaga ttagctatag gcaattctaa tggttcattt aatgaagtat ttgtttaccc   36060
tgaaaatatt aaagatggta tagtagatat tacttacact tctagagatg ataattacgc   36120
agaaggaaaa caaaggctta ataatgatta tagagtttac gctcaaccat gcgatagtaa   36180
agtagtaaca atttacagtt tagagttaat aaaagtttaa taaataagtt gacagaaagt   36240
taataatatg gtatacttat aaagtaatat ttagtgggta taccatgtta tattaataaa   36300
gaaaacaaca gatgaaagga attaaaaaat atggcaattg caacgtataa ttctcatgtt   36360
gagttagcaa aatatctagt tagtaaagct gattcagttt acttaacaat tggaaagagc   36420
acaccgtggt ctaatgaaac aaacccaccg caacctgatg aaaatgcaac agtattacag   36480
gaggttatag gatacaaaaa agctactaaa gtaactttag ttagaccttc taaatcacct   36540
gaagatgata ataagaattt aatttcttat ggtaataaat catgggtaga agtaacacct   36600
gaaaatgcta aagatgaagg agctaaatgg gtttacttag aaagcagtat tgttggtgac   36660
gaactacctc ttggaacata tagacaagta ggatttgtta tggacttagt agcaaaaagt   36720
ggtattagta aatttaactt agtacctagt gaagtagaat caattggaac attgttattc   36780
tttgataata aacaattcca aaatagaagt gagcaaacaa ctgctaaaga aagatttatt   36840
gtagaagttt aaagaaaggg agataattct aaatggcaat taattttaaa ggttcacctt   36900
atttagatag atttgacccg tctaaagata gaacaaaagt attatttaat cctgatagac   36960
ctctacaaca ggcagaatta aatgaaatgc agtctataga ccaatattat ttaaaaaatc   37020
taggagacgc tattttttaaa gacggagata aacaatcagg tcttggattc acattatctg   37080
aagataatgt attgacagta aatcctggtt atgtatatat caacggtaaa ataagatatt   37140
acgataatga cgattcagtt aaaataactg gcgtaggtaa agaaactatc ggtattaagt   37200
taacagaacg tattgttaca cctgatgaag atgctagcct actagaccaa actagcggag   37260
taccaagtta cttctctaaa ggtgcagata gattagaaga gaagatgtca ttaactgtta   37320
atgaccctac atcagcaact atttatactt tcatggatgg agatttatat atccaatcaa   37380
ctaatgctga gatggataaa atcaataaag tattagctga acgtacttat gatgaatcag   37440
gttcatataa agtaaatggt ttcgagctat tctcagaagg taatgctgaa gatgatgacc   37500
acgtttctgt agttgtagat gcaggtaaag cttacgtaaa aggtttttaaa gtagataaac   37560
cagtatctac aagaattagt gtacctaaat cgtatgactt aggaacagca gaaaatgaaa   37620
gtactatctt taataagtct aataattcta ttagtttagc tatagccct gtaaaagaaa   37680
ttagacgtgt tacaggtcaa gtacttattg aaaaagaacg agttactaga ggagcagaag   37740
gtgatggaca agacttctta tctaataata cagcgtttga gattgtaaaa gtttggactg   37800
aaacaagccc tggagttact acaaaagaat ataaacaagg agaagacttc agattaacag   37860
atggtcaaac gattgactgg tcacctcaag gtcaagaacc ttcaggaggt acttcatact   37920
atgtttctta taaatataat aaacgtatgg aagttggtaa agattatgaa gtaacaactc   37980
aaggtgaagg gctaagtaag aaatggtata ttaattttac acctgaaaat ggggctaaac   38040
ctattgacca aacagtagta ttagtagatt atacttacta cttggctcgt aaaagattcag   38100
tgtttattaa taagtatggt gacattgcaa tattacctgg tgaacctaat attatgagat   38160
tagttacacc accattaaac acagaccctg agaatttaca attaggtaca gttacagtat   38220
tacctgattc agatgaagca gtatgtgtattt catttgcaat cactagattg tctatggaag   38280
acttacagaa agttaaaaca agagtagata acttagagta taaccaagca gtaaatgctc   38340
tagatgatgg tgctatggaa ggacagaacc ctctaacatt acgttcagta tttagtgaag   38400
gtttcattag tcttgacaaa gcagatatta cacatcctga cttcggaatt gtatttagtt   38460
ttgaagatgc agaagctact ctagcttata cagaagcagt taaccaacct aagattattc   38520
caggagatac cacagctcat atttggggta gattaatttc agcaccattt actgaggaac   38580
gtacaatcta tcaaggtcaa gcatcagaaa cattaaatgt taacccttat aatattccta   38640
acaaacaagg tgtgttaaaa ttaacaccta gtgaggataa ctggattgat actgaaaatg   38700
ttacaatcac tgaacaaaaa actaaaaaag taactatgaa acgatttggg agacataatg   38760
aaagttacta tggtgagact gagcattact tgtattctaa cttacagtta gatgcaggac   38820
aaaagtggaa aggtgaaact tacgcttatg atagagagca tggtcgtact ggtactttat   38880
tagaatcagg aggacaacgt actctagaag aaatgattga attcattaga atcagagatg   38940
tatccttcga agttaaagga ctaaacccta atgataataa cttatatta ttatttgatg   39000
gagtaagatg tgctataaca cctgcaactg gttatagaaa aggctctgaa gatggtacaa   39060
taatgacaga tgctaaagga acagctaaag gtaaatttac tattcctgca ggtattcgtt   39120
gtggtaaccg agaagttacc cttaagaatg ctaactctac aagtgctaca acttacacag   39180
ctcaaggacg taaaaaaatc gttcaagata ttattatcag aactcgtgta acagtaaact   39240
tagtagaccc gttagcacaa tcattccaat atgatgagaa cagaactata tcatcattag   39300
gattatactt tgcttctaaa ggtgataaac aatctaatgt tgttatccaa attagaggta   39360
tgggtgacca aggttatcct aataaaacaa tctatgcaga aacagttata aacgctgatg   39420
atattaaagt atctaataat gctagtgctg aaactagagt atactttgat gaccctatga   39480
tggctgaagg cggtaaggaa tacgctattg ttattattac tgagaacagt gattatacaa   39540
tgtgggtagg tactagaact aagcctaaaa ttgataaacc taatgaggtt atctcaggta   39600
accccatacct tcaaggtgta ttattcagtt catcaaacgc atcaacatgg actcctcatc   39660
aaaactctga ccttaaattt ggtatttaca cttctaaatt taatgagaca gcaacaattg   39720
aattcgaacc aattaaagat gtatctgcag atagaatagt tcttatgtct acgtacttaa   39780
ctcctgagag aacaggatgt acatgggaaa tgaaaataat tctagatgat atggcatctt   39840
ctacaacatt cgaccaattg aaatgggagc ctattggtaa ctatcaagat ttagatgttt   39900
tagggctagc aagacaagtt aagttaagag caacttcga atctaataga tatatctcac   39960
cattaatgag ctccagtgat ttaacattca ctacattctt aacagaatta acaggttcat   40020
atgttggtag agctattgat atgacagagg ctccttacaa tacagtaaga tttagttatg   40080
aagctttctt acctaaaggt actaaagtag ttcctaagta ctctgatgat gatggaaaaa   40140
cttggaaaac atttactaaa tccccctacaa ctactagagc caataatgag tttacacgct   40200
atgtcattga cgagaaagta aaatcatcag gaacaaaatac taaactacaa gttagattag   40260
atttatcaac tgaaaatagc tttttacgtc ctcgtgttcg tagacttatg gttactacta   40320
gggatgaata aactagaggg gttgattgac ccctctttat ttaataagga gagatttata   40380
tgcctagaga agttagagac ccttattctc aagctaaatt atttatacct acagttgagg   40440
aaaaatcaat taaggaatta gaaaaaacat acaaagaaaa aattgatgaa gctactaaat   40500
taatcaatga attaaagaaa gagagaggag aaaaatagat ggcatttaac tacacgcctc   40560
ttactgaaac acagaagcta aaagacatgt atcctaaagt taatgatata ggtaattttt   40620
```

-continued

```
taaaaacaga agttaacctt agtgatgtaa aacaaatatc acagcccgac tttaataata  40680
ttttagcatc tatacctgat agtggtaact attatgtaac taattcaaaa aatgcaccca  40740
gtggagaatc tacggcagga tttgtaatac tggataaaag aaatgtaaat tattataaaa  40800
tttactattc accatatagc agtaataaaa tgtatatcaa gacttatgct aatggtactg  40860
tatatgattg gattagtttt aaattagatg aaggtaacct ctacgatgaa ggtaatactt  40920
taaatgtaaa ggaacttact gaatctacaa cccaatatgc aactcttatt aaccctccaa  40980
aagagagctt aaatacggga tgggttaatt acaaagaaag taaaaacggt gtttcttctt  41040
tagtagaatt taacccggtt aactctacct caactttcaa gatgataaga aagttaccag  41100
tacaagaaca aaaacctaac ttattgagag atagtttatt tgtttatcct gaaactagtt  41160
cttcaaatat caaaacagat aattggagta cgcctccttt ttggggatac acagctaata  41220
gcggtcgttc aggggttaga tttagagggg aaaatactat acagcttgat gatggcagta  41280
gtacctaccc tacagcaatg actaatagat ttaaaatggg taacgagcta tctgtaggag  41340
atacaataac tgtatctgta tatgctaaaa ttaatgaccc aacgttactt aaagataata  41400
aagcatactt tgagatagcg gggtatgata cggtagatag agctgataat ccttatacag  41460
gaggacgtag agaaataaca gcaagtgaga taacaactga gtggaaaaaa tactctttca  41520
cattcacgat acctgaaaat acaataggtg aatcaggtgc aaaagttaat tatatttcat  41580
tactcttaag aatgaattgt tcatctagta aaggtaatg tgctgtagta tactatgctc  41640
tacctaaatt agaaaaatca tctaaagtta caccgtttat cacacatgca actgatgttc  41700
gtaaatatga tgagatttgg tctaactggc aagaagttat tagtaaagat gaattaaaag  41760
gtcactctcc tgtagatata gaatataatg attactttaa gtaccagtgg tggaaagctg  41820
aagttaatga aaagaactta aaagatttag ctatgacagt acctcaaggt tatcatacat  41880
tttattgtca aggttctatt gaaggaacac ctagaggacg ttctattaga ggaactattc  41940
aagtagacta tgacaaaggt gacccatata gagctaataa gtttgttaaa ctattattta  42000
ctgacacaga tggtatacct tatacattat actatggagg gtacaaccaa ggttggaaac  42060
ctttaaaaca acaaagaaca tctacaatac tttgggaagg tactttagac tatggttcaa  42120
aagaaaatat aactttaaat gaccccttgga ctaactata tatgttagaa gttgtgtatc  42180
taacacaatc agcaggtcac tataaaacaa tgttttttaga cttaagaacg cctacaacgc  42240
catatttata tataagagac ttcaatctag ctaatagttc tacaggctca ggggtagact  42300
ttttttgaagg gtatctatct ttcccaacaa caacttcagc tacacctact atggttaaaa  42360
aagttacttt aaatgggtct acaaatacga catctgtatc tgatttcaat gctcaaggaa  42420
taataactat atatagaata gcaggaatta atacacttta ggaggataaa taggatgact  42480
agacaatttg atattggcag agatgagata gtattacatc taagagaagg taaatatatt  42540
acagggttca caacagcagg ggcttatgat acagattttg ggcagataaa agttaataga  42600
gaaattttac ctgcttactt ctttgataat tttgcctatg aaagatactt gtattatagt  42660
aaacctgaag aggttatga aaaataaagac tatgtaccac ctcaaatcaa taatggtgat  42720
gaggaatctc aacaaaatac tgtacctaaa gaacaatatg atagtttaaa agaagaacta  42780
gaacttatga gaaaacaaca agaagctatg atggaaatgc ttcaaaaaact cttaggtcaa  42840
aaggggtaat aataaatggc attaaatttt actacaataa cggaaaacaa tgttattaaa  42900
gacctgacta ctcaggtcaa taacattgga gaagaattaa caaaagaaag aaatatattt  42960
gacattacag atgatttagt ttataatttt aataaatcac agaagattaa actaactgat  43020
gataaaggat taactaaatc gtatggaaac ataacagctc ttagagatat aaaagaacca  43080
ggttactact atataggcgc tagaacatta gcaacattat tagatagacc tgatatggag  43140
tctcttgatg ttgttttaca tgtagtacct cttgatactt ctagtaaggt agttcaacat  43200
ttatatacgc tatctactaa caataaccaa attaaaatgt tatataggtt tgtctcagga  43260
aactctagtt cagaatggca atttattcaa ggattaccga gtaataaaaa tgctgttata  43320
tcaggaacta atattctaga tatagcttca ccaggtgttt attttgttat gggaatgaca  43380
ggagggatgc ctagtggtgt agattcaggt tttttagatt taagtgtaga tgctaatgac  43440
aatagattag ctagactaac tgatgctgaa actggtaaag aatatactag tattaagaag  43500
cctacaggag tatacacagc ttggaaaaaa gaatttgagc caaaagatat ggagaaaatat  43560
ttactaagta gtatcagaga cgatggtagt gcatcattcc cactcctagt ttatactagt  43620
gataataaaa cgtttcaaca agctattata gaccatatag atagaacagg tcaaacaacc  43680
tttactttct acgttcaagg tggtgtatca ggttccccta tgtctaatag ttgtcgaggg  43740
ttattcatgt cagatacacc taacacttct agtttacatg gtgtgctataa tgctataggt  43800
acagatggta gaaatgtaac aggttcagtg gtaggaggta attggacttc accaaagaca  43860
tcaccttccc ataaagaatt atggacggga gcacaatcat tcctatctgt aggtactact  43920
aagaatctag cagatgatat tagtaattac tcttatgtag aggtttatac taaacataag  43980
acagtagaga agactaaagg taatgatgac tcaggtacaa tttgccacaa gttctacttta  44040
gatggtagcg gtacttacgt ttgctcagga acttttgttt caggagatag aacagataca  44100
aaaccacctg ttacagagtt ctatagagta ggtgtatctt tcaaaggttc aacatggaca  44160
cttgtagata gtgcagtaca aaatagtaaa actcaatacg ttacaagaat tataggtatt  44220
aatatgccat agactaggat aagtttccta gtctttttttt cttgacttga aaaggattct  44280
atggtatact ataactcgtg taaggatata aggagattaa aatgagatta agaattaaaa  44340
acttatatac ctatgtagaa tttgaggagg atgataaata cttaaaagat atatttttaa  44400
agagagtcca tacaactata ggagcaaggc aagaaggttt tcagtatagc cctgcttaca  44460
aaagaggcag ttgggacggg tatgtagact tttatgttta tgaggaagat aaaattcccta  44520
ctggactttt atttaaaatt gagttattat taggtgagct acaatcaagg tataacttcc  44580
agtttgaaac aattgatgag cgtgatgaaa gtttcttatc tgaagaagat attgatgatg  44640
agataacatt gcttgataat aatgtaggtc aaattacctt acgagattat caatatgagg  44700
cagtgtacaa cagcttaaca ttttacaatg gtattgctca tttagctact aatggaggta  44760
aaactgaggt tgctagtggt attatagacc aactattacc tcaattagaa aaaggtgaaa  44820
gagtagcatt cttcacaggc tctacagaga tattccatca gtctgcagat agactacaag  44880
aacgtttaaa tatccctatc ggtaaagtgg gtgcaggtaa gtttgatgtt aagcaggtta  44940
cagttgtaat gatacctact ttaaatgcaa accttaaaga cccaacacaa ggggtaaagg  45000
ttacacctaa acaaaatatt agtaaaaaga ttgctcaaga gatattacct aaatttgaag  45060
gtggaacaaa tcaaagaaa ttactaaaag tattacttga taacacaaca cctaaaacaa  45120
aagtagaaca aaacgtatta agtgccttag agataaattta ccaaaacagc aagacggatg  45180
cagaagtttt attaaactta agaaatcata atgcacattt tcaaaaaatt gttagagaaa  45240
agaacgaaaa gaaatatgat aaatatcaag atatgagaga tttttttagac tcagttacag  45300
ttatgatagt tgatgaggca caccattcta aatctgattc ctggtacaat aatctaatga  45360
```

```
catgtgaaaa agctttatat agaattgcat taacagggtc tatagataaa aaagatgaat   45420
tactttggat gagattgcag gcgctattcg gtaatgttat tgcaagaact actaataagt   45480
ttttaattga cgaaggtcat tctgctagac caacaataaa tattataacct gtagctaatc   45540
ctaatgacat agatagaatt gatgattata gggaagctta cgataaaggt ataacaaata   45600
atgattttag aaataaactt attgcaaaac taacagaaaa gtggtataat caagataaag   45660
gtacattgat tattgtaaac ttcatcgaac atggagatac aatatcagaa atgttaaatg   45720
atttagatgt agagcactac ttcttacatg gagaaataga ctctgaaact cgtagagaaa   45780
aattaaaatga tatgagaagt ggtaagctta aagtaatgat agctcacatca cttattgatg   45840
agggtgtaga tatatccggt attaatgcgc taatattagg tgcaggaggt aaatcgttaa   45900
gacaaacatt acaacgtatt ggtcgtgcgt tacgtaagaa gaaagacgat aatacaacac   45960
aaatatttga ttttaatgat atgacaaata gattttttata tactcatgct aatgagcgta   46020
ggaaaattta tgaagaggaa gattttgaaa taaaagactt aggaaaatag gagggtaaga   46080
gatggcaaca agaacacaac gaaagttata ccaatatcta gaagaaaatg ctacagaaaa   46140
taaatttcat atttctacta agaaagagtt agcagattct ctaggcgttt ccatctctgc   46200
tttatccaat aaccttaaaa agttagaaga agaaaataaa gttgttactg tttctaaaag   46260
aggaaaaaat ggtggagtaa taataacttt agttagggaa tatgcacag aagaattgaa   46320
agaatttaat aattctacag ataatatcat tacttctgat ttacagtatg ctaaagcatt   46380
aagagaaaag cactttcctt cttatagata cgagaggaaa gaacagcgta gacgtactaa   46440
gttagaaatg gcacagtata atgctattaa agatgaaaag agaagaatta tagcagatat   46500
gaactttcat tcagaaggtc ttccttatcc ttctaaagat atatttaata tgtcttatga   46560
cccggaagga ttttataaag catacattct atgtaagtta tatgaccaat atgctatttc   46620
tcatatggat gctaaacata caagccatct taaagcaagt agtaaggcaa caactaaaga   46680
tgaatatgat taccatcaac atatgtctga atactataga aataaaatga ttcaaaattt   46740
acctagaaat agtgttagtg ataatttctt cggtagtaaa atgtttaata ctttctataa   46800
ttttttattta aaaataaaag ataaaaatat taatgtattt aaatatatgc aaaacgtatt   46860
taagaatgta acattttatt atgagaatgg tatgcaacct aatccaatac cttctcctaa   46920
cttctttagt tcagataagt attttaaaaa ctataataat tatattaaag gaataaaaaa   46980
aggtgttaat agtacaaata gacacttagg ggatacagat agtattatta attcatcaga   47040
ttatgttaag aaccctgctg tattacattt acatcaatta tatactacag gattaaattc   47100
tactttacat gatattgata ctatgtttga gcaagcctta gaccttgaga atgcttctta   47160
tggactattt ggagatatga aacatattat tttactacaa tataattcta tgattgaaga   47220
agaaattaag aacttaccta cagaagagaa aagtattatt aataaaatatg taaaacaatg   47280
cataattaat gattactccc caacaagcat atcaccatct gcaagattat caatgtttac   47340
tatgcagaaa gagcatatag tttataataa acagttaaac agaggaatca agagagaaga   47400
tttattacca ttaagtctag gaggtatagt gaataaagat tcactaagtg gtatggtat   47460
acaaaactta gagcagaatg gtaatgagta cctatatatg agacaacata cttcaactta   47520
ttatatacta agaatgtttg gtgattatct aggatatgaa gtaaacttaa gagaagtaaa   47580
atatattgta gagaaatata atttaattga taaaatacca ttgacaaaag agggtatgtt   47640
ggattataat aaacttatac atttagtaga ggaagaggtt aataactatg agtaagaaga   47700
taaaggagct tatccttcat aaatcaatga aggatataca ttttgcaaga gaagtactag   47760
ataacttacc taagaaccta ttttcagcag aatctgaaga tatgggttac ttatttacag   47820
ctataaaaag aacagcacat atttccgata agatgtctaa tgaagcatta gcaattaaag   47880
tagaacgact tatgggaaat aataaggaag atgaagaaaa agtaaccaag acattgactt   47940
acttagaaga tttatataaa gtagatgtta atgaaaaaga tgaatctgtt aattatgaaa   48000
tagagaaata tattaaaaca gaaatgtcta aggaagtatt agttaagttt attgcagaaa   48060
ataaacaaga agactcagac aatttacatg aacttgtaga taaattaaaa caaatagaag   48120
taagtgatat ttcaggaggt aacggagaat ttattgattt cttcgaagac actgaaaaga   48180
aacaagaatt attaagtaat ttagctacaa ataaattctc tacaggattt aactctattg   48240
ataatcatat tgaaggtggt atagcaagag gagaggttgg attaattata gctccaactg   48300
gtagaggtaa atcattaatg gcttctaact tagctaaaaa ttatgtgaag agtggattaa   48360
gtgtttttta tattgcatta gaggaaaaaa tggatagaat ggtattacgt gcagagcaac   48420
aaatggcagg agcagaaaaa agccaaattg taaaccaaga catgtcttta aacagtaaag   48480
tttatgatgc aatacaaaac cattatcaga agaatagaaa gttactaggt gactttttata   48540
tttctaaaca tatgccagga gaagttacac caaaccaact agagcaaatt attgttaata   48600
caacaatcaa gaaagataag catattgatg ttgttattat tgactaccct cacttgatga   48660
gaaatccata tgctaaatat cactcagaat cagatgcagg aggaaaaactg tttgaagata   48720
ttcgtagatt atcacagcaa tatgggtttg tatgttggac tttagctcag accaaccgtg   48780
gagcttatgt ttcagatgtt attacaagtg agcatgtaga aggttctcgt aagattgtca   48840
atgctgttga ggtttctcta gcagtaaacc aaaaagatga agaattcaag agtggtttcc   48900
taagattata cttagataaa attcgtaaca gttctaatac aggggaacga tttgttaatc   48960
ttaaggtaga accaactaag atgattgtaa gagatgaaac accggaagaa aaacaagaac   49020
atatacagct attatctgac aatggaaaag aagatacaag taaattccaa aataaagata   49080
ataaaataga agctataaat aacacattcg gaggattacc gggagtttaa atttttacta   49140
tataccactt gacattttat atgttaggtg gtataattat tttataaaga ataaaaggag   49200
agattaatat gaaaattaaa caaatattac ctagtaataa tccaaacaaa tatcacctt   49260
tgattgagag caagctaata cctagttact actcaacaag agatgatgtt tataatgatt   49320
attatgattt aaatctatat ggtatgtttg atgatagtaa aaatttatta tgttcatgtg   49380
caatagaaaa gtataatgaa ttagtattta tgaaaaggt tgttatggtt ggggaacatg   49440
gtaatggata tttttaaacag tggtttctc ttataataaa agagaacct catatatgtt   49500
taactataaa taaagataat attaaagtag ctgatatctt aaatgaacta ggatttatta   49560
atgcaggaga agtaattgat agaacaggaa agtatactta tgaattatac caaggaggaa   49620
gagcttaatg aagtttgtat tttttacaga tagtcatttt catttattta caaactatgc   49680
aaaacctgat gatgaatttg taaatgatag atttaaagag caaatagaag cattacgaaga   49740
agttttgat attgctagga aagaaaaggc taatgttatt ttcggaggag atttattcca   49800
caaacgtaat tcagtagata ctagagtata taacaaagta tttagtacat ttgctaaaaa   49860
taaagatgtc cctgtattat tacttcgagg taatcatgat gctacaacta attccattata   49920
taccgattca agtatagata catttgagta tttatctaat gtaagtgtaa taaagtcatt   49980
aaatacaatt ttaaaagata atgttaatat tgtatttaca gcttatggag atgaaacaga   50040
agaaataaaa acctacatta acagtaacta tgataaagat atggttaata tactagtagg   50100
```

-continued

```
tcatctaggt gtagaagggt cattaactgg taaaggttcc catagattag aaggagcctt   50160
tggatatcag gacttattac ctgataaata tgattttatt ttactaggtc attatcatcg   50220
tagacaatat ttccaaaacc caaaccattt ttatgggggt tcattaatgc aacaatcatt   50280
ttctgatgaa caagaagcta acggtgttca cctaatagat acagaaaaga tgaccacaga   50340
atttattcca attcatacac gtagatttat tactatccag ggagaagata tacctgaaaa   50400
ctttgaacaa ttaatagagg aagataattt tattagagtt attggtacct caaaccatgc   50460
taaagtttta gagatggatg atagtatgaa ggataaaaac gttgaagttc aaattaaaaa   50520
agaatatact gtagagaaac gtatagatag tgatgtatct gatgaccctc taacaattgc   50580
tagcacttat gctaagcaat actcacctga atcagaacaa gaaatacttg aatgtttgaa   50640
ggaggtttta tagtgagaaa atataaagaa tatctaaaca agtcagatga agaaaattta   50700
gcagaagatt gggaacggat aaaagaagat ttatggaaag tgtttaaaga tatgaaacct   50760
aaaattaata cattagacat cagtaatgta gtaagtaaag acttagataa aagtaagcct   50820
attttacaat ttcaagattc agacagagta atagagaaca tttgtaatgt tgaaggttta   50880
gaagatggt tatctaaaat gaaaaagatt tttgacgata gtaattttga aaaacattac   50940
tataatagaa ttgtagaaca tgatgaatat tattggattg attatggttc tcatcattgt   51000
ttctttaggg ttacgaaagg agataagtaa tggtcgtatt taaacaagta gaagttaata   51060
attttttagc aattaaagag gctacactag agtttagataa tagaggttta atacttattg   51120
aaggtgaaaa taaatccaat gagtcattcc attcaaatgg ttccggtaag tcaactttaa   51180
tatctgccat tacttatgct ttatatggta aaactgaaaa aggattaaaa gcagatgatg   51240
tagtaaataa tattgagaag aaaaatacat ctgttaaact taagtttgat attggagaag   51300
atagctattt aattgaacgt tatcgtaaag ataaagagaa taagaacaaa gtaaaattat   51360
ttgttaatga taaagaaatt acaggctcaa caaatgatgt tactgataaa cagatacagg   51420
atttatttgg tattgagttt aatacgtatg ttaatgctat catgtatggt caaggagata   51480
ttcctatgtt ctctcaagca acagataaag ggaaaaaaga aattcttgaa tctattacca   51540
agacagacgt atataaacaa gcacaagatg tagcaaaaga gaaagttaaa gaagtagaag   51600
aacaacagaa taatctaaga cacgaaatag ataaactagg gtatcagtta tctacaaaag   51660
atgaatactt tcaaaaggaa attgaacagt ataatcaata taaagaacaa ttggctcaaa   51720
tagaaaatag taataaggaa aaagataaat taagggagca agaggagaag caaatagaag   51780
ctcaaataga gcaattaact tcacagatac caacaatacc tgaagatgaa tttaagcact   51840
cagaggagta taataaagct tctctcaaagcc tagatttact ttctaataaa ttaactgaac   51900
taaatcaagt atatgcagag tataatacta aagagcaggt actaaaatct gaaatagcta   51960
cattaagtaa tagcttaaat caattagata caaatgacca ttgtccggtt tgtggttctc   52020
ctatagataa ttctcataaa ttaaaagagc aggaaaatat taataatcag attgagaata   52080
agaaacaaga gattactagt gtactagaaa ttaaagatac gtataaagaa gctattgata   52140
aagtaaataa taaatcacaa gaaattaaag acaaaatgtc tcaagagac caacaagaac   52200
gagagcacaa cactaggatt aataatatca ttcaagaggc ttccaagatt aaatcagata   52260
ttagttcatt agagaataat aaaacttatt taaaagtgaa atatcaacat caatctgttc   52320
aaggattaga aagagaagaa ccaagtaaaa agaaacatga agaagataaa aaagaattac   52380
aagaatctat tgacaaacat gaagagaatg tagtacaatt agaaactaag aaaggtaagt   52440
atcaacaagc tgtagacgct tttagtaata aaggtatacg ttcagtagtg ttagactta   52500
ttacaccctt cttaaatgag aaagccaatg aatatcttca aactttatca ggttcagata   52560
ttgaaataga gtttcaaact caagtgaaga atgctaaagg agaactaaaa gataagtttg   52620
atgttattgt taaaaatagt aaaggtggag gctcatataa atcaaactca gcaggagaac   52680
aaaaacgtat tgacttagca attagttttg caatccagga tttaattatg agtaaggatg   52740
agatatctac aaatattgca ctttatgatg aatgtttttga tgggttagac actataggt    52800
gtgaaaatgt aattaagtta ttaaaggata gacttaatac agtaggaact atatttgtaa    52860
ttacccataa tacagaactt aaaccactgt ttgagcaaac aattaaaata gtaaaagaaa   52920
atggagtatc aaaactggag gaaaaataat gaaattaaag attttagata gagataatgc   52980
aacacttaat gtgtttcatc gtaataagga gcacaaaacg atagataatg tacctactgc   53040
taacttagtt gattggtatc ctttaagtaa tgcttatgaa tataagttaa gtagaaatgg   53100
agagtatttta gaattaaaaa ggctacgttc taccttacct tcttcttatg gcttagagga   53160
taataaccaa gatattatta gagataataa ccatagatgt aaaataggat attggtataa   53220
tcctgcagta cgtaaagata atttaaagat tattgagaaa gctaaacaat atggtttacc   53280
ggttataaca gaagaatatg atgctaatat tgtagaacaa gggtttagag acattggagt   53340
tatattccaa agtcttaaaa ctattgttgt tactagatac ctagaaggta aaacagaaga   53400
agaattgaga atttttaaca tgaaatcgga gagtcacaca ttaaatgaag cacttaaaga   53460
gagtgatttt tcggtagatt taacttatag tgacctaggg cagatttata atatgttact   53520
attgatgaaa aaaattagta aatagtaagg aaggatatta tgaggtttga agacttttta   53580
acccaagaat taggagaacc aaaaagaaaat actataggtg aactaagata ctgttgtccg   53640
ttttgcggag aaaaaagtta taagttctat gttaagcaag ctttagactc tagtaatggt   53700
cagtatcact gtaaaaaatg tgatgaatca ggtaatccta ttacatttat gaagacttat   53760
tataacatta caggtaaaca agctttttgat ttattagagt ctaagaatat agatatagag   53820
agagcccctt tacttacaac taataataag gatttaacag aatcagagaa acttatatta   53880
atgcttagg gcgtacacca agataaagga aacactaatc ttaaacctcc tagattacct   53940
gagggatata agttattaaa agataactta aataataaag agattatacc ttttttaaaa   54000
tacttaaaag gcagaggtat aactttagaa caaataatta ataataatat aggttatgtt   54060
attaatgggt gcttctataa agttgatgga gaatcaaaag tctcattaag gaatagcatt   54120
atattttta cgtatgacta tgatggaaac taccagtact ggaatacacg aagtatagag   54180
aagaaccctt atatttaaatc tatcaatgcc cctgctaaac aagtagaagt aggaagaaaa   54240
gatgtcatat ttaaatttaaa tatagcaaga aagaaaaaaat tcttagttat aaccgagggt   54300
gtctttgatg ctttaacctt tcatgaatat ggagtagcaa cactaggtaa acaagtaaca   54360
gaaaatcaaa taaaaaaaat aattgattat gttagcatag atacatcaat atatattatg   54420
ttagatactg atgcgttaga taataatata gatttagctt ataagctaaa aacgcacttt   54480
aacaaagttt attttgtacc gcatggtgat gaagatggtt atgatatggg aacaaggaaa   54540
gcttttgagc tattaaaaca gaaccgagta ctagtaacac ctgaaagtat acagagttac   54600
aaaatacaac aaaaacttaa actttaggct tgacctagagagaagtttat gttatactaa   54660
taattaagta attaataaag gagaaaaaat aatgtcaaat aataaaaag atattttaga   54720
atttgtagat gaatacatta cagctttaag agttggtaat gagcaacgac aacatcaatt   54780
agaagaaatg ggtaaagaag aaacagcaac attaacagat gtagctaaag ctattactaa   54840
```

-continued

```
ccttatgtta ggtgttaatg agcaaatgac agacttggaa tacaacaatg agttaaattt   54900
aaatattta attgacgctt tatataaagc agaacttatt aatgaagatg tactagatta   54960
catccaagaa tcaattgata aatcacaaga agaacctaaa aatgaagaag aaaaaggaga   55020
acaagaataa tggaaaaaaa tattagcaca cacacaaaag gtattagtca agcagacatg   55080
gagaaatgga ttgaagctgt agtccaagga actgttgatg gtaaacaagt tgatgaaaaa   55140
acagctaaac aactagatag aattggttca cgcagtgttt ctttagaaga agcaactcgt   55200
attgctaaag tcattaatgc tgttacagtt caagagatgt caggagattt taatgacgca   55260
tttaacgcaa ttgacttaat gatgattgtt atggaagatg agttaggagt aactcaagaa   55320
caagttggaa aagctaaaga taagttaaat gagaaacgag aagcttattt aaaagagaag   55380
caagaagaat tacgtcaaaa acaacaagaa gagacacaaa aagaaactga atctgacagc   55440
aatgaaaaag taattcagtt gaagaaaaat gacgaacagt aagaaaaaag gagatacatt   55500
cgaacgtaaa atagctaaag aattaactgc ttggtgggga taccaattta ataggtctcc   55560
tcaatcaggt ggtgcctctt ggggtaaaga taataatgct gtcggagaca tagtagtacc   55620
tcaggaagct aattttcctt tagtagtaga atgtaaacat agagaagaat ggactataga   55680
taacgttctt ttaaacaata gagaaccaca tacatggtgg gaacaagtaa ttaatgatag   55740
tagcaaggtg aataagacac cttgcttaat atttactaga aacagagccc agagttacgt   55800
tgctttacct tatgatgaga aagtatatga ggacttaaga aataatgaat atcctgttat   55860
gagaacagat tttattattg ataatattag aaaagataaa tttttttatg atgtccttat   55920
aactaccatg aatgggttga cctcatttac accttcttat attatatctt gctacgacaa   55980
aaaagatata aaaccataca agaaggttga gtctaattta tctgaggtaa gtaagcatga   56040
agatgaattg attaatgacc ttcttaatga tatataagga agggtaagat aggtatgaca   56100
agtaaagaaa gaccattaat tgtatatttt tcaggtacag ggacgacaga aagactagta   56160
aacaaaatta atattaataa ctcatttgaa acgtttaggg ttaagagtgg aaaagagaaa   56220
ataaataaac cttttatact aataacaccg acttatatga agggtgcaat acctaaacaa   56280
atagaaagat tcctagaaat taatgggagc cctaaggaag tcattggtac aggaaataaa   56340
caatggggct ctaatttctg tggagcaagt aaaaagatt cagagatgtt taagattcct   56400
ttaattgcta aagtagagca atcaggacac tttaacgaga tacaaccaat attagaacac   56460
tttagtaata aatataaagt agcgtaaagg atgagagata tatggcaaca tatggaaaat   56520
ggattgagtt aaataatgaa ataactcaat tagatgacaa tggaaaaaat aaactctata   56580
aagaccaaga agctttagat gagtatttaa aatatattga agataataca agaaagttta   56640
ataatgaagt agaaagaatt agagtattga caaaagaagg aacatatgat aaaatatttg   56700
ataaagttcc tgatactatt attgatgaaa tgactaagct agcttacagt tttaatttta   56760
aatttcctag ttttatggca gggcaaaagt tttatgagtc ttacgcatca aaacagtatg   56820
acgagaataa aaaacctatt tttgttgaag actatgagca acataacgtt cgagtagctt   56880
tatatttatt tcaaaatgat tatgtaaagg ctagagagtt attagtacaa cttatggagc   56940
aaacatttca accatctaca cctacgtata ataactcagg gcaagctaat agaggtgaac   57000
taagttcatg ttatctattt gtagtagatg attcaattga gtccttaaat tttgttgagg   57060
atagtgtagc taatgctagt tctaatggtg gcggagttgc aattgattta actagaatta   57120
gaccgaaagg tgctccagta cgtaatagac ctaattcaag taaaggtgtt attgcttttg   57180
ctaaagctat tgaacataaa gtaagtatat atgaccaagg cggggttcga caaggtagtg   57240
gtgcagtcta ccttaatata ttccataatg atattttgga tttattaagt tctaagaaaa   57300
taaatgctag tgaatctgtt agacttgata aactatctat aggtgttaca atacctaata   57360
agtttatgga attagttaaa gaaggtaaac ctttctacac gtttgacact tacgatatta   57420
acaaagtata tggtaaatat ttagatgaat taaacattga tgagtggtac gaagaattat   57480
taaataatga taaaattggt aaagtaaaac atgatgctag agaagtcatg acagatattg   57540
ctaaaacaca attagaatca ggttaccctt atgtatttta tattgataat gctaatgaca   57600
atcaccctct taaaaatcta ggtaaagtta aaatgagtaa cttatgtaca gaaatttcac   57660
aattacaaga ggtatcagaa atttatccat attcctatag taatcagaat gttattaata   57720
gagatgttgt ttgtacatta ggttcactta acttagttaa tgtggttgaa aaaggtttat   57780
taaatgagtc cgtagatatt ggtacaagag cactaacaaa agttactgat attatggatt   57840
taccatatct acctagtgtt caaaaagcaa atgatgacat tagagctatc ggtttaggtt   57900
caatgaattt acatggactt ttagctaaga atatgattag ttatggttct agggaagctc   57960
tagacctagt aaacagttta tatagtgcta ttaacttcca gtctattaag acatctatgt   58020
taatggctaa agaaacagga aaaccattta aagggtttga aaagtctgat tatgctacag   58080
gtgaatactt tgtaagatat gttagagagt ctaaccaacc taaaacagat aaagctaaga   58140
aagtcctaag caaggtctat attccaacac aagatgattg ggatgaatta gctaaagcag   58200
ttaaagtata tggactgtat aatgggtata gaaaagcaga agcacctact caatctatat   58260
catatgtaca gaatgctaca agctcaatta tgcctgtacc tagtgctata gagaacagac   58320
aatatggaca catggaaaca tactatccaa tgccttattt aagtcctata actcagtttt   58380
tctatgaagg agaaacagct tataagattg ataataaacg tattattaat acaagtgcag   58440
tagtgcaaaa acatacagac caagcagtat ctactatact ttatgtagaa tcagaaatac   58500
cgactaataa gttagtatca ttatattact atgcttggga acaaggatta aaatcattat   58560
attatacacg ttcacgtaaa ctttctgtta ttgaatgtga aacatgttcg gtttagaaag   58620
gaaatagata tggatattac acaaaaagta aacaacata ataaaaatgc agtttaggca   58680
gcaacaaatt ggaatattga agatgacggg atgtctgata tttattggga gcaaggaatc   58740
tcccaatttt ggactcctga agagtttgat gtatcaagag atttaagttc ttggaacagt   58800
ttaactgaga gtgaaaagaa cacttataag aaagtccttg cagggctcac agggctcgat   58860
acgaagcaag gaggggaagg tatgaactta gtatcttatc atgaaccaag acccaaatac   58920
caagctgtat ttgcgtttat gggtggtatg gaagagatac atgctaaatc ttatagtcat   58980
atctttacaa cactattaag taataaagaa acaagttatt tactagatac ttgggttgaa   59040
gaaaatgact ttttaaaagt aaaagctcag tttattggat attattatga ccaattatta   59100
aaacctaatc ctactgtatt tgatagatat atggctaaag tagctagtgc cttcttagaa   59160
agtgcattat tctactcagg attttattac ccactacttc ttgcaggaag agggcagatg   59220
acacaatcag gagctattat ttataaaatt acccaagatg aagcttatca cggttcagca   59280
gtaggattaa cagctcaata tgattacaat cttttaacag aagaagaaa aaaaattagca   59340
gatagagaaa cttatgaatt attaaatatt cttttatacta atgaagtagc gtatacacat   59400
agtctatatg acccgctaga gttaagtgaa gatgtaatta actacgttca gtataacttt   59460
aatagagctc ttcaaaacct tggaagagaa gactatttta accctgaacc ttataaccct   59520
attgtagaaa atcaaactaa tgtagacaga ttaagaaatg ttgatttctt tagcggtaaa   59580
```

```
gcagactacg aaaaatctac aaacattaaa gatattaaag atgaagattt ctcattctta  59640
gatagtaaag agtatagtac tgctaaggaa ttcctataaa aaggagaaaa gatattatgg  59700
atagaaaaga agcaatggat ttattaagta aaacagaaat attatttaaa aaacatgatg  59760
agttttcatg tgtgagtgat atcaatgacc ctatgaagtt atttagtaac tctaaagatg  59820
ccaaagctga tgatacgtct aagtcttttc agttagagtt tatgcatgat atgactatgt  59880
atactttatc ttatggctca ggacagttaa aactcattga tttatcagaa ggttatgaag  59940
cacaaaaagc tacagcagtt aactcatttc ccgaaattat taaaacatta gaaaaggatg  60000
actcagaaga tggaaaaaat gaataattta gtagatttaa atacagcaat tagacaaaag  60060
aaagatgtta ttgtcatgat tacacaagat aattgtggta agtgtgagat tttaaaaagt  60120
gtaatcccta tgtttcaaga gtcaggtgac attaaaaaac ctatcttaac attaaatcta  60180
gatgctgaag atgtagatag agaaaaagct gttaagttat tcgatatcat gagtacacca  60240
gtattaattg ggtataaaga tggtcagtta gttaaaaagt atgaagacca agttacacct  60300
atgcaattac aagaattaga gtcactttaa tttggaattt cctactatct gtgctatact  60360
ataatagtac aaggtagtag gattttttaa tggaaggaag atgacatatc gcaaagaata  60420
aaacattaac gatatataat agtgatagat attttaatat acacacaaaa gataaagata  60480
aaattaatga ggctattaaa gtcacacatg gtaatgaaga agaaattgaa aagaatatgg  60540
atgaattaat atctaagtct agacgatata tcatgagaga tgaaaatcat tatatgttat  60600
ttaatgagaa gtacaataat gatagactta tagaaaaagt atgtaaacac ggtggcaaag  60660
ttacatacta tactgattca gtattaccct attatgtttt aaaagactta tctagtcacc  60720
ctgactcaga agttgtttat cgtatgcgca atggtttttac tgcaaaagaa gtagataata  60780
tagctttatc attcatgggt acaaaagtta ttattgatat ttctgtagta tttccttatg  60840
taaacccita tgatattatt agaagtttac atgatattaa aacaaatgta gatgaagttc  60900
atttatcatt tccacgaata ttagaggtag atgaaaaaca agaaaagttt tatttctttg  60960
atggtgaagc ttatgattta aaacctgaat ataaagtcga ttttgcagat aaaattagag  61020
tatctttatc agtatggaaa atgtatatct atatcttaac aagtagtcgt gattttgagg  61080
atgtagacaa tgtaattacg aaactaaaac aacaacgaaa gattaagata taaggtgatt  61140
atatgagtac agcaaataga agagacatag caaggaagat atcagagaac acaggttatt  61200
atatacaaga tgtagaagag atactaagtg cagagacaga tgctatttct gacttactag  61260
aagaagggta tactaaagta aagaatcata aatttatgca aatagaagtt attgaaagaa  61320
aagtaaaaa agcttgggat gggctgaata aagaatattt ccatttacct aatagaaaag  61380
ctataaaatt taaaccactt aaagaattag aagaggttat tgatagactt aatgaagaag  61440
agaaataatt ctcttctttt tttattgaca agatttaaaa tatatggtat agtattatta  61500
agttaaaaaa ggagaggaat taaatgaaag tattaatctt atttgaccac attagagaag  61560
aacatttttc tgtaagtaaa gatgggagtg tgaaatctaa tgtattaaat acacctaatg  61620
gaaaaacact taagaaatta cttgagaagt gttctaactt aaagagagat aaaacaaaca  61680
gagactatga tattgatttt ctctataacg cagtacctac acctattaga aatgattatg  61740
gtaaaattat taaataccaa gatgttaaac aagcagaagt aaaaccatat tatgaaagaa  61800
tgaataacat tattattgat aactcctatg atatgataat tcctgttggt aaactaggtg  61860
ttaaatactt attaaatgtt acagctatag gtaaagtaag aggagtacca agtaaagtaa  61920
caattgaaaa tgaaatatct tctcatgatg tatgggtact acctacgtat agtattgaat  61980
atacgaatgt aaataaaaat agtgaacgtc atgttgtatc agatttacaa acagtaggaa  62040
aatttgtaga acaaggtgaa gaagcattta aacctaaaga agtatcttac gaattagtag  62100
ataacattga aagagtaagg gaaatattta ataaggaagt aattatgatg aattatgatg  62160
gtgtagatat caccgcatgg gacttagaga ctaactcatt aaagcctgat aaggaaggaa  62220
gtaaaccttt agtattatca ctatcatgga gaaatggtca aggtgtgact atacctttat  62280
acaaatcgga ctttaattgg gaaaatggtc aagaagatat tgatgaagta ctagaattac  62340
ttaagaattg gttagctagt aaagaagata ttaaggtggc acataatgat aaatatgata  62400
ttaaatttt aatgagtact gagaacttta aagattttga gaacattcaa gatactaaag  62460
taggttggta tttagctgtc acacaagaag ttaaagaatc tttggagatta tctgacttag  62520
cttacgaggt aacagatgtc ggaggttatg ataaaccact agaagatttt aaaattatggt  62580
ttgttactaa gttattaaga tttttctctg ataaaattaa agaaatacag aaagaaatta  62640
aaaaaattgc taagaaagag tatgatgtta aagctcctga atacaaagag tggttagaga  62700
ctaaattaaa tgaaacaata gtagaattag atgatactga gaagaaattt agagttagtg  62760
aattagaaa aaaatacatt cagttaggtc tttcacctga aattgtaaac atgaatttag  62820
ttatgaacaa cgatgaattt attagtattg cagagccatc acctgaatat atgggattat  62880
ctgattacgc taaatcttac acactgaata ctgcaattga tttaattaac aagtatagag  62940
atgtaaaaga tgtaattaat gatattgatg gaggtaactt taactatgat tggttcccta  63000
ttgagttat gcacccgtac gcatcaggag acactgatgt atgtagaaga attcattgtg  63060
atgttgttaa gaaacttaaa gagcaagata gacctaagtc aatgcattta ttagaagtta  63120
attacccaag acttactaaa tcattagcta gaattgaatc aaatggttta tactgtgatt  63180
tagattacat gaaagaaaat gatgagtcat acgaatctga gatggctaag aaccacgcta  63240
ctatgagaga acatttgggct gttaaagaat ttgaagagta tcaatataac ctttaccaaa  63300
tggcgttaga agagcatgag aaaaagccaa aagatagaga caaagagatt catcagtata  63360
gagataagtt taaagatggt aaatggatgt tttctcctga ctcaggagac cataaggcta  63420
gagtaatttta tgatatttta ggaattcagt taccttatga taaagagtat gttaaagaaa  63480
aaccatttaa cgctaatgtt aaagaagcag accttacttg gcaggattat aaaacagata  63540
agaaagctat tggttatgca ttagataact tagaattaaa agatgatgtt aaagaacttc  63600
ttgaattact taaatatcat gctagtatgc agacaaaacg taactcattt actaagaaat  63660
tacctaatat gattaataaa caaaaacgaa cattacatgt ttcttttct gagacaggta  63720
cagagacatc aagattaagt agtagtaatc ctaacttaca aaacttacct gctcatacat  63780
cagatgtaaa caagtttgat tataaacatc caattaaacg ttcatttgtt tctagatttg  63840
aaaatggagt actactagga gccgactata gtgccctaga gatgcgtatt attggattat  63900
ttactaaaga ccctgatatg ctacaatcat tcttaaatgt tgaggatatt cataaggcta  63960
cggcaagtat tgtttataat aaaccagtag aagaagtaac taaagaagag agacaagcaa  64020
ctaaagcagt taactttggg ctagcctttg gagaatcacc attctcattt gcaggtaaaa  64080
ataatatgga agtaagtgaa gcagaagaaa tatttgaaaa gtacttccaa acaaaaccta  64140
gtgtaaaaaac ttctattgac aatgtacatg aatttgtgca acaatatggt tatgttgata  64200
caatgcacgg tcatagaaga tttatacgtt cagcacaatc aacagataaa aagataaaaaa  64260
atgaaggtct aagacaatca tttaatacta ttatccaggg ttcaggtagt ttcctaacaa  64320
```

-continued

```
atatgtcttt aacttactta gatgatttta ttcagtctcg taacttgaaa tcaaaagtta  64380
ttgctacagt acacgatagt atcttaattg attgccctcc tgaagaggct aagattatgg  64440
ctaaagtgac aattcatatt atggagaatt taccgtttga tttcttaaaa gcagaaattg  64500
acgggaaaga agtacaatac ccaatagaag ctgatatgga aattggttta aattataatg  64560
atatggttga atacgatgaa gaagaaattg atacatttaa ttcttaccaa ggttatatta  64620
agtacatgat gaatttacag acttttagaag attataaaga gtcaggtaaa ttaactgatg  64680
aacaatttga aaaagctact aatgttgtta aaagtgaaaa acatatctat caagaaattt  64740
aataaaagta ttgacaatat gtttcactta tgttatacta tataggtaat aagtataagg  64800
aggaaaaaag agtgaataca ggagagatta gatttaatcg ttctatggat gaatggatta  64860
taacaagtat gtaccaggat gaattaggtg aaatgaatat tgttgttaca ttctataata  64920
gagaagaaaa taaacatggc tctaccgttt taccaacaga gtcatctact ggagaagtaa  64980
cagaagaatt agcaagtctt gaagaagaat atcctttagc tttaccgtta agtagtattt  65040
cagttaatat ttaaaaggag gaactgataa atggagatac acattgattc cctagatttt  65100
acaaatttta ctattaaaga tagaaatggg aactcacaag agtttgatat tacagatgaa  65160
ttaaagatta cagaatatac aatacaagaa gattttatgc aacaatcagc taagtacgct  65220
tttttgggctt ctatattaga gaaggtcaga gcatattctg aaatggagca aagaaattta  65280
gaaacaattg gtagtaagct taatctcaca attagacaag agtatgaaca acaaggtaaa  65340
aagcctacta aagatatgat tgagtctagt gtgtatattc atgattccta tcaacaacaa  65400
cttaaagttg ttgaggcttg gaattataaa gttaaacaac ttcaatatgt tgtaaaagct  65460
tttgaaacaa gaagagatat gatgattcaa ttaggtgcag agttacgaca aacaaataaa  65520
aatggtggaa ttactaaccc attttcacat taaaaaagaa agtaaagaat ataattgaca  65580
aatataaaa actatgttat aataaataag taaattaatt aaaaggagaa aagataatta  65640
tggatttcaa tcaatttatt aacaatgagg caagcaaatt agaaagtaat aacagttctt  65700
ttaacaacaa tgtagagagc tataaaccta aaaaccctgt attacgatta ggtaatatta  65760
aagatgcaaa tggaaataaa gttactaaag aaaatgcttt tgtacgagta ttacctcctg  65820
cacaaggaac aaatgttttc tttaaagaat ttagaacaac aggtattaac tactctaaga  65880
aagatggttc tcaaggattc acaggactaa cattacctgc agaaccaggt tcatctgtcc  65940
ttgacccttta cattcaggac tggataacaa atggcgttca atttagtaga ttccctaata  66000
aacctggagt acgttattac attcatgtta ttgaatactt taataataac ggacaaattc  66060
aacctaaaac agatgagcaa ggaaatgtaa tgattcaacc tatggagtta tcaaacacag  66120
gatataaaga attggtagca aaccttaagg atactatgtt aaaaccgtca cctaatgcac  66180
ctcatagttt tatttcagca aatgaagcat tcttagttaa tattgctaaa gctaaaaaag  66240
gtgaaatgtc atggaaagta agtgtttatc ctaatgctcc tttaggtgca ttacctcaag  66300
gatgggaaca acaattatca gacttagaac aattagcaaa accaacagaa gaacaaaacc  66360
ctaacttttgt taacttctta atcaataacg ttaataacac agagttaagt catgataact  66420
ttaaatttaa ccgtgagtct aatgtattag gtgaagaacc ttcagaacct aaacaagctc  66480
ctactcaaca agatattgat agtcagatgc caagtaatat tggaggtcaa cctaaccaac  66540
cacaacaagg tcaagtaggt cagtatactc aacaaggtca aaataatggt caaggacagc  66600
agttacaagg taaccaacag ccaattagta atactcaatt tggtcaagga acaccttcag  66660
gacaacaacc taataataca ggttcagttg attgggataa cttagctcaa caacaatcac  66720
aaccggattc aaaatccttt aatgactttg atgtaaacag tgttgatgat tcacaagtac  66780
cttttgagac acaacctcaa aacacacaac aagcacctga accacaacaa actactcagg  66840
agcctccaaa acaaaaacaa acacaaagta ttgacgatgt attaggtggt ctagacttag  66900
ataacctata agatatagag tgccttagg cactctttta tttgagatat aattactagg  66960
aggatattaa atggcaagag caaaaaaagg taaagaagta gatttaacag atttaaatac  67020
aattgattta ggtaaagaat taggattaac attattatca gatacaaata gagcagatat  67080
taagaatgtt atacctacaa tggtacctca gtatgactat attttaggtg gaggtatacc  67140
gttaggtaga ttaacagagg tttatgggtt aactggtagt ggtaaatcaa catttgcagt  67200
tcatttgtct aggattgcaa cacaattagg tgttattacc atttggattg atattgaagg  67260
aacagcagac aataatcgta tggaacaact tggagtagat gtttcaaaat tattctctat  67320
tcaatcagga gaaggtagac ttaaaaatac agtagaatta tctgtagagg ctgtaggtaa  67380
agaattagag tactggattg acacatttaa tgaaaagata cctggagtac ctattgtgtt  67440
tatttgggac tcactaggag ctacacgaac tcagaaagag attgacggcg gtattgatga  67500
gaaacaaatg ggtcttaaag catcagctac tcaaaaagta attaatgcag taacacctaa  67560
attaaatgat acaaatacag ggttaattgt tattaatcaa gcacgtgacg atatgaatgc  67620
aggtatgtat ggtgaaccta ttaagtctac aggtggtaga gcatttgaac atagtgctac  67680
tttacgtatt aaggttcata aagcatcaca attaaaacaa aaaagtgaat taactggtaa  67740
agatgaatat catggtcata tcatgcgtat tgaaactaag aaatctaaat tatcgagacc  67800
gggacaaaaa gcagaagcag acttactatc tgattatatg gtaggtaaag aagatgaccc  67860
tatattatta aatggtattg acttagaaca tactgtatat aaagaagcag ttgaaagagg  67920
tttaattact aaaggtgcat ggagaaacta tgttacattg aatggtaag agattaaact  67980
tagagatgct gaatgggttc ctgtattaaa agataataga gagttatatt tagaattatt  68040
cagtagagta tatggagagc atttccctaa cggttactca ccattgctta ataataaagt  68100
aattgtaact caactagaag agtatcaagc tcttgaaaat tactataaag aatggggctac  68160
agataataaa caaaggaac aagaggaaga actaaaagga gaatctcaag aaaaggattc  68220
tgaataataa atggataatt taatagataa aaacatgaat caggtaaaag aatctttggg  68280
gaatgcaaat tcctcagatg ttcttccttt accttataaa gatatagcaa agaaatttga  68340
agaagtaaaa gaaaaaggtg aatcaattat cattgaagaa ggtggattcc cttacacaga  68400
ttctacagtg atgtatatag aacatgtaac agatagtatg gcaggaggat actccttaat  68460
tagacatgaa ggtgaagagg ttaaagtgcc taaaactatc catttctctg atatatatgt  68520
taaggataag tcacataaag taagaataat cttcgagggg gctaatcctt atgaagaag  68580
ctaacaatgg taatagatat gtaatagata tagatgtgta tcctgttgat tttgaaagag  68640
acttggatag tttacttaac aggtataaaa accttagatg gtcgttgtat catagatatg  68700
caggtatatt atctaatgac tttgaaagac aagaattaag aaatatatt gatgagcaat  68760
ttattaaact agtaaagaa tataatatta gaagtaaagt agattttcca gggtatatta  68820
aagctaaatt aactttgaga gttcaaaata gttatgttaa aaagaatgaa aagtataaac  68880
gtactgaaat tatcggtaaa aaagattata cggtagagtc cttaacagaa gatttaaatg  68940
aggactttga ggataatcaa attatgagtt atgtatttga tgatatagaa tttacagaag  69000
ttcaaagtga gctacttaaa gaattactta ttaatcctga aagagaagat gatgcctta  69060
```

-continued

```
tagtttctca agtagcgag  aagtttgata tgaaaagaaa agaagtagca agtgaattga  69120
cagaattaag agattatgtt agatttaaaa taaatgcata tcatgagtac tacgcaaaga  69180
aagaattaaa taatcataga gttaatactg aaaatcatat ttgggaaaac tagttacagt  69240
gccttccttg tgttatatta ttatcgagaa ttcaataata aagcatagg  aaggcttttt  69300
tctatgtctt atagaatgct ttaaaataga ttactaaaat aaagattgga gattaagctt  69360
atggctaaaa agaatgttaa tgatgtatta caacaagaat ctgttacagt agcagataag  69420
tatttacaag ttaaagttaa ccgtgacggt tatactcgta cacacgaagg acaatatgcg  69480
tacaaagtag tttcagaggg agaagagtta ttcttatacc cagtacaaac agatggtaaa  69540
ggtacattaa atgtaatgaa gaaatcacct attgcttaca ctgatggaga caatatccat  69600
tttgtagtaa atacagtagt agacccttat aatcactcat ttatccgtac tgaagatatt  69660
aaaggattag ataaaggtaa acaacttatt caagctttct tagctttcgt tgaagaccgt  69720
ttcaaatttg gtgtttataa cgtatttgtt gcaaataaca aagaagatgt attatctatc  69780
gtagaccctg cagataatga tgcagatgaa gttaaagata gtttagagca tgcacatgaa  69840
gatgtaattg cggatttccc tgctagccct gctcgtaagg acgttaaagg cgtagattca  69900
ggagaaggtc aaggagacac ttcagaacca tcagcaccta agaacgttca agttactcct  69960
aaggaagacg gagcagacgt atcagcagaa taatatagat aaaggatggt aaatttggct  70020
aagttaaatt tatacaaagg taatgagtta ctaaacagcg tagagaaaac agaaggaaaa  70080
tcaacaatca cgattgagaa tttagatgct aacacagatt accctaaagg tactttaa  70140
gtatcattct caaatgattc aggagaatca gagaaggtcg atgtccctca gtttaagaca  70200
aaagcaatta aagttatttc agttacccctt gacgttgata gtttagacct tacagttgga  70260
gatactcacc aactatcaac aactatcacg cctagtgaag catctaacaa aaatgtgtca  70320
tttgaatcag acaaatcagg tgttgctagt gtaacatcag aaggattaat tgaagcagtt  70380
agtgcaggaa cagctaatat tactgtaact actgaggatg gtagtcatac tgatattgtt  70440
gcggtaacag ttaaggaacc tattcctgaa gcacctacag atgtaacagt tgaacctggt  70500
gaaaatagcg cagatattac tgcataggag gacaataaag aatggaaaag acattaaaag  70560
tttatagtaa tggtgaagtt gtaggctctc aagtagctaa taacgatgga gctactacag  70620
tatctattac aggcttagaa gccggaaaaa cttatgctaa gggagctttt aaagtagcat  70680
ttgctaatga ttcaggtgaa tcagaaaaag tagatgttcc tgaatttaca actaaaactc  70740
ctgctgaaga accttcagaa gaagcataat aattaagacc aactaaaaag ttggtctttt  70800
tttattgaca atttataata tctatgatac actatataag aattaagaaa aggagggaaa  70860
gtaatggata ttccaacaat attatttaga aatccatatg attacacaaa agtaaaaaaa  70920
ttaatggaaa acaaagaaca gtacattgta gtaaaatttg attcagtttc tgttcataat  70980
ttaaatgttc aaggtatgat gaatgttatt caagattacc tgcacatcta tggttacaga  71040
gtcaaagaat acggacaaga aaatgcttct aaagtgatg  aaagagacgt taaaggttac  71100
ttatacgaaa gagtaggtga gtaaggtatg ggtgttataa taaattctaa ccatattcag  71160
tcagatactt tatatgagta cgatagtttt tttgatattg agaaagtaga tacgtttgaa  71220
gaaggattac tatcaataca ggatgaacca actgtttttag caggatttat ctatgatgat  71280
attacattta ataaggttat taactctaat tcaaatattg ataacaatat taagaataat  71340
gatatttatt atgtttctga tatagg-gtta cttccggata cttttatcac tgttgattct  71400
aataaaaaat actattcatt attacagcag atagttgagt taagtaaaga ccctttccct  71460
aaatgggtag aaacggatgc aaaagattta actaggtatt ataactttca agattttgaa  71520
gatgtattcg atttaaatag tttttataaa aaagaagttg acatggtaag agaaaagtgc  71580
tataataatg gtaatgtata tttattatat gaagtcttgc ctgattataa attacctcta  71640
gcttatagtt tactttcaaa taaagagcat ggtattgtta ttatcggttc acagacacgt  71700
tctaataatg atatactgac tttttacgtt aaaggtatgg atgctaaggc aatagctagc  71760
atgtttaatg tagaacatga ttatgattct aatattttc atacattcgt aaatagtcac  71820
attaatattt taggaaatca aataactaag tttataaagg agaaaggaaa cagttatgag  71880
taactataaa acaatagaag aagtacaagc agttattatc ggagtattat ttaaagatga  71940
aggtaaaatt gtaacatcta agtttataa  aattactaaa gagtttggtt tagatagaat  72000
tggtaaagac gaccttaaag aaattgttga agatattaga caagatgcct atctaaatga  72060
gcttaagaat aaagcaatta aaggtaaggt aactttagga gaccttaaag atgttgcaga  72120
taatcaagta ttcgaaggta ataactatca tgaagaagtc tctacttatg tagtagctaa  72180
agaaaaagaa ctatctcact tgagagaaca acgtaagcac aacagacata ccgcatacc   72240
tcaaattatg tttgatgaac ttaaagaaca tatggttaaa gaattacaag gggaaacatt  72300
agtagagcat catggaagta aagttaacat taatgataca agttaattg tattactatc  72360
agatttccat attggaagta ttgtatccga tatgactaat ggtaaatatg attttgaagt  72420
attgaagtca agactaaatc actttattga tacgacagtt aaagagattg aggatagaga  72480
gatttctaat gtaactgttt actttgttgg agacttagta gaacatatta tatgagagga  72540
cgttaaccag gcatttgaaa cagagtttac tttagcaagaa caaatctcta aaggtactcg  72600
attacttatt gatatcttaa atgtactatc taatgtagtt acaggagaat taagatttga  72660
tattattggt ggtaatcatg accgtatgca aggtaacaaa aatcagaaga tttataatga  72720
taatattgct tatgtagtac tagactcttt attgctattc caagagcagg gattattaaa  72780
cggtatagat attattgata atcgtgaaga tatttatact attagggata atttcggagg  72840
taaatctatt atcgttaacc aacggatggg attaaaagct aaaggcaatc atattaataa  72900
atttatctta gatagccata ttgattract aattacaggt cacgtacacc attctcagt   72960
aaaacaagaa gattttaaata gaatgcatat tgtagcttca tctccgatgg gatataataa  73020
ttatgctaaa gagctacatt tatcaaaaac taaaccttca cagcaattat tatttgtaaa  73080
taaagaaaat aaagatattg atattaaaac agtatttttta gattaaggat ggttaataaa  73140
tggatacaat tttattatta ggtgtagcgt ttataacttt tgcaacattt aatatagtct  73200
ttagattatt tgatttatgg actacagaga agaaaatgt  aagtcaagga caacctccac  73260
taagtaattt tgagtactat catgtgatag taccctactt agttggtgtt attgttatta  73320
tactgagtat tatttttaga gattccttgt attctgcgca atcaggattc ggtgttatta  73380
ttacaagctt tatttatatg ctagtttatg ttataatcgg tcttgtaggg tcgtttgtac  73440
ttacaatatt ccaagctaga aaggctagac agtatcaaac acaggaggat aataatgaag  73500
ttcaatgata tttatgagca attaattaaa aatgatacaa tacaaaacat tcatgaatct  73560
caagatgatg aaggaaatat ttatacaata caatttgata aaggtaatga taagtattta  73620
tttaatgtta tcaatgatgg attcttgaaa gaaatgacaa atggtatggt agaccatcct  73680
aaaggtcaac catattcagt aagtctaatc aataaagaaa ctcctagtat gtcagtgaaa  73740
caatattaa  cagacgtaga agatattgta cctactatta gaaaaatgga aaaggatttc  73800
```

-continued

```
ttatagagtc aagtctttac ttgactcttt ttactatata tggtatatta atatagaggt   73860
gacttaaaaa tggattttaa ttttagtgct tttgataata gctcattagc aatgagaatt   73920
agtgagggtg tatactattt caatgatacc ccttattact ttattgaaca tatagaagaa   73980
gaaatgtctg agtatgttat tgtgtatgac atacatgata gagaggaaaa agaaaatcct   74040
cagaagaaat atagagtaga accttaccaa cggacaatac ctggaggtac acctcttagt   74100
aatttgatta agagtatgat gcctcaacgt aaatatccta agaaggttgt agaagaccct   74160
atatttgtag ctaatgttat tcctttagga acagatacag ttacaggtaa aactggaaaa   74220
ggttttttttg aaagagataa ggatagaact atttactcac agaaagaacc aactaaggta   74280
gtccatggtc aatacacagg tgttttcata ggtctaacaa gtgttaaatg gaatagaaca   74340
tatactcctt tagaaagtgt tgttgagtat tgcaagagag taaaaggaga taggttaaat   74400
gtctaatgat gtagttaagt tttatgaaaa agatattaaa gaccttataa gaactaaaaa   74460
acacatgttt aaagacgatg agataactag tgatataaat gatatacgta tatttaatga   74520
gaaagtaatt tgtcaaggta agtgtagaac agattgctta gtactagacc gtaatggtac   74580
tgtcatgggt atagaaataa aaacggaaag agattctaca cagagattaa ataaccaatt   74640
aaaatattat agtctagtat gtaagtatgt atatgtaatg tgccatgata aacatgtacc   74700
taaagtagag cagatactta aaagatataa acataatcat gtaggtataa tgagttacat   74760
taattttaaa ggtaaacctg ttgtaggtaa atataaagat gctacaccat caccacatag   74820
aagcccttat catacaatga atatactatg gaagacaaat ttaatgacaa tacttaggtt   74880
gattagagac cctcatactt atagaacagg gtatagttat aatgctagcg gtaggtatag   74940
tggtggggaa ggcaacttct ctcaaacaac tcaaagtaaa agaatgaaaa aacctgctat   75000
tattaaccaa ataattcatt atgtaggggt agataatact tataaactct ttacaagagg   75060
tgttatttat ggttataata atagatggga agttatagaa gaagatttct ttaatactat   75120
gaaaaatggg gtaagagtaa tcaatgagca aagacaaacc aaatagacgt aaagagatac   75180
agcatcaacc tgttaacttt gccccaacaa atactttaac aggagctaat aatagtttct   75240
ttgctaaaaa gccctcagaa cctaaggata caacatctgt tattgaatat agaatacttt   75300
ttattaaaag atttgataat gtaacaagta cagatgttaa gttacaaaaa aaatatgcat   75360
taaatcttat tagtgaggca cttgatgtta aagaaactta tctatctctt aaacaaaaag   75420
gaaagaaaac agaatctatt ttacacacag atagagttta ttatgtgcat agaggtaaaa   75480
aacttattgg aaaatgtagt attagggagc aaagaacatt taaaggtaaa catttgatat   75540
ttatatttaa gacaagacat agagttaaag cagaaaggaa agataaataa tgttaaaagg   75600
attttcagaa catgtagata aacctacaac tattaaaacc ttatataaga ccttaacaag   75660
tggtaaagta gaattactag gtgtatctta tggtagtgat tacttccctt caggtgttac   75720
agtacaagct tatattgaag atataggtaa tgaagatgaa ggtctgcagt ttgttaataa   75780
agtaaacgta gtggaatcaa tgaaacaggc tgtagtaggt atgaacaatc aattaggttc   75840
ctcaggtctt ggatatgtta gaactgaaca acttaaaaaa gagctagaag aaactggatt   75900
aatgacagat ttacttgcta gaggtactaa cttaacttct actaagaaag tggatattgt   75960
aagtactttt attgagcctg aagtaacata tcaagacatt actatagcta aagatattaa   76020
gttacgtcta tacaaactag aagaagagtc accattaaac ggttatacac atattgtata   76080
tcttcttact acagagaaat tatatgatgg tcaaacacta tttggtatgc tatctaagaa   76140
agataagtta tctaaaggag atactgataa attattagca ttctttagaa ataatagttt   76200
aataagtaaa agtgtatttt gtgttaagtt attaagtaaa gactactact tcaatttata   76260
taatacacat gaaacaggta tattcttttt agaagatacg gatattatta ctattgcttg   76320
tggtcagtca tacgttaaag ttaatactaa agatattaaa tctagtcatg ttaaaatgta   76380
agatgagact cataaaattaa ctgagctagt aattaactta aaaggtgacg acacattaac   76440
tatttttattc taatagaatg ttataaatat gtgataatta agtataaaata tacgttatat   76500
agaaagtttt cataatgttt ttaatacaga aactagttaa gttttttaca cttgtcctag   76560
tttctgtgaa attatattta tgaaaagtta aaatatcttt taggtaaagg ctttgtaaat   76620
agttaaaaaa tatattaaaa ttttatacaa agtagttaat aaaattatat tacatttata   76680
tattatgaaa taataacaga aattgtgata tattatatag tgtaaccttg aaacagttga   76740
tgttgtaggg tttgtttatg ttcgttaaac tggtttcaga acatcagtta ccataaataa   76800
atgacagtta aggagagcta tataatggct agaaaaaaga atttacgaaa taaaaacgat   76860
gatataaaag ttgttcctga taaagaaaaa gaaagtatat tatctaagct ataccataat   76920
aaattactac gctcaaaggt agataatgct ttagatgaag atatgagtta tgatgatatt   76980
atagaactat gtaaagaata tgatttagaa ttgtctaaat cagctattac aagatacaaa   77040
agtaaaagaa aagaagctat tgaaaatggt tgggatttag gagaattaat tgataaacgt   77100
aaaaaaacaa gcgtaaaaga tattaaggaa aaagaaactc ctatattaga agaggagcaa   77160
ctttctccat ttgaacaatc aaaacatcac acacaaacaa tctatgatga tattcaagta   77220
ctagatatga ttatttctaa aggtgcaaaa ggattagaat ttgtggaaac tttagaccct   77280
gctttaatga tacgtgcaat ggaaactaaa gataagatta ccggaaacca attaaaaggt   77340
atgtcattta ttggacttag agaattacaa ttaaaacaaa cagctcaaga tacggctatg   77400
agtgaagtat tattagagtt tatacctgaa gaaaaacatg aagaggtatt acaacgatta   77460
gaagaactac aaaatgaatt ctacaaaaat ctagatttag atgaagaaag tagaaaatta   77520
aaagaagctc ttgatagagt aggctataca atttagatag tgaggttaga gtaatggcag   77580
atgagattag tttaaatcca atacaagatg ctaagccaat tgatgatata gtagatatca   77640
tgacatactt aaaaaacgga aaagtactga gagttaaaca agacaaccaa ggggatatcc   77700
ttgttagaat gagtccaggg aaacataaat ttactgaagt atctagagac ttggataaag   77760
aatcattcta ctataaaaga cattgggttc tctataatgt atctgttaac tctcttataa   77820
catttgatgt ttacctagat gaagaatact cagaaacaac taaggttaag tatcctaaag   77880
atactattgt agaatataca agaagaagacc aagaaaaaga tgttgctatg attaaagaaa   77940
tacttacaga taataatggt aattatttct atgcacttac aggagaaaca atgctctttg   78000
atgaaaataa attaaataaa gttaaagatt agggttgaca gttctgaaag tatatgatat   78060
agtatatgta tactaaaaat aaaggagcta acaattatgt ttatttcatt aaatcaagaa   78120
gagaaagaat tattaactaa agaggaaaac aagtatacac cattagaaac atcaagagag   78180
tttaacacac ctaaagaaga attcattgta acaagttata atgaaggtaa accttttagat   78240
tacattgcaa aagaagctaa agtaagtatg ggattaattt acacagtctt aaactactat   78300
aaagtaggta agcgtaacaa gaaatcacct gtagaagaaa gaattgcaca tatcttgaaa   78360
gacaaaaact tagttaaaga gattattaag gattaccagt atatgaattt acaggacatt   78420
tatagtaaat ataatcttca taagaatggt ttatattaca tcttggattt ataccatgtg   78480
gaaagaaaat ctgaacttaa ggacaaagca ttggaagagg ataatattgt cgttgagtaa   78540
```

-continued

```
gtaaagaggt tataatatga gaaataaaaa atcatttcaa gagcaattaa atgacatgcg    78600
taataaagag aaatgggtat ctgaagagga gttcactgaa gaagtgactc cttctgaaga    78660
acctgaagta gaagaagaaa agttatatac tttaaatgag ttaaaagaaa atttattgga    78720
tgctcaggga ttaaaagatg ttgtcgataa ttttcctgca tctaagccag tatatgaatc    78780
taataagctt tatatttgta caataccaaa aggatatcgt tctacagaag tacaaccagg    78840
tcaatatatt ggtatcagta cagggttatt atcagaatca gaagatttta gtcatttaag    78900
aggtcaaatg cctagaaatc tttatgaaac ttctcatgtt ttaaaacctt tagtacgtat    78960
taataataca aatctcgaat atcaacagca tgagttactt gaagatatta aagatgacaa    79020
gaagatatat gatgttgaat tagaagacct gaggttagta acaggagaag aaatatccca    79080
tttagaaatt gtcgatagta agttttttga aagtcgtatt aatgaaattc tcgaccgcta    79140
tactgaatta acggattccg atgatttgct tatatactat agtaaattac gagaattagt    79200
aggcagtgac aaaatgattt attgctcact tctagataaa tgtgttaaaa ttatagatta    79260
atagttagtc tcctcttata ttataactgt aagaggagac attttttata gaggtgttaa    79320
ttatgtcaag aaaagcaagt atattctata tactagtagt tattgttttg gcttttctta    79380
tttcatctta ttatatatct tctttcatgt atcacgacaa agcaaagaat gaagtctcta    79440
ctgagttatc aaacacggga aagattaaag aagaaaagaa cgtagaattt gtcggtgact    79500
atacacttaa aaaagtggaa aataataaag cttactttat ggaaacatta cctacttacc    79560
tacccggtag aacaggagat aacagcatag atatgaggta ctacaaaaca agtagatttta    79620
aagaaggggt aaatttcaag cttattaggg tatatactga agatggggaa gataatccaa    79680
ttcataagta taggtttgaa gcagtaccaa ccaaaaagta ataaggaggt gacttaaatg    79740
acaacattaa ttgtcgtcat ctttattgct atcatttatt acttatggaa cagtgattga    79800
gtcaagttaa ttcttgactc tctttttgtt ttatggtata ttaatatata gaaaggagag    79860
attaattatg gaaatggcag atttagaaag atttgatacg tttgtaagat tagtttcaga    79920
cgatgagctt tcggaggaaa gaatattaga attgagtgta gacttattaa atccgatact    79980
agaaggaggt acagcttacc aagctaaaaa acgcattaga agtaagttcg gtaaaataga    80040
agcaaaaaac tttaaaagaa attataaatt cttactcaag tcgatagctc aaatagacca    80100
agggagatag gacaatgaca gaaagggaaa agttagttaa agagattgaa gatgctaata    80160
gggacataca attaaggtta aaagaagtag atgattataa ggatagtata cgttctaaag    80220
gaacaagaaa ctatgtatct actaaggtat tagattcagt tatggtaggg ctaattataa    80280
gtttctttat tcttgtaatg ttacgtgtac ttgaatattt tgtaacaggt aatgctgttt    80340
attcaccttt agcgcctgca gttattatta tgtttgtttt agccttaggt acatggaaag    80400
taagtaaaat gaataaaata gtatcctaca ggggaactat taaaatgtat tgggaattaa    80460
gtaatgctga gcagaaccaa gctaagatat ttaagtatcc taatgatgaa gtagatatcg    80520
tatcaaaaca taacttaaga caaataactt ttagtgagat taatatcctt catcttaaat    80580
atatgagata taataaggca gtagaacagc atactaagtt atctaaagaa ctttttaaaa    80640
aagataaaga aactattgac aagaacaaat aagtgtagta tagtattact aaaggaggag    80700
agatattatg gttataccta gtattaaagc acaaaataaa ttcaagaatg aattagagta    80760
ttataagcaa ggtcacatta gtgaaagtaa aatgttagaa ttagcttttg attacattca    80820
agaattagaa caaaataatg aatatgttac taatttgcta gaagaggaga gatatggtga    80880
gtaaatttat cggagtgtac ttatttaatt tattagtagt agcgctaatt tatacagtag    80940
gatttttatt ctttttatggt gtagctagtt tagttattat tataactcat gccactattg    81000
acccatttgt attagctact ttcttaggaa taggattctt ggttattaga actgcacaca    81060
gaatcatggc acgagtaatc aatgatgcag tagcccaagc cattaaggat aaagaaaatg    81120
aataaagggg aatttattat ggataaaaca ttaccaaagt ttagtgtata tgaagttatt    81180
gtaaagactg taattatgac accaacagaa ggaagttctg accgagaatc attttactttt    81240
tcaactcaag agttagcaga aagatttgtt aaagaaaacc aagtagaaac aaaagatgga    81300
aagcgtgtat cttttttctat taaagagcgt aagtaaatc aaccaggcta acattaattt    81360
gttagctttt tttattgaca aatcatttta tatagtgtat agtaatatta tactgaaaag    81420
gaggaattat tatgaaagtt tcagaagaag taaaacagag ctacttagag aataaagcta    81480
atactaaaat ggataagata agttggtctg agttaaggtc tagtcctgca ggtagaacat    81540
taggagactt aatatacttt agtgtagtta taataaataa tatcatagct atagcattaa    81600
cattaatgct tggagatatt atcaaagatt taacggatag taccctagta aaaataataa    81660
gtatattact tattatcatc gttgtatacg gtatactatc ggctttaata cctatactaa    81720
tatttaaatc tgtatttcct ggatgggaat atactgaatg gaataattct tactatttga    81780
gattacctgg agaaaaagat tataaatact atagctactg gtatttaaat ttattaggtg    81840
ttactgagtt ttatcggaca aatgatgagg gtaaagaaat taaagaaact agtttaagtt    81900
gggtttttta tactaaggtt gatagacctg aggatattga ccattggaaa aatcaattaa    81960
taactaatag accttttaaca atttctgagt acaaaaaact aaagaagcta gataaagaaa    82020
gtgaaattag aaaacaagaa gatttagaag aatacaagca atacaatagt aattaaagag    82080
gtgaaaaacc aatgataagt tcatttgata gtgtattact tgtaatatac attattatag    82140
cttttgcagt agctatggca atactttatt tagtatttaa aggtatgacc cttttattag    82200
ataaactaat gatgttatta ctaagtaaaa ctaccttaga tgtagaagct tgctccatga    82260
taatggcagt agtcagtaca attgtgtttg gaattattgt acttttaata tggttagcag    82320
taaataatat tttattgtaa ggagttttac tatggatttt aatgacttta taaacagtga    82380
atcagataga gtgggtaaac ctaaacaaaa gaagaaggta gaaaataaac taccttcttc    82440
tactcctatt gaagagaagg aaaaaatgtt gaaaagaata agagaaaaat cattatacat    82500
tgatttaagg agaaaaagaa atgactaaag aaacaaatgt actttacaaa gataagtata    82560
gagattatac tatagttgta agactagtag gtaatattat tgttactgta gtagataaga    82620
agcataaaac aaaattttca cctattatat ttgataatgg tcgagaaggt gtagagcttg    82680
taatgcgtat cggctcagaa gaacttgata tgaaagaact tagagaattt actaaagagg    82740
tatcaacagc tcagaaagct ttagaatatt ttaataaaaa actttacatt aaaggcttga    82800
cagatgaagc ctttttaatat atactaagat tataactaaa acaagaaaaa gaggaatgat    82860
tattatgtta ttaggaattt tatggtttat atggggattt gtatcttatt ttgtagtgat    82920
gtttggaatt gaattttgga aagacagatg gttaccagga gttattggtg caggagtttt    82980
attaatattc ttattttgga ttatgaagtc tattcataat gctatgacag tagtttactt    83040
gtattaggag gtaatataga tgaatatatt agttatccat tatgaagaaa caaataaacg    83100
agttctaaaa gaaacaataa aaacaataca aaatcattta aacgatgaac atggtttggt    83160
taaaatgaca gcaacaagac ttagtagaaa agccatagaa gaagagttta atgattacaa    83220
tatagttatt gcagaaaatg accctgatag tttttacagc tactcagatg cagtagacga    83280
```

```
tgtagatttt gttatagata taccaatttc atatttagat atacatgcag gtgtagagtg   83340
ggatgttgat aatcctgtag atatgctaga taggaaccct gattttatag aagctatggg   83400
tcaattaaac gaggacttaa tgttataagg aggaaataaa atgttaaatg aaaaactaaa   83460
aaatttagaa gatacgaaag tgtatatgat taatagtatt gcaagtttac taagtgcaag   83520
tacaggtaaa tcaagtaaag tatttttga tgaaggaact attaaaattg taagtggtga   83580
tacaaaagcg gtagaagtta ttgataattt agttcaccct cattcaggac gtttacctat   83640
taaaacaaca gaacgtattg ctcttggtag actaacagat tctttacagt ttgttatttc   83700
agaaatagag tcggttaaag accaaattat agatgaagaa aatgaagctt acattgattt   83760
tgtaatggaa gactggaatt gggattaatg cctatggact taatgacaat agcttctgtt   83820
gcctttatag ctgtcgttat tattgattta attaatgatg atatgagcta tatgttaact   83880
ggtactgcaa tattaataaa catttgggca ggttttttatg gatggttctt tttactacaa   83940
gcaggtatgc tactttctt actcttagct agaaaagtta aagatgataa ggaatcaata   84000
ctatactcag gtgcttcgtt aatatgtgca ttagggatga taataaatct tcttatattt   84060
tcttaaaaat aagtgttgac acttctaaac ttttgtatta tactataagt ataacaagta   84120
caggagatga ttaatatgag taaagaaaca attagaagac aattttcaaa cgcaattgag   84180
attatgcaa caactaagga atggtggaat ttccctaaaa gctttaatac aaataaagag   84240
tttaaaatta aaacttttaa aaatgacaca cttgtatttg aagttcgaga aggtaataga   84300
aacttaggaa gctttgtagt tttcacatgt attgactttg attatgataa acttgaagga   84360
acttcaacac agtatatgat taattacttt gctaagaaat taactaaaga tatgtttaac   84420
tatcataagt tacaactata gtaggaggtg gaaagatgag agaggaatta aaaccttta   84480
atagaaaaca agttaatgtt aaagggtact tagatgatgt taagtactca aagcgtagaa   84540
gacataaagg taatcaacat ggatgtgtaa aaataacagt tactgacgta aagattaatg   84600
gtatatctat tgaccatgtt aatattgaag ttggaatttc tttttatgaa aaactaaaag   84660
aattacaagg aaaaagaatt caatttgtag gtactgtcta caaatacgtt aaacatgcta   84720
gaggtcataa aggtagaatt aaaggatttt ataaagagga ttatagtgta actttggata   84780
agaagttaca aaaggaggaa aaataatgat taaaagaaga aaacatttag accatacagt   84840
acaacctgag aaaggatgga gaacagtacc ttttaatggt tactatgaag cccacccttc   84900
aggtttaatt agaaataaag taacaagaaa actaattaaa ggaacacaga caaggaaaaa   84960
tcatcctaag tggactgctc atgagattgt atatttaatt aaccctaaga aaacaagtta   85020
ttcacgaggt gttgttattg cacatacctt tcctgaaatg attagccaat cacgaggaga   85080
ccttaagaac ggtcacgtat gttttaaaga tggtgacaga agtaattgtc atgtaaataa   85140
tatgtttatt ggtaaaggta atgttaataa gaatatctac aaattaaatg attcctattt   85200
gactagaaaa gatattgaag aggatatcaa caacttagtt aatgagagac tattctctca   85260
gttagagtta cttattaaga aaaatgaacc tgaaagaatt acacctagca atcacttat   85320
taaaagagat aataatgtat tcagtatcac ggatttatct aaaaactctt tagtagaatt   85380
tgaattagaa atcaaaaata ttaaataagg tggctatata aatgaatgag tggtatgctt   85440
tatgttacta tgataaagta ggtaaaaaga aaataccttag gcaagttaga gcacacagag   85500
atatttcagt attagaagag ctaaaagaaa gattagaaga aagaaatcct agtacagaat   85560
actctataaa aacaacaaaa gaatttgatg aggagagata gggatgttaa caccacagca   85620
aaaagattca ttaaaaaagc aacaaaagaa attaagtaaa aagaagaaat aactgttgac   85680
aaatgagtgt acataggtta tacttaagtt aacaaataaa gaggaggtat gacctatgtt   85740
attcataatt ttttttctag cagtattctt tgtattagga tttattaacg gatggaactc   85800
agaagactaa aaaaggagtg gttatagtga agttagaaga taaagtatta gaaagaattg   85860
attctcttgg aggtaagtta ggtgatatta gccaacatgc ttgggaagct ttagtaaagt   85920
atcaaattat atatggtatt atagaccta tagtaggtat tatagtttata gcattaactg   85980
tatttttatg gaagttattt attaaccaac ataaaaaggt aaatgatata gatagagatg   86040
atgattatag tttactattt gaagattgtg aagatttcac aggtataggt ttgttttatg   86100
taatagctac atcaatcata tcactatttg catttatata cttagtatat ggaataccta   86160
tggatattat aaaaaatactg aaccctgagg tatttgcagt aaaagattta atcgaacaag   86220
ctaaaggagg aaactaaaat gaaacaaaga gattttgaat ttgaggaaga ttttgtatta   86280
acttacgagt gtgaggattg caaacatttt gaagattggg gtcatgatga agagcctgaa   86340
gaatgtagtg aatgtggtag tagtgactta attaacaata caagtcatga agacactgag   86400
tgtgacatgt gtaaagggta cattgatatg tggcaagatg gatatagata catgggagat   86460
aataaagcat accttgaaaa agaagattca ggtttaattt gtgaagattg ttatgagaaa   86520
ttagatattt aataaggagg aaattaaaat gaacaaagca gtagacaag caagtagtgc   86580
attagggcaa ggtttttcag ctatggtatg gcaccaggtg ttagtaggtt taggatttat   86640
tttactaggg gtgttattat cttttattag ttgggtacta gtaaaaaaat tacaggtacc   86700
atttaaccat ccaacagctt ttgtagtata ctcaattatg ttagttagta ttgttgctag   86760
ttttatttgg ggtggtttac acgtaattaa ccctgagtat tatgctattt tagaacttaa   86820
agggtttata aagtaggagg aattctatga ctaaagaaga gttagagcaa agagtaaaag   86880
aacttgaagc agagaataaa gaacttaaaa aacaaataga acgtttgaa gacgagggag   86940
gaaaaacaaa agatgaatag tagacaaaag aaaattctaa cattaacaat aaataatttt   87000
ttaatgttag ccttagatac tgtagcacta attagatata aaaaaggtaa aattaaacaa   87060
gagaactata atacaggaca gattacaaga acaatagtta caacagctaa ctcattaggt   87120
attctttact tagaagaaca agagcgtaaa gaagttaaag atattaaaat aggtactttt   87180
gaaactggag accttaaaag atttatgaat acaaataaat aaaaagttta agaaacctat   87240
tgacattagg tttcttttat tatatactaa tattataaga aataaggagg ttaacttatg   87300
aaaggtatta ttatatttta caagaagag accaaagagg atttaggata ttttcttggg   87360
tttataaact ttaagctaga aggattatct tacacaactg aaggtacttt agtagataat   87420
gatgtagtag ttttaaagga taaccaaatt aatgaggata atttagaaca gtttagtatg   87480
tcaaacaata atttagttat tggaatacta ggtcattcat ctcttttcagt acgtatctat   87540
gaaaaaggta ttagacaaga aattgaaaga gtagaagaat atttagagga gttgagacaa   87600
taatgttagc aatatttgca ttaattttg gttttactatt tattttatct ttattaggta   87660
ttttttattta ttctatattt ttacggaaaga aaaaaacatt aatagaagaa agagaatcaa   87720
ttggtatttta taatagaacg aaaagaaaac tgggtgatgt aacacgttta gggtatgagg   87780
aagatgtata taagttaatc cataaccaat ctaataagac aatcatagag gataaaaaga   87840
gtaaagttgt agatacaatt aaaaagatgt atgaattaga attaacatct gtagatgttt   87900
ctaaggtaga aggattatct ccactcgata cagaacctat gacaaatatg aaattacttt   87960
catataagct agatagagaa ggattatata gtttgagtaa atttattttag gagtgataca   88020
```

-continued

```
atggaattta tagataaaaa taatgtgatt aaagcttacg atataccaaa tgtttattta  88080
aaaggttatg tattacaggc atgtgataaa aatggagata caacagctta tgatggttat  88140
gaccaaatac actataaaaa aggtagagta ttaacattcc cttttgataa accattaaga  88200
aagataaatg tactatcagg atattacaaa ctatttaaaa aggaggacat aatatgattt  88260
attttgttag tgatttacat tttggtcatg ataatattag agaatttgaa gcacctacaa  88320
gaagtcactg gaactcagta gaagagatgg atgaaggttt aattgagttg tggaataata  88380
caattacaaa taacgatatt gtttataata ttggagactt cttttttcaat atgaaaccgt  88440
ctaaagtaga agatatactt aatagactaa attacaaaga gatgatactg attgcaggta  88500
accatgacca taagaaactt ataaaactat atgaacgtaa tggtattaca gtaaagtacg  88560
cagatatgat taaaaaggat ggtaaaagat tttatctaag ccattaccct acgctaaatg  88620
gtagaaaaaa catgtttaat attcatggtc atatacattc acagttaatg gatacagagt  88680
atcacattaa tgtaggttat gatgtagagg gtaagattgc ctatagtttt gatgatatta  88740
taagtagagc aggtgaatat aatggagaaa ttcaaaggta aagatttata taaaactaga  88800
attagaaagc aaacaattaa aaatttagtt ataaaaacag agaagctaca taataaacat  88860
ggaaagtata gacctatcgg tcatgtctat tattacccga aaacaaaaga gtttacttta  88920
tccaaacctg agcagaaaat atttatagag tacatgaagg cattaggttt tagtgttaaa  88980
cacaagagac gtaagaaaat aattatagta tacaagaatg tgttagatga atatcttagt  89040
atgtatcagg aagcaattga aagtacgtgt tgacaattaa ggtatactat gttatagtat  89100
agaaaaggag gttaactgat gaagcatttt attttgattt taggaattgt aattctagtt  89160
attgcattag gtattgtttt acctgcatgg attttacaat tagtgttatc tgcatttggt  89220
gttaaagtaa gtatttgggt atgtatcggg atatttatct taatcagtgc agtaggaagt  89280
atgtttagta gaaattaaag gaggaactat aaatggcaaa aaatatcaac gaatcaacg   89340
gagaaaatta tattgcaaca ccatcacaag ctttaagaga ggcactagca gaattaatta  89400
aagaagaaaa gaactttgca gattaccaaa ctaagggtga ggaacagtat gaatcacagt  89460
tacaactaag acacttcgat gcaatgattt ctcagtatga agaagctatt cgagtattag  89520
aggatagata tttatctcag attttttattc caaaagataa taaggaggaa aagtaattat  89580
gaaagcagag tcaatagcac gatttttttca ggataaggta ttacaaatag aagggtataa  89640
ggtaagattc actcaagcta gttcatcata tatttttagat atagatacta tggatgaatc  89700
agtattgttt ttagatactg tagttttcac tctatcaggc aagtacttat tagatacaca  89760
tattcgatt aataaacctg aaacactaag ctctaaggaa ttatacacag agattggtaa  89820
taaactacaa gagattgtag gagaccaaac gaaaacagat atcgaattaa ctcgatactt  89880
taaggaggta aaataaatga aatcagatgc tattataaat tcattattaa atatgaaaca  89940
tataaatata caaaaacaca atataaaagt aacacttgag aaaggtagat ataagggtgt  90000
agggtatcta atagagtttg aaacctcaat acaatacaga aataattata aattacaatc  90060
tccaataatt atatcttacg aaaatgaaga gcctaaagaa atcattactc aaattaaaga  90120
taaagtattg aaaattgtag aagagcagat aaagacagat gatttattta ttgaagcaat  90180
tgatgatatt aataaggaga cagctcttag aaaactaaag ccttatatta atgaagaata  90240
ctactcagtg tttaaatcat ctattgataa gggagtacct gtagtttac cttctgaact   90300
tttagataga tgcacaggaa aaacatcaac aatggcttat ttagctatag aatatgattt  90360
acctcttata gtatcaaaca cagtcatggt tagagtgcta ttaaatgatt atccgactat  90420
taaagttaca tcgaaaaaaa gagaaggtta caaagactca atagtgttaa ttgacgagcc  90480
tgactctgaa atactaaatc tttacttagg tatgcctgag tgtgatatta ttggtattac  90540
gaaaaaataa ataaatttat aaatacctgt tgacaacagg tattttttat agtatacttt  90600
agatataaag aaaaaggaga ggttaacatg aataacaaac aaattgaaag attacacaag  90660
aaagcaaacg aggtagtaag taaatcagaa gatattgaag atttaggtta tgtgcaggca  90720
cataaaatta ttaaaggata tcttgattta ccagtgtctg attttgaaaa gagagatgta  90780
atgactgaat tactattagc gttagataaa gctaataaat ctatagatta ataagggggt  90840
agtaatatgg tagatattat aattttaatt gtcggtttaa tattattttt agctagcgga  90900
tataaaattag ttttaggtaa atattatgat aacacagatt taaaaatgtt atttacaatc  90960
tttggtatcg gtactatact attacttgta ggatttatat tataaaggag gaaattataa  91020
atgaactaaa aagaagtact agaagttatt aaaaagaata agccatgtaa ggttagattt  91080
actgaagta ttttagcaat tgttaataag gaatttaacg cagatactga taaaggtgtg  91140
ttacaaattg atgtatcaaa tattaataaa aatgactaca ttaagttaca acagtattgt  91200
ttagaaagag atgattatac tgtagcagga gctattttat tttaaggggg agtaattatg  91260
aattatagag attttattac ggattgtatt agcggggtt ataacgtcca cattagtgtt   91320
actgagaaaa gagttcatat tatttcagaa atgacatcag catcttatcc gaagaagaa   91380
attaatttgg atgaactgca agcttatgtt tattatatga ataattttgg aagtcagatt  91440
acaacggagg gattataaat ggaattagtt attaatatta tagcagtatt aattggtatg  91500
tacggtattt actttttatgt tacaaaattt agtactggtc tatcaggtat tttaattgta  91560
ctaggtatgg ctgtaggtct ttacttttac ttagattact taaatgttag agagaatgtt  91620
attcgattag tatctgtaat gtttggtgct ttcttatta gtatcgagat gatttataat  91680
aagattatgt tcgaaattaa aaaatctaag tatgataaga ctgttagaac gtacagagga  91740
gaccaataag aattttacta taaagagtac ttaaaatagg ttaagtgctc tatatggtac  91800
cttaaaatgg cttagaattg aaattaagga gatgaaaagt tatgtatcct gatataggtc  91860
agttagctta taaattaaaa agtactagag aaagactaga aggtattatg atggaggaag  91920
tttgggaaat acatcataga gagacaggaa aattagtttt taaaggtgga tacttagaag  91980
taaaagaaat attaagaaaa atgtataagg agaatttaac attagtagat gtagacacaa  92040
tgttaaatat cggtcaaggg tttttgatg ttgctaaaag tatatcagca gaaaatgtat   92100
ttcaaataaa ctataaaaag gagttaccac gatgattaaa gtattttcag aaatggatac  92160
aaaatataaa acgattgtac cggagaaatt ccctaatgga gaaattaatt ttaaatatga  92220
tgacctaaaa tatttagtag aaggagaact atggtttgat gttttcttta aatgggaaac  92280
tgatgcgagc ttaatgcatt tgtatatgtt tactaagtat ctagaacaat taggtattaa  92340
aaataatgtt tccttcctgg aaattgcgta tttaccttat agtagaatgg atagagtaga  92400
agaaggtcat agcaatatgt ttagtcttaa gtatattgca gaatttatta acaatcttaa  92460
ttataaatct gtgttgatag cagaagctca tagccctgtc acagaaaatc taattaaaaa  92520
ttctgtttct ataggtgtca cacttaaatt attagaccaa tatattgaaa tgtctgaaga  92580
acctgtaaca attgtactac cggataaagg agcttatgac aggtacctat ctgatgtgga  92640
agacatctta agggattcca atattgaaaa ttattcaatt gtatatggtg aaaagaaacg  92700
tgattttgaa acaggtaaaa ttaaaggtat taaaaattgtt aaggataaaa atactttata  92760
```

-continued

```
tgataactgt attatactag atgatttaac aagttatggt ggtacatttg taggttgtaa   92820
aaaagccctt gacaatctta aggtaaatag tgtatcatta atattgaccc atgcagagaa   92880
agtatttaaa aacggtaaat tactcgattc aggatttaaa gatattattg taacagactc   92940
aatgttacct gatagccagt gggaaaaagc tattgctaaa catagagcac aagaaaacgg   93000
aacagaatta caaataaaga gtatcgaaag atatctataa aaggagaaga ataaactatg   93060
ctaaatccaa cattaatgtg tgactttttat aaattaagtc acagagaaca ataccctgaa   93120
ggtacagaaa ttgtatacag tacacttgta cctagaagta ataagtacta tgaacatagt   93180
gataatattg tagtatttgg tattcaatca cttgttaaaa aatattttat tgatatgttt   93240
aataaagaat tctttaatag acctaaagag gaagttatta atgaatataa acgtacagtt   93300
aaattcacat taggacaaga aaaccctgac gctaaacatt tagagcagtt acatgaccta   93360
ggttacttac ctattgatgt aagagcttta aaggaaggta cagtagttca ccctaataca   93420
cctgttatga caattgaaaa tactcactca gatttctttt ggctaactaa ctatttagaa   93480
actattatta gtactcaaac atggcaagca atgactagtg ctacactagc atatgatatg   93540
cgtaaaatgt tagataagta tgcattagaa acagtaggta atattgaagc agtagatttc   93600
caaggacatg actttagtat gcgtggaatg agttcattag aaacagctca attaagctca   93660
gcaggacatg caattagttt taaaggtagt gacactgtac ctgtagtaga cttttttagaa   93720
tcttactaca atgcagatgt agaaaaagaa atggttgttg cttccatccc tgctactgaa   93780
cattcggtta tgtgtgcaaa tggtgattac gagacaatgg atgaatatga aacatacaaa   93840
cgtatgttaa cagaaattta tccaacagga gtattctcta ttgtatctga tacttgggac   93900
ttttggggta atatgactaa aactttacct aggttaaaag atattattat ggaacgtgac   93960
ggtaaagtag taatcagacc tgatagtgga gaccctgtta agattatttg tggtgaccct   94020
gatgcagata ctgagtatga acgtaaaggt gctgtagaag tactttggga tactttttgga   94080
ggtactgaaa ctgaaaaagg atataaagta ctagatgaac atgtaggatt aatctatggt   94140
gattctatta actatgagcg tgctcagcaa atttgtgagg gattaaaagc aaaaggtttt   94200
gcaagtatta acgttgtatt aggtgtaggt agtttctctt atcaatttaa tactcgtgat   94260
actcatgggt ttgcaatcaa agcaacatat gctaagatta aaatgaaga gaaacttatc   94320
tataagaatc ctaaaacaga cagtggtaaa cgttcacata aaggtagagt agctgtttac   94380
aaagatggtt catgggaaga taacctaaat cttcaccagt ggttaaataa acagaattta   94440
aatcaattag aacgagtatt tgaagacggt aaactataca gagaccagtc actaagtgaa   94500
attagagaaa gaattaaaaa taattaataa atatttaaac tccctattga caaagggagt   94560
tttttattat atagtataac tatagtaaat aaaggagtga aagagatgat ttataaaata   94620
tcaaaacata attattatag taggtttgag tattctactt accctcctga tgaagggttt   94680
gcgtatgtag attatgtaga tgtgattctt atcggtgtag ataatcctaa gaaaaaaaag   94740
gttattacct taaaagtaaa tgagttcaat tcggatgact ataaagtagg tcataagtac   94800
aatattataa aaatactatg gtttgaaaaa tgggaatggt taaagccata agtaaaagga   94860
gagaaataaa atgattatag ataaaattaa tggagttaaa ctagaaataa gcggtcatgt   94920
cgtatcattt agtgtaagaa agtttgatac aattaatggt gagagacaat taatagacta   94980
ccatcatatt aaaagaaata gacaaaagta ctttagaact actgaagaat tttataatga   95040
atataaagaa attaagcctg acaaaaatga aatagatgaa atgtttgaat ctctaggtta   95100
cgtagatact gagttagatg atgtagtaag acacctggaa aaggttactg aaatattagg   95160
agttagtgaa caatatttaa atcagttatc ttataaagct atagaagagt atgtagataa   95220
agtagttaca cttgaaatta aagagttgaa aggagagaaa tagcatgaat aataactggg   95280
aaaaagaaag ggttaactat tgggaaaacg aagactgtcc gagggaatac ttagaaaaag   95340
cattcattga cctagtagaa tatgtcgaag gagttacagt atcatctaaa gatgttaagc   95400
agttaagaga agataaactt agagaagata ttgggttta tgagtacgta gctgataaat   95460
aaaattagtat ctacctattg acttaggtag atatctatta tataatagta tacaaggaga   95520
tgaaaatatg aaaaagttaa tagtattact tacaattact atttctctat tactaggagg   95580
ttgctctcct gataaccatg agggtaaagt agtaggggta ggtgaataca gagaaccaac   95640
tacttatata aaatcaggta gcgttactgt cccagtcatt ggtgaaatga aatattatgt   95700
agatttagag acagataaag gagaagaccg tgtatatctt aataaagagg tctatcataa   95760
gtttgaaaga ggtgatggtt tctctaatgt aggtaagaaa gtgtacaaga atgatgaatt   95820
aatatataaa ggagactaag tagtatgaca caatttatac atgataagaa agatagttat   95880
aatagtacaa atcgtaattt tgatactcaa tattataaaa atataccttt acaacaaatt   95940
gataggggct atggtcaagc aaaagctagg aggtttacaa taaataatac gaaccaaaat   96000
atatggatac ctatgacata tttaagacct aacggtactc ttaaaaataa tattgatata   96060
gattggatat ttgttaaaga aaaaaatagt ttaaagaaag caggattaga aataaaaata   96120
gaaattacag aaggtggatt ataatgtata tactagagag aacaattaaa ggttttgtag   96180
gtcaaaaaga tgatatctta ccttattact tcagaagtaa aagggaaatt gttcatttct   96240
taaaattaat ggaattccgt aagaaagaaa caaattattg ggttaaaaag aatggtgatt   96300
ttactattat aataagagct aaaaaattat tatatattga agaatataa caaaaactaa   96360
aggagtggga aaatgactta tgatgtgttt gtattataca aaagaagaga acctattgca   96420
caaggtagta tggaacattg tttagatgtc tattattggg aaagattaca tggatatagt   96480
aataaaegggt atgagctatt acctagaaga tatgaccagg aggaacaatt atgaatagta   96540
caaaattagt agattatttt acaagtaaac aaggtaaata tctaatatta cctgatgaaa   96600
ctaaagttag gttatctaat gtagatttaa tgtcttacat tatgagactc acttttactt   96660
ataacacaga agttgtgtct atagatattg ataagttata ttcagattct atagaaatgc   96720
atataccaca aggtctttat atgacaactg ttgttaaaat tcctaataca cagagtgtta   96780
gttcagttct tcataaggta ttagaggaat gggtaagaca agtacaaaat gatggtatat   96840
tcggattcgt atgggaggaa ttttaaatgta tagattttta ttctgatta attctgatta   96900
ttacccttgc ggtgggatgg atgatgtaga gcttaagttt aatggttttt ctgagttaat   96960
aagtaacaaa gatgatttgt atttaagtga aaatattgaa atatacgata ctaagtatga   97020
caatatacta tatattagta acaaagaaac gatattaagt gaatttagag actatttagg   97080
ataatggtaa aaataattaa aaaataaagg agaaatgtaa aatggcaaga gaagctaaac   97140
aaacagtaaa tacattatta caaagatcaa gaagcaaag aaaattattt   97200
ttaacttaac agatgaccaa attgaagaaa tggacttaga agtaacactt actacaaagt   97260
atagtaatag tgtgacaaat caggtaatta aaggtactga caaggatgtt tcaatgctta   97320
tcctgattttt aagtaacgaa gaattttaatg ataaggttat taatattgaa attgaagaaa   97380
tcaatattat tttataaaaa ctttaactct attaagagaa gggcaactag tatttaatttt   97440
taaatgggag gaattaatat gataaaataga tataaaaagg tatgggatga aataacccaa   97500
```

-continued

```
caaattgtta atgtagaaat tattaacttt aaaaatgaaa cagtaacaat agaatctaca 97560
gatgattcag gattatcaga gataagaggt tttgaagaag tagagtttat agattactat 97620
ggataagatg tttaaagtat ataatttata aggaggaaac atatggactt gtttgcaaaa 97680
ataattatta tgtctatagg agttgtccct ttaattacat ttatggtatg tttagctata 97740
acagattatt ataatagaca ttaggactaa taggagtatg ttgactaata aggaagatat 97800
ataggagagg agttaatcaa gtaaaaccaa taaaatcaat taaaaccaag taaagtaact 97860
aaacaatacc tagagcctgg gaaaactttt acctctccca ctcagcctat tacttactac 97920
cgacttccct aactatgtat tctatagtta taatattcat ttattataca atacttaaac 97980
tatagtattg taaccttaat ctatactgaa gcggtattaa tctattgtta ttatataata 98040
atcttatata atggtggtat aatctaggtt attacattag aatcattcta atctagaatt 98100
ttaatctttta gaccctagga aaagtggtac taaaatatag aaccctatag gtatgggatt 98160
cttattttta aaattactaa aaagtattag gttttcccta gggtaaagtt ttaatgtacc 98220
taaaatcgta agtagctcct tatcatttag gtctgtttaa ttgagaatat tagaagatat 98280
ccgcttcaat tacaattaaa ggttgacaac tatgaagcgg tatgttatac ttagtattgt 98340
aggggtggtt ccctacagac ctagactatg gtcgtgattt tggtttgcat attagtgtca 98400
ttcataacct ctattccagt aggggttatt tttatttaag tgttgacata ctctaagtag 98460
tatggtatga ttagtatata aggagatgaa taatatgatt gatatatact taggggaaaa 98520
ctataatact gattacttat ctactattat gaatattata agacttccg cttcaagaga 98580
gttaagttat gggtttaata ataaagaagc ggatgtaaat atagaggata tgaagtatga 98640
aggtgatgtt ctgcatgtat atggtacgat gtctatggat tatccaggct gtattattat 98700
atgtattact agagatgaga ctaaggttat acatggtggt aactttctaa caggtacagg 98760
tcttagtcaa gaagttagag aaaaattcta gggggagtta ttatgattat accattaatt 98820
atattcatga tgaccttcgg tacatttgca ttcagttatg ttgcacatga tgcatacaaa 98880
gtagatgaaa aaggtatcat gtatgctatg gtagttggta ttgtagttat aaatgggatt 98940
ggtttagaaa tgataattgt agaatgttta taaaggaggg agtaaaatga taggtcaaat 99000
tatactatta gctattgtta gtatagttac aataggttgt gtaggattat ttttctatga 99060
gacgttcaag agtattaagt atgatgctaa tgataaaatc tttatgatta ctgggagtat 99120
attaatgtta gttattatcg ttagtggtgc attagctata cttggcattt agagctcatt 99180
taagaagcgg ttaagtagtt catgataaat tggtctagaa atatatgacc gcttctctat 99240
ggaaggctga gagggtttag aattgaaagg agagatataa tggctatatt ttttagtatt 99300
ttattattga ttaacatata cttaatatac tatgaatgta cttcagttac gtttgattgg 99360
tgtgcactgc ttatttacgt atgctcatta tgctcttgta tttatttaat agtatatttt 99420
gtataaaagg aggagatata atgcaagcaa ctatatactg tgctaatagg tatagtaaaa 99480
atacattaaa gagtctttta gaaaaattag aagcggagaa tagaaactta acatatagta 99540
ctgacatatc agatatggag gaagtggatg ttattgtaca acacactgac ttatctttg 99600
cagagttaat ggattcttgt gatagagtaa gtaaagggtc tgaccgcttc caagtatttg 99660
taggtaatca cgcagggtat tatataaacg gtgatttata tattaacgaa gtaggtaagt 99720
ttattgtacc taggaaaacg aatatgatga tgtaaggagg aaatataatg attcatatat 99780
ttgtaaaaga ggattataat aaagaaacat taaggagttt acttgaatat attaatgata 99840
ctgtaggtag ggaattaact tatggtatta atacagacta tgataaggat gtagtgattg 99900
aaaccgatga ccctatagat gaggagaata cgattgattt atcaaatctt cctcactta 99960
aagatgactt atgtattctt atagaagaat tatactgtaa ggcatttgtt aatgggggaac 100020
ctattattat acgtaagtat gtagagggga tgttataatg tttataacta ttttaactga 100080
aaaatatgat gccaaggctt taaagaaagt attagaacat attgataatt gtagtagcag 100140
aggtcttagc tatttaatgg gaaaaggaga agcggatgta tgtatagaga agaatgtatt 100200
cagagaaaga gatgatgtaa ggattaactc aaacattatt gatgaaggta aactttgtat 100260
actcataaat aaaaatggtt tagaatgtag ttactataga ggtgatcat gtaatattgg 100320
tgcctttgta aaggagagat tataatgata gaaatatatc tcagtgaaaa ctatgatagg 100380
gatttactca aagcagaatt aaaatggatt aaagagaccg cttcaagaga actaacttat 100440
gatgttaata gaagcccagg attagatgta catattagtc cttttagata taccaaggat 100500
gaggttgaag aatgagctt acatcctcag tttgaagatg atgtatgtgt atttatagct 100560
gaaacatgga tacatgagta tcgtaatggt aaatcaatag gtgtgagatag tatggaagaa 100620
tatgtaaagg agatgtaatt aatggtagaa acttattata cagtatatca taagaatagt 100680
atgaaaacta ttaaggatta cttaagtaga agtgatttaa ttgacttctt atataagact 100740
tggcataagg atataagtaa tatataccca acagattata ctacgtatga aacaaaattc 100800
tgtatagaca tagatgtagt tagattaatt gaagcggtta atgaagaagg tgtattactt 100860
attaatgaag gtaatattgt agagtggtag gaggagataa atatgagtca gtttttcacg 100920
tatacagtgt atcatacaga aacagctaaa gtagtagcta agaatttgtt tgatgcatca 100980
ttggtgcacc ttattaacaa gatgatagag aaagatatag ttaaggatat taatttagaa 101040
tattcatga atacacgtgg tgtagttata gatatgagta gactactgga tgatatagaa 101100
tcacagggtg tatttctatt caaacgtaag ctacatggat aataggttag accctaaaaa 101160
gtttgagata caataggatg cttaggataa taggataaaa ataacttagg atgcttagga 101220
tgaaatacga tacgataggg aggttaagtt aagatgcaag agttaataac ttatataatt 101280
taccataaag aatcaggtaa agtagtagca caggatttaa gtgaattaga aactattgaa 101340
cttatataca aaatgataga agagggatta gtaaaagata tagaattatc taactaccgt 101400
cttttttagtg ggaatataga tatacttaac ttattagtag acatacgtaa acaaggtata 101460
tttgattttg aacatacttg gcacacaaga taaggaggga taggatgata gttatatatt 101520
cagatgagtc tagggattac ttaagagatg agttcttacc ttggcttaat gatagagata 101580
gatatttaaa atattataag aatgagttac ctgaagatat agactcttct tatgttgtat 101640
cagttgtata ctgtagggat atggaaggtc ttatgaatag gaaagatatt cttattggta 101700
atagttatag agagcctgta gctgtattag gtgttcctga atttttggt aactattcta 101760
attattacta ttataaagga gagcatataa gtaagcatga cctaggagag ataattaggt 101820
taaaggcttg gcaacgtaat tttgactaag tagctctctc taatttcact aagtagctcc 101880
ctaggaattg cctaagtagc tcggtgtgat tttaccctaa gtagctctct ctgttttcta 101940
ttagtttatt ttaaccgctt cacgtgtcta tatatagaca atcggaataa tagcagaccg 102000
caaaaagaaa tacactagga tattattccc agtgtattgt ataatttttt tatagaatat 102060
ttataacatt gtattcaaat tcatttactt catgttgtga tttaattaaa ttttaattta 102120
atccgttttg tgtttatag tcttttacta gtttttcatt ttctataatt aaattattaa 102180
attcttcttt tgttgtatcc tcatctacat aaaatttact ttcatatatt tcataatatt 102240
```

-continued

```
ttttatctgt tccgttatca atatcatctg atatttgata attttttgaat acaatttctt 102300
ttgtttctaa ttcatttact aataattgtg attttgcata ttgtaatacg tcttcattgt 102360
cccacattgg aatatagttt attttcattt aaatcaaacc cttttctata atttttttat 102420
ataatatttg tagaagcggt tggggtttgt cccttgcctt actacactta atatattaca 102480
gtatagttat tcagaagtca atactttttga gtaacttttt tttaaattct tttttcttct 102540
atataatagt agtttttagc cctaaaaaaa gttttttaaa agaatttaca ttttcttatt 102600
gacttattaa tcatatgata gtaatataaa ggtacagcaa gagaacagca acaaggtatt 102660
agaattatat aaaaaaatta tttaattgga gatgatttaa atggatgtaa aagaaattgc 102720
agacactata atggagttgt ggcaaatgga cggatacaga tgtacagaac cgccattata 102780
tgaaagcaca ttaaaccaca cacgcacata tacggcttta atcgtaagca ttaagggaaa 102840
ctatgacact gttcaaatgt tccgtaaaac gcctataatg agcatgagag ggcaagcgca 102900
accggctagc atgttagtaa atgtaattga tgacgtgatt ataatcgtat atgaaaatac 102960
ggtttacggg gtacagaata aagaaataaa atttattgaa gaaatttaaa aatagggtt 103020
gcaataccccc ttaagatgta gtaatataat agatgtaagg gatagcaaca caccttaaaa 103080
aactttttaa aaaagttaaa gaaaagtgtt gacaccttac aagatacatg ttaatattag 103140
tatagaagtt aagacaagcc acatagcaaa taacgaaatt aaataaaaaa attatagaat 103200
aggatttgat tattatgaca aacaaaaatt acttatacga agaaactcac acagtacaag 103260
ggcaagacat tacggctttc agaattccaa atgacacaaa cggcaacccca cgttatgtag 103320
tgcatttcat ggatttagac attaaactag cagactatga caacatcaat aagctatacg 103380
gatttaaaaa atatactgct aaatggtttg gcggtggtgt agtattccaa agctataata 103440
ttgaagatac attaaaattac gcactatcta atgttaaaga aatagaagcg gttaagaatt 103500
aaaaccgctt ctgaattaaa taaaaaaatt atataaaaag gatatgatat tatgaaattt 103560
aaaatagaaa aaaataacag tgatataaaa actttatgga atttagctaa aaatggatat 103620
atgagttatc aaactgtaca caatatattt aaaaatgaat cagatgaatt tattatattt 103680
aacagtaaac aaacttataa taaatttatg gaattaagat ataatagaag tgcaattcaa 103740
tagtataaaa aagttatata attccctagg attaaattcc tagggatttt tatttgtttag 103800
aatttatata aaaaaaattat ttaataaata aattagtgta aaattgactg ttgacaaggt 103860
tgtattttttt atggtataat gaagtgaaga ccttttttag tataaaaaaa ttattatata 103920
aaaaatttat attaaatggt tttaaaaccg ctctttctcc ccaccttgtc atatttatag 103980
tggaagggtt aggcgggtta ccactgtttt actttctata tatagtatac tatgaataat 104040
ggtaattgtc aacacctttc agaaactttt tttactttct tttattatta tataaaaaaa 104100
ttatacatat tttagggctc cacttccatt atataataat tcggtcttaa tgtcaatact 104160
tttattcaaa aaagtttttt aaattaattt caacaaatct attgacttat gtttttttct 104220
atagtaatat ataggtatac caacaaggga ggcaatacaa atgctaaaat ttaaatggaa 104280
aaacaaaaca atcaaatcaa ctcaaaaaac ggataacatt attttacttc ttataggtgg 104340
tttagttgca acagtcacgc ctaaacttgt aaactggttt ttactactac aagataatat 104400
aaaatatttt ttaagataac tattgacaac ttagaaacaa cgtgttaata ttaagataca 104460
aggtaaggga agcggtcaac cgcttccgac ctaaataaaa aaagtttaaa aaaactattg 104520
acagtcactt gaaaccatga tattattaag ataacaaaaa acaaacagaa aaggaattga 104580
ttataatgaa atttatcaaa actatcgaaa acttattaga aaaagcagaa aacaaagggc 104640
aagcaatttt aaacggtcgt tactttgacg ggtatagcaa aggtgagctt gaggaaaaat 104700
atgcaattga aattgatggc aacaaattga ttatgcgtca ctggggtaca caaacaattg 104760
agattgactt aagcataaat gagattgttt catattacgg tgaaagcaat tcagaccgtg 104820
acagtttaaa cacacttgta tattgcttag gaattgcgcc aaactttaga tacttaccaa 104880
gcaaaaactt attcatttac gaaaattaat taaataaagg gcttgacttc caagccctac 104940
catgttatta ttaaattgta aggtaatcaa gcacaacgac aaaatcaaact gaaaaggaat 105000
tgatgaaaat gttcaaatta caaaataaag tggaaattat cgtacctaag gaagataaca 105060
acggcgttga gattgcagac aaacgtatta aagaatatgt aaatagcatc acaatggaag 105120
cgggcggttg tactattaca gaaattaaag ggcaatggta ctcagaagat gaaaaacgta 105180
taatggaaga taacaactta aatcttgagt ggtattatct gcaagacagt gcaaaattca 105240
tgacagttga gttaaaaggt attgtaagac gtttaattga agtttacgga caagaggcta 105300
tcagtatcaa agttaatggc acattgtaca ttgtagacca atcagacatt gaagaattac 105360
acacaacatt attaaaatatc atgaaataaa aaatttatat aaaccgcttc ggattaaatt 105420
cttgaagcgg tattttttgtg taaaatttat gcttgacaaa tgtattaaaa aatgagataa 105480
tagagtgacg acttttttta gtataaaaat aatattatat aaaaaagtta tagagttttt 105540
agggctccaa gtccattata tcaattttgc tactagttgt caatactttc ttttttttata 105600
taataattta attatcttaa agataccgtc cacctccatt atctcaaatt ttgccccctaa 105660
agtcaagaac tttcttttcaa ataatttatt taaaaaagtt tacaaaaagg gttgacttat 105720
tttgtactat ggtgtaatat ataaagtgta gtaaggaagc ggaggaaata acctaaaaaa 105780
agaatttaaa aaacttttaa aaaggtgttg acaaacttcc aaatacatga taatattaag 105840
atagttagaa aaacaaaaaa acgaaaagga attgataatt atgaacagat tagaaatagt 105900
aaaagatacg gcaatggaat atatccttat gatggataat agcgttatgg acggcgttat 105960
gacacaagag gaatacaacg aagcggttag ctttgaaaag gtgtatgact acactctatc 106020
agaagcaaat caagaagtta aattcttagg tggtaaggtt ttaactttcc tagtacatga 106080
agcaatcgaa gaatacgcat aaaaaaaactt aataaaaggg gttgacattc aaccccctacc 106140
atgttaatat taatatatac caaatgagag gaattgataa ttatgagata cgaaattgta 106200
acgttagtta atcaagaatt gtttatgtat gcaacattca acaagcagga agcagaagcc 106260
aaatatcaag aatggtgtga cttatatggt caagaaaatg taagcatgga aaaaaattaa 106320
aataagctgt tgacaaacta accgcttcat gataatatta aactatacta aagaaaagga 106380
aatgattaca atgacaaaaa caatcaaaca attagaaagc caattagaga gtctagaaag 106440
aaaatcagat gaggaattag caaacggata ctatgacaga tttgaaagaa cttgtgcaca 106500
gattagagaa ttagacctac aaatcgaatt aaaaaagaac tcagaaactg tttaaaaaaa 106560
tctaaataag gggttgacac ttaacccctt acatgttaat attaagatag ttaaaaaata 106620
caaataagaa aaggaattga tacaaatgaa attaatcaat agagataaatg aaatcgtaat 106680
tagcatagca acacttgaga gcgtaaaaca agccctaatt tgggagtaca tcgaccactt 106740
agataataac atcctagaca gtaaaattta cgaccaagaa gcggttgtgg tgacttctga 106800
cactctacag tcaatcaaat ttgcggacac tatggaagaa ctagaagaat atgtaaacga 106860
catcggttgg aaattaattt aaaaaaaggta ttgacaccct agcatataga tggtaatata 106920
agagtataga aaaaataaaa aaagaaaagg atttgattat tatgacaaat acaatacaag 106980
```

-continued

```
cattttttaca aggacaagaa gcaagcacag ttaaggacgt agcaactcat ggagtacaaa   107040
gcggagcaat tggcaaatta atctacacat cagacatagt aaacttcttt gatagatacg   107100
agcaggacat tgaagccgtc atcactgaat acattgaaga ggttacggga caacaatatt   107160
atgacttatt gaactatgag cttatgagag acctcgagaa ttatgcaaat gtagaatttg   107220
aagacgaaga cgaatataat aacattcaat ttgacctagc agaaaacatt gcttctgatg   107280
aggttgaagg atttgaagac atggacgaag cagaccaggc ggaagcaatc tatgaggcta   107340
tggatgatgt tgaattagaa ctacaagaaa cggacaaggt tcaatatgtt aatctagcgg   107400
ttgagattgt agcgcaaaga atggcactat aggaagcaca cagacacaca cagagaagct   107460
taaccgcttc tctaatacaa ttaatcagga gatgttgaag atgaaaatta accaattaaa   107520
caatgctaaa aaactatacg aaacattatt tgctatcgag tttgatagta ctatcgagga   107580
agattggaca atagataatg actctctaga agctaaacta ttcttggagt tatcagatga   107640
gggcaaaaag gtttatgcaa tgagtcacgc taagcaatgg gcaaatattg ttatggatat   107700
ggaagaagag gaatatagaa gctattacgg aaatgattta gattatattt tagaggagat   107760
gtaaaacatg aatacaagaa gggtaaacaa agcgttaaac gaagcggttc gattattaga   107820
tgagcaaata gcagacactc aaaagactat gcaggagttg aataaacaac tcgagaagca   107880
aataaaggct aagcaagagc taatgatatt agttgatgtt atgactggtg atgatgagta   107940
atgagcatta gagaggttca taatgtcgtt aagagtgcaa agagcaaact cctgcaggaa   108000
cataataata ttaataatgt aatcatagat gactacatca cagaagagct acacagacgc   108060
acacagggaa gcggaacaat acagatgaac aataacaccg cttcatatag taatggctca   108120
tatggtagct tagaagagct tagagaagct tatgacctat cttcattatc tactgaggag   108180
attaaagaac taatacaaac atttgtttaa attattttat caaaacgctt tacaatcttt   108240
taatttgtat gatataatga acttaacaaa ttaaaagaaa aggaaatgat gaacatgaca   108300
aacttattag aacaggaaca attagaaaaa gacgtaaaag atattatttg ggtattagac   108360
agaatgattg ctagaggaga acaatacact gaagcttacg atattttagt taacaaatta   108420
gaaagacaag aaaaaagaat cgtagaaata aaaaaacaaa acggaatatt ttaaataaca   108480
aatagaggga ataaaatccc tcttttattt ttatcttatt atataatttt tttatattat   108540
acgggggcag gggtaaaatg ccactcaatg ggggtgggtc tatataccc tatggtctac   108600
ccaggtactt atttttttggg gaaaattatg aaaataaata tttaaaagtc aacacataaa   108660
atatagaaag taagtcaaca tcccttataa taagtcaaca atttatagta caaatataaa   108720
gcctctaaat ataaagtcaa catatctaaa ataagaagag aggtatatcc tctcttctct   108780
taactatata agtacgcttc tattatttag ttcctgttct attctattta aatgctccca   108840
aacctcaatc caatttactc ttgaatcatc ataataaagg tggaaatctt gagggttttc   108900
taaatacgct tctagttcat catagtatag aacatcaaaa gctgtgtcat caagacctat   108960
ttgaatcttt agtatatctt tatatcctaa ttgtttatta ccgcaataag ctgtatcttc   109020
taaccgcttc tctagtttat taaatagtgt ttgtatacct tgtagttcat tcataatgta   109080
tgacctccta attgattata tacttagtat aaaggatagg tgttagaatg tcaaccttta   109140
tatataaaaa aagagaaaga atattattct tcctctaagg tattactaat aacttctaat   109200
tcatgaatag taatcatatc cattctatcg aatcctcttg ggtctccttt aatgaactct   109260
tgttctcctc tatgagttat actttcttta tatccttctt ctttaatacg tttaattaag   109320
ttctccttat ttgtgtatat ctcatcttcc ctgaaatgga aattatcttc ataggggttca   109380
caattatcat gttctacttg atatagtttc atattagtta tcctcctatt ctctatagta   109440
atcatatatt tctaaataag gtgaaaatgg tgagtcacct ctagtattaa taataacttc   109500
tccctcttga ttacttaact ctataagctc ttctaagcta ttaatttcta cacaccaacg   109560
ttctatagta aatgtattac ctttttggtc tacacgttct aattcccttta tgtaggcacc   109620
ttctataggc tttttattaa ttgtgcttgt tctatctata aaaaattcca ttactttttcc   109680
tccttataca cttatacgca tgattaaata aaaaattataa aacttactgt tatgatgttc   109740
tatattacaa aggtataaca ttagtctata ataatactct aaatcatgag tatgtttaaa   109800
agttttttca ttaaactcag attccagtag gttaataagt ttttcatgag ttaaaacata   109860
tgcaccctcg tcaccaaatt catcaaattt atcataatat atttctgcat ctcttagtaa   109920
gagttccata aaatatcctg gttttctaaa atcatcttca aaattaaatc tttgataata   109980
gtttttttct aactgatttc tatatttcga attgttaata aaatgttgta atcctttttg   110040
ttctactttt cttttacttta aagttacacc aattacttca aaatctaatc ccattacttt   110100
tcctcctttt cgtaagtcca ttcaccatat tctgcgttaa aatgagctgt gtctgttccc   110160
tcatcttcat attctacact ataccatgca tcttcttctg tttctgcatc tatatatctt   110220
atttcttctg tagtaatagt acgtttttacc ttaaatctct ccatttgttt ttcctctcct   110280
ctaccttcat agatattacc tataacacat aattctaagg tatttgtata tgattttaaa   110340
tagaaatcac taagcaaagt aatcttatta ccttcataat tttctataaa gaaaaaccct   110400
ttacctttt taacgatacc tgagtttata tagttaccat taatatcttg tatttctaca   110460
atatctcccct caaatatttc tacactattt ctatcactaa gacctgtgaa ttgcataatt   110520
tcaaggtttt ctcctaaata accatcacaa gcaaatagat gtgaatatac tgtgtaatct   110580
gcaaagtcaa acctagcaat atcaaacatt ctttgtgatt cttcatccca tgctctaaat   110640
ttaatcatct actttactct cctttatatt ctcttctaat atttgtttta atgtttgaca   110700
atcttttttgg tctagggtgt cccaactctc tagattctgt aattgatagt ataattcatt   110760
tacaatttca tcgaaggctt ctgcttttttg atagacttct tgtaactctt ctaattcttt   110820
ttcattatca atacaccagt agttctcgtt gtcagttata atatcttgaa ttttatttttt   110880
atattcataa gccattattt atccctccta tcttctatcc tttgttttat ctcttctcga   110940
ttacggtggt gttctttact catttctttta cgttccttat ttgttaatct tattctataa   111000
ataaggtagt taatatataa tgttccggct gaccatagta gtaggaatga tattaggtaa   111060
gtccatgaga cacttatttc tatcattgtg agtcctcctt atattcttta taactttaa   111120
taacaatctt acagataccct ctattaacag ctaagaataa cataaatgat aatagagtta   111180
taactgctct aatgtctcca gtaaagggta ataatttaaa tagtaaaaca ctttctaaaa   111240
cacttgtagc tgtaataatt gtaagatata agatagatag taaataatcc tttaatttta   111300
gtttaacgaa aggttttttta ttatcttgag ttcttgttat accatataga attataaacc   111360
atgcaacagg tatgagctga gttataaagt cattgtttat gcctaataca tataaaccat   111420
aaatgatacc ggcaggaata ccaataatga atgctaagaa tacagagaat ataattagca   111480
ttaaaggaag agctacaagt aatcctaatc cttgtattga atactctagt gtattcttttc   111540
ctaaggcttt aaagaatgtt ttattcatct tctacctcct tgtaatatac agtatctata   111600
tgagtaatat tatcttaaa ccatagagac ttatccccctt tgttagattc taaagtttta   111660
gcaccattaa aaacaagacc ctcaataaaa gaatttaaat tagtttttagt atcttttttgt   111720
```

```
tgtacgataa tagaagaccc tgatacatca caaattctta taaaattaat atcttttttt   111780
atttcttttt ctactttatt attttaaat atcattataa ttcctcctct atataatcaa   111840
ctgtttaat atactcacta tttttagta ccttttcac attttcacta ataaatttt   111900
cttgctctat ttcatctatt ttttcctgta ttctaagata cagaatttca ggaacacagg   111960
caggctttg taattcttct tctgtaactg agtttgtaaa acttgccatt ccatcattag   112020
ctagaataag accatctgta attctagtta atttatctcc attaggttta taatatataa   112080
cttcgtaaac ctcttcatct ttaaataact cttcacgagg tattcttcta gaggagaagc   112140
tataaccatt tttaaaggtg ataattgtat tttgagtttc tcttaaaaat actcttaaag   112200
tattttcaaa aatatcccat ttttctttt cttcatctgt tatagttata ttttccttgc   112260
tttttttaaa catcgttatt attcctcctc ttcttctata gaattacttt ccgtaatagt   112320
tacttctagc atactattgt aatactcatt cttttgatta atattatagt tatcattata   112380
ttcattgaag tctacataaa tgtattcatt tgttccattt tcataaataa tatctatagc   112440
tgtaaatatct gagtacgctg taatcatttc ataagcattt gtattatcag ggtaagcaaa   112500
accaacttga ggtatttctt taggcttatt aatgagaata ccaaagtaag tacaatgacg   112560
tgttctattt atgtgtgaag ttcctttata cgtaccatag taatttattc cttctgtaac   112620
accttctata tggaacctgt ttacatcttt aggttctaac cttactacat cacaatttttc   112680
taatactaag tctatatatt ttatattcat tttaattctc ctttttttatt tgtatttgtt   112740
gtatacacaa tgtactcgaa cgtcttccat tactttacct aatagattct gacctttcca   112800
gttactctca tctaatatttt tagggtcact ttctttaaga cctactcccc atatttttatc   112860
ataagatgat gcctctacga aatctttacg taaatctgta tcgagtattt cccgtttttaa   112920
gtgtgtagtc ataaatttat ctttaaccac ttctaccata atgtcatatc ttaccttatt   112980
ccattgctct tcattaaaat tacgaacttt acgacctaga cttttagcat ggttcggatt   113040
cttagcattt aatatttctc ctgctatttg ccagtcttta aaatattgcg ctttgtgcca   113100
cataaaagct tgttctgagt tattaaatgt tctcccttta tgtttaaatg ttattgggta   113160
aaagttagaa taaatatctt ccttacccca aaacataatg tatctgcttg tttctttcat   113220
aatatctccc ctttaattcc ataatgatgg taacacaatt ttgaaattat ctaatatttt   113280
attttgtact tgttcaagct catcatattt atccatatca aaatcatcca tttcttcatg   113340
ataatattgt attaagctta aaaatatattt tatcatatct atttgtgttc tttcttcacc   113400
atctacatct acaaaagtat tccattccat atctatacaa gaacgttcac tactttctat   113460
aaaggcattt aaatcggcat atattgaac aaaaaaagac atatcatagt tccaatactt   113520
aggttcattt cttcctaatt tttattcat tttttttatac tttctatttc tctttaaccc   113580
aaaaacttct ttttcaaaat catttaattt taaacctttta aaatattttt tcttcatatc   113640
taatcctcca atttaataag tggtaaatct atatctctaa atacagaacc tacgtcacat   113700
agcagtatat cattatgttc ttctacttca ccactactag taggtgtatg accacataca   113760
tatataaatc catcttttct aggttggaag tctctagacc atattaactg gtctactgtt   113820
tgctcttcta taggtttcca actaactccc cctgaatggg aaaatatata cttaccttct   113880
ttataataccc ttctacaatt aaccataaat attttaaatt ttctataatc ttcagattct   113940
ttaagtttct ttagttcact tttaataaaa tcataatgat ttcttaaatt atcttctaca   114000
ctttatatt ttaaagttac agtactaaca ccgtaagagt taagtgtttc tatacaatac   114060
cttgataacc attcaatatc atagatactt aaccggtcta cgttttccat aatatttataa   114120
aactcatcat cgtgatttcc taataaagct actacattat catcatttga tagtaaatca   114180
aacatgtagt taacaacgtc ttttgacctt ttacctctat ctacataatc tcctaaaaat   114240
acaatagtat cctcgggtct tcttttttca tttatcttat ccataatttt cagtaattta   114300
ttgtattcac cgtgaatatc aggaaccacg tatatagcca tttaatctcc tccttattgt   114360
atataactat cttaccatac ttatttataa aagtcaataa aaaaacacct attaatgaaa   114420
ataggtgtcc gacagagctc ccgtacttag attacggtta ataatatttt acgacaatta   114480
tatgagaccc tctatcgttg aaacgctcgt cactgcgtta gatacggaat ggagggatac   114540
taccatccgg agtctacggt cagatacaaa gcctctgccg ggcaacatac ggtatctctc   114600
gtacatcagg ttgactagac ctttagagat tttcactcct tctcttataa ccagtaactt   114660
aagagaaata ggttttactt agtagatatg aaacaataaa tctacatata atattaaatc   114720
atagtcaagt gattgcacat atgtctaata cctataagtt ttttgctagc ctggtatatg   114780
gactctgtag gattcgaacc tacagtcaaa ccgttatgag cggttggctt taccttttaag   114840
ctaagagtcc tagaaaatatc ctgagagagg actcgaacct caacgactag gtagctacaa   114900
ctagccagtg ccattactca ggattgctag taacgctaaa tagagtcata acgttaccgt   114960
agaccttttc tactcttggt agataggtaa aatataatga tttcaaagta cctatatagt   115020
caggctctta ctctcattat aaggttaaaa aggttaactg tgtttagcat tatataagag   115080
gctttagtta actactatac taatagtata tcataaatag tacttagtgt caagataatt   115140
tatcaattga atccataatt tttgatgtac ttcttatatc cgcttcttta ctgtgtttaa   115200
gaagtatttt taatttcatt agaaaagaat tcttttcctt ttctatagta tctttcttgt   115260
tactatattc tgaatacatc ataaattcta taaatatact atttctgtca gatgaaaaca   115320
tatcatagaa aaatggacaa tcaaaactta tgtcatcttt attaatacta aaacattcag   115380
taacatttaa atcatttatt tcatatacct cgaaatatcc atcaactctt ttaagttcta   115440
tagcactatt atatctataa taacgttgtt cctctattaa cttatctttt gttagataag   115500
gatattcatt tataaatata ggattacttg ttccatagtt attttcagcat tattcagcat   115560
cttctaagga atcagtataa cctaaaactt cgtaacttgt tgtatacaca gtatcttctt   115620
cccacaagtc atagtccatt tcctctattt cttcctctag tatataaatt tttttcatat   115680
attactccca aacaccaata agatttttaa gtttagctat aacctcttct tctgtttgat   115740
aagaaaatac tcctgtaatg tgttcatagt tacctacaat ttcataatcc tgcgtaccgt   115800
gtctgtctac tagatacgag gtacccataa catttaaact atcttctgaa taactgaaat   115860
ttatattata gtctactaaa aaattaataa ttttttttcat ttacataacc tctcctatcg   115920
gatattgtcc taacattctt gttccatttt cattataaaa agtatattct actacaataa   115980
tattcatcat atctacatat atagcttcta tataaggttt aatattttct tcttcttgta   116040
tatgcttacc tataatatca tataataatt cagagtgtat tctttttatct ctcattgtag   116100
acctccgtaa gaaatgatac cgcttttatct tttaaagatt tttctactag ttccatagca   116160
tctttataat gttttatgct agattcatta gatttaagtt tatctttttac ttcttggatt   116220
aaaggttcta ctttattaac caaatctttt ttctttttcaa tacttacatt acttctctta   116280
ttatctaata cttctttttgg catatactta acttttgcaa agtctttata gctaacattt   116340
aagttatcta aatcatctaa taaatcatta taatattcta aatgattata gaatgtgtaa   116400
aacttaacaa ggtctttacc agttaattct tcttttttta atatattatt gatattacca   116460
```

```
ataacagagt atgctatagg cttaaaatta gctctaacat aagttaaaaa tataaaatca 116520
tcataaaaca agtctaaaac agttttattg aatctagtgt ttttagcttg ctctaattga 116580
gcacataaat taagaacatt atcaaatcca ctctttaata ccaaagaaat aaatctctcc 116640
actgcatagt atcgagatac ttctgtatgt ttacttgcct tttcactatt tctaaatata 116700
gtatctgata aaggttgaac tactaaactc atgtaatctt tatctgaata ctcatctgat 116760
gttccttgat aggtacttcc aaattctatt gttgataata agaaactttt ttctaagttc 116820
attataacat cctcctttta cttgttattt aaataataac atatgttgat agtaatgtca 116880
aacattaaat atcttctgtt gtgtcaactt catcttgttt atatttaaag tgttcataaa 116940
ctttaaatag aatagcccct agtgttatta attctaaaat atatttcata acaatcctcc 117000
ttaataaccg tgtttagtta cccatcctgc taaagcatcc atagccatat catattcttc 117060
ttcatttttta attcttataa ttttctctat ttcttctttt gcgtgtttag aattcataaa 117120
atcaatatct actgtatcta aatttgtata atcaatattt tcttttataa actctttttg 117180
cggtaggggtt atagaattaa ctcgtacatt ttcgtgattt aaaaattgat agaagtccat 117240
actattcacc ttctttttaaa cagtctgcca tatctttaa agtattaagt acatatttca 117300
aatctctata ataactatca gaaaaactaa taacagcata tggtgtcata tcactatagt 117360
gtgcacaatc aaaacctaat accctatagt caccttcatg ttcatcgtat gttatacctc 117420
catgagaaca atcttctata ctattaaact gttctttggt tatattcgta ggcacattaa 117480
tataaccatt tagatgtcct gaatgagggt gacgtttaac agttaggttt attccccttat 117540
aatctatatt taaagttaag tcctctccta atatattatc ctctttatct ataatttcca 117600
taatatgttc cggtgctttt ccaaacatca taattcctcc cttttattta tactttttact 117660
atacactact ttttctattt tgtcaacaaa aaaaggctac taattaaagt agcctaagaa 117720
ttaattattt agcgttatat ttccattgcc aataaccatt tttctgtgag aactcaaagt 117780
gaaaaccgtc atagtcaaat tcaatattat agtctccatc ttgaagtggt tttgaattta 117840
gtacaggact attactcttt gccaattctg ctagaaactc atgatttact ttttccatag 117900
ggtttattcc tcctaattat tcttacagta ctaatatatc acaggtcttt ttctaggtcg 117960
tttttaaact tctcctcgta agagctagca taagtaacct catatcctat tatcttagta 118020
taatctatgc aaagtaattt ataattggat tttacttaa tatcttctga ttgttctatt 118080
ttgttgataa tttcatttaa ttcatctgaa gagtagtgtt cattatcaac ttttattgtt 118140
tttccctggg tatagatatc aatttcttgt atcatcattt catccttttg attattcatt 118200
atttgattat aagtttctaa atcatcaata ttatctgtat ctgaaccttt tactaaccat 118260
tctcctctct ttttaaggag gtcatcaaac ttctcatgct cttttaattat cttctctact 118320
tcactcggta ttagaacagc tctagcgtaa tttatatgcc acatagacat attatcaata 118380
agataattaa ccattcttat aagttccttc tcatttgcca tataccaacc tccttatatc 118440
taatactaat ataagagaaa agcagactta ttaaaagtct gcttctgtac ctaattctaa 118500
tcttctattt ttcatatgag gaatcgtttt tctatctcct gttaatagag ataattctct 118560
agcttttttct ttagataatg ttaatagtcc attataatta tctactttac tattatattg 118620
tcttactaag tactctagtt catcttctat atctgatagc tctcctgatt taactccaag 118680
taactttcta tacatatcat aatcttcaga aagactttct actttatttt tagatacaga 118740
atcataaact gcttgtaaat taccttcttc aataagttta aagttatgtt cacctatgat 118800
taattctttc tcagaagaat caagtgtcac taacccactt gtattacctg taaagtcacc 118860
tttataatct acaacaatac cttcagttac tttgtcacct aattcaatag tcccatcttc 118920
attttctttta aatttatgag catcatatac ttctactttg tcacctaatc tcaaatcttg 118980
agttaagtta tgtttaccaa taattctatc cattactcaa tctctccttt attaataggg 119040
tcttgtgtta agaacatttc tagattctct tttgtaatag gtaaccaaaa atatttactt 119100
tccggaattg taactgtata gaaatcctca tctttgttaa ctttaatatt aacatctgta 119160
aactcatctt gcattaacca atgagttaca gttaagttat atgacccatc actaacatac 119220
cctaaatcaa tatcatgttt aaaagctaaa tcttctaagt gctctaataa atcattcttt 119280
tcattttgtt cttcttctgt attatttttg attggattaa ttaactctgt acaaacgata 119340
tcatacaact caccatctgt aacttcataa ttctttttcta ttaatacatc ttgtatttta 119400
ttgattgaat ttgtaactac tgctccatat tcttcttctg taaaattaca tttatctaaa 119460
tcaacatctg taattaaatc tgcaatccat ttatttaaaa ttgataccgc cattgttcta 119520
gaaataaatac tatcatatac catatttatt taatctcctt gtttaggtga atgtggtctt 119580
ctaatgaaaa atcaaaaggc gctacaccat ttcttttatt gtttgtttct tttttaagta 119640
taacataagt tagtgaaaaa gtcaagatag ttactacaac cattaataaa agtttaatca 119700
gattcttcat aattactcta actccttaag tttatttttt actttttctt tatcatactt 119760
ataatctttt tctgagtttt catttttttc tttctcttct tcattaagtt ctctgtattg 119820
agcttcttct acctcttgtt ccttattatc tttgcctgcg tctgcttttt gaatttctac 119880
attttttacta ctaccgccac tcacctttt tctaaaaaga aaccaaagta ttaataaaat 119940
gatgagtaaa ataataatgc ttaatacaac cgcccaaata ttattagcca ttacaaccta 120000
cctccaaata gtttttttac agctcttaag ttttctgctg actcattgtt tatatgaata 120060
cctgtacttg aatcgaaaat aacagcatta tcaagtaagt gttttttaag ttcattttca 120120
taacttcctt tacctactac actaccataa ccatcgtgtg ttaaatcagt catatcagat 120180
tcaacttcta atactctaaa cgatactcta cgtaaaaatg atgggtttac taagtaaaag 120240
gatgatttaa aaacatttaa tctttgataa gaatgttttta tattaacaac aaacccagta 120300
agttatcat tataacttga gtttgatagc ttacctaaat ataaatttat actataccct 120360
tttgtttcta aagtttgtat agcactaagc agtatagctc ctctataagc aagattctca 120420
gggtcttcca tccaacttat actagaatta tagaatacat caataacttt cttctctgct 120480
ttaatctct gttgagacat catagaatta ggtaaacctt ttatagcgtt aggtacatga 120540
ggttgataac cttcaggagc cacaactggt tttcttttta cagatttatc cattctgaat 120600
aatgcatctg tcatcttttt aagcttaaca accatatcat aagactctct atctccttta 120660
accattaagt tataggcttc attaaagcta tgagtgcctg tgaagtcgta gctacctgta 120720
tctgatgaat tgtctctacc tgaaactcta ttcttttttta aagcagaaaa gaaatcaggt 120780
agaccatcat atttaattac atttaattct gagttatcta ttaatcgtct acccattgtt 120840
ttttcctcct attctaatcc tagtttatcc atgatagtgt caagtgccat tgaatcacta 120900
gatgaacttt gagtttttct tggttcttgt ttaggttctt gtttgatacc taaaagattt 120960
tttgttgctt ctgtatatct gttatcttta ggtaaagaac taataaattg attaatttca 121020
tctttaggta cagacttgaa gatgatgctt tctacaacaa actcatcgtc cattactcca 121080
tctaatttac ttccattaat aattgcacgc attgaaaaga cataaggtaa tccttttttca 121140
tcgttctcat atcttaattt ttgtacaaag tttactaaat cctcattact tgatagttgg 121200
```

-continued

```
tgttctacct tattatcata atcaaattca acttgagcaa aacggtctaa tgtagctcca   121260
tccagttgct gtcttccac ataaatatgg tctgctccag ttcccatagt attacctgct    121320
gatactactc taaagtcttc atgtgctgtc acacgaccaa tagggaagtc aaagtattta    121380
tttgcaaatag ctgagttaag aattaataat acttcaggga tagatgcatc catctcatct  121440
aggaagaata atcctccatt tgtaaatgct ttataaaact gagtttcatg aaacttacca   121500
tttgcatcaa taaatcctgt taatttaaat tcttgagtaa ttgcattact gaaatagaaa    121560
tctaagtcta gagcttctgc tacttgctct aatacatggt tctttcctga acctgctcca   121620
ccttttaaaa acactggaat attttgatta actagtttta atatatcttg atatctataa    121680
tggaagattc ctgagatatc tttaattgtt ttaccttctt gttgtaattc aatcttaact   121740
ggtaaattat taagttgctc ctctacgtat tcttcaattt gttttttaac atcagtaata   121800
attatttctc tactctcagt tcctgctttc tctacaattg catccacaat tgcttgttca    121860
taagggttag agtttttctc tcctagttta tctgctaagt ctttcgttgt ctgcatttgt    121920
tgttctacca atctctctaa tctttcaata gtatcttgct ttgccatatt tatcattctc   121980
ctttgatttg ttatacattt attataatac aagtattttc atttgtcaac aactttctaa    122040
aactttttta gttgttaata aaaaaattac cttataccta taacttaaca tagggtaagg    122100
taattgtcaa cactttatc taaaaataca ttaatttaaa aaagtcatca atgtcttcag      122160
ttccatgtgt atccatatta tacataaaca tacaattata tgtatgttta ttcactattt    122220
ctagcatatt gtgcatagaa gttgcattat tgaattcttc taaatcaata gttatcgtaa    122280
gttcttgacc ttcgtaaagt atgtttgcta tatagtatgt tttaacacct tccattgttc    122340
cgtgggaagt ttcattatga ttaagaactt ctatacctaa tgaaggtaaa taatctgaaa    122400
aatagtattt gcagaaatat ataaaattgt ctgttctttt agacacgagt actatcccca    122460
tattttatat ttctttctaa tcttacataa tatgtttttaa tctttttgaac ttctttgtct  122520
actgcatctt ttcttcctaa tcttgtagta tattttacaa tattaaatat catagaatca    122580
acaaaaccat cataagaaaa gtgttcttct agaaaagaaa taacatcctt actacctta     122640
tagtgctcag gtaaatgtgc atctacttgt atattatagt aatcttctaa aagccctata    122700
ctttcaccaa gactagataa agcataacct aaatcattag agtcattaga ccattcttta   122760
gatactgata aagcatcttc tataattgtt attttttaatt tatctaagta atcttctact   122820
tgagcttgtg ttttcataaa ttcttttgca ttcatttaat accctcctaa attgtataaa    122880
aaaaacaccc tgcttggata caagcaaggt gaaaaaggaa agatattatg gaagtgtact    122940
atctaagtac acctcataat ataacagttt tccttgctag ttattactta tttttttaagg   123000
tcttcttctt taacaaacac tccgttaata agcttacctt tcctgtcttt tatctcatca    123060
taagccatat caatacactc ttcaatatct atatctaatt gtaaacatag tactgttaat    123120
actacaaaaa tatctcctac actatctcgt gttacatggt cattacttt agcaatacct     123180
gaagctaatt ctcctgcttc ttctaataac tttaacattt gaccttcagg tttacctgtt    123240
tgtaaatttc tatcttttgc ccattgctta ataagttcta cttttttccat tattctatat   123300
ctcctttaat ttctgtatct tttataatta gattatcaga atcacttatt acagttaagt    123360
tatcttcgac taattcatgt aggttattag taatatcttc ttcataccta taacctacac    123420
gaacataagc tttcaccctg acatctatat taacataatc ttcttggaat ttttccattt    123480
ctaacttcct ttattatacc atattgttat acctttgtca attaatctga gtagtttcct    123540
ttggcaagtt gatacttttt gtgtaattct tcatataatt ctctcatacc ttcgtagttt    123600
ctcatatcat cttccaagaa actaagataa tctaataata atttagtttc ttctacttct    123660
aaagttataa ctggtttgac catttatgca acctccttaa attcttcttt atttattttc    123720
ttaatatctt tttctaatgc ttcttttagt tcattaggta atttatatgc atcaattgat    123780
tgttgctgtc ctaacacata accattatct gtaatacgta tttcaactgt aaaccatgaa    123840
ttatctaaat cttcttctaa tcttgctaat aatattaaac agctattctt tagaattcta    123900
ttagcatatc ctccaacaca atgagataac attctacctt catctttaa tttacttaca     123960
gtatctgcag gaaggaattt tactttttcta ccatctttta atttatcaatt tttatcaatt  124020
attttttcta acttattatc atacttagct ttaagttctg catcatctaa ttgttgttga    124080
atggattgtt tttcatctgt aactatatca tgctctaact tcagtgaaaa aggcgttaag   124140
ttaacactct ctaatgttct atacccttct cggattagta ttgataaatc ttgtaaatag    124200
tcaaggtaat atctatctag tgcatatcct gttatacgtt gtctgtcttg agcatctaca    124260
tctaaatagt gcgtcatctt tttgtagtta gcaaaagata tagataatat ttgatttaca    124320
ataggtttaa ctttaaagc atcagtaaca tctcttgaat ctcgaaccat taaaaaagta     124380
tcatcaaata attggtgtaa attaacctca ttgtgtaaat gattatagta cttatataga    124440
gtattagcaa atcttaagta attaccttgc tcaaatttat ttaaagttag taatttttta    124500
taagtctgtt ttgtaagatt gaaagcttca tgaacttttcc atttaggatt tttaggtata   124560
tgaaatagta atgcatttct ttcaaataat ccaaattcct ctaagttatt tattttgtca    124620
atatttttaa caatatctgt taaagttgtt aagtaattag aagttgaatt ttctcctata   124680
aaaatcctat atttgtctcc tctataattt atatgaccat aaacatctat attatccgga    124740
caccaactag aaaaatcaaa attatggtgt tctaatgttt gttctattat ctttattata    124800
accctctat ttaagttagg ttgtgagtaa ttttttaaaa taacatttaa taaaacagat     124860
aatgtcaatt catttttata ttcactttta cttatatcat ctttatacaa atttaaagtt    124920
agttcttat taacaaggct atctgttaag aaaactttaa cctcccctgt tttaacatca     124980
aatgaacttt tattttctaa aacccattta ttacccatat tatgtttatc tctgatatgt    125040
ctaactttaa gaccgaaaga tgaattattc tcagtacctg gatgcatgta ccaagcacta    125100
ctatacaatg aatctgatat ttccttataa tacttacttg agcctttttc tgtatcttca   125160
ttcatataag aagtaataga tgattttatt aaaccgtact taccttggtc tagaaatatcc   125220
ataatatcat catttaaact ctctactact tccttatact catctaattg tctagcttca    125280
taccccata atcgggtttc attttctaat tctttaattt tttcttctac ataacctta     125340
gattttattt gtcttctgct cttattacca tataaaggaa attcttttct ttcttctcta    125400
ctggattcaa tatattcttt gtaatttctt cctttatttt ctccaattac accttcaact   125460
aattttttcaa ctgtttcata agggttacct gtaaagtttg ttacttcttt attaccacat   125520
agtgctaaga ataaatgtat ttctgtagca gtatcaaaac taaatatatt atgaatatct    125580
ctaaataatt ccttagagcc taagttaatt atattatttt tcttcttctt aaggaataca   125640
tcttcttctc ctatgtagat acatccttta ttaactttag gtaaattaat aatttcttgt    125700
tctgttaatc cttttttgttt atatgttatt gccatttaaa atcactcctt atttgttatg   125760
tactaatcat atcatagtaa gtcatatttg tcaacaaaaa aaaagaagaa cttttttaaag   125820
ttcttctaaa tgagtttcgt atataacctt ttgaatttta tttagtggtt ctaaatctaa    125880
attcctaata agttttcgt attttcttga attcttgaag ttaatagtat taggcatagc      125940
```

```
aagagcttca tcaacgtctt tagtatagct tacaacatct gaatagatat ctacttcttt   126000
tacatataga ccctgagtta aacttctaaa tactacctca ttatgtgcta taacttcttc   126060
tttctttttct atgctcattt gtaaacctcc tggtttattc tacccaaaca agtacgtact   126120
ctaagctagt taatgatact gatttaatat tatttaattc ttgcaatttc ttaatatcta   126180
catcatagtt tttacttata gtccataatg tctctcctgc tcttacttta tggtaatact   126240
tattcccctc tttaataagg tcatccaata ttacctacct ccttgagtaa taattagcct   126300
gtagataaca tataagtata agaacaaagt ttacaaattc agtagctata atatgaacat   126360
aggtatgtga taaaaccata cttactatca acgaagctaa tcctaatcca ataataagga   126420
atagaaatct gtttgtccct tctgaacttt tagtttttata aaatgttgtt atctgagtta   126480
catacgcaag gataatagta atagttgcta cagtttgtgt taaggctgta aagtcactta   126540
ataaaaatag taacaatgag aacacaataa taaaaggtat agagaaataa tcctttttttc   126600
tatatgaagc tactaataag caaacaatac ctagagttaa attaagacca actgatacta   126660
cttgaaacat tgtagcatca gttaatagta aattgtaaaa actaatacct actgtagcta   126720
caattaaata ccaaaaataa ctactaactc ctttaacact atccgattta actaaagcta   126780
ttagacctgg tatataacct actgtaacta atatagcata taatatactc aagtaatgtg   126840
ataaattatc catcttgttc tcctaatttc tctaatattt ctaaaacttc ttcccaagag   126900
ataaatcctt ctccgtctgt taattccaaa accataccat aaacaaattg atttgtacta   126960
aattcagctc tgtccgggtc gtcataacct tttccatgtc cttgacgaat atccgagcaa   127020
taaattaaaa caggtttatt tacaatattt tcaagttttt ctacgattaa ttcctcttct   127080
tcacttaacc aagtttcaaa tctatctgat atataattaa agtgttcttc tccattatca   127140
tatatatggt taatagtttc ttgtgcttga tgcttcatac ctagtaaaat accaagttct   127200
gcaatcgttc ctagcccctc attaagaata tcaaacacaa atatatctga gtcttgcata   127260
gctttaaagt cattgtttaa aatgcgctct gctaaaccag tttgttctgc attagccttta   127320
tcattaattg atttatcttt atgagggctg taaggagtga ctcctacaat accttctact   127380
tgcttatgct gtttgtctct ataatctacc atagcttggt taagtagatg acctcccata   127440
taaattactt tgtctttaat ataattaacc atttatagta tctccttttt cttctagaat   127500
acctcttaaa atgtgtggca tcttttttctt aatttgtttt tctataattt tcatcatatt   127560
ttctttttct tcttccataa tatcatcaac aaaattttga cctacttgtt tcataattaa   127620
accaaaattt tctaattcta aatcatcttc agacaatctg ttttcttcta tagctctaaa   127680
aatcattttt tccattcttg attttgtgat agcataatct gccacagaat cattacttct   127740
aacttctgat ttcattttct tacgactaaa ctctttaaat tccttagata ctaatttaaa   127800
gtaatcatca tgttctgatt taccatctaa atatttaata acaatacctt ctcctgtatt   127860
aggtttaaca gtcatatctg attgtcctac taaatcttga atttcttgag gatttaattc   127920
attaagataa aaagatggtt ctacaatcat taaagtttta acagttttca aacctaatgt   127980
ttctgataaa gaaatgactt ctgaatgagg taaataggtt tcactatcct tatcgtatac   128040
atcgaataca taaaaatcat tataacaatc ttctttataa tttaccttat gtttaactaa   128100
ccattctcca aatataataa taccttctaa tatagataaa tctaatttat ctgtcatgtt   128160
ttcatgtacc caattataaa aaccgtttaa tgtttcgttt tcatttaatt tttttctacg   128220
agagaaacag actaactcac cattctcggt agtaaaactt gcgttgcttc catctaattt   128280
ttcttgaatt acaaaacctc tatctttaaa tttgtctaaa gataatcctt tatttttttac   128340
tttagtataa gatttcatta attagttatc ctcctttgaa ttatgtacta ttgaaaataa   128400
aataagactt acacttgcta aaaatgctaa taccactaaa ccaggtaaat ttagaactgt   128460
tgataagaat aatgatattg cacttataat ataaactaaa ccgcttagaa ataaagttaa   128520
taatacaatt gttataagtt ttaccaacca actgttatta ataaatacct tagctaaata   128580
attcataaaa aatcctcctt agttattata aagtaagtat atcataacta aagaggtttg   128640
tcaacatatt attttaccat ttaaaattgt ctgcgtactg agctaactta gaacggaaat   128700
taactgtaaa attatggaat accgcaccat cataattttt aaaatattcc atataatctc   128760
caaaacctga tttactttca tttttttaaat ctatttgctt gaaatttcct tcaactatta   128820
ctgtagaatt ttttgtatga atccttgtaa gtactttctt aagttcactt cgtttaaagt   128880
tttgtgcttc atttataatt atagtagcat cccttaaatt accgcctctt aaaaataaat   128940
gtgatatttg ggatacccaa cattcaccta atttatcttc tttgacatta tcttccatca   129000
ttaacatttc ggttatttgt tgttcaggac tcatattaag ttcaataagg gcatcatgta   129060
atcccatgaa ataagccatt tcttttttctg tttggttacc aggtctacta cctaaatctt   129120
ctgatacagg tgaaattaca aatactaatt ttctgttctt atttagataa tcagcataag   129180
cacaagctac tgaacacatt gttttacccg taccggcttg actttcattc caaagtattt   129240
caacattatc attaaagaaa tcctcacaga aatctaattg ctcagttgta gcttttttcaa   129300
ggaattcatt gaatactaga tgttctccca tgttatatct tacattagga taatcctttta   129360
acttaaagtc taactctttt agttgtattg ccatattttta aagttccccct atctataaat   129420
agtttactc tcttttaata tagtactaat tacctatata ttcacctgtt gaagaacaat   129480
agttactgca gttacattca ggataatttt cacaaacttc ttcatcttca tcatcaaata   129540
agtcttcatg ataaatacta gaatcaaaat ctacaataca attttccct ttacctttag   129600
atatgcctgt gtaaataact tcatcaacca tatcccaatc attacttact aagtaattta   129660
cagtatttga tactgaatca ttatcaggta agtagatatc accatctgta aacttaatta   129720
aaatatctcc ttgagggagt acatcattaa ttaaatcaat ttctgtttct tcttcaattg   129780
taaatacagt tccttctagc tttttcaggag tagtatgtgt taaatgttta acatcttctc   129840
ctgattcttc ataaaatcct actgcattca tttttccttgtt atactttgca ataaatttac   129900
cattatcact gactaaatat tgactgtttg cattataatc ttctgcatct tctaaagtca   129960
tagatgggtt atggtcttta acataataac taattttct aacatctgtt gtttgaattt   130020
tctttccttc acctttaatt actgaattaa tttttttcat aatatttttct cctttttata   130080
tatcaattga ttttttttgca agattatcag cgtagtcatt ccattatca tttgagtggc   130140
ttttttacttt tacaaagttt atatctatta cttttttggta ttctcgtatc atattaatat   130200
atgttttact tagaatattt cttgcagacc aagtaccttc ataccaatgt attaaaccaa   130260
tataatctat ataaactatt gcctgattgt atcctaattt tatagcctct tcgataccat   130320
aacaacaagc taatatttca cctgcaacat tattatactt tatcaatcct ggtttgtcaa   130380
cactttttact aatttccgct attatatttc cttcttttact tactaagaca gcacctgagc   130440
ctactttacc tttattataa gatgagctac cgtctgtgta tatatttaca ctatcctgca   130500
tatttataat cctccataaa ttgagggaat tcacaatctg aatatacttc tctgcagaaa   130560
gatactgaaa tataattaaa atcaaaacat ttgaaacagt gttcttgaac ttctttttttg   130620
tctttagcaa tcacattaaa tttaaaacca tcagctatta ctgtaaatac tcctttttttc   130680
```

-continued

```
ataaaacaaa tacctccact aattttattt taaattaata actaactcaa taaacgattt   130740
aatagtttta tttttacctt catcaatatc tgaaaagaaa ttaattaaac tatcatcttc   130800
atcaaataaa tcttcaacat catcaaattt atttaatata tctgtaacac tataaccttc   130860
ttctgatata tactcatgca agtcttctcc atcctctgac agagttgctt ctatcttacc   130920
attcttactt tcaattaaat acaaagtatt taatacttta atagaatcta ctactacact   130980
gtaattacta atagtaggat actctgtata aagtatttcc acattagtat tcatataact   131040
atcaattaca gaattaactg tgtccctttt taattcagat acattatgtt ttcgtatagt   131100
agggaattct tcgtcatatt ctactaattc ttttctatct gtattcaata atttgtctaa   131160
agaagataat aatactattt tatattgatt gtccggtaga ctatctgtaa tttccataat   131220
ggttaaaaaa gtatcttcac ctaaaacttt atttatatct tgtaattcaa atgaatctac   131280
catttcaata gtatcatcta tatcatctgt agtcattaaa aaattaacta aattattatt   131340
ctccatcgtc ttcctccaat tctttaaata gctctttacc tggagtattt aacgccttct   131400
ctaacctcat taaattagca cttcttggtt tcttttacc atactcccaa taagatataa   131460
gagaataatg gactcctatc tcagaagcta ggcttcttaa tgtatgtcct ttttctactc   131520
taatttttg aagatttaga ggtttactt cctttttttc atccataact atttctcctc   131580
tacttttaaa aatttaaaat cctcagatgc ttttgcattt tttagtatat actcttgtga   131640
tttatttctt gcctctgctt tactttagc atataactct atatgaaata catgaggttt   131700
ttttaaagat ggtgattcat atctccaata aactttaaaa agtagtgttt ctttttttag   131760
aacattaatt ctaaaccatc ttttaaattt attcattcat tatcctcctt tatttatttg   131820
ttaaactaat tatagcatag ttaacttatg aagtcaacta taatatacaa aaaagactaa   131880
gaaattaatc ttagtcttaa tatattaata actattatgt gcgttgtggt atgcaagagc   131940
tcctgatgtt gaaccgtaac ggtcaatcat atattgtttt gcacctttag tttgttctgc   132000
tatagaaccc ccactccatg atttacctaa tccttggaat agtccttgag ctcctgatga   132060
tgcattaacg gcattaggat tcagtgtaga ttcacgcata gcaatttcaa tcattgcctc   132120
gtctccacct gcttgtctaa tttgttctgc tacagaacct cctgtagaac tagttgattg   132180
tgtaggttgt ttagtttctt tttgaactgg tgctgatgtt ggttgtactt cttttttagt   132240
atcttgttta ttttgagtat caaattgcgc ttgttgttgg tctacttttt gttcaggtgt   132300
ttgttcttct cctgctaatc tagatactgt attatctact tgagttgaac ctgagtgata   132360
ttcgtatcca aaattaccat tataattata gaaatgataa gtaaattctc cgtcactgaa   132420
tgagaaatca tagttacctt cttgaattgg ttttgtattt acttctactg aatttgattt   132480
agcttgttct gctaacttat tataatcaat ttcgtctgca ctagcttcgt ttgtagcaat   132540
acctccaaaa gtaatagccg tacctaatgc taatgttgca aaaattgttt tcttcataaa   132600
tttaaaactc cttaaataat tttttagaat tgtttatttg taaatcgaca taagtaatca   132660
taacatatat ctttaaataa cgcaagtata atatagcact aattagtgta atattattaa   132720
agttttatta caaacattac agttatcaga taattaaaga caaaaaaaga gaggtattaa   132780
cctccctaat ttattatttc cctgttacgt ctacgatagt tccgtctccg ccaatttgaa   132840
taggttgttt accatcccat ttttcaatta actgttgacg taatatctta tcagataaag   132900
aagattctct aatctcattg gctttttat caccattagc ttctacttct ttttttcttag   132960
cattttgttc agcaatttgt ttatcaactt tagtacgttc taactcttgg ttagctttaa   133020
cacggctgtc aattgctttt tgagtgttct tatctgcttt agggctagat aatgcaatat   133080
cctcaattac aaatccttgt ttttctaagt tatcatttaa gctatctaaa gtatcttttt   133140
taatttctcc tgtcttaaca ccaaatgcat caattacaga atatttagat actgcctgac   133200
gaacattatc ttgcacacgt gaacgcaagt atccttttc tagttcttca atatctgcaa   133260
taccaaaacg attaaataaa tctacagctt tagttgcatc tactttataa gatacatcaa   133320
tatccatttg taaattttg ccgtctgaag ttgctacatt taaatcttta tatttatgtg   133380
tttgtgtttt agttggatat ttatttacct tatcaaaagg tgctgttaag tgccaaccag   133440
gtgatttagt atcttcctta acaccattta ctgagtatac aactccaaca tgaccttgtg   133500
gaatctttgt aatacacatt aataaaaataa taaatcctat aattgctaaa aaccctaata   133560
ctcctgaaat aactactgac tttctcatta catttctcct ttttctattt cttttattaa   133620
gctatttaaa gcttttttcct cttggtctat ttcttgctta tcggctctag ttacaattga   133680
ttgtctgcgg tcgtttaaga attgttttt atactttaca tattgttcta aaccgtattc   133740
atctaatgta ccttgcctaa ctaattccct gtattgtttt cttatgttac ttttcttttc   133800
tttcattgaa agaaaatcga atacataact tataccaaaa cctacaagga ctagaaaaac   133860
aataaaaata gcaaagtatg ttaaaaataa tgccatgtaa ttcctccttt atttgattac   133920
atatataact atacactatg tatttaattt tgtcaacact tttttgcaaa aaaaaaatag   133980
acggatttta aatccgtcta aatttctatt ctatttgaat actccccaag caaccccagg   134040
tatatgatta ggtggaactc cttgacaagt tctaacaggg caatatactc tgttaccatt   134100
gtaagcattg taacctatcc aaatgtgacc tgcttggata caaacttcgt catatacaat   134160
tgtagctcct gccggtaagt tacctcctac tggagcattt aagaatggag aacctattct   134220
agttactata ggttggttac cattaacaaa tgttgcattt tccggtttgt accaagttcc   134280
gtactggttc ttttttccaag agcctgttac tggtctagtt gccggtgtac ttgcgctact   134340
tgtttttaccg tctttaacta ctgtagaact tgaagttcct ttatccatgt agtttttaat   134400
ttgtttaatg aaataatctt ttagtttatt cattattgct tgagatggtc ttccttgtgt   134460
tactggatta aatcctgtat gaagaaccat agaacgatga ggacaagctg ttggaacaaa   134520
ttccatatgc aatcttacag ttttacgatt aggagtaaga ccccattctt taaatttctc   134580
tgcagtaaat tggaatactg cttgttcgtt tttaaggaat tgagcatcac tagcactcat   134640
tgattgacag acttcaatac ctgcaaatct aaagttacct gagtttgctc ctgttccatc   134700
tcctgtgtgc caagcaattt gattcttagc atctattgct tcccatacat aaccttcaga   134760
gccatagtaa tgagcaatac cattagcata tctagcataa cctgcgttag ctaatgaatt   134820
ctcgtattgt tgccctgaag aacgacctgc atcgttgtgt attaccattc cttcaggttt   134880
cttaccacgt ttatccattg tatagttaat atggttctta gaaacttta gtgttgcttt   134940
cttttaggt gcaggtgttt tacttgcact tttcttagct gtttctttttt taacagtagt   135000
tcctgctttt acaggtatct caataaaatg agttaatccg taataattat ctacacgttt   135060
tgtaggtttt ttattagcgt aaccgttcca gttttgcttt aaaatagtaa atgtagaagt   135120
attacctcca tcatatacaa tacctatgtg accccattgc tgataactac cggatgtaaa   135180
tacagcaatc catccttttt taggtactgt agaaggttta ttttcatgta ttttaaatcc   135240
agtaccataa ctttgtttga tttggtcttt agcattaccc caagttctaa ctttattatc   135300
tgttaaccat aatacataat cagtaattaa gtcttggcac tgtgcatgat agtaaccatc   135360
tgcgtcaatt gctcctgctt ccattacacc aaacgatggg tcatagcttg tagcttttttt   135420
```

```
aattctataa ggactgtcta ctgtaccttt tgcataagcg tctaaacgtt tatttatttc   135480
tgcttgagtc ttagccatta cttaacttcc tcctctgcaa atactttacc gtgttcctcg   135540
gtatcttctt catcttgaga aggtgctgaa ccgccatcaa tttcatcttc aatagcaggt   135600
acttcatcac tatcatctgt atcaggttct gcattgtttt catagttgtc taattcgaaa   135660
gtgctagctg tgtttgcatt tgcttgccat tgaacaaatt cattagggtc tttactatca   135720
cgaggtttta tataatctgt ttgaacaata tcactatctt taagacccttt agtattatta   135780
tcaacaataa tacctaaacc tgctaataat gttagtatag aacctatgat atttacacct   135840
tgctcaattt gagctgagta gtctaaacca aaagcacctg taatttgatt agcaaatact   135900
gctactgctg atataattgc tacccaaaat gttttactct tagttcttgt gctaaagttt   135960
attcctccaa caactttagg ttgtttagtt tcattagcca ttaaaaaacc gacctttcta   136020
ttatatttat ttctaacaat aatataacag taggtcggtc atgtttatct atattaattt   136080
aacacttact cattaatttg atttagtttt ttgataactt cagacatttg tttgttatct   136140
aaatcttcta atttagtttc aggtaataac tctaatttat cccaaacttc ttctttattta  136200
gatactttat tattaataat tgccttacca actaaacttt ccgtataata taattgcttt   136260
gctgatgcca tttgtatctc tccttttaaa tatgtaaagt atatagctag tatcgtatcc   136320
taggaacaaa cacttgcgct atatactcaa tgaaactcta ccctcattcg aggacacagc   136380
aaaccgattc gtcaaccgca catgtgaatt ctcaagtttc atttatgtaa cacaccctct   136440
ttgatttgca caaagactaa gggttttgga gacccttgta ctactaatta tactaagggt   136500
gtttattatg gtttctattg gatttggaacc aatgacacct agagcttcaa tctagtgctc   136560
taccatctga gctaagaaac cttgtaacga ctcatacgag actcgaactc gtactctctg   136620
ccgtgacagg gcagtgtgtt aaccagttac accaatgagc caaaataaat gctataccct   136680
aaccttacct taatgtatag caggtttca taagctcga agcaacgat tattaccact   136740
cataacaact atatattaag tgaaggagg tgaaatgaac aaaacgtggt aattggtact   136800
tatataggaa gtatgtataa tctacaagga gtaagttatt ggttcataaa ggagtgtgaa   136860
caataaatac atgaaagagt gaaagtctac tccttgtaga ttcttttttta attatcaatc   136920
aaaggaggaa actgataatt gttaataata aactataaag aggaaaatat ttatagtcac   136980
attctgatat aatgcaacta aatatccaag cataacccgt ctcacgagga acctacctat   137040
aagacctgtt attaagtgaa tcactacgat tgactctatt aaggagctac cttaagtcca   137100
tctcacgcaa tttaaaaggg acttacaaac cgtataacga tagtaagttt attaaataat   137160
gtgatattaa catattagtt aataactttc acatggtcga agaaaagtaa atttatttga   137220
tttccaaatt atttttatca aatatagctt ctttttgaacc tgtagattta tgctactcat   137280
actaataacc tctattatct aacacatttc tgtgctccaa ctacagttag tcgttacagc   137340
gtatctttct aggattccgc taagacccta gaaagaaatt aaaccctagc cgttatcata   137400
ctctacagac cttataagta agtaccaagt ataccaatcg tatttaacaa tactaatgac   137460
gacccatcct accgatatat ttccgatagg tttttgattcg tttgattatc ttgtacctta   137520
tgactaccaa atcattattc agtcactatg ctcagatatt tagttgtatt attatatatt   137580
aattataaca taatttttag tacttgtcaa gttaattttta aaaaaaatta tagaagtaag   137640
ataaaattct tacttccaat taaaattata aggatgatac acattgttat tgtttaaact   137700
ggaaaacaat gtaagaaaaa acagtgatgt gtaaggtatt tgttttattg ttaattacat   137760
tatagcatat actgatacct ttgtcaagtt aatttaatac tttttttaaa atattagtta   137820
tcttttgtta gttcttcctg aatagcatcc catcttcttt ctgcttcact acgattatct   137880
tctatatgtt ttgtagtttt acaacatttg atacagtata tatctttgat atgaccttct   137940
tctctttat ttgctctttt tcttggtact ttgaatacat taccacattc tttacatatt   138000
aaacttgagt aaaacatttt ttgtcttttc ataattaatc aattccttt cttgttttat   138060
ttgataatttt aactatatac tatattgata aataagtcaa cagtttttcta aaaataattt   138120
aaattatttt gaagaatcct ttaataccaa gggttacaag agaaaaagta cgtatttaga   138180
aaataaggag tactcctatt atatataatt atattctgat ataagtaatt aataatatta   138240
aatatataat tataattaat aaggttggga aaattgaatt aaatataatc tgatacttgg   138300
taaaactact caatatagaa gtaaaatcct ttagtatcag tacttacaga caaaaaagta   138360
cgtatttaga aaataaggaa ctctcctatt atagttatat atacttatta attattatta   138420
attactatct aaatatataa ttataattaa taaggttaga gagtcaacaa aaagacaaat   138480
aaaaaagtga ctacttaaag tcacttgtta atttaaaaaa ctattttaaa tgattcaatc   138540
attcttgggt taatataaat taaactagaa ctagcatctt cagttgtatt aacttttatt   138600
gatgctgaat cagaaccact aatcatatag tctatatctt ttctagtgta acccttttcg   138660
tcagatgata ctaaaaaata tttagcacca cttaacattg tatttcaat atgtttttgac   138720
atctacaatc tctcctatgc aaatttgtta aagacaaagg atagtatagc acctagaacg   138780
agtaaaagaa ccttctcagt agtatccttc ttcctagtat ctttagtttt tgtactttca   138840
gcaagttctg aaatcttttc atcaagtctt tctaattgga cgtaaattgc tgattgtttt   138900
tcactattga cagctacatc tttatctata ctaactatca tttttcttag ttcagctacc   138960
tcaacttcta aatctttgaa agttcctcta tctatataat taccttcttg tatcttagac   139020
ttaatagttt ctacttgaga aacaaggttg tttatctcct tatccaacta gaatcacctc   139080
taaggtctaa ccgtttcaga ttcagaatgg atatcataat tttctaagaa atcattgata   139140
atctccatat aattatccgt aacgactttt ccgtaagatg tttttgtatc aatttcaaac   139200
ctaagcttac caaaactttg gaggtctaat tcttttatta caatattagg gtcatcagaa   139260
ggaaggtaat aatagtcgaa gtatataatt gagccattta ttaatactct gtctattcta   139320
tagacgtgga aatagcgtct gtctctttta aaatgggcta gtgcatcttt aaactctaac   139380
ttaaggatat ccttatattt agtcaaagtg gtaacctcct tactattaat ttttaaattt   139440
acttatttg tggtataata gttatgataa aggcagttat tataattata ttaagaataa   139500
tgataataat tattttttct gagaaaataa gccaaatact aaaaacagat aaagcataga   139560
tagctgatag atatactata ttaagagtta ccttacttt atcttcttta tagatagaat   139620
aacctaaaga cgttgtaaca ccactaagta taaaataata gaaacaaaaa agaggtatag   139680
acagaaaaaa agatacgata atcattgtta aacacctatt tcttttttgac ctattattta   139740
tagaactttt agattacacc actaatataa cattaaaagc cagtcataaa agtcaattgt   139800
tagattaata atataataaa aaaagacaat aggaggttaa agtggttgaa taataacata   139860
gctatattca tattcaaaac actggttatc attatattct tactactaat tttgtctgtt   139920
attaattcct tgtcccttat ttattcaata agaccgagtg tagttatgac atactttata   139980
tttggtggta ttgtttctaa tgtcgcactt actataacag ataagttctt actgaagaaa   140040
gaagacccccc tacctgaata tgttcttaaa aaagtagaga taaatgataa agaaataaga   140100
ataatcaaga aaatcataga aagtaactac ggtataacag cagaagagat aaaagttagg   140160
```

-continued

```
gctaaagcac aaagaagaat agaggaagat agtaaaaagg aagattacga tgaaaacaaa   140220
gaaagaaatt aaagaacaaa ggaaagagct taaggatggt gctacatctg tttctttagt   140280
aaaaaaagga gataagagaa tagctagccc tagtagaatt tgtagcctat gcggtcagca   140340
gttatcaggt atgaattaca ctaaaggaaa agcattatca aaagttaatc attttcattt   140400
acagtattct aagtatattt attttgatat ttgcgcagat atcaacaatt gttataagaa   140460
tttaagaaaa agaggtgaaa tggattgagt gcagaaaata ttagagatat aattaacaag   140520
aaaaagttag aagaagagga tacaagaaaa tatatagctg atggatttat gaatggtata   140580
ggtaaattaa tgtatgaatt caataaaaaa gtagataata aagaaataga agttaaagac   140640
cctaatgatt tatataaact attcgtgata ttctctcaaa tgcaaaatat ggttaatgaa   140700
acttctgaag gtggagcaat acctcagcta tctagacctc agcaagaatt atttgacgag   140760
attacaacag aagatagtaa tggagaatct acagttgatt tacagaagat acaagaaatg   140820
acagcagaag atattacagc aatgatttct gaaaaagaaa aagtaatgaa tgaggaaaat   140880
tcagaaacat tctaaggaga aagatataa                                     140909
```

COMPOSITIONS AND METHODS FOR THE TREATMENT OF SKIN DISEASES AND CONDITIONS INCLUDING ECZEMA

CROSS-REFERENCE TO RELATED APPLICATIONS

This application is a continuation of International Application No.: PCT/US2024/022657 filed Apr. 2, 2024, and which claims priority to U.S. Provisional Appl. No. 63/493, 834, filed Apr. 3, 2023, the content of each of which is incorporated herein by reference in its entirety.

REFERENCE TO AN ELECTRONIC SEQUENCE LISTING

A Sequence Listing accompanies this application and is submitted as an xml file of the sequence listing named "177601.00023.xml" which is 257,338 bytes in size and was created on May 2, 2025. The sequence listing is electronically submitted with the application and is incorporated herein by reference in its entirety.

FIELD

The field of the invention relates to therapeutic compositions comprising bacteriophage and colloidal oatmeal, and methods of using the compositions for the treatment of skin diseases and conditions including eczema.

BACKGROUND

Eczema is a common skin condition characterized by red, itchy skin and small blisters also known in the art as skin rash or rash or dermatitis. There is no cure for eczema, but there are many treatments, ranging from special diets to emollients and immunosuppressive ointments like e.g. corticosteroid ointment. While corticosteroids, such as hydrocortisone or clobetasol propionate (topical, oral or intradermal administration) usually bring about improvements, they also may have side effects. Prolonged use of topical corticosteroids is thought to increase the risk of side effects, the most common of which is the skin becoming thin and fragile (atrophy). Because of this, if used on the face or other delicate skin, a low-strength steroid should be used or applied less frequently. Additionally, high-strength steroids used over large areas, or under occlusion, may be absorbed into the body, causing hypothalamic-pituitary-adrenal axis suppression (HPA axis suppression).

Due to the impaired skin barrier in atopic dermatitis an increase in skin infections with bacteria such as *Staphylococcus aureus* or fungi might be the result. For more severe cases, dermatologists may also prescribe either topical or oral conventional antibiotics such as penicillin, streptomycin and chloramphenicol. The antibiotics prevent infection that can result from impaired skin barrier such as cracked skin. *S. aureus* colonization or infection is the most common cause of increased eczema severity. The effectiveness of antibiotic treatments varies from person to person. The well-known disadvantages of conventional antibiotics are specificity, i.e. also non-pathogenic and/or beneficial bacteria are killed, and the risk of developing resistance, not only by the target bacterial cells but possibly also by other pathogenic bacteria. Furthermore, conventional, systemic antibiotic treatment can interact with other drugs, including contraceptive pills. Certain antibiotics cannot be combined with the use of alcohol. Accordingly, there is a need for improved treatment of eczema.

SUMMARY

Disclosed herein are compositions, kits, and methods for the prevention and treatment of skin disease and disorders, such as, but not limited to eczema.

In some embodiment, compositions disclosed herein are formulated for topical administration and comprise bacteriophage, and colloidal oatmeal. In some embodiments, the bacteriophage comprises a *Staphylococcus* bacteriophage. In some embodiments, the bacteriophage comprises or consists of one or more *Staphylococcus aureus* (*S. aureus*) bacteriophage. In some embodiments, the *S. aureus* bacteriophage comprises or consists of one or more of SEQ ID NO: 1 (MESA-01), SEQ ID NO: 44 (MESA-05), SEQ ID NO: 45 (MESA-11), and/or SEQ ID NO: 46 (SaGU1).

In some embodiments, the composition further comprises one or more additional active agents. By way of example, but not by way of limitation, the one or more additional active agents comprise a ceramide, hyaluronic acid, glycerin, petrolatum, niacinamide, an enzyme, and/or a probiotic bacteria.

In some embodiments, the composition comprises one or more enzymes, such as, but not limited to a bacterial cell wall degrading enzyme, an endolysin, and/or an anti-aging enzyme.

In some embodiments, the compositions disclosed herein consist of one or more *S. aureus* bacteriophage and colloidal oatmeal. The bacteriophage are free in the composition and are not linked to a solid support such as a bead. In some embodiments, the page are encapsulated, or occluded in suspension in the medium.

In some embodiments, the *S. aureus* bacteriophage comprises or consists of SEQ ID NO: 1, SEQ ID NO: 44, SEQ ID NO: 45, and/or SEQ ID NO: 46. In some embodiments, the *S. aureus* bacteriophage comprises a sequence that is at least 90%, 91%, 92%, 93%, 94%, 95%, 96%, 97%, 98%, or 99% identical to one of SEQ ID NOs: 1, 44, 45, and/or 46.

In some embodiments, the bacteriophage comprises a nucleic acid sequences at least 90% identical to one or more of SEQ ID NOs: 1, 2, 4, 6, 8, 10, 12, 14, 16, 18, 20, 22, 24, 26, 28, 30, 32, 34, 36, 38, 40, 42, 44, 45, and/or 46. In some embodiments, the bacteriophage comprises a nucleic acid that encodes a polypeptide at least 90% identical to one or more of SEQ ID NOs: 3, 5, 7, 9, 11, 13, 15, 17, 19, 21, 23, 25, 27, 29, 31, 33, 35, 37, 39, 41, and/or 43.

Also disclosed herein are methods of treating skin diseases or disorders, e.g., eczema, in a subject in need thereof. In some embodiments, the methods comprise topically administering a composition of any of the embodiments described above to a region of the subject's skin comprising the skin disease or disorder, e.g., eczema. In some embodiments, administration comprises once daily, twice daily, three times daily or four times daily administration. In some embodiments, the composition is administered for one week, two weeks, three weeks or more. In some embodiments, the treatment reduces one or more of the following eczema symptoms: itchy skin, dry skin, redness, and swelling of the region of the subject's skin administered the composition. In some embodiments, reducing the one or more eczema symptoms occurs more quickly in treated subject than in a control subject (e.g., a subject not treated with a composition as described herein, e.g., including one or more *S. aureus* bacteriophage).

For example, in some embodiments, the treated subject exhibits improvement 5%, 10%, 15%, 20%, 25%, 30%, 35%, 40%, 45%, or 50% faster than a comparable control subject. In some embodiments, the treated subject exhibits at least about 5%, 10%, 15%, 20%, 25%, 30%, 35%, 40%, 45%, 50% or greater improvement in at least one symptom as compared to a comparable control subject, in the same amount of time.

In some embodiments, the eczema is selected from contact eczema, allergic contact eczema, seborrheic eczema, nummular eczema, neurodermatitis, stasis dermatitis, dyshidrotic eczema. In some embodiments, the eczema comprises atopic eczema.

In some embodiments, the subject to be treated is human.

BRIEF DESCRIPTION OF THE DRAWINGS

Non-limiting embodiments of the presently systems, methods, and kits may be described by way of example with reference to the accompanying figures.

DETAILED DESCRIPTION

Figure 1A:
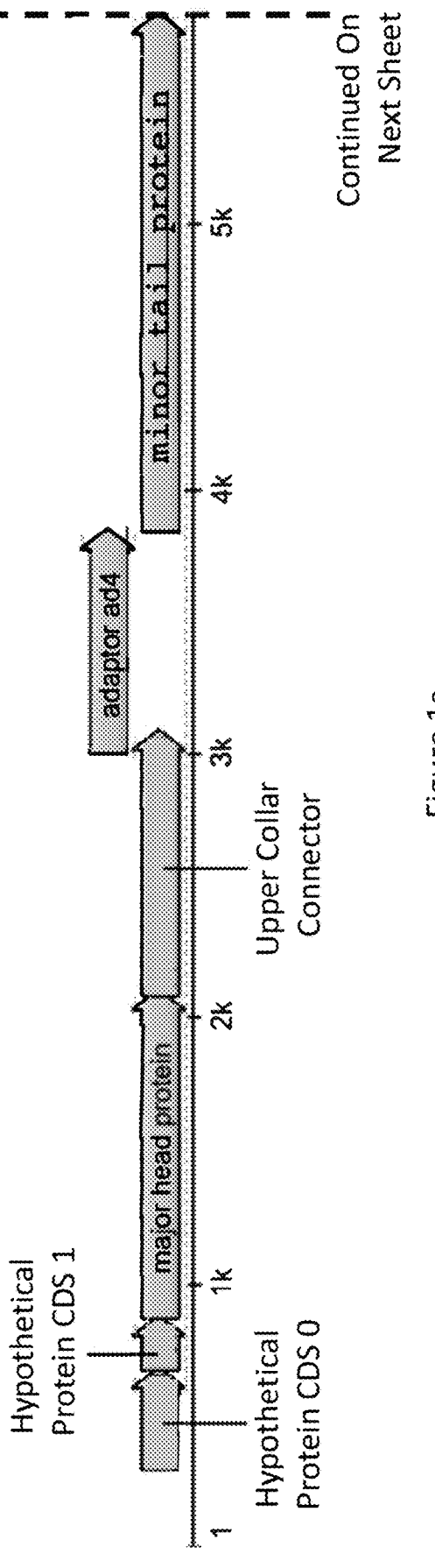
FIG. 1A, FIG. 1B, FIG. 1C. An annotated schematic of an exemplary full-length bacteriophage DNA sequence (SEQ ID NO: 1). Twenty-one segments are shown with the following SEQ ID NOs: 2 (CDS 0 hypothetical protein), 4 (CDS 1 hypothetical protein), 6 (CDS 2 major head protein), 8 (CDS 3 upper collar connector), 10 (CDS 4 adaptor Ad4), 12 (CDS 5 minor tail protein), 14 (CDS 6 endolysin), 16 (CDS 7 tail protein), 18 (CDS 8 tail protein), 20 (CDS 9 holin), 22 (CDS 10 hypothetical protein), 24 (CDS 11 DNA polymerase), 26 (CDS 12 terminase), 28 (CDS 13 hypothetical protein), 30 (CDS 14 hypothetical protein), 32 (CDS 15 hypothetical protein), 34 (CDS 16 hypothetical protein), 36 (CDS 17 hypothetical protein), 38 (CDS 18 hypothetical protein), 40 (CDS 19 hypothetical protein), and 42 (CDS 20 hypothetical protein). These sequence segments can be transcribed and translated into the representative polypeptides of SEQ ID NOs: 3, 5, 7, 9, 11, 13, 15, 17, 19, 21, 23, 25, 27, 29, 31, 33, 35, 37, 39, 41, and 43, respectively.
Figure 1B:
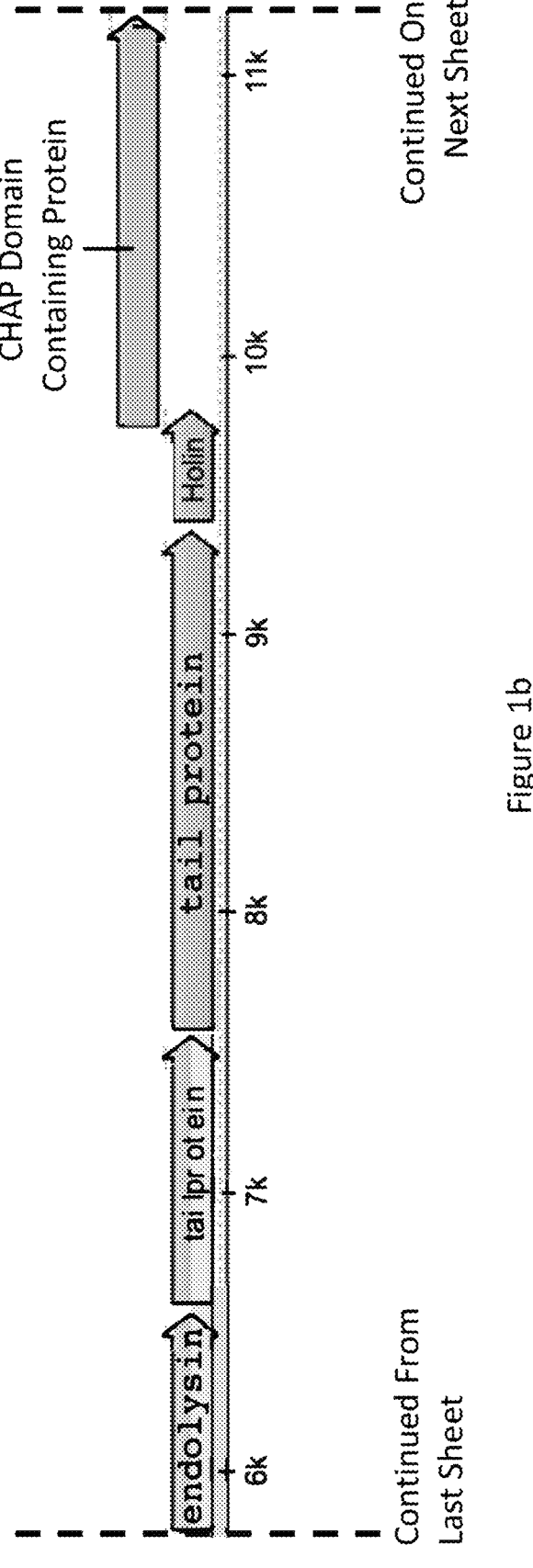
Figure 1C:
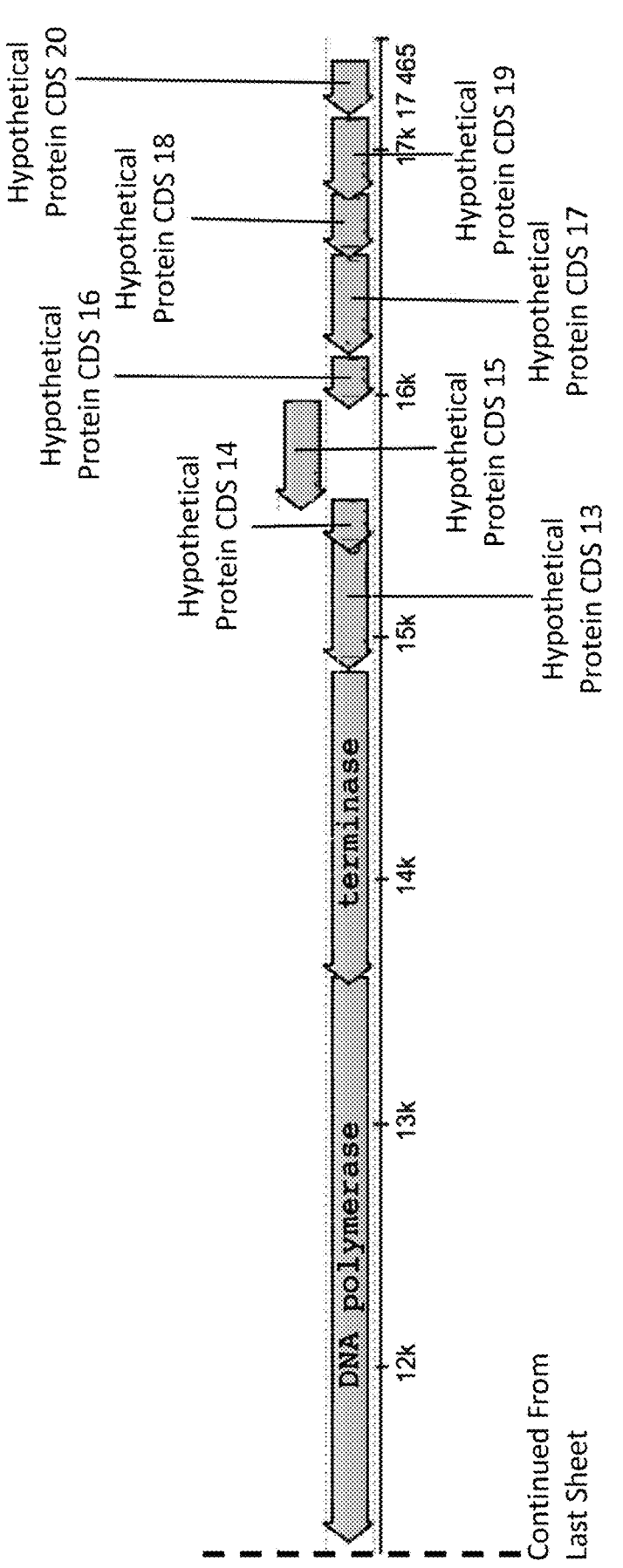
Figure 2:
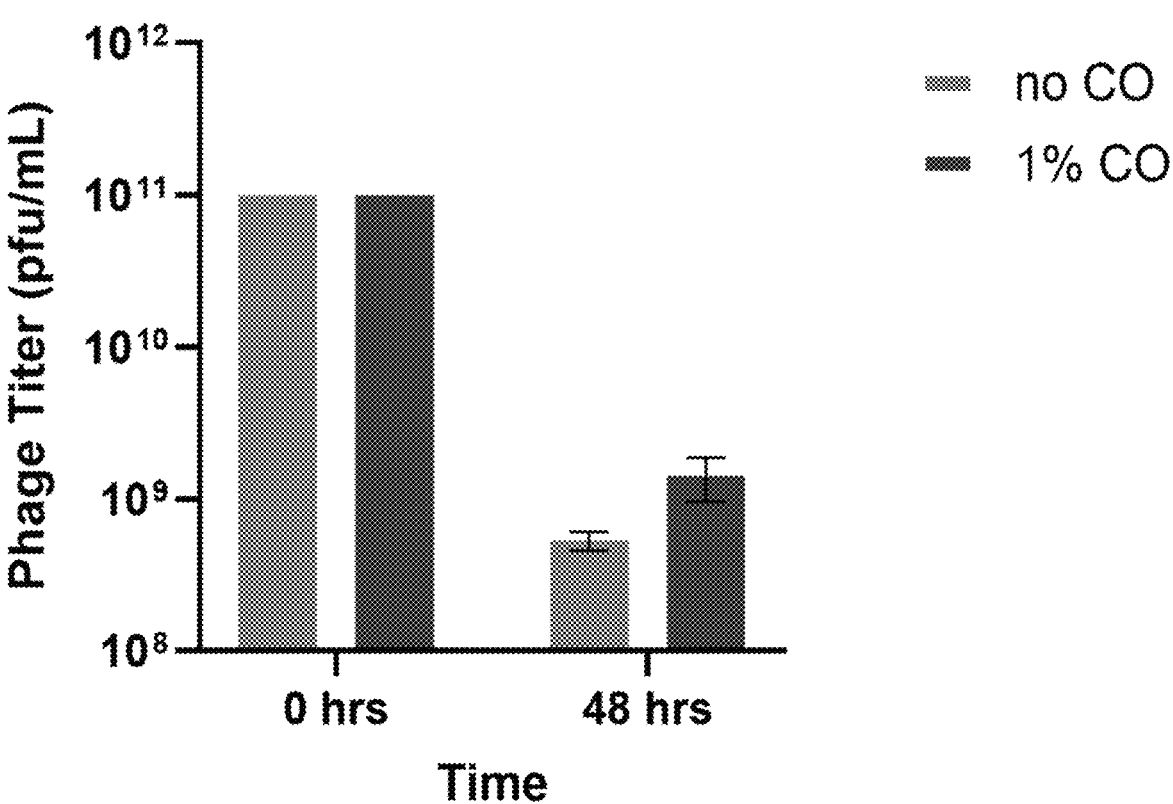
FIG. 2 is a graph showing *S. aureus* bacteriophage is more stable in the presence of 1% colloidal oatmeal (CO). *S. aureus* bacteriophage were incubated at 30° C. for 48 hours with and without 1% CO. Without CO: $0.53 \times 10^9$ pfu/mL. With 1% CO: $1.4 \times 10^9$ pfu/mL. Thus, 1% CO confers 2.64× (264%) higher stability to *S. aureus* bacteriophage.
Figure 3:
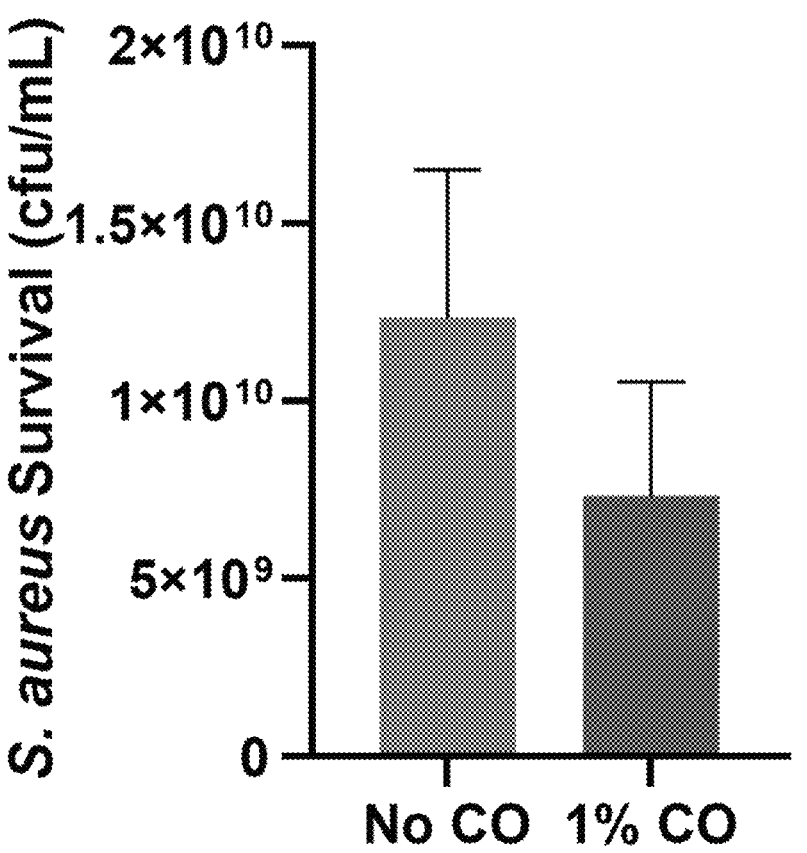
FIG. 3 is a graph showing *S. aureus* bacteria survival is lower in the present of 1% colloidal oatmeal. Bacteriophage killing of *S. aureus* bacteria was measured with our without 1% CO. Lower *S. aureus* bacterial survival indicates better killing. *S. aureus* survival was lower in the presence of 1% CO. No CO: $1.23 \times 10^{10}$ cfu/mL. With 1% CO: $0.73 \times 10^{10}$ cfu/mL. Thus, CO enhances the bacteriophage killing of *S. aureus* bacteria.

Disclosed herein are compositions and methods for the treatment of skin disease or conditions including, but not limited to eczema. The disclosed compositions comprise bacteriophage and colloidal oatmeal and in some embodiments, such compositions are topically administered to a subject suffering from a skin disease or condition, such as, for example, eczema.

In some embodiments, the method of treatment is a method for preventing, delaying and/or curing a skin disease or condition, such as, but not limited to eczema, acne, rosacea, pimples, impetigo, boils, furuncles, cellulitis folliculitis, hidradenitis suppurativa, psoriasis, carbuncles, scaled skin syndrome, and abscesses. Preferably, said method of treatment is a method for preventing, delaying, treating, and/or curing eczema such as atopic dermatitis, allergic contact eczema, contact eczema, dyshidrotic eczema, neurodermatitis, nummular eczema, seborrheic eczema, stasis dermatitis, preferably atopic dermatitis. In some embodiments, the method of treatment is topical treatment of eczema.

To aid in understanding the invention, several terms are defined throughout the specification.

Unless defined otherwise, all technical and scientific terms used herein have the same meaning as commonly understood by one of skill in the art. Although any methods and materials similar to or equivalent to those described herein can be used in the practice or testing of the claims, the exemplary methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

The term "about" means within a statistically meaningful range of a value or values such as a stated concentration, length, molecular weight, pH, time frame, temperature, pressure or volume. Such a value or range can be within an order of magnitude, typically within 20%, more typically within 10%, and even more typically within 5% of a given value or range. The allowable variation encompassed by "about" will depend upon the particular system under study.

The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range, and includes the endpoint boundaries defining the range, unless otherwise indicated herein, and each separate value is incorporated into the specification as if it were individually recited herein.

"Nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a linear sequence of nucleotides. Oligonucleotides are typically from about 5, 6, 7, 8, 9, 10, 12, 15, 25, 30, 40, 50 or more nucleotides in length, up to about 100 nucleotides in length. Polynucleotides are polymers of any length, including longer lengths, e.g., 200, 300, 500, 1000, 2000, 3000, 5000, 7000, 10000, 20000, 30000, 40000 etc. Polynucleotides and oligonucleotides will generally contain phosphodiester bonds, although in some cases, nucleic acid analogs are included that may have alternate backbones, that include, e.g., phosphoramidate, phosphorothioate, phosphorodithioate, or O-methylphophoroamidite linkages (see Eckstein, Oligonucleotides and Analogues: A Practical Approach, Oxford University Press); and peptide nucleic acid backbones and linkages. Other analog nucleic acids include those with positive backbones; non-ionic backbones, and non-ribose backbones, including those described in U.S. Pat. Nos. 5,235,033 and 5,034,506, and Chapters 6 and 7, ASC Symposium Series 580, Carbohydrate Modifications in Antisense Research, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made.

The term "bp" and the like refer, in the usual and customary sense, to the indicated number of base pairs.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. In embodiments, the percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., 50%, 55%, 60%, 65%, 70%, 75%, 80%, 85%, 90%, 91%, 92%, 93%, 94%, 95%, 96%, 97%, 98%, 99%, or more identity over a specified region, e.g., of an entire nucleic acid or polypeptide sequence or individual portions or domains of a nucleic acid or polypeptide), when compared and aligned for maximum correspondence over a comparison window, or designated region as measured using one of the following sequence comparison algorithms or by manual alignment and visual inspection. Such sequences are then said to be "substantially identical." This definition also refers to the complement of a test sequence. In embodiments, the identity exists over a region that is about or at least about 20, 50, 100, 1000, 2500, 5000, 7500, 10000, 15000, 20000, 25000, or 30000 amino acids or nucleotides in length to about, less than about, or at least about 31000, 32000, 33000, 34000 or 35000 amino acids or nucleotides in length. Optionally, the identity exists over a region that is at least about 10 to about 100, about 20 to about 75, about 30 to about 50 amino acids or nucleotides in length. Optionally, the identity exists over a region that is at least about 50 amino acids in length, or more preferably over a region that is 100 to 500 or 1000 or more amino acids in length. Included herein are phages comprising nucleic acids (e.g., a genome or a portion thereof) having sequences that are substantially identical to any of SEQ ID NOs: 1, 2, 4, 6, 8, 10, 12, 14, 16, 18, 20, 22, 24, 26, 28, 30, 32, 34, 36, 38, 40, 42, 44, 45, and/or 46. Non-limiting examples of phages provided herein comprise genomes having sequences that are substantially identical to SEQ ID NO: 1, 44, 45, and/or 46. In addition or alternatively, included herein are phages comprising polynucleotides encoding polypeptides having sequences that are substantially identical to any of SEQ ID NOs: 3, 5, 7, 9, 11, 13, 15, 17, 19, 21, 23, 25, 27, 29, 31, 33, 35, 37, 39, 41, and 43.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions in which a sequence may be compared to a reference sequence of the same number of contiguous positions after the two sequences are optimally aligned. In embodiments, a comparison window includes about or at least about 20, 50, 100, 1000, 2500, 5000, 7500, 10000, 15000, 20000, 25000, or 30000 to about, less than about, or at least about 31000, 32000, 33000, 34000 or 35000 contiguous positions. In embodiments, the comparison window is the entire length of a reference sequence, such as the sequence of a bacteriophage genome. Methods of alignment of sequences for comparison are well-known in the art. In embodiments, optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

An example of algorithms suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively. As will be appreciated by one of skill in the art, the software for performing BLAST analyses is publicly available through the website of the National Center for Biotechnology Information (NCBI). In embodiments, BLAST and BLAST 2.0 are used, with the parameters described herein, to determine percent sequence identity for the nucleic acids and proteins.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions to a peptide, polypeptide, or protein sequence which alters a single amino acid is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)).

As used herein a "*Staphylococcus aureus* (*S. aureus*) bacteriophage" is a bacteriophage that infects, replicates within, and kills *S. aureus* cells. In some embodiments, an *S. aureus* bacteriophage is a lytic *S. aureus* bacteriophage. In embodiments, an *S. aureus* bacteriophage is capable of lysing an *S. aureus* bacterium and incapable of lysing any bacterium which is not *S. aureus*. In embodiments, an *S. aureus* bacteriophage is incapable of sustaining lysogeny in a bacterium. In embodiments, the use of a bacteriophage that can lyse *S. aureus* but is incapable of sustaining lysogeny has the advantage that the bacteriophage cannot lie dormant within a bacterium, but must lyse the bacterium and hence kill it. In embodiments, an *S. aureus* bacteriophage lacks the ability to express at least one gene necessary for sustaining lysogeny. The term "lacks the ability to express at least one gene necessary for sustaining lysogeny" is intended to indicate that the *S. aureus* bacteriophage lacks the ability to produce a fully functional protein product necessary to sustain lysogeny, for example, as the result of one or more point mutations or full or partial deletions of the genome. In embodiments, the *S. aureus* bacteriophage has a genome that lacks all or part of at least one gene necessary for sustaining lysogeny (e.g., artificially or naturally, e.g., the strain is or is derived from a strain that lacks all or part of at least one gene necessary for sustaining lysogeny). In embodiments, the *S. aureus* bacteriophage may comprise modification (e.g. mutations, insertions or deletions) in the genome in non-coding regions that may, nonetheless, affect the ability of the phage to sustain lysogeny, for example defects in the genome integration site(s) (e.g. a/att/site) or in a repressor binding site. In embodiments, an *S. aureus* bacteriophage is naturally occurring and isolated, with the added advantage that artificial mutations need not be introduced into the bacteriophage. In embodiments, an *S. aureus* bacteriophage is capable of lysing a plurality of strains of *S. aureus* bacterium. In embodiments, an *S. aureus* bacteriophage is capable of lysing at least about 5, 10, 15, 20, 25, 30 or more strains of the *S. aureus* bacterium. Non-limiting examples of *S. aureus* bacteriophages are disclosed herein and include, without limitation those described in References 1-9, incorporated herein by reference in their entireties.

In embodiments, the *S. aureus* bacteriophage has a genome having sequence identity of at least about 80%, 81%, 82%, 83%, 84%, 85%, 86%, 87%, 88%, 89%, 90%, 95%, 99%, 99.1%, 99.2%, 99.3%, 99.4%, 99.5%, 99.6%, 99.7%, 99.8%, 99.9% identity with SEQ ID NO: 1, SEQ ID NO: 44, SEQ ID NO: 45, or SEQ ID NO: 46. In some embodiments, the *S. aureus* bacteriophage has a genome comprising the sequence of SEQ ID NO: 1, SEQ ID NO: 44, SEQ ID NO: 45, or SEQ ID NO: 46 or consisting of the sequence of SEQ ID NO: 1, SEQ ID NO: 44, SEQ ID NO: 45, or SEQ ID NO: 46. In embodiments, the genome of the *S. aureus* bacteriophage has no insertions or deletions compared to SEQ ID NO: 1, SEQ ID NO: 44, SEQ ID NO: 45, or SEQ ID NO: 46. In embodiments, the genome of the *S. aureus* bacteriophage has no insertions or deletions, and only conservative substitutions compared to SEQ ID NO: 1, SEQ ID NO: 44, SEQ ID NO: 45, or SEQ ID NO: 46.

Additional non-limiting examples of *S. aureus* bacteriophage, well known in the art, are provided in References 5 and 11-13, which are incorporated herein by reference in their entireties and include without limitation the following bacteriophages (GenBank/NCBI Accession Number in parenthesis): vB_SauM-A (No. MN539736), vB_SauM-C (No. MN539737), vB_SauM-D (No. MN539738), JD007 (No. JX878671), MCE-2024 (No. KJ888149), phiIPLA-RODI (No. KP027446), SaGU1 (No. LC574321), Stau2 (No. NC_030933), IME-SA1 (No. NC_047729), PT1028 (No. AY954948), 66 (No. AY954949), 44AHJD (No. NC_004678), P68 (No. NC_004679), 187 (No. AY954950), 69 (No. AY954951), 53 (No. AY954952), 85 (No. AY954953), 2638A (No. AY954954), 77 (No. AY508486), 42e (No. AY954955), 3A (No. AY954956), 47 (No. AY954957), 37 (No. AY954958), EW (No. AY954959), 96 (No. AY954960), ROSA (No. AY954961), 71 (No. AY954962), 55 (No. AY954963), 29 (No. AY954964), 52A (No. AY954965), 88 (No. AY954966), 92 (No. AY954967), X2 (No. AY954968), K (No. AY176327), G1 (No. AY954969), Twort (No. AY954970), PG-2021_1 (No. MZ417323), PG-2021_3, PG-2021_4 (No. MZ417338), PG-2021_7, PG-2021_8 (No. MZ417350), PG-2021_9 (No. MZ417354), PG-2021_10 (No. MZ417315), PG-2021_11, PG-2021_12 (No. MZ417316), PG-2021_13, PG-2021_14 (No. MZ417317), PG-2021_15 (No. MZ417318), PG-2021_16 (No. MZ417319), PG-2021_17 (No.

MZ417320), PG-2021_18 (No. MZ417321), PG-2021_22 (No. MZ417324), PG-2021_23 (No. MZ417325), PG-2021_24, PG-2021_27 (No. MZ417326), PG-2021_28, PG-2021_33 (No. MZ417330), PG-2021_34, PG-2021_37, PG-2021_38 (No. MZ417332), PG-2021_39, PG-2021_40 (No. MZ417333), PG-2021_42, PG-2021_43 (No. MZ417335), PG-2021_45, PG-2021_47 (No. MZ417337), PG-2021_48, PG-2021_49, PG-2021_50, PG-2021_51, PG-2021_52, PG-2021_53, PG-2021_63, PG-2021_64 (No. MZ417340), PG-2021_68 (No. MZ417342), PG-2021_78, PG-2021_84 (No. MZ417345), PG-2021_86 (No. MZ417346), and PG-2021_87 (No. MZ417347). In embodiments, the *S. aureus* bacteriophage has a genome having sequence identity of at least about 80%, 81%, 82%, 83%, 84%, 85%, 86%, 87%, 88%, 89%, 90%, 95%, 99%, 99.1%, 99.2%, 99.3%, 99.4%, 99.5%, 99.6%, 99.7%, 99.8%, 99.9% identity with one of the above-referenced phage. The terms "phage" and "bacteriophage" are used interchangeably herein.

*Staphylococcus aureus* (*S. aureus*) is a Gram-positive spherically shaped bacterium and is a common member of the microbiota of the body, frequently found on the skin. While typically commensal, it can also be pathogenic, causing skin infections and/or exacerbating diseases and conditions affecting the skin. *S. aureus* strains are known in the art, and a non-limiting example of a well-known exemplary *S. aureus* bacteria strain UAMS-1, is described in Reference 10, which is incorporated herein by reference in its entirety.

The term "isolated," when applied to a bacterium or bacteriophage, refers to a bacterium or bacteriophage that has been (1) separated from at least some of the components with which it was associated when initially produced (whether in nature or in an experimental setting), and/or (2) produced, prepared, purified, and/or manufactured by the hand of man, e.g. using artificial culture conditions such as (but not limited to) growing on a plate and/or in a fermenter. Isolated bacteria include those bacteria that are cultured, even if such cultures are not monocultures. In embodiments, the isolated bacteria are bacteria that are cultured as a monoculture (e.g., on a plate or in liquid culture such as in a fermenter). Isolated bacteria and bacteriophages may be separated from at least about 10%, about 20%, about 30%, about 40%, about 50%, about 60%, about 70%, about 80%, about 90%, about 95%, about 96%, about 97%, about 99% or more of the other components with which they were initially associated (e.g., by weight). In embodiments, isolated bacteria are more than about 80%, about 85%, about 90%, about 91%, about 92%, about 93%, about 94%, about 95%, about 96%, about 97%, about 98%, about 99%, or more than about 99% pure (e.g., by weight). In embodiments, isolated bacteriophages are more than about 80%, about 85%, about 90%, about 91%, about 92%, about 93%, about 94%, about 95%, about 96%, about 97%, about 98%, about 99%, or more than about 99% pure (e.g., by weight). In embodiments, a composition provided herein includes one or more isolated bacteriophages. In embodiments, a composition provided herein includes an isolated bacteriophage. In embodiments, a bacteriophage that is administered is an isolated bacteriophage. In embodiments, a composition provided herein includes one or more isolated bacteria. In embodiments, a composition provided herein includes an isolated bacterium. In embodiments, a bacterium that is administered is an isolated bacterium.

The bacteriophage disclosed herein (e.g., *S. aureus* bacteriophage) are active agents. In some embodiments, the bacteriophage active agent consists of bacteriophage (i.e., bacteriophage alone, e.g., not linked to a solid support; bacteriophage that are free in solution). In other embodiments, a bacteriophage active agent may comprise or consist of bacteriophage linked to another component, such as a bead or other molecule. In still other embodiments, a bacteriophage active agent may include both free bacteriophage and bacteriophage linked to another molecule, such as a solid support. In some embodiments, phage may be encapsulated or occluded in suspension; such phage may be free or linked to a solid support.

A "control" sample or value refers to a sample that serves as a reference, usually a known reference, for comparison to a test sample. For example, a test sample can be taken from a test condition, e.g., in the presence of a test compound (e.g., enzyme) or phage, and compared to samples from known conditions, e.g., in the absence of the test compound, phage, or bacterium (negative control), or in the presence of a known compound, phage, or bacterium (positive control). A control can also represent an average value gathered from a number of tests or results. One of skill in the art will recognize that controls can be designed for assessment of any number of parameters. For example, a control can be devised to compare therapeutic benefit based on pharmacological data (e.g., half-life, the degradation of a biofilm or a component thereof, or bacterial cell lysis, or symptoms of a disease, condition, infection, etc.) or therapeutic measures (e.g., comparison of side effects). One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant. A control may also comprise, for example, a subject or a subject population that is suffering from or afflicted with the same disease, symptoms, or condition, etc. as a test subject or a test population, but receives a placebo, partial treatment, or no treatment.

The term "disease" refers to any deviation from the normal health of a mammal and includes a state when disease symptoms are present, as well as conditions in which a deviation (e.g., dysbiosis, infection, gene mutation, genetic defect, etc.) has occurred, but symptoms are not yet manifested. In embodiments, the disease is eczema. In embodiments, the disease includes dermal dysbiosis. In embodiments, methods, compositions, systems, phages, and probiotic bacteria provided herein are suitable for use in a subject that is a member of the Vertebrate class, Mammalia, including, without limitation, primates (such as humans), livestock, work animals, and domestic pets (e.g., a companion animal). In embodiments, a subject is a human subject. As used herein, a "symptom" of a disease includes any clinical or laboratory manifestation associated with the disease, and is not limited to what a subject can feel or observe.

As used herein, the term "dermal dysbiosis" means a difference in the skin microbiota compared to a healthy or general population. In embodiments, the dysbiosis is on the surface of the skin, within skin (e.g., within a skin region or layer of skin cells), within a gland, and/or within a pore of the skin. In embodiments, the dysbiosis is within sweat and/or sebum. In embodiments, the skin is on the face (e.g., the forehead, one or more cheeks, the nose, or the chin of a subject). In embodiments, the skin is anywhere on the body, including but not limited to on the shoulders, chest, arms, elbows, legs, and back. In embodiments, dermal dysbiosis includes a change in microbiota commensal species diversity as compared to a healthy or general population and may include decrease of beneficial microorganisms and/or increase of pathobionts (pathogenic or potentially pathogenic microorganisms) and/or decrease of overall microbiota species diversity. Many factors can lead to dysbiosis, including hormonal changes, infrequent washing, cosmetic use, antibiotic use, psychological and physical stress, radiation, and dietary changes.

As used herein, "eczema," is a general term for many types of skin inflammation, also known as dermatitis. The most common form of eczema is atopic eczema or dermatitis (many practitioners use the terms eczema and dermatitis interchangeably). However, there are many other different forms of eczema including, contact eczema, allergic contact eczema, seborrheic eczema, nummular eczema, neurodermatitis, stasis dermatitis, dyshidrotic eczema, among others.

Atopic dermatitis is a chronic skin disease characterized by itchy, inflamed skin and is the most common cause of eczema. The condition tends to come and go, depending upon exposures to triggers or causative factors. Factors that may cause atopic dermatitis (allergens) include environmental factors like molds, pollen, or pollutants; contact irritants like soaps, detergents, nickel (present in jewelry), or perfumes; food allergies; or other allergies. Around two-thirds of those who develop the condition do so prior to one year of age. When the disease starts in infancy, it is sometimes termed infantile eczema.

Contact eczema (i.e., contact dermatitis) is a localized reaction that includes redness, itching, and burning in areas where the skin has come into contact with an allergen (an allergy-causing substance to which an individual is sensitized) or with a general irritant such as an acid, a cleaning agent, or other chemical. Other examples of contact eczema include reactions to laundry detergents, soaps, nickel (present in jewelry), cosmetics, fabrics, clothing, and perfume. Due to the vast number of substances with which individuals have contact, it can be difficult to determine the trigger for contact dermatitis. The condition is sometimes referred to as allergic contact eczema (i.e., allergic contact dermatitis) if the trigger is an allergen, and irritant contact eczema (i.e., irritant contact dermatitis) if the trigger is an irritant. Skin reactions to poison ivy, oak and/or sumac are examples of allergic contact eczema. People who have a history of allergies have an increased risk for developing contact eczema.

Seborrheic eczema (i.e., seborrheic dermatitis) is a form of skin inflammation of unknown cause. The signs and symptoms of seborrheic eczema include yellowish, oily, scaly patches of skin on the scalp, face, and occasionally other parts of the body. Dandruff and "cradle cap" in infants are examples of seborrheic eczema. It is commonplace for seborrheic dermatitis to inflame the face at the creases of the cheeks and/or the nasal folds. Seborrheic dermatitis is not necessarily associated with itching. This condition tends to run in families. Emotional stress, oily skin, infrequent shampooing, and weather conditions may all increase a person's risk of developing seborrheic eczema. One type of seborrheic eczema is also common in people with AIDS.

Nummular eczema (i.e., nummular dermatitis) is characterized by coin-shaped patches of irritated skin—most commonly located on the arms, back, buttocks, and lower legs—that may be crusted, scaling, and extremely itchy. This form of eczema is relatively uncommon and occurs most frequently in elderly men. Nummular eczema is usually a chronic condition. A personal or family history of atopic dermatitis, asthma, or allergies increases the risk of developing the condition.

Neurodermatitis, also known as lichen simplex chronicus, is a chronic skin inflammation caused by a scratch-itch cycle that begins with a localized itch (e.g., an insect bite) that becomes intensely irritated when scratched. Women are more commonly affected by neurodermatitis than men, and the condition is most frequent in people 20-50 years of age. This form of eczema results in scaly patches of skin on the head, lower legs, wrists, or forearms. Over time, the skin can become thickened and leathery. Stress can exacerbate the symptoms of neurodermatitis.

Stasis dermatitis is a skin irritation on the lower legs, generally related to the circulatory problem known as venous insufficiency, in which the function of the valves within the veins has been compromised. Stasis dermatitis occurs almost exclusively in middle-aged and elderly people, with approximately 6%-7% of the population over 50 years of age being affected by the condition. The risk of developing stasis dermatitis increases with advancing age. Symptoms include itching and/or reddish-brown discoloration of the skin on one or both legs. Progression of the condition can lead to the blistering, oozing skin lesions seen with other forms of eczema, and ulcers may develop in affected areas. The chronic circulatory problems lead to an increase in fluid buildup or edema in the legs. Stasis dermatitis has also been referred to as varicose eczema.

Dyshidrotic eczema (i.e., dyshidrotic dermatitis) is an irritation of the skin on the palms of hands and soles of the feet characterized by clear, deep blisters that itch and burn. The cause of dyshidrotic eczema is unknown. Dyshidrotic eczema is also known as vesicular palmoplantar dermatitis, dyshidrosis, or pompholyx. This form of eczema occurs in up to 20% of people with hand eczema and is more common during the spring and summer months and in warmer climates.

Eczema occurs in people of all races and can affect people of any age, although the condition is most common in infants, and about 85% of people have an onset prior to five years of age. Typically, eczema will permanently resolve by age three in only about one-half of affected infants. In others, the condition tends to recur throughout life. People with eczema often have a family history of the condition or a family history of other allergic conditions, such as asthma and/or hay fever. Approximately 20% of children and approximately 1%-5% of adults are believed to have eczema. This means that more than approximately 15 million people in the United States alone express symptoms of the disease and over 32 million people have eczema. Present statistics suggest that eczema sufferers have tripled in the past 30 years and one in five children suffer. It is generally accepted in medical opinion, that there is currently no known cure for eczema, and symptoms can endure a sufferer's lifetime.

While eczema is not known to be contagious, it is believed to be at least partially inherited. As such, it is not uncommon to find members of the same family affected.

Skin diseases such as eczema can be painful and embarrassing. Eczema symptoms generally include incredible itchiness and sufferers typically have poor sleep and liken it to "sleeping on an ants' nest." In numerous instances, children and infants suffering from congenital eczema have been reported with significant delayed development in speech and growth.

A normal skin barrier is thick and in the stratum corneum the corneodesmosomes are intact and the outermost layers of dead skin cells flake off in a barely detectable manner, as the outermost binders snap and release the unwanted cells. However, in atopic eczema or dermatitis, and other dry skin disorders, the skin barrier is typically thinner than normal so the skin's protective and regulatory capacities are compromised. As the skin barrier breaks down, cracks appear in the skin barrier which allows allergens and infectious agents, such as dust mites and bacteria to enter the skin, thereby causing a worsening of the skin disorder.

Present treatments for eczema include the application of moisturizers between four to six times daily. Healthcare professionals prescribe topical hydrocortisone however this treatment is usually discontinued after seven days, and it is considered a risk for use on children under two years or on irritated or broken skin. Eczema is irritated and broken skin, and sufferers are often under two years. In any case it is known that topical steroids do not cure eczema and often they are applied for years which can result in permanent thinning of the skin, stretch marks, cataracts (if used near eyes) and Cushing's syndrome.

Topical immunosuppressants (topical calcineurin inhibitors) are sometimes prescribed to reduce eczema symptoms. Such products however do not provide a cure, and medical practitioners are hesitant to prescribe immunosuppressants due to documented side-effects. In particular, in 2006, the U.S. Food and Drug Administration warns on product packaging that "a small number of malignancies (skin cancer and lymphoma) have been reported in patients using topical calcineurin inhibitors."

Typically, more than half of eczema sufferers present with salicylate sensitivity, which worsens after ingesting salicylate-containing foods (found in many healthy foods, fruits and vegetables, sauces and juices). Salicylate- and multiple chemical-sensitivities reduce a person's quality of life and long term adherence to low salicylate diets can be restrictive and can lead to nutritional deficiencies. Eczema sufferers are also known to have elevated histamine levels in the blood combined with a reduced capacity to detoxify these histamines.

Accordingly, the present compositions and methods address these shortcoming, and provide unexpected, rapid, long lasting relief of eczema symptoms.

The term "diagnosis" refers to a relative probability a subject has a given metabolic disorder. Symptoms and diagnostic criteria are summarized herein. Similarly, the term "prognosis" refers to a relative probability that a certain future outcome may occur in the subject. For example, in the context of the present invention, prognosis can refer to the likelihood that an individual will develop eczema. Prognosis can also refer to the likely severity of the disease (e.g., severity of symptoms, rate of functional decline, etc.). The terms are not intended to be absolute, as will be appreciated by any one of skill in the field of medical diagnostics.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the bacteriophages, probiotic bacteria, and/or compounds of the invention. One of skill in the art will recognize that other pharmaceutical excipients are useful in the present invention.

Additional component that may be added to a therapeutic composition of the present disclosure comprising colloidal oatmeal and a bacteriophage include but are not limited to enzymes, ceramides, hyaluronic acid, glycerin, petrolatum, and niacinamide.

As used herein, "colloidal oatmeal" refers to finely powdered, ground oat grain (e.g., *Avena sativa*) that is heat treated, e.g., boiled, to extract colloidal materials. Currently, the use of colloidal oatmeal as a skin protectant is regulated by the U.S. Food and Drug Administration (FDA) according to the Over-The-Counter Final Monograph for Skin Protectant Drug Products issued in June 2003. Its preparation is also standardized by the United States Pharmacopeia, and is well known in the art. Colloidal oatmeal includes a diverse array of functional molecules, such as starches and betaglucan, which contribute to the protective and water-holding functions, different types of phenols, which confer antioxidant and anti-inflammatory functions, and saponins, which contribute a cleaning function. Colloidal oatmeal also has an ability to act as a pH buffer, and can assist in modulating skin pH to provide symptom relief and potentially optimize the stability and activity of *S. aureus* phage. Thus, its many functional properties make colloidal oatmeal a cleanser, moisturizer, buffer, as well as a soothing and protective anti-inflammatory agent. Available exemplary sources of colloidal sources (brands) include, without limitation: Aquaphor, Cetaphil, Cerave, Exederm, Eczema Honey.

"Patient" or "subject in need thereof" refers to a living member of the animal kingdom suffering from or who may suffer from the indicated disorder. In embodiments, the subject is a member of a species that includes individuals who naturally suffer from the disease. In embodiments, the subject is a mammal. Non-limiting examples of mammals include rodents (e.g., mice and rats), primates (e.g., lemurs, bushbabies, monkeys, apes, and humans), rabbits, dogs (e.g., companion dogs, service dogs, or work dogs such as police dogs, military dogs, race dogs, or show dogs), horses (such as race horses and work horses), cats (e.g., domesticated cats), livestock (such as pigs, bovines, donkeys, mules, bison, goats, camels, and sheep), and deer. In embodiments, the subject is a human. Thus the methods are applicable to both human therapy and veterinary applications.

The terms "subject," "patient," "individual," etc. are not intended to be limiting and can be generally interchanged. That is, an individual described as a "patient" does not necessarily have a given disease, but may be merely seeking medical advice.

As used herein the abbreviation "sp." for species means at least one species (e.g., 1, 2, 3, 4, 5, or more species) of the indicated genus. The abbreviation "spp." for species means 2 or more species (e.g., 2, 3, 4, 5, 6, 7, 8, 9, 10 or more) of the indicated genus. In embodiments, methods and compositions provided herein comprise a single species within an indicated genus or indicated genera, or 2 or more (e.g., a plurality that includes more than 2) species within an indicated genus or indicated genera. In embodiments, 1, 2, 3, 4, 5, or more or all or the indicated species is or are isolated. In embodiments, the indicated species are administered together. In embodiments, each of the indicated species is present in a single composition that includes each of the species. In embodiments, each of the species is administered concurrently, e.g., within about 1, 2, 3, 4, 5, 6, 7, 8, 9, 10, 30, or 60, 1-5, 1-10, 1-30, 1-60, or 5-15 seconds or minutes of each other.

As used herein, "treating" or "treatment" of a condition, disease or disorder or symptoms associated with a condition, disease or disorder refers to an approach for obtaining beneficial or desired results, including clinical results. Beneficial or desired clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean inhibiting the progression of the condition, disorder or disease, slowing the progression of the condition, disorder or disease temporarily, although in some instances, it involves halting the progression of the condition, disorder or disease permanently.

As used herein, the terms "treat" and "prevent" are not intended to be absolute terms. In embodiments, treatment can refer to a 10%, 20%, 30%, 40%, 50%, 60%, 70%, 80%, 90%, or 100% reduction in the severity of an established disease, condition, or symptom of the disease or condition. In embodiments, a method for treating a disease is considered to be a treatment if there is a 10% reduction in one or more symptoms of the disease in a subject as compared to a control. Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition. In embodiments, references to decreasing, reducing, or inhibiting include a change of 10%, 20%, 30%, 40%, 50%, 60%, 70%, 80%, 90% or greater as compared to a control level and such terms can include but do not necessarily include complete elimination. Treatment can refer to any delay in onset, amelioration of symptoms, improvement in patient skin appearance, etc. The effect of treatment can be compared to an individual or pool of individuals not receiving the treatment, or to the same patient prior to treatment or at a different time during treatment. In embodiments, the severity of disease is reduced by at least 10%, as compared, e.g., to the individual before administration or to a control individual not undergoing treatment. In some aspects the severity of disease is reduced by at least 25%, 50%, 75%, 80%, or 90%, or in some cases, no longer detectable using standard diagnostic techniques. In embodiments, treatment is effective to reduce at least one symptom of eczema. In embodiments, treatment is effective to reduce the level of one or more symptoms such as, but not limited to itching, burning, stinging skin, redness or rash on skin, flaking skin, trouble sleeping due to skin discomfort, rough bumpy skin, skin discoloration, oozing and crusting. Thus, a treated subject will exhibit a greater alleviation of symptoms in the same amount of time as a corresponding control subject, and/or will exhibit reduced symptoms more quickly as compared to a corresponding control subject (e.g., a subject who is afflicted with eczema but who has received treatment comprising bacteriophage alone, or comprising colloidal oatmeal alone, or a placebo, or no treatment).

In embodiments, compositions of the present disclosure are administered to a subject suffering from eczema in a "therapeutically effective dose." Amounts effective for this use may depend upon the severity of the disease and the general state of the patient's health. Single or multiple administrations of the compositions may be administered depending on the dosage and frequency as required and tolerated by the patient, and/or as determined by a physician or other medical professional.

The terms "effective amount," "effective dose," "therapeutically effective amount," etc. refer to the amount of an agent that is sufficient to ameliorate a disorder, as described herein. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Compositions and Combination Therapy Comprising Bacteriophage

In an aspect, provided herein is a composition comprising, consisting essentially of, or consisting of at least one *S. aureus* bacteriophage, colloidal oatmeal, and optionally, one or more pharmaceutically acceptable carriers, and/or optionally, one or more additional active agents, ingredients, or components. The *S. aureus* bacteriophage is not bound to another molecule or a solid support, such as a bead, and is free in the composition.

In an aspect, provided herein is a composition that comprises at least one *S. aureus* bacteriophage, and colloidal oatmeal, and optionally, one or more additional active agents.

In an aspect, provided herein is a composition that includes active agents consisting of at least one *S. aureus* bacteriophage and colloidal oatmeal.

In an aspect, provided herein is a composition that comprises at least one *S. aureus* bacteriophage, colloidal oatmeal, and one or more additional active agents, wherein the one or more additional active agents comprise a ceramide, hyaluronic acid, glycerin, petrolatum, niacinamide, an enzyme, probiotic bacteria, aloe, mineral oil, humectants, lanolin, antihistamines, alpha-hydroxy acids (e.g. glycolic acid), and optionally a pharmaceutically acceptable carrier or excipient.

In an aspect, provided herein is a composition that comprises at least one *S. aureus* bacteriophage, colloidal oatmeal, and wherein the composition does not comprise a probiotic bacterium.

In embodiments, the at least one additional active agent includes a ceramide. In embodiments, the ceremide is present at a concentration of 2.5% to 10% (weight/volume). In embodiments, the ceremide is present at a concentration of less than 2.5% but greater than about 0.1%, 0.5%, 1%, 1.5%, or 2% (weight/volume). In embodiments, the ceremide is present at a concentration of 2.5% to 10%, e.g., about 2.5%, 3%, 3.5%, 4%, 4.5%, 5%, 5.5%, 6%, 6.5%, 7%, 7.5%, 8%, 8.5%, 9%, 9.5%, or 10% (weight/volume). In embodiments, the ceremide is present at a concentration of less than 2.5% but greater than about 0.1%, 0.5%, 1%, 1.5%, or 2% (weight/volume).

In embodiments, the at least one additional active agent includes hyaluronic acid. In embodiments, the hyaluronic acid is present at a concentration of 0.5% to 2% (weight/volume). In embodiments, the hyaluronic acid is present at a concentration of less than 0.5% but greater than about 0.1% (weight/volume). In embodiments, the hyaluronic acid is present at a concentration of 0.5% to 2%, e.g., about 0.5%, 0.6%, 0.7%, 0.8%, 0.9%, 1%, 1.1%, 1.2%, 1.3%, 1.4%, 1.5%, 1.6%, 1.7%, 1.8%, 1.9%, or 2% (weight/volume). In embodiments, the hyaluronic acid is present at a concentration of less than 0.5% but greater than about 0.1% (weight/volume).

In embodiments, the at least one additional active agent includes petrolatum. In embodiments, the petrolatum is present at a concentration of 3% to 10% (weight/volume). In embodiments, the petrolatum is present at a concentration of less than 3% but greater than about 0.1%, 0.5%, 1%, 1.5%, 2%, or 2.5% (weight/volume). In embodiments, the petrolatum is present at a concentration of 3% to 10%, e.g., about 3%, 3.5%, 4%, 4.5%, 5%, 5.5%, 6%, 6.5%, 7%, 7.5%, 8%, 8.5%, 9%, 9.5%, or 10% (weight/volume). In embodiments, the petrolatum is present at a concentration of less than 3% but greater than about 0.1%, 0.5%, 1%, 1.5%, 2%, or 2.5% (weight/volume).

In embodiments, the at least one additional active agent includes glycerin. In embodiments, the glycerin is present at a concentration of 2%, or 3% to 8% (weight/volume), (e.g., about 2.5%, 3%, 3.5%, 4%, 4.5%, 5%, 5.5%, 6%, 6.5%, 7%, 7.5%, or 8%) (weight/volume).

In embodiments, the at least one additional active agent includes niacinamide. In embodiments, the niacinamide is present at a concentration of 2% to 8% (weight/volume). (e.g., about 2%, 2.5%, 3%, 3.5%, 4%, 4.5%, 5%, 5.5%, 6%, 6.5%, 7%, 7.5%, or 8%) (weight/volume).

In embodiments, the $S.$ $aureus$ bacteriophage is present in an amount of about $1\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times108$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, or $1\times10^{11}$ plaque forming units (pfu). In embodiments, the $S.$ $aureus$ bacteriophage is present in an amount of about $1\times10^6$ to $1\times10^{11}$ pfu. In embodiments, the $S.$ $aureus$ bacteriophage is present in an amount of about $1\times10^6$ to $1\times10^8$, about $1\times10^8$ to $1\times10^9$, about $1\times10^9$ to $1\times10^{10}$, about $1\times10^9$ to $1\times10^{11}$ or about $1\times10^{10}$ to $1\times10^{11}$ pfu. In some embodiments, the amount of $S.$ $aureus$ bacteriophage is provided or described as a concentration (e.g., pfu per mL (pfu/mL)).

In embodiments, a probiotic bacterium is present in the composition. In some embodiments, the probiotic bacterium is present in an amount of about $1\times10^5$, $1\times10^6$, $2\times10^6$, $3\times10^6$, $4\times10^6$, $5\times10^6$, $6\times10^6$, $7\times10^6$, $8\times10^6$, $9\times10^6$, $1\times10^7$, $2\times10^7$, $3\times10^7$, $4\times10^7$, $5\times10^7$, $6\times10^7$, $7\times10^7$, $8\times10^7$, $9\times10^7$, $1\times10^8$, $2\times10^8$, $3\times10^8$, $4\times10^8$, $5\times10^8$, $6\times10^8$, $7\times10^8$, $8\times10^8$, $9\times10^8$, $1\times10^9$, $2\times10^9$, $3\times10^9$, $4\times10^9$, $5\times10^9$, $6\times10^9$, $7\times10^9$, $8\times10^9$, $9\times10^9$, $1\times10^{11}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, or $1\times10^{11}$ colony forming units (cfu). In embodiments, the probiotic bacterium is present in an amount of about $1\times10^6$ to $1\times10^{11}$ cfu. In embodiments, the probiotic bacterium is present in an amount of about $1\times10^6$ to $1\times10^8$, about $1\times10^8$ to $1\times10^9$, about $1\times10^9$ to $1\times10^{10}$, about $1\times10^9$ to $1\times10^{11}$ or about $1\times10^{10}$ to $1\times10^{11}$ cfu. In some embodiments, the amount of probiotic bacterium is provided or described as a concentration (e.g., cfu per mL (cfu/mL))

By way of example, but not by way of limitation, a probiotic bacterium may be one or more of the following: $Staphylococcus$ $epidermidis,$ $Staphylococcus$ $aureus$ 502A, $Staphylococcus$ $hominis,$ and Roseomonas mucosa.

In an aspect, provided herein is a composition that includes an $S.$ $aureus$ bacteriophage, colloidal oatmeal, and an enzyme. In some embodiments, the enzyme comprises an endolysin, an SH3 domain-containing protein, a CHAP domain-containing protein, a lysin, a tail lysin, and/or an anti-inflammatory cytokine. Enzymes such as endolysin can be contributed by the phage itself, and/or can be exogenously added. Exemplary, non-limiting enzymes are well-known in the art, for example, as shown in GenBank AHB79986.1 (putative endolysin of $Staphylococcus$ phage K); NCBI Reference Sequence: YP_009780264.1 (SH3 domain-containing protein of $Staphylococcus$ phage ISP; NCBI Reference Sequence: YP_009780266.1 (CHAP domain-containing protein of $Staphylococcus$ page ISP); NCBI Reference Sequence: YP_008873573.1 (putative endolysin of $Staphylococcus$ phage Sb1); NCBI Reference Sequence: YP_007002194.1 (putative lysin of $Staphylococcus$ phage G15); NCBI Reference Sequence: UP_009275797.1 (tail lysin of $Staphylococcus$ phage Stau2); NCBI Reference Sequence: YP_009275798.1 (tail lysin of $Staphylococcus$ phage Stau2); NCBI Reference Sequence: YP_009275799.1 (putative tail lysin of $Staphylococcus$ phage Stau2); NCBI Reference Sequence: YP_009275801.1. Each of these publicly available NCBI and GenBank sequence entries is incorporated herein by reference in its entirety.

In an aspect, provided herein is a combination comprising, consisting essentially of, or consisting of at least one $S.$ $aureus$ bacteriophage, at least one additional active agent comprising an enzyme (e.g., as described above), wherein each of the at least one $S.$ $aureus$ bacteriophage and the at least one additional active agent comprising an enzyme is in a composition that further includes a pharmaceutically acceptable carrier.

In an aspect, provided herein is a combination that includes a $S.$ $aureus$ bacteriophage, colloidal oatmeal, and an enzyme (e.g., as described above).

In embodiments, the composition or combination includes an $S.$ $aureus$ biofilm degrading enzyme. In embodiments, the enzyme is a glycosidase, a protease, a DNAse, or a restriction endonuclease. In embodiments, the enzyme is a glycosidase. In embodiments, the glycosidase is a glycoside hydrolase. In embodiments, the enzyme catalyzes the hydrolysis of linear polymers of N-acetyl-D-glucosamines. In embodiments, the enzyme is a β-hexosaminidase. In embodiments, the enzyme hydrolyzes β-1,6-glycosidic linkages of acetylglucosamine polymers. In embodiments, the enzyme is a DNAse I, a restriction endonuclease, papain, bromelain, Trypsin, Proteinase K, Subtilisin, serratiopeptidase, dispersin, alginate lyase, amylase, or cellulase. In embodiments, the enzyme is Dispersin B. In embodiments, the enzyme is a protease, and the protease is proteinase K or subtilisin.

Additionally or alternatively, in embodiments, the composition or combination includes a bacterial cell wall degrading enzyme. In some embodiments, the cell wall degrading enzymes comprises a bacterial endolysin. In some embodiments, the endolysin is specific for $Staphylococcus$ and by way of example but not by way of limitation, comprises one or more of GenBank AHB79986.1 (putative endolysin of $Staphylococcus$ phage K); NCBI Reference Sequence: YP_009780264.1 (SH3 domain-containing protein of $Staphylococcus$ phage ISP; NCBI Reference Sequence: YP_009780266.1 (CHAP domain-containing protein of $Staphylococcus$ page ISP); NCBI Reference Sequence: YP_008873573.1 (putative endolysin of $Staphylococcus$ phage Sb1); NCBI Reference Sequence: YP_007002194.1 (putative lysin of $Staphylococcus$ phage G15); NCBI Reference Sequence: UP_009275797.1 (tail lysin of $Staphylococcus$ phage Stau2); NCBI Reference Sequence: YP_009275798.1 (tail lysin of $Staphylococcus$ phage Stau2); NCBI Reference Sequence: YP_009275799.1 (putative tail lysin of *Staphylococcus* phage Stau2); NCBI Reference Sequence: YP_009275801.1.

Additionally or alternatively, in embodiments, the composition or combination includes an anti-aging enzyme. In embodiments, the anti-aging enzyme is a superoxide dismutase or a peroxidase.

In embodiments, the *S. aureus* bacteriophage has a linear double stranded DNA genome.

In embodiments, the *S. aureus* bacteriophage is within the bacteriophage order Caudovirales.

In embodiments, the bacteriophage is a wild-type bacteriophage. In embodiments, the bacteriophage has a genome with a nucleotide sequence that is at least about 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% identical to the genomic sequence of a wild-type *S. aureus* bacteriophage. A non-limiting example of an *S. aureus* bacteriophage useful for the present comprises SEQ ID NO: 1, SEQ ID NO: 44, SEQ ID NO: 45, and/or SEQ ID NO: 46.

The therapeutic compositions disclosed herein, comprising colloidal oatmeal, bacteriophage, and optionally, one or more additional active agents, e.g., endolysin. By way of example, but not by way of limitation, therapeutic compositions comprising phage at concentration between $10^1$ and $10^{12}$ pfu/mL with 1% colloidal oatmeal in one or a combination of the following formulations: an aqueous phase, an organic phase, a water-in-oil emulsion, in an oil-in-water emulsion, in biphasic phase-separated form, or in one of the above formulations with the phage or another ingredient encapsulated or occluded in suspension in the medium.

The combination of bacteriophage and colloidal oatmeal exhibits a synergistic effect in treating a subject's dermal dysbiosis (e.g., eczema). That is, the combination exhibits a treatment effect (i.e., relief from and/or reduction of symptoms), that is greater than each component alone, i.e., bacteriophage alone, or colloidal oatmeal alone, as demonstrated in the Examples.

By way of example, but not by way of limitation, the combination of colloidal oatmeal and bacteriophage allows for increased bacteria killing. In addition, the combination of colloidal oatmeal and bacteriophage will provide at least one or more of the following unexpected effects: increased penetration of phage into the subject's skin and increased persistence of the phage on the subject's skin, thereby increasing contact time of the phage with the target bacteria. The increased phage contact time will allow for increased destruction of the target bacterial and faster treatment/recovery from eczema than provided by prior art compositions and methods, or provided by treatment with phage alone, or provided by treatment with colloidal oatmeal alone. That is, the known benefits of colloidal oatmeal (such as soothing, moisturizing, providing a barrier against further infection, an anti-inflammatory properties), will contribute to the alleviation of symptoms, while allowing the phage a greater opportunity to lyse target cells and treat the dysbiosis, not simply relive symptoms.

By way of example, but not by way of limitation, it is anticipated that at least one symptom of a treated subject's eczema will exhibit a statistically relevant reduction, or reduction in a statistically relevant faster time, as compared to the eczema symptoms of a comparable control subject (e.g., a subject treated with placebo, or treated with phage alone, or colloidal oatmeal alone). By way of example, a subject treated according to the compositions and methods disclosed herein will show at least about 5%, 10%, 15%, 20%, 25%, 30%, 35%, 40%, 45%, 50% or greater improvement in symptoms as compared to a comparable control subject, in the same amount of time. Additionally or alternatively, in some embodiments, a subject treated according to the compositions and methods disclosed herein will show improvement in at least one eczema symptom in at least about 5%, 10%, 15%, 20%, 25%, 30%, 35%, 40%, 45%, 50% less time than a comparable control subject.

In embodiments, a subject diagnosed with, suffering from, or suspected of having dermal dysbiosis, such as eczema, is treated with a composition of the present technology, i.e., a composition comprising a bacteriophage and colloidal oatmeal. The composition is applied topically to the skin of the subject. In some embodiments, the composition is applied to at least the affected area of the subject's skin (e.g., the area exhibiting eczema), and in some embodiment, the composition is applied to the skin surrounding the affected area.

In some embodiments, the composition is administered once per day, twice per day, three, four, five, or six times per day, or as needed. In some embodiments, the composition is applied over a period of one week, two weeks, three weeks, one month, two months, three, four, five, six, seven, eight, nine, ten, eleven months, or for a year or more. In some embodiments, the composition is applied, daily, as needed, e.g., until symptoms of the dermal dysbiosis (e.g., eczema) are reduced or absent. It is anticipated that the subject treated with the compositions of the present technology will exhibit reduced symptoms of dermal dysbiosis (e.g., eczema) sooner than a comparable subject that is not treated with the disclosed compositions.

Miscellaneous. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect a person having ordinary skill in the art to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

The following examples are illustrative and should not be interpreted to limit the scope of the claimed subject matter.

Example 1: Higher Stability: Phage is Preserved for Longer in the Presence of Colloidal Oatmeal (CO)

*S. aureus* phage MESA-11 (SEQID 45) was prepared in either PBS or PBS+1% colloidal oatmeal (CO). Each formulation was incubated in triplicate at 30 C for 48 hours, the phage concentrations were determined by titer assay and compared to the initial concentration at t=0. It was found that despite starting from the same concentration, 1% CO conferred 2.64× (264%) higher stability than phage in PBS alone.

Temperature: In a first experiment, *S. aureus* bacteriophage formulations with or without CO are tested for stability by incubation at room temperature and elevated temperatures. In one or more of these conditions, it is anticipated that the presence of colloidal oatmeal will prolong the stability of the *S. aureus* bacteriophage.

pH: In a second experiment, *S. aureus* bacteriophage formulations with or without CO are incubated in buffers at different pHs. It is anticipated that the *S. aureus* bacteriophage will show better survival at alkaline pHs (as is found on eczema skin) due to the acid-buffering capacity of colloidal oatmeal.

Example 2: Protects the Phage: CO Prolongs the Presence or Activity of Phage on the Skin Several topical formulations (A-F) will be prepared and evaluated as follows:

A: Phage with 1% CO in aqueous phase formulation.

B: Phage with 1% CO in organic phase formulation.

C: Phage with 1% CO in oil-in-water emulsion formulation.

D: Phage with 1% CO in water-in-oil emulsion formulation.

E: Phage with 1% CO in discontinuous aqueous and organic phase formulation.

F: Phage with 1% CO in a formulation where the phage is encapsulated or occluded and in suspension.

*S. aureus* bacteriophage formulations A-F, prepared with or without CO are applied on the skin of human subjects. After a certain period of time, the area of application is swabbed and the surviving phage is quantified using a phage titer assay. It is anticipated that the colloidal oatmeal will positively affect the survival of the *S. aureus* bacteriophage on the skin.

Example 3: CO Enhances Phage Penetration into the Skin

*S. aureus* bacteriophage formulations A-F, prepared with or without CO are applied on the skin of human subjects. Upon complete absorption, the area of application is subjected to tape stripping to isolate layers of stratum corneum. Each tape strip is titered to quantify the *S. aureus* bacteriophage within successive layers of the stratum corneum. It is anticipated that the formulations containing colloidal oatmeal will show deeper penetration into the skin, evidenced by the persistence of *S. aureus* bacteriophages in deeper layers of the stratum corneum in formulations containing colloidal oatmeal.

Example 4: CO Enhances the Killing of Bacteria

*S. aureus* phage (MESA-11 SEQID45) was added to a logarithmic phase culture *S. aureus* strain UAMS-01 in BHI broth, in the presence or absence of 1% CO. The cultures were incubated aerobically at 37 C in triplicate. After 24 hours of incubation, the survival of *S. aureus* bacteria was measured by plating serial dilutions on a BHI agar plate. After overnight incubation at 37 C, the *S. aureus* survival was calculated by counting colonies in the relevant dilution and multiplying by the dilution factor and the inverse fraction of 1 mL plated. It was found that on average in the presence of 1% CO, *S. aureus* survival was 59% of the comparative survival in its absence ($0.73 \times 10^{10}$ pfu/mL vs $1.23 \times 10^{10}$ pfu/mL, respectively).

*S. aureus* bacteriophage formulations A-F, prepared with or without CO were incubated with *S. aureus* host bacteria. The formulations will be assessed and compared for their efficiency in killing *S. aureus* bacteria, by determining the growth kinetics, phage expansion, and survival of host bacteria. It is anticipated that the presence of colloidal oatmeal will enhance the killing of bacteria by *S. aureus* bacteriophage.

Example 5: CO Calms the Skin Upon Phage Application

*S. aureus* bacteriophage formulations A-F, prepared with or without CO are applied on irritated or inflamed skin. After repeated applications, the affected area is evaluated to quantify the inflammation. It is anticipated that the presence of colloidal oatmeal will reduce inflammation more than *S. aureus* bacteriophage alone.

It is anticipated that the combination of the *S. aureus* bacteriophage with colloidal oatmeal will achieve more than an additive effect, i.e., a synergistic effect (the combined effect of the bacteriophage and the colloidal oatmeal is greater than the sum of the effects of the bacteriophage and the colloidal oatmeal when each agent is used separately) in treating skin irritation or inflammation, such as with eczema. The effectiveness of treatment is measured by evaluating the patient's skin for decreased pain, itchiness, bumps, oozing, discoloration, and general discomfort.

REFERENCES

1. Estrella, Luis A, et al., Characterization of novel *Staphylococcus aureus* lytic phage and defining their combinatorial virulence using the OmniLog® system, Bacteriophage, 6(3), e1219440 (13 pages) Aug. 5, 2016; doi: 10.1080/21597081.2016.1219440.

2. Ajuebor, J. et al., Comparison of *Staphylococcus* Phage K with Close Phage Relatives Commonly Employed in Phage Therapeutics, Antibiotics (Basel) 2018 Apr. 25; 7(2):37. doi: 10.3390/antibiotics7020037. PMID: 29693603; PMCID: PMC6022877.

3. Gu, J. et al., Genomic characterization of lytic *Staphylococcus aureus* phage GH15: providing new clues to intron shift in phages, J Gen Virol. 2013 April; 94(Pt 4):906-915. doi: 10.1099/vir.0.049197-0. Epub 2012 Dec. 19. PMID: 23255621.

4. Ganaie, M. Y. et al., Isolation and characterization of two lytic bacteriophages against *Staphylococcus aureus* from India: newer therapeutic agents against Bovine mastitis, Vet Res Commun. 2018 December; 42(4):289-295. doi: 10.1007/s11259-018-9736-y. Epub 2018 Sep. 15. PMID: 30219981.

5. Natalia Lubowska, et al., Characterization of the Three New Kayviruses and Their Lytic Activity Against Multidrug-Resistant *Staphylococcus aureus*, Microorganisms, 18; 7(10); 471, October 2019.

6. Sue-Er Hsieh, et al., Wide host range and strong lytic activity of *Staphylococcus aureus* lytic phage Stau2, Hsieh, Sue-Er et al. "Wide host range and strong lytic activity of *Staphylococcus aureus* lytic phage Stau2." Applied and environmental microbiology vol. 77, 3 (2011): 756-61. doi:10.1128/AEM.01848-10.

7. Kim, M S, et al., Complete genome of *Staphylococcus aureus* phage SA11, J Virol. 2012 September; 86(18): 10232. doi: 10.1128/JVI.01574-12. PMID: 22923794; PMCID: PMC3446589.

8. Gill, J J. Revised Genome Sequence of *Staphylococcus aureus* Bacteriophage K, Genome Announc. 2014; 2(1): e01173-13. Published 2014 Jan. 23. doi:10.1128/genomeA.01173-13.

9. Gu, J, et al., Complete genome sequence of *Staphylococcus aureus* bacteriophage GH15, J Virol. 2012; 86(16): 8914-8915. doi:10.1128/JVI.01313-12.

10. Sassi, M. et al., Genome Sequence of the Clinical Isolate *Staphylococcus aureus* subsp. *aureus* Strain UAMS-1, Genome Announc. 2015; 3(1):e01584-14. Published 2015 Feb. 12. doi:10.1128/genomeA.01584-14.

11. Shimamori Y., et al., Isolation and Characterization of Novel Phage SaGU1 that Infects *Staphylococcus aureus* Clinical Isolates from Patients with Atopic Dermatitis, Curr Microbiol 78, 1267-1276 (2021).

12. Kwan, T. et al., The Complete Genomes and Proteomes of 27 *Staphylococcus aureus* bacteriophages, PNAS 102 (4), 5174-5179, Apr. 5, 2005.

13. Göller, P. C., et al., Multi-species host range of staphylococcal phages isolated from wastewater. Nat Commun 12,6965 (2021)

We claim:

1. A composition formulated for topical administration comprising:
    a) one or more *Staphylococcus aureus* (*S. aureus*) bacteriophages, and
    b) colloidal oatmeal,
    wherein the one or more *S. aureus* bacteriophages comprises the nucleic acid SEQ ID NO: 1, 44, and/or 45.

2. The composition of claim 1, further comprising one or more additional active agents.

3. The composition of claim 2, wherein the one or more additional active agents comprises a ceramide, hyaluronic acid, glycerin, petrolatum, niacinamide, an enzyme, and a probiotic bacteria.

4. The composition of claim 3, wherein the enzyme comprises a bacterial cell wall degrading enzyme.

5. The composition of claim 3, wherein the enzyme comprises an endolysin.

6. The composition of claim 3, wherein the enzyme comprises an anti-aging enzyme.

7. The composition of claim 1 consisting of the one or more *S. aureus* bacteriophage and the colloidal oatmeal.

8. A method of treating eczema in a subject in need thereof, the method comprising: topically administering a therapeutically effective amount of the composition of claim 1 to a region of the subject's skin comprising the eczema.

9. The method of claim 8, wherein administration comprises once daily, twice daily, three times daily or four times daily administration.

10. The method of claim 9, wherein the composition is administered for one week, two weeks, three weeks or more.

11. The method of claim 8, wherein treating comprises reducing one or more of the following eczema symptoms: itchy skin, dry skin, redness, and swelling of the region of the subject's skin administered the composition.

12. The method of claim 11, wherein reducing the one or more eczema symptoms occurs more quickly than in a control subject.

13. The method of claim 12, wherein the treated subject exhibits improvement 5%, 10%, 15%, 20%, 25%, 30%, 35%, 40%, 45%, or 50% faster than the control subject.

14. The method of claim 11, wherein the treated subject exhibits about 5%, 10%, 15%, 20%, 25%, 30%, 35%, 40%, 45%, 50% or greater improvement in at least one symptom as compared to a comparable control subject, in the same amount of time.

15. The method of claim 8, wherein the eczema is selected from the group consisting of contact eczema, allergic contact eczema, seborrheic eczema, nummular eczema, neurodermatitis, stasis dermatitis, and dyshidrotic eczema.

16. The method of claim 8, wherein the eczema is atopic eczema.

17. The method of claim 8, wherein the subject is human.

\*   \*   \*   \*   \*